United States Patent
Hartung et al.

(10) Patent No.: US 7,846,928 B2
(45) Date of Patent: Dec. 7, 2010

(54) SUBSTITUTED PYRAZOLOPYRIDINES AND SALTS THEREOF, PHARMACEUTICAL COMPOSITIONS COMPRISING SAME, METHODS OF PREPARING SAME AND USES OF SAME

(75) Inventors: Ingo Hartung, Berlin (DE); Stuart Ince, Berlin (DE); Georg Kettschau, Berlin (DE); Karl-Heinz Thierauch, Berlin (DE); Hans Briem, Bremen (DE); Ulf Boemer, Glienicke/Nordbahn (DE)

(73) Assignee: Bayer Schering Pharma AG, Berlin (DE)

( * ) Notice: Subject to any disclaimer, the term of this patent is extended or adjusted under 35 U.S.C. 154(b) by 716 days.

(21) Appl. No.: 11/761,672

(22) Filed: Jun. 12, 2007

(65) Prior Publication Data

US 2008/0058326 A1 Mar. 6, 2008

Related U.S. Application Data

(60) Provisional application No. 60/816,626, filed on Jun. 27, 2006, provisional application No. 60/890,937, filed on Feb. 21, 2007.

(30) Foreign Application Priority Data

Jun. 13, 2006 (EP) .................................. 06090109
Feb. 15, 2007 (EP) .................................. 07090020

(51) Int. Cl.
| | |
|---|---|
| A61K 31/44 | (2006.01) |
| A61K 31/501 | (2006.01) |
| A61K 31/535 | (2006.01) |
| A61P 43/00 | (2006.01) |
| C07D 401/00 | (2006.01) |
| C07D 413/00 | (2006.01) |
| C07D 471/02 | (2006.01) |

(52) U.S. Cl. .............................. 514/234.2; 514/252.16; 514/303; 546/118; 544/117; 544/362

(58) Field of Classification Search ............... 514/234.2, 514/252.16, 303; 546/118; 544/117, 362
See application file for complete search history.

(56) References Cited

FOREIGN PATENT DOCUMENTS

| WO | 02/060900 | * | 8/2002 |
|---|---|---|---|
| WO | WO 2004/113304 A1 | | 12/2004 |
| WO | WO 2006/050109 A2 | | 5/2006 |
| WO | WO 2007/000241 A1 | | 1/2007 |

OTHER PUBLICATIONS

D. Albert et al., "Preclinical Activity of ABT-869, A Multitargeted Receptor Tyrosine Kinase Inhibitor," Mol. Cancer Therapeutics, vol. 5, No. 4, (Apr. 2006) pp. 995-1006.

* cited by examiner

*Primary Examiner*—D. Margaret Seaman
*Assistant Examiner*—Niloofar Rahmani
(74) *Attorney, Agent, or Firm*—Millen, White, Zelano, Branigan, P.C.

(57) ABSTRACT

The invention relates to substituted pyrazolopyridines according to the general formula (I):

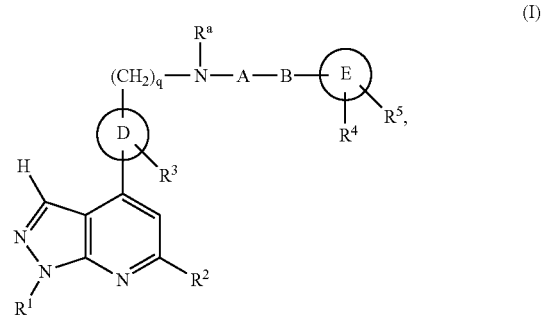

in which A, B, D, E, $R^a$, $R^1$, $R^2$, $R^3$, $R^4$, $R^5$ and q are as defined in the claims, and salts thereof, to pharmaceutical compositions comprising said substituted pyrazolopyridine compounds, to methods of preparing said substituted pyrazolopyridines, as well as to uses thereof for manufacturing a pharmaceutical composition for the treatment of diseases of dysregulated vascular growth or of diseases which are accompanied with dysregulated vascular growth, wherein the compounds effectively interfere with Tie2 signalling.

39 Claims, No Drawings

SUBSTITUTED PYRAZOLOPYRIDINES AND SALTS THEREOF, PHARMACEUTICAL COMPOSITIONS COMPRISING SAME, METHODS OF PREPARING SAME AND USES OF SAME

This application claims the benefit of the filing date of U.S. Provisional Application Ser. No. 60/816,626 filed Jun. 27, 2006 and U.S. Provisional Application Ser. No. 60/890,937 filed Feb. 21, 2007, which is incorporated by reference herein.

The present invention relates to substituted pyrazolopyridine compounds of general formula (I) and salts thereof, to pharmaceutical compositions comprising said substituted pyrazolopyridine compounds, to methods of preparing said substituted pyrazolopyridines, as well as to uses thereof.

SCIENTIFIC BACKGROUND

Dysregulated vascular growth plays a critical role in a variety of inflammatory diseases, in particular psoriasis, delayed type hypersensitivity, contact dermatitis, asthma, multiple sclerosis, restenosis, rheumatoid arthritis and inflammatory bowl disease. Aberrant vascular growth is also involved in neovascular ocular diseases such as age-related macular degeneration and diabetic retinopathy. Additionally, sustained vascular growth is accepted as one hallmark of cancer development (Hanahan, D.; Weinberg, R. A. *Cell* 2000, 100, 57). While tumors initially grow either as an avascular mass or by co-opting existing host vessels, growth beyond a few $mm^3$ in size is depending on the induction of vessel neogrowth in order to sufficiently provide the tumor with oxygen and nutrients. Induction of angiogenesis is a prerequisite that the tumor surpasses a certain size (the so called angiogenic switch). An intricate signaling interaction network between cancer cells and the tumor microenvironment triggers the induction of vessel growth from existing vasculature. The dependence of tumors on neovascularization has led to a new treatment paradigm in cancer therapy (Ferrara et al. *Nature* 2005, 438, 967; Carmeliet *Nature* 2005, 438, 932). Blocking tumor neovascularization by small molecule or antibody-mediated inhibition of relevant signal transduction pathways holds a great promise for extending currently available therapy options.

The development of the cardiovascular system involves two basic stages. In the initial vasculogenesis stage, which only occurs during embryonal development, angioblasts differentiate into endothelial cells which subsequently form a primitive vessel network. The subsequent stage, termed angiogenesis, involves the remodeling of the initial vasculature and sprouting of new vessels (Risau, W. *Nature* 1997, 386, 671; Jain, R. K. *Nat. Med.* 2003, 9, 685). Physiologically, angiogenesis occurs in wound healing, muscle growth, the female cycle and in the above mentioned disease states.

It has been found that receptor tyrosine kinases of the vascular endothelial growth factor (VEGF) family and the Tie (tyrosine kinase with immunoglobulin and epidermal growth factor homology domain) receptor tyrosine kinases are essential for both developmental and disease-associated angiogenesis (Ferrara et al *Nat. Med.* 2003, 9, 669; Dumont et al. *Genes Dev.* 1994, 8, 1897; Sato et al. *Nature* 1995, 376, 70).

In adults the Tie2 receptor tyrosine kinase is selectively expressed on endothelial cells (EC) of the adult vasculature (Schlaeger et al. *Proc. Nat. Acad. Sci. USA* 1997, 94, 3058). Immunohistochemical analysis demonstrated the expression of Tie2 in adult rat tissues undergoing angiogenesis. During ovarian folliculogenesis, Tie2 is expressed in neovessels of the developing corpus luteum. Four endogeneous ligands—angiopoietins 1 to 4—have been identified for the type 1 transmembrane Tie2 (also named Tek) receptor, while no ligands have been identified so far for the Tie1 receptor. Binding of the extracellular Tie2 domain to the C-terminal fibrinogen-like domains of the various angiopoietins leads to significantly different cellular effects. In addition, heterodimerizations between Tie1 and Tie2 receptors have been postulated to influence ligand binding.

Binding of Ang1 to Tie2 expressed on EC induces receptor cross-phosphorylation and kinase activation thus triggering various intracellular signaling pathways. The intracellular C-terminal tail of the Tie2 protein plays a crucial role in Tie2 signaling (Shewchuk et al. *Structure* 2000, 8, 1105). Upon ligand binding, a conformational change is induced which removes the C-tail out of its inhibitory conformation thus allowing kinase activation by cross-phosphorylation of various Tyr residues in the C-tail, which subsequently function as docking sites for phosphotyrosine-binding (PTB) site possessing down-stream mediators. Cellular effects initiated by Ang1 activation of Tie2 include inhibition of EC apoptosis, stimulation of EC migration and blood vessel reorganization, suppression of inflammatory gene expression and suppression of vascular permeability (Brindle et al. *Circ. Res.* 2006, 98, 1014). In contrast to VEGF-VEGFR signaling in EC, Ang1 activation of Tie2 does not stimulate EC proliferation in the majority of published assay settings.

The anti-apoptotic effect of Tie2 signaling was shown to be mediated mainly by the PI3K-Akt signaling axis which is activated by binding of the regulatory p85 subunit of PI3K to Y1102 in the Tie2 C-tail (DeBusk et al. *Exp. Cell. Res.* 2004, 298, 167; Papapetropoulos et al. *J. Biol. Chem.* 2000, 275, 9102; Kim et al. *Circ. Res.* 2000, 86, 24). In contrast, the chemotactic response downstream of the activated Tie2 receptor requires crosstalk between PI3K and the adaptor protein Dok-R. Membrane localization of Dok-R via binding of its pleckstrin homology (PH) domain to PI3K and simultaneous binding to Y1108 in the Tie2 C-tail via its PTB domain leads to Dok-R phosphorylation and downstream signaling via Nck and Pak-1 (Jones et al. *Mol. Cell. Biol.* 2003, 23, 2658; Master et al. *EMBO J.* 2001, 20, 5919). PI3K-mediated recruitment of the adaptor protein ShcA to Y1102 of the Tie2 C-tail is also believed to induce cellular sprouting and motility effects involving activation of endothelial nitric oxide synthase (eNOS), focal adhesion kinase (FAK) and the GTPases RhoA and Rac1. Other downstream mediators of Tie2 signaling include the adaptor protein Grb2, which mediates Erk1/2 stimulation, and the SHP-2 phosphatase.

In conclusion, basal activation of the Tie2 pathway by Ang1 is believed to maintain quiescence and integrity of the endothelium of the adult vasculature by providing a cell survival signal for ECs and by maintaining the integrity of the EC lining of blood vessels (Peters et al. *Recent Prog. Horm. Res.* 2004, 59, 51).

In contrast to Ang1, Ang2 is not able to activate Tie2 on EC unless Ang2 is present in high concentration or for prolonged periods. However, Ang2 functions as a Tie2 agonist in non-endothelial cells transfected with Tie2. The structural basis for this context-dependence of the Ang2-Tie2 interaction is to date not understood.

In endothelial cells, however, Ang2 functions as Tie2 antagonist and thus blocks the agonistic activity of Ang1 (Maisonpierre et al. *Science* 1997, 277, 55). Ang2 binding to Tie2 prevents Ang1-mediated Tie2 activation which leads to vessel destabilization and results in vessel regression in the absence of pro-angiogenic stimuli such as VEGF. While Ang1 is widely expressed by periendothelial cells in quiescent vasculature such as pericytes or smooth muscle cells, Ang2 expression occurs in areas of ongoing angiogenesis. Ang2 can be stored in Weibel-Palade bodies in the cytoplasm of EC allowing for a quick vascular response upon stimulation.

Ang1 and Ang2 are expressed in the corpus luteum, with Ang2 localizing to the leading edge of proliferating vessels and Ang1 localizing diffusively behind the leading edge. Ang2 expression is inter alia initiated by hypoxia (Pichiule et al. *J. Biol. Chem.* 2004, 279, 12171). Ang2 is upregulated in the tumor vasculature and represents one of the earliest tumor markers. In the hypoxic tumor tissue, Ang2 expression induces vessel permeability and—in the presence of e.g. pro-angiogenic VEGF—triggers angiogenesis. After VEGF mediated EC proliferation and vessel sprouting maturation of the newly formed vessels again necessitates Tie2 activation by Ang1. Therefore, a subtle balancing of Tie2 activity plays a pivotal role in the early as well as late stages of neovascularization. These observations render the Tie2 RTK an attractive target for anti-angiogenesis therapy in diseases caused by or associated with dysregulated vascular growth. However, it remains to be shown if targeting the Tie2 pathway alone will be sufficient to achieve efficacious blockade of neovascularization. In certain diseases or disease subtypes it might be necessary or more efficacious to block several angiogenesis-relevant signaling pathways simultaneously.

Various theories have been discussed to explain the differential effects of Ang1 and Ang2 on Tie2 downstream signaling events. Binding of Ang1 and Ang2 in a structurally different manner to the Tie2 ectodomain could induce ligand-specific conformational changes of the intracellular kinase domain explaining different cellular effects. Mutational studies however point toward similar binding sites of Ang1 and Ang2. In contrast, various publications have focussed on different oligomerization states of Ang1 vs. Ang2 as basis for different receptor multimerization states upon ligand binding. Only Ang1 present in its tetramer or higher-order structure initiates Tie2 activation in EC while Ang2 was reported to exist as a homodimer in its native state (Kim et al. *J. Biol. Chem.* 2005, 280, 20126; Davis et al. *Nat. Struc. Biol.* 2003, 10, 38; Barton et al. *Structure* 2005, 13, 825). Finally, specific interactions of Ang1 or Ang2 with additional cell-specific co-receptors could be responsible for the different cellular effects of Ang1 vs. Ang2 binding to Tie2. Interaction of Ang1 with integrin $\alpha 5\beta 1$ has been reported to be essential for certain cellular effects (Carlson et al. *J. Biol. Chem.* 2001, 276, 26516; Dallabrida et al. *Circ. Res.* 2005, 96, e8). Integrin $\alpha 5\beta 1$ associates constitutively with Tie2 and increases the receptor's binding affinity for Ang1 resulting in initiation of downstream signaling at lower Ang1 effector concentrations in situations where integrin $\beta 5\beta 1$ is present. The recently solved crystal structure of the Tie2-Ang2 complex suggests however that neither the oligomerization state nor a different binding mode causes the opposing cellular effects (Barton et al. *Nat. Struc. Mol. Biol.* 2006, advance online publication).

Ang1-Tie2 signaling plays also a role in the development of the lymphatic system and in lymphatic maintenance and sprouting (Tammela et al. *Blood* 2005, 105, 4642). An intimate cross-talk between Tie2 and VEGFR-3 signaling in lymphangiogenesis seems to equal the Tie2-KDR cross-talk in blood vessel angiogenesis.

A multitude of studies have underscored the functional significance of Tie2 signaling in the development and maintenance of the vasculature. Disruption of Tie2 function in Tie2$^{-/-}$ transgenic mice leads to early embryonic lethality between days 9.5 and 12.5 as a consequence of vascular abnormalities. Tie2$^{-/-}$ embryos fail to develop the normal vessel hierarchy suggesting a failure of vascular branching and differentiation. The heart and vessels in Tie2$^{-/-}$ embryos show a decreased lining of EC and a loosened interaction between EC and underlying pericyte/smooth muscle cell matrix. Mice lacking functional Ang1 expression and mice overexpressing Ang2 display a phenotype reminiscent of the phenotype of Tie2$^{-/-}$ mice (Suri et al. *Cell* 1996, 87, 1171). Ang2$^{-/-}$ mice have profound defects in the growth and patterning of lymphatic vasculature and fail to remodel and regress the hyaloid vasculature of the neonatal lens (Gale et al. *Dev. Cell* 2002, 3, 411). Ang1 rescued the lymphatic defects, but not the vascular remodeling defects. Therefore, Ang2 might function as a Tie2 antagonist in blood vasculature but as a Tie2 agonist in developing lymph vasculature suggesting redundant roles of Ang1 and Ang2 in lymphatic development.

Aberrant activation of the Tie2 pathway is involved in various pathological settings. Activating Tie2 mutations leading to increased ligand-dependent and ligand-independent Tie2 kinase activity cause inherited venous malformations (Vikkula et al. *Cell* 1996, 87, 1181). Increased Ang1 mRNA and protein levels as well as increased Tie2 activation have been reported in patients with pulmonary hypertension (PH). Increased pulmonary arterial pressure in PH patients results from increased coverage of pulmonary arterioles with smooth muscle cells (Sullivan et al. *Proc. Natl. Acad. Sci. USA* 2003, 100, 12331). In chronic inflammatory diseases, like in psoriasis, Tie2 and the ligands Ang1 and Ang2 are greatly upregulated in lesions, whereas a significant decrease in expression of Tie2 and ligands occur under anti-psoriatic treatment (Kuroda et al. *J. Invest. Dermatol* 2001, 116, 713). Direct association of pathogenesis of disease with Tie2 expression has been demonstrated recently in transgenic mice overexpressing Tie2 (Voskas et al. *Am. J. Pathol.* 2005, 166, 843). In these mice overexpression of Tie2 causes a psoriasis-like phenotype (such as epidermal thickening, rete ridges and lymphocyte infiltration). These skin abnormalities are resolved completely upon suppression of transgene expression, thereby illustrating a complete dependence on Tie2 signalling for disease maintenance and progression.

Tie2 expression was investigated in human breast cancer specimens and Tie2 expression was found in the vascular endothelium both in normal breast tissue as well as in tumor tissue. The proportion of Tie2-positive microvessels was increased in tumors as compared to normal breast tissue (Peters et al. *Br. J. Canc.* 1998, 77, 51). However, significant heterogeneity in endothelial Tie2 expression was observed in clinical specimen from a variety of human cancers (Fathers et al. *Am. J. Path.* 2005, 167, 1753). In contrast, Tie2 and angiopoietins were found to be highly expressed in the cytoplasm of human colorectal adenocarcinoma cells indicating at the potential presence of an autocrine/paracrine growth loop in certain cancers (Nakayama et al. *World J. Gastroenterol.* 2005, 11, 964). A similar autocrine/paracrine Ang1-Ang2-Tie2 loop was postulated for certain human gastric cancer cell lines (Wang et al. *Biochem. Biophys. Res. Comm.* 2005, 337, 386).

The relevance of the Ang1-Tie2 signaling axis was challenged with various biochemical techniques. Inhibition of Ang1 expression by an antisense RNA approach resulted in decreased xenograft tumor growth (Shim et al. *Int. J. Canc.* 2001, 94, 6; Shim et al. *Exp. Cell Research* 2002, 279, 299). However, other studies report that experimental overexpression of Ang1 in tumor models leads to decreased tumor growth (Hayes et al. *Br. J. Canc.* 2000, 83, 1154; Hawighorst et al. *Am. J. Pathol.* 2002, 160, 1381; Stoeltzing et al. *Cancer Res.* 2003, 63, 3370). The latter results can be rationalized by the ligand's ability to stabilize the endothelial lining of vessels rendering vessels less sensitive for angiogenic stimuli. Interference with the dynamics of Ang1-Tie2 signaling either by over-stimulation or by stimulus deprivation seemingly leads to similar phenotypes.

The pharmacological relevance of inhibiting Tie2 signaling was tested applying various non-small molecule approaches. A peptidic inhibitor of Ang1/2 binding to Tie2 was shown to inhibit Ang1-induced HUVEC migration and angiogenesis induction in an in vivo model (Tournaire et al. *EMBO Rep.* 2005, 5, 1). Corneal angiogenesis induced by tumor cell conditioned medium was inhibited by a recombinant soluble Tie2 receptor (sTie2) despite the presence of VEGF (Lin et al. *J. Clin. Invest.* 1997, 100, 2072; see also Singh et al. *Biochem. Biophys. Res. Comm.* 2005, 332, 194). Gene therapy by adenoviral vector delivered sTie2 was capable of reducing tumor growth rates of a murine mammary carcinoma and a murine melanoma and resulted in reduction of metastasis formation (Lin et al. *Proc. Natl. Acad. Sci. USA* 1998, 95, 8829). Similar effects were observed with related sTie2 constructs (Siemeister et al. *Cancer Res.* 1999, 59, 3185) and a Tek-Fc construct (Fathers et al. *Am. J. Path.* 2005, 167, 1753).

Adenovirus-delivered anti-Tie2 intrabodies were shown to inhibit growth of a human Kaposi's sarcoma and a human colon carcinoma upon peritumoral administration (Popkov et al. *Cancer Res.* 2005, 65, 972). Histopathological analysis revealed a marked decrease in vessel density in treated vs. control tumors. Phenotypic simultaneous knockout of KDR and Tie2 by an adenovirus delivered intradiabody resulted in significantly higher growth inhibition of a human melanoma xenograft model than KDR knockout alone (Jendreyko et al. *Proc. Natl. Acad. Sci. USA* 2005, 102, 8293). Similarly, the bispecific Tie2-KDR intradiabody was more active in an in vitro EC tube formation inhibition assay than the two monospecific intrabodies alone (Jendreyko et al. *J. Biol. Chem.* 2003, 278, 47812). Systematic treatment of tumor-bearing mice with Ang2-blocking antibodies and peptide-Fc fusion proteins led to tumor stasis and elimination of tumor burden in a subset of animals (Oliner et al. *Cancer Cell* 2004, 6, 507). For a recent report on an immunization approach, see Luo et al. *Clin. Cancer Res.* 2006, 12, 1813.

However, from the above studies using biochemical techniques to interfere with Tie2 signaling it is not clear, whether similar phenotypes will be observed with small molecule inhibitors of the Tie2 kinase activity. Small molecule inhibitors of kinases by definition block only those cellular effects which are mediated by the receptor's kinase activity and not those which might involve the kinase only as a co-receptor or scaffolding component in multi-enzyme complexes. So far, only a single study using a small molecule Tie2 inhibitor has been published (Scharpfenecker et al. *J. Cell Sci.* 2005, 118, 771). It remains to be shown that small molecule inhibitors of the Tie2 kinase will be as efficacious in inhibiting angiogenesis as e.g. ligand antibodies, soluble decoy receptors or receptor intrabodies. As discussed above, in certain settings inhibition of Tie2 signaling alone might not be sufficient to induce an adequate antiangiogenic effect. Simultaneous inhibition of several angiogenesis relevant signaling pathways could overcome such inadequacies. In conclusion, there is a great need for novel chemotypes for small molecule inhibitors of the Tie2 kinase. Fine tuning of additive anti-angiogenic activities as well as pharmacokinetic parameters such as e.g. solubility, membrane permeability, tissue distribution and metabolism will finally allow for choosing compounds of accurate profiles for various diseases caused by or associated with dysregulated vascular growth.

PRIOR ART

To date, a small number of therapeutic agents with antiangiogenic activity have been approved for cancer treatment. Avastin (Bevacizumab), a VEGF neutralizing antibody, blocks KDR and VEGFR1 signaling and has been approved for first-line treatment of metastatic colorectal cancer. The small molecule multi-targeted kinase inhibitor Nexavar (Sorafenib) inhibits inter alia members of the VEGFR family and has been approved for the treatment of advanced renal cell carcinoma. Sutent (Sunitinib), another multi-targeted kinase inhibitor with activity vs. VEGFR family members, has been approved by the FDA for treatment of patients with gastrointestinal stromal tumors (GIST) or advanced kidney tumors. Several other small molecule inhibitors of angiogenesis-relevant targets are in clinical and pre-clinical development.

AMG-386, an angiopoietin-targeting recombinant Fc fusion protein, is in phase I clinical development in patients with advanced solid tumors. Several multi-targeted small molecule inhibitors with activity against Tie2 are (or have been) in preclinical evaluation for cancer therapy, including ABT-869, GW697465A and A-422885.88 (BSF466895). The first and most recent compound, however, was reported to possess higher inhibitory activity against other kinase targets including non-angiogenesis kinases and oncogenic kinases. This agent is therefore not considered to be a purely antiangiogenic agent and its applicability to non-cancer diseases remains to be shown.

Pyrazolopyridines have been disclosed as antimicrobiotic substances (e.g. Attaby et al., *Phosphorus, Sulfur and Silicon and the related Elements* 1999, 149, 49-64; Goda et al. *Bioorg. Med. Chem.* 2004, 12, 1845). U.S. Pat. No. 5,478,830 further discloses fused heterocycles for the treatment of atherosclerosis. Pyrazolopyridines have also been described as PDE4-Inhibitors (WO2006004188, US20060004003).

A single 3-amino-1H-pyrazolo[3,4-b]pyridine with modest EGFR inhibitory activity has been published by Cavasotto et al. (*Bioorg. Med. Chem. Lett.* 2006, 16, 1969). 5-aryl-1H-3-aminopyrazolo[3,4-b]pyridines have been reported as GSK-3 inhibitors (Witherington et al. *Bioorg. Med. Chem. Lett.* 2003, 13, 1577). WO 2003068773 discloses 3-aminopyrazolopyridine derivatives as GSK-3 inhibitors. WO 2001019828 discloses 125 templates, including 3-amino-1H-pyrazolopyridines, as modulators of the activity of receptor and non-receptor tyrosine and serine/threonine kinases. WO 2004113304 discloses 3-amino-indazoles as inhibitors of protein tyrosine kinases, particularly as inhibitors as KDR kinase. WO 2006050109 discloses 3-aminopyrazolopyridines as tyrosine kinase inhibitors, particularly as KDR kinase inhibitors.

WO 2002024679 discloses tetrahydropyridine-substituted pyrazolopyridines as IKK inhibitors. WO 2004076450 further discloses 5-heteroaryl-pyrazolopyridines as p38 inhibitors. WO2005044181 discloses pyrazolopyridines as Abl kinase inhibitors.

TECHNICAL PROBLEM TO BE SOLVED

There is a high demand for active compounds which can be used as potent inhibitors of Tie2 kinase for the treatment of diseases of dysregulated vascular growth or diseases which are accompanied with dysregulated vascular growth, in particular solid tumors and metastases thereof. However, it would be desirable to have compounds at one's disposal which display potent inhibition of Tie2 while being less active as inhibitors of other kinases, particularly as inhibitor of the insulin receptor kinase (InsR). Inhibition of InsR kinase may result in disadvantageous effects on the liver. The insulin/IGF-1 receptor inhibitor NVP-ADW742 for example at concentrations which inhibit both the insulin and IGF-1 receptors strongly potentiated deoxycholic acid-induced apoptotic cell death, which as a consequence predicts strong liver toxic effects in case of impaired bile flow (Dent et al. *Biochem. Pharmacol.* 2005, 70, 1685). Even worse, inhibition of the neuronal insulin receptor causes Alzheimer-like disturbances in oxidative/energy brain metabolism (Hoyer et al. *Ann. N.Y. Acad. Sci.* 1999, 893, 301).

Inhibition of kinases by using ATP-competitive heteroaromatic compounds is well precedented in the patent and scientific literature (Parang, K.; Sun, G. *Curr. Opin. Drug Disc.* 2004, 7, 617: *Design Strategies for protein kinase inhibitors.*). It is known to the person skilled in the art that ATP-competitive compounds bind to the ATP-binding site in kinases by forming a hydrogen bonding network to a distinct region of the enzyme (the so called hinge region). 3-Aminopyrazoles were shown to form such a hydrogen bonding network to a kinase hinge region including the amino group of the 3-aminopyrazole moiety (Witherington et al.: "5-arylpyrazolo[3,4-b]pyridines: Potent inhibitors of glycogen synthase kinase-3" *Bioorg. Med. Chem. Lett.* 2003, 13, 1577). The person skilled in the art would expect that removing this amino group should disrupt this hydrogen bond network in part and therefore should lead to compounds with significantly reduced activity as kinase inhibitors.

DESCRIPTION OF THE INVENTION

Surprisingly, it was now found that compounds of the present invention, which feature a pyrazole hinge binding moiety lacking the 3-amino group not only display potent activity as inhibitors of Tie2 kinase. Even more surprisingly, compounds of the present invention display a more selective inhibition of Tie2 kinase relative to not desired target kinases, particularly the insulin receptor kinase (InsR).

Such a pharmacological profile is highly desirable not only for treating diseases of dysregulated vascular growth or diseases which are accompanied with dysregulated vascular growth, in particular solid tumors and metastases thereof, but for treating non-oncological diseases of dysregulated vascular growth or non-oncological diseases which are accompanied with dysregulated vascular growth, such as retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel, diseases such as coronary and peripheral artery disease, wherein treatment of the said non-oncological diseases are preferably accomplished with less side-effects than in the treatment of oncological diseases.

The solution to the above-mentioned novel technical problem is achieved by providing compounds derived, in accordance with the present invention, from a class of substituted pyrazolopyridines and salts thereof, methods of preparing substituted pyrazolopyridines, a pharmaceutical composition containing said substituted pyrazolopyridines, use of said substituted pyrazolopyridines and a method for treating diseases with said substituted pyrazolopyridines, all in accordance with the description, as defined in the claims of the present application.

The invention thus relates to compounds of general formula (I):

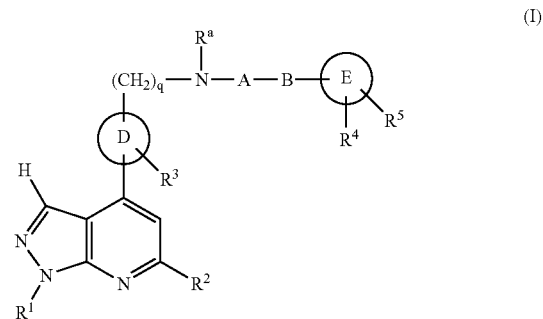

in which:
R$^1$ represents H or —C(O)R$^b$, or is selected from the group comprising, preferably consisting of, C$_1$-C$_6$-alkyl, C$_2$-C$_6$-alkenyl, C$_2$-C$_6$-alkynyl, C$_3$-C$_{10}$-cycloalkyl, C$_3$-C$_{10}$-heterocycloalkyl, wherein said residues are unsubstituted or substituted one or more times, independently from each other, with R$^6$;

R$^2$ stands for hydrogen, —NR$^{d1}$R$^{d2}$, —C(O)R$^b$, or is selected from the group comprising, preferably consisting of, C$_1$-C$_6$-alkyl, C$_2$-C$_6$-alkenyl, C$_2$-C$_6$-alkynyl, C$_3$-C$_{10}$-cycloalkyl, C$_3$-C$_{10}$-heterocycloalkyl, aryl, heteroaryl, wherein said residues are unsubstituted or singly or multiply substituted independently from each other with R$^7$;

R$^3$ is selected from the group comprising, preferably consisting of, hydrogen, C$_1$-C$_6$-alkyl, C$_1$-C$_6$-alkoxy, C$_1$-C$_6$-haloalkyl, C$_1$-C$_6$-haloalkoxy, hydroxy, amino, halogen, cyano;

R$^4$, R$^5$, R$^6$, R$^7$, R$^8$ independently from each other, are selected from the group comprising, preferably consisting of, hydrogen, C$_1$-C$_6$-alkyl, C$_3$-C$_{10}$-cycloalkyl, C$_3$-C$_{10}$-heterocycloalkyl, C$_1$-C$_6$-haloalkyl, C$_1$-C$_6$-haloalkoxy, aryl, heteroaryl, hydroxy, amino, halogen, cyano, nitro, —C(O)R$^b$, —S(O)$_2$R$^b$, —OR$^c$, —NR$^{d1}$R$^{d2}$, —OP(O)(OR$^c$)$_2$, wherein C$_1$-C$_6$-alkyl, C$_3$-C$_{10}$-heterocycloalkyl and C$_3$-C$_{10}$-cycloalkyl of R$^4$, R$^5$, R$^6$, and R$^7$, are optionally substituted one or more times, in the same way or differently, with R$^8$, and wherein C$_1$-C$_6$-alkyl, C$_3$-C$_{10}$-heterocycloalkyl and C$_3$-C$_{10}$-cycloalkyl of R$^8$, are optionally substituted once with R$^8$;

R$^a$ is selected from the group comprising, preferably consisting of, hydrogen or C$_1$-C$_6$-alkyl;

R$^b$ is selected from the group comprising, preferably consisting of, hydroxyl, —OR$^c$, —SR$^c$, —NR$^{d1}$R$^{d2}$, and C$_1$-C$_6$-alkyl;

R$^c$ is selected from the group comprising, preferably consisting of, hydrogen, —C(O)R$^b$, C$_1$-C$_6$-alkyl, C$_1$-C$_6$-haloalkyl C$_3$-C$_{10}$-cycloalkyl, C$_3$-C$_{10}$-heterocycloalkyl, wherein C$_1$-C$_6$-alkyl, C$_1$-C$_6$-haloalkyl, C$_3$-C$_{10}$-cycloalkyl, C$_3$-C$_{10}$-heterocycloalkyl are optionally substituted one or more times, in the same way or differently, with hydroxyl, halogen, aryl, or —NR$^{d1}$R$^{d2}$, and wherein C$_1$-C$_6$-alkyl, C$_1$-C$_6$-haloalkyl, C$_3$-C$_{10}$-cycloalkyl, C$_3$-C$_{10}$-heterocycloalkyl are optionally substituted once with —OR$^c$, or —OP(O)(OR$^c$)$_2$;

R$^{d1}$, R$^{d2}$ independently from each other are selected from the group comprising, preferably consisting of hydrogen, C$_1$-C$_6$-alkyl, C$_3$-C$_{10}$-cycloalkyl, C$_3$-C$_{10}$-heterocycloalkyl, aryl, heteroaryl, or for a —C(O)R$^c$, —S(O)$_2$R$^b$, or —C(O)NR$^{d1}$R$^{d2}$ group, wherein C$_1$-C$_6$-alkyl, C$_3$-C$_{10}$-cycloalkyl, $C_3$-$C_{10}$-heterocycloalkyl are optionally substituted one or more times, in the same way or differently, with halogen, hydroxy or an —$OR^c$, —$C(O)R^b$, —$S(O)_2R^b$, —$OP(O)(OR^c)_2$ group, and wherein $C_1$-$C_6$-alkyl, $C_3$-$C_{10}$-cycloalkyl, $C_3$-$C_{10}$-heterocycloalkyl are optionally substituted once with an —$NR^{d1}R^{d2}$ group; or $R^{d1}$ and $R^{d2}$ together with the nitrogen atom to which they are attached, form a 3 to 10 membered heterocycloalkyl ring, whereby the carbon backbone of this heterocycloalkyl ring is optionally interrupted one or more times, in the same way or differently, by a member of the group comprising, preferably consisting of, NH, $NR^{d1}$, oxygen or sulphur, and is optionally interrupted one or more times, in the same way or differently, with a —C(O)—, —S(O)—, and/or —$S(O)_2$— group, and optionally contains one or more double bonds;

A is selected from the group comprising, preferably consisting of, —C(O)—, —C(S)—, —C(=$NR^a$)—, —C(O)$NR^a$—, —C(=$NR^a$)$NR^a$—, —$S(O)_2$—, —S(O)(=$NR^a$)—, —$S(=NR^a)_2$—, —C(S)$NR^a$—, —C(O)C(O)—, —C(O)C(O)$NR^a$—, —C(O)$NR^aC(O)$—, —C(S)$NR^aC(O)$—, and —C(O)$NR^aC(S)$—;

B is a bond or a group selected from the group comprising, preferably consisting of $C_1$-$C_6$-alkylene, $C_3$-$C_{10}$-cycloalkylene, $C_3$-$C_{10}$-heterocycloalkylene;

D, E are, independently from each other, arylene or heteroarylene; and q represents an integer of 0, 1, or 2;

or a salt or an N-oxide, thereof, wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a preferred embodiment, the present invention relates to compounds of general formula (I), in which:

$R^1$ represents H or —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, wherein said residues are unsubstituted or substituted one or more times, independently from each other, with $R^6$;

$R^2$ stands for hydrogen, —$NR^{d1}R^{d2}$, —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, heteroaryl, wherein said residues are unsubstituted or singly or multiply substituted independently from each other with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen;

$R^4$, $R^5$, $R^6$, $R^7$, $R^8$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, hydroxy, amino, halogen, —C(O)$R^b$, —$S(O)_2R^b$, $OR^c$, $NR^{d1}R^{d2}$, OP(O)(OR^c)_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is selected from the group comprising, preferably consisting of, hydrogen or $C_1$-$C_6$-alkyl;

$R^b$ is selected from the group comprising, preferably consisting of, hydroxyl, $OR^c$, $SR^c$, $NR^{d1}R^{d2}$;

$R^c$ is selected from the group comprising, preferably consisting of, hydrogen, —C(O)$R^b$, $C_1$-$C_6$-alkyl, $C_1$-$C_6$-haloalkyl $C_3$-$C_{10}$-cycloalkyl, $C_3$-$C_{10}$-heterocycloalkyl, wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted one or more times, in the same way or differently, with hydroxyl, halogen, aryl, or —$NR^{d1}R^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —$OR^c$, or —OP(O)(OR^c)_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, $C_6$-$C_{11}$-aryl, $C_5$-$C_{10}$-heteroaryl, or for a group —C(O)$R^c$, —$S(O)_2R^b$, or C(O)$NR^{d1}R^{d2}$, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —$OR^c$, —C(O)$R^b$, —$S(O)_2R^b$, —OP(O)(OR^c)_2$ group, and wherein $C_1$-$C_6$-alkyl, $C_3$-$C_{10}$-cycloalkyl, $C_3$-$C_{10}$-heterocycloalkyl are optionally substituted once with the group —$NR^{d1}R^{d2}$; or $R^{d1}$ and $R^{d2}$ together with the nitrogen atom to which they are attached, form a 3 to 10 membered heterocycloalkyl ring, whereby the carbon backbone of this heterocycloalkyl ring is optionally interrupted one or more times, the same way or differently, by a member of the group comprising, preferably consisting of, NH, $NR^{d1}$, oxygen or sulphur, and is optionally interrupted one or more times, the same way or differently, with a —C(O)—, —S(O)—, and/or —$S(O)_2$— group, and optionally contains one or more double bonds;

A is selected from the group comprising, preferably consisting of, —C(O)—, —C(O)$NR^a$—, —$S(O)_2$—, —S(O)(=$NR^a$)—, —C(S)$NR^a$—, —C(O)C(O)—, —C(O)C(O)$NR^a$—, —C(O)$NR^aC(O)$—, —C(S)$NR^aC(O)$—, and —C(O)$NR^aC(S)$—;

B is a bond or a group selected from the group comprising, preferably consisting of $C_1$-$C_6$-alkylene, $C_3$-$C_{10}$-cycloalkylene, $C_3$-$C_{10}$-heterocycloalkylene;

D is phenylene;

E is phenylene or 5- or 6-membered heteroarylene; and q represents an integer of 0 or 1;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a particularly preferred embodiment, the present invention relates to compounds of general formula (I), in which:

$R^1$ represents H or —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, wherein said residues are unsubstituted or substituted one or more times, independently from each other, with $R^6$;

$R^2$ stands for hydrogen, —N$R^{d1}R^{d2}$, —C(O)$R^b$, or is selected from the group comprising, preferably consisting of, $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, heteroaryl, wherein said residues are unsubstituted or singly or multiply substituted independently from each other with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen;

$R^4$, $R^5$, $R^6$, $R^7$, $R^8$ independently from each other, are selected from the group comprising, preferably consisting of, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, hydroxy, amino, halogen, —C(O)$R^b$, —S(O)$_2R^b$, O$R^c$, N$R^{d1}R^{d2}$, OP(O)(O$R^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$; or more times with $R^a$ is selected from the group comprising, preferably consisting of, hydrogen or $C_1$-$C_6$-alkyl;

$R^b$ is selected from the group comprising, preferably consisting of, hydroxyl, O$R^c$, S$R^c$, N$R^{d1}R^{d2}$;

$R^c$ is selected from the group comprising, preferably consisting of, hydrogen, —C(O)$R^b$, $C_1$-$C_6$-alkyl, $C_1$-$C_6$-haloalkyl $C_3$-$C_{10}$-cycloalkyl, $C_3$-$C_{10}$-heterocycloalkyl, wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted one or more times with hydroxyl, halogen, aryl, or —N$R^{d1}R^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —O$R^c$, or —OP(O)(O$R^c$)$_2$;

$R^{d1}$, $R^{d2}$ independently from each other are selected from the group comprising, preferably consisting of hydrogen, $C_1$-$C_6$-alkyl, $C_3$-$C_{10}$-cycloalkyl, $C_3$-$C_{10}$-heterocycloalkyl, $C_6$-$C_{11}$-aryl, $C_5$-$C_{10}$-heteroaryl, or for a group —C(O)$R^c$, —S(O)$_2R^b$, or C(O)N$R^{d1}R^{d2}$, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —O$R^c$, —C(O)$R^b$, —S(O)$_2R^b$, —OP(O)(O$R^c$)$_2$ group, and wherein $C_1$-$C_6$-alkyl, $C_3$-$C_{10}$-cycloalkyl, $C_3$-$C_{10}$-heterocycloalkyl are optionally substituted once with an —N$R^{d1}R^{d2}$ group; or $R^{d1}$ and $R^{d2}$ together with the nitrogen atom to which they are attached, form a 3 to 10 membered heterocycloalkyl ring, whereby the carbon backbone of this heterocycloalkyl ring is optionally interrupted one or more times, the same way or differently, by a member of the group comprising, preferably consisting of, NH, N$R^{d1}$, oxygen or sulphur, and is optionally interrupted one or more times, the same way or differently, with a —C(O)—, —S(O)—, and/or —S(O)$_2$— group, and optionally contains one or more double bonds;

A is selected from the group comprising, preferably consisting of, —C(O)—, —C(O)N$R^a$—, —S(O)$_2$—;

B is a bond or a group selected from the group comprising, preferably consisting of $C_1$-$C_6$-alkylene, $C_3$-$C_{10}$-cycloalkylene;

D is phenylene;

E is phenylene or 5- or 6-membered heteroarylene;

and q represents an integer of 0 or 1;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a more particularly preferred embodiment, the present invention relates to compounds of general formula (I), in which:

$R^1$ represents H or —C(O)$R^b$, or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ stands for hydrogen or is selected from the group comprising, preferably consisting of, $C_1$-$C_6$-alkyl, $C_3$-$C_6$-cycloalkyl, $C_3$-$C_6$-heterocycloalkyl, aryl, heteroaryl, wherein said residues are unsubstituted or singly or multiply substituted independently from each other with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, O$R^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, O$R^c$, N$R^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, —C(O)$R^b$, —S(O)$_2R^b$, O$R^c$, N$R^{d1}R^{d2}$, wherein $C_3$-$C_6$-heterocycloalkyl is optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, O$R^c$, N$R^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, halogen, —C(O)$R^b$, —S(O)$_2R^b$, O$R^c$, N$R^{d1}R^{d2}$;

$R^a$ is hydrogen;

$R^b$ is selected from the group comprising, preferably consisting of, O$R^c$, N$R^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times, in the same way or differently, with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —$C(O)R^c$ or $C(O)NR^{d1}R^{d2}$ group, wherein $C_1$-$C_6$-alkyl, and $C_3$-$C_6$-cycloalkyl are optionally substituted one or more times, in the same way or differently, with an —$OR^c$, or —$C(O)R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen;

A is selected from the group comprising, preferably consisting of, —$C(O)$—, —$C(O)NR^a$—, —$S(O)_2$—;

B is a bond or a group selected from the group comprising, preferably consisting of $C_1$-$C_3$-alkylene, $C_3$-cycloalkylene;

D and E are phenylene;

and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

In accordance with a first variant of the more particularly preferred embodiment, supra, the present invention relates to compounds of general formula (I), in which:

$R^1$ represents H or —$C(O)R^b$, or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ stands for hydrogen or is selected from the group comprising, preferably consisting of, $C_1$-$C_6$-alkyl, $C_3$-$C_6$-cycloalkyl, $C_3$-$C_6$-heterocycloalkyl, aryl, heteroaryl, wherein said residues are unsubstituted or singly or multiply substituted independently from each other with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, $OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —$C(O)R^b$, —$S(O)_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, —$C(O)R^b$, —$S(O)_2R^b$, $OR^c$, $NR^{d1}R^{d2}$, wherein $C_3$-$C_6$-heterocycloalkyl is optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —$C(O)R^b$, —$S(O)_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, halogen, —$C(O)R^b$, —$S(O)_2R^b$, $OR^c$, $NR^{d1}R^{d2}$;

$R^a$ is hydrogen;

$R^b$ is selected from the group comprising, preferably consisting of, $OR^c$, $NR^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —$C(O)R^c$ or $C(O)NR^{d1}R^{d2}$ group, wherein $C_1$-$C_6$-alkyl, and $C_3$-$C_6$-cycloalkyl are optionally substituted one or more times, in the same way or differently, with an —$OR^c$, or —$C(O)R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen;

A is —$C(O)NR^a$—;

B is a bond or a group selected from the group comprising, preferably consisting of $C_1$-$C_3$-alkylene, $C_3$-cycloalkylene D and E are phenylene; and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

Preferably, the first variant of the more particularly preferred embodiment, supra, of the present invention relates to compounds of general formula (I), in which:

$R^1$ represents H or —$C(O)R^b$, or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ stands for hydrogen or is selected from the group comprising, preferably consisting of, $C_1$-$C_6$-alkyl, $C_3$-cycloalkyl;

$R^3$ is selected from the group comprising, preferably consisting of, hydrogen, methyl, fluoro, or chloro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, $OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —$C(O)R^b$, —$S(O)_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, —$C(O)R^b$, —$S(O)_2R^b$, $OR^c$, $NR^{d1}R^{d2}$, wherein $C_3$-$C_6$-heterocycloalkyl is optionally substituted one or more times with $R^8$;

$R^8$ is selected from the group comprising, preferably consisting of, $C_1$-$C_6$-haloalkoxy, hydroxy, amino, halogen, —$C(O)R^b$, —$S(O)_2R^b$, $OR^c$, $NR^{d1}R^{d2}$;

$R^a$ is hydrogen;

$R^b$ is selected from the group comprising, preferably consisting of, $OR^c$, $NR^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —$C(O)R^c$ or $C(O)NR^{d1}R^{d2}$ group, wherein $C_1$-$C_6$-alkyl, and $C_3$-$C_6$-cycloalkyl are optionally substituted one or more times, in the same way or differently, with an —$OR^c$, or —$C(O)R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen;

A is —$C(O)NR^a$—;

B is a bond or a group selected from the group comprising, preferably consisting of $C_1$-$C_3$-alkylene, $C_3$-cycloalkylene;

D and E are phenylene; and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

More preferably, the first variant of the more particularly preferred embodiment, supra, of the present invention relates to compounds of general formula (I), in which $R^1$ represents H or $C_1$-$C_6$-alkyl;

$R^2$ stands for hydrogen or is selected from the group comprising, preferably consisting of, $C_1$-$C_6$-alkyl, $C_3$-$C_6$-cycloalkyl, $C_3$-$C_6$-heterocycloalkyl, aryl, heteroaryl, wherein said residues are unsubstituted or singly or multiply substituted independently from each other with $R^7$;

$R^3$ is selected from the group comprising, preferably consisting of, hydrogen, methyl, fluoro, chloro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, $OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —$C(O)R^b$, —$S(O)_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —$C(O)R^b$, —$S(O)_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, halogen, —$C(O)R^b$, —$S(O)_2R^b$, $OR^c$, $NR^{d1}R^{d2}$;

$R^a$ is hydrogen;

$R^b$ is selected from the group comprising, preferably consisting of, $OR^c$, $NR^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of, hydrogen, $C_1$-$C_6$-alkyl, $C_3$-$C_6$-cycloalkyl, or for a —$C(O)R^c$ or $C(O)NR^{d1}R^{d2}$ group, wherein $C_1$-$C_6$-alkyl, and $C_3$-$C_6$-cycloalkyl are optionally substituted one or more times, in the same way or differently, with an —$OR^c$, or —$C(O)R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen;

A is —$C(O)NR^a$—;

B is a bond or a group selected from the group comprising, preferably consisting of $C_1$-$C_3$-alkylene, $C_3$-cycloalkylene;

D and E are phenylene; and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

More particularly preferably, the first variant of the more particularly preferred embodiment, supra, of the present invention relates to compounds of general formula (I), in which:

$R^1$ represents H or $C_1$-$C_6$-alkyl;

$R^2$ stands for hydrogen or is selected from the group comprising, preferably consisting of, $C_1$-$C_6$-alkyl, $C_3$-$C_6$-heterocycloalkyl, aryl, heteroaryl, wherein said residues are unsubstituted or singly or multiply substituted independently from each other with $R^7$;

$R^3$ is selected from the group comprising, preferably consisting of, hydrogen, methyl, fluoro, chloro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, $OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, halogen, —C(O)$R^b$, —S(O)$_2R^b$, $OR^c$, $NR^{d1}R^{d2}$;

$R^a$ is hydrogen;

$R^b$ is selected from the group comprising, preferably consisting of, $OR^c$, $NR^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —C(O)$R^c$ or C(O)$NR^{d1}R^{d2}$ group, wherein $C_1$-$C_6$-alkyl and $C_3$-$C_6$-cycloalkyl are optionally substituted one or more times, in the same way or differently, with an —$OR^c$ or —C(O)$R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen A is —C(O)$NR^a$—;

B is a bond or a group selected from the group comprising, preferably consisting of $C_1$-$C_3$-alkylene, $C_3$-cycloalkylene;

D and E are phenylene; and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

More particularly preferably, the first variant of the more particularly preferred embodiment, supra, of the present invention relates to compounds of general formula (I), in which:

$R^1$ is H or $C_1$-$C_3$-alkyl;

$R^2$ stands for hydrogen or is selected from the group comprising, preferably consisting of, $C_1$-$C_6$-alkyl, $C_3$-cycloalkyl;

$R^3$ is selected from the group comprising, preferably consisting of, hydrogen, methyl, or fluoro;

$R^4$ is selected from the group comprising, preferably consisting of, hydrogen, halogen, $C_1$-$C_3$-alkyl, or $C_1$-$C_3$-haloalkyl;

$R^5$ is selected from the group comprising, preferably consisting of, hydrogen, $C_1$-$C_3$-alkyl, $C_1$-$C_3$-haloalkyl, $C_1$-$C_3$-haloalkoxy, halogen, —$OR^c$, —$NR^{d1}R^{d2}$, wherein $C_1$-$C_3$-alkyl is optionally substituted by $R^8$;

$R^8$ is selected from the group comprising, preferably consisting of, —$OR^c$, and —$NR^{d1}R^{d2}$;

$R^a$ is hydrogen;

$R^c$ is selected from the group comprising, preferably consisting of, hydrogen, and $C_1$-$C_3$-alkyl, wherein $C_1$-$C_3$-alkyl is optionally substituted one or more times with —$NR^{d1}R^{d2}$, and wherein $C_1$-$C_3$-alkyl is optionally substituted once with —$OR^c$;

$R^{d1}$, $R^{d2}$ independently from each other are selected from the group comprising, preferably consisting of hydrogen, $C_1$-$C_3$-alkyl, wherein $C_1$-$C_3$-alkyl is optionally substituted one or more times, in the same way or differently, with an —$OR^c$ group, and wherein $C_1$-$C_3$-alkyl is optionally substituted once with an —$NR^{d1}R^{d2}$ group; or, $R^{d1}$ and $R^{d2}$ together with the nitrogen atom to which they are attached, form a 6 membered heterocycloalkyl ring, whereby the carbon backbone of this heterocycloalkyl ring is optionally interrupted one time, by a member of the group comprising, preferably consisting of, NH, $NR^{d1}$, and oxygen;

A is —C(O)$NR^a$—;

B is a bond;

D is para-phenylene;

E is phenylene;

q represents an integer of 0;

wherein, when one or more of $R^a$, $R^b$, $R^c$, $R^{d1}$ or $R^{d2}$ is (are) present in one position in the molecule as well as in one or more further positions in the molecule, said $R^a$, $R^b$, $R^c$, $R^{d1}$ or $R^{d2}$ has (have), independently from each other, the same meanings as defined above in said first position in the molecule and in said second or further positions in the molecule, it being possible for the two or more occurrences of $R^a$, $R^b$, $R^c$, $R^{d1}$ or $R^{d2}$ within a single molecule to be identical or different. For example, when $R^a$ is present twice in the molecule, then the meaning of the first $R^a$ may be H, for example, and the meaning of the second $R^a$ may be methyl, for example.

In accordance with a second variant of the more particularly preferred embodiment, supra, the present invention relates to compounds of general formula (I), in which:

$R^1$ represents H or —C(O)$R^b$, or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ stands for hydrogen or is selected from the group comprising, preferably consisting of, $C_1$-$C_6$-alkyl, $C_3$-$C_6$-cycloalkyl, $C_3$-$C_6$-heterocycloalkyl, aryl, heteroaryl, wherein said residues are unsubstituted or singly or multiply substituted independently from each other with $R^7$;

$R^3$ is selected from the group comprising, preferably consisting of, hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, O$R^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, O$R^c$, N$R^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, —C(O)$R^b$, —S(O)$_2R^b$, O$R^c$, N$R^{d1}R^{d2}$, wherein $C_3$-$C_6$-heterocycloalkyl is optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, O$R^c$, N$R^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, halogen, —C(O)$R^b$, —S(O)$_2R^b$, O$R^c$, N$R^{d1}R^{d2}$;

$R^a$ is hydrogen;

$R^b$ is selected from the group comprising, preferably consisting of, O$R^c$, N$R^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —N$R^{d1}R^{d2}$, and wherein $C_1$-$C_6$-alkyl, $C_3$-$C_6$-cycloalkyl, $C_3$-$C_6$-heterocycloalkyl are optionally substituted once with —O$R^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —C(O)$R^c$ or C(O)N$R^{d1}R^{d2}$ group, wherein $C_1$-$C_6$-alkyl, and $C_3$-$C_6$-cycloalkyl are optionally substituted one or more times, in the same way or differently, with an —O$R^c$, or —C(O)$R^b$ group, and wherein $C_1$-$C_6$-alkyl, and $C_3$-$C_6$-cycloalkyl are optionally substituted once with an —N$R^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, N$R^{d1}$, and oxygen A is —C(O)— or —S(O)$_2$—;

B is a bond or a group selected from the group comprising, preferably consisting of $C_1$-$C_3$-alkylene, $C_3$-cycloalkylene;

D and E are phenylene; and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

Preferably, the second variant of the more particularly preferred embodiment, supra, of the present invention relates to compounds of general formula (I), in which:

$R^1$ represents H or —C(O)$R^b$, or is selected from the group comprising, preferably consisting of, $C_1$-$C_6$-alkyl, $C_3$-$C_6$-cycloalkyl, $C_3$-$C_6$-heterocycloalkyl, wherein said residues are unsubstituted or substituted one or more times, independently from each other, with $R^6$;

$R^2$ stands for hydrogen or is selected from the group comprising, preferably consisting of, $C_1$-$C_6$-alkyl, $C_3$-cycloalkyl;

$R^3$ is selected from the group comprising, preferably consisting of, hydrogen, methyl, fluoro, or chloro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, O$R^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, O$R^c$, N$R^{d1}R^{d2}$, wherein $C_1$-$C_6$-alkyl and $C_3$-$C_6$-heterocycloalkyl are optionally substituted one or more times with $R^8$;

$R^6$ is selected from the group comprising, preferably consisting of, hydrogen, $C_3$-$C_6$-heterocycloalkyl, $C_1$-$C_6$-haloalkoxy, hydroxy, amino, —C(O)$R^b$, —S(O)$_2R^b$, O$R^c$, N$R^{d1}R^{d2}$, wherein $C_3$-$C_6$-heterocycloalkyl is optionally substituted one or more times with $R^8$;

$R^8$ is selected from the group comprising, preferably consisting of, $C_1$-$C_6$-haloalkoxy, hydroxy, amino, halogen, —C(O)$R^b$, —S(O)$_2R^b$, O$R^c$, N$R^{d1}R^{d2}$;

$R^a$ is hydrogen;

$R^b$ is selected from the group comprising, preferably consisting of, O$R^c$, N$R^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —N$R^{d1}R^{d2}$, and wherein $C_1$-$C_6$-alkyl, $C_3$-$C_6$-cycloalkyl, $C_3$-$C_6$-heterocycloalkyl are optionally substituted once with —O$R^c$;

$R^{d1}$, $R^{d2}$ independently from each other are selected from the group comprising, preferably consisting of, hydrogen, $C_1$-$C_6$-alkyl, $C_3$-$C_6$-cycloalkyl, or for a —C(O)$R^c$ or C(O)N$R^{d1}R^{d2}$ group, wherein $C_1$-$C_6$-alkyl, and $C_3$-$C_6$-cycloalkyl are optionally substituted one or more times, in the same way or differently, with an —O$R^c$, or —C(O)$R^b$ group, and wherein $C_1$-$C_6$-alkyl, and $C_3$-$C_6$-cycloalkyl are optionally substituted once with an —N$R^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen;

A is —C(O)— or —S(O)$_2$—;

B is a bond or a group selected from the group comprising, preferably consisting of $C_1$-$C_3$-alkylene, $C_3$-cycloalkylene;

D and E are phenylene; and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

More preferably, the second variant of the more particularly preferred embodiment, supra, of the present invention relates to compounds of general formula (I), in which:

$R^1$ represents H or $C_1$-$C_6$-alkyl;

$R^2$ stands for hydrogen or is selected from the group comprising, preferably consisting of, $C_1$-$C_6$-alkyl, $C_3$-$C_6$-cycloalkyl, $C_3$-$C_6$-heterocycloalkyl, aryl, heteroaryl, wherein said residues are unsubstituted or singly or multiply substituted independently from each other with $R^7$;

$R^3$ is selected from the group comprising, preferably consisting of, hydrogen, methyl, fluoro, chloro;

$R^4$ is selected from the group comprising, preferably consisting of, hydrogen, $C_1$-$C_6$-alkyl, $C_1$-$C_6$-haloalkyl, $C_1$-$C_6$-haloalkoxy, hydroxy, amino, halogen, $OR^c$, wherein $C_1$-$C_6$-alkyl is optionally substituted one or more times with $R^8$;

$R^5$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^7$ is selected from the group comprising, preferably consisting of, hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, $OR^c$, $NR^{d1}R^{d2}$, wherein $C_1$-$C_6$-alkyl and $C_3$-$C_6$-heterocycloalkyl are optionally substituted one or more times with $R^8$;

$R^8$ is selected from the group comprising, preferably consisting of, $C_1$-$C_6$-haloalkoxy, hydroxy, amino, halogen, —C(O)$R^b$, —S(O)$_2R^b$, $OR^c$, $NR^{d1}R^{d2}$;

$R^a$ is hydrogen;

$R^b$ is selected from the group comprising, preferably consisting of, $OR^c$, $NR^{d1}R^{d2}$;

$R^c$ is selected from the group comprising, preferably consisting of, hydrogen, $C_1$-$C_6$-alkyl, $C_3$-$C_6$-cycloalkyl, $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, $R^{d2}$ independently from each other are selected from the group comprising, preferably consisting of hydrogen, $C_1$-$C_6$-alkyl, $C_3$-$C_6$-cycloalkyl, or for a —C(O)$R^c$ or C(O)$NR^{d1}R^{d2}$ group, wherein $C_1$-$C_6$-alkyl, and $C_3$-$C_6$-cycloalkyl are optionally substituted one or more times, in the same way or differently, with an —$OR^c$, or —C(O)$R^b$ group, and wherein $C_1$-$C_6$-alkyl, and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of this heterocycloalkyl ring is optionally interrupted one or more times, the same way or differently, by a member of the group comprising, preferably consisting of, NH, $NR^{d1}$, and oxygen;

A is —C(O)— or —S(O)$_2$—;

B is a bond or a group selected from the group comprising, preferably consisting of $C_1$-$C_3$-alkylene, $C_3$-cycloalkylene;

D and E are phenylene; and q represents an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different. For example, when $R^a$ is present twice in the molecule, then the meaning of the first $R^a$ may be H, for example, and the meaning of the second $R^a$ may be methyl, for example.

More particularly preferably, the second variant of the more particularly preferred embodiment, supra, of the present invention relates to compounds of general formula (I), in which:

$R^1$ is H or $C_1$-$C_3$-alkyl;

$R^2$ stands for hydrogen or is selected from the group comprising, preferably consisting of, $C_1$-$C_6$-alkyl, $C_3$-cycloalkyl;

$R^3$ is selected from the group comprising, preferably consisting of, hydrogen, methyl, or fluoro;

$R^4$ is selected from the group comprising, preferably consisting of, hydrogen, halogen, $C_1$-$C_3$-alkyl, or $C_1$-$C_3$-haloalkyl;

$R^5$ is selected from the group comprising, preferably consisting of, hydrogen, $C_1$-$C_3$-alkyl, $C_1$-$C_3$-haloalkyl, $C_1$-$C_3$-haloalkoxy, halogen, —$OR^c$, —$NR^{d1}R^{d2}$, wherein $C_1$-$C_3$-alkyl is optionally substituted by $R^8$;

$R^8$ is selected from the group comprising, preferably consisting of, —$OR^c$, and —$NR^{d1}R^{d2}$;

$R^a$ is hydrogen;

$R^c$ is selected from the group comprising, preferably consisting of, hydrogen, and $C_1$-$C_3$-alkyl, wherein $C_1$-$C_3$-alkyl is optionally substituted one or more times with —$NR^{d1}R^{d2}$, and wherein $C_1$-$C_3$-alkyl is optionally substituted once with —$OR^c$;

$R^{d1}$, $R^{d2}$ independently from each other are selected from the group comprising, preferably consisting of hydrogen, $C_1$-$C_3$-alkyl, wherein $C_1$-$C_3$-alkyl is optionally substituted one or more times, with an —$OR^c$ group, and wherein $C_1$-$C_3$-alkyl is optionally substituted once with an —$NR^{d1}R^{d2}$ group; or, $R^{d1}$ and $R^{d2}$ together with the nitrogen atom to which they are attached, form a 6 membered heterocycloalkyl ring, whereby the carbon backbone of this heterocycloalkyl ring is optionally interrupted one time, by a member of the group comprising, preferably consisting of, NH, NR$^{d1}$, and oxygen;

A is —C(O)—;
B is $C_1$-alkylene or $C_3$-cycloalkylene
D is para-phenylene;
E is phenylene;
q represents an integer of 0;

wherein, when one or more of R$^a$, R$^b$, R$^c$, R$^{d1}$ or R$^{d2}$ is (are) present in one position in the molecule as well as in one or more further positions in the molecule, said R$^a$, R$^b$, R$^c$, R$^{d1}$ or R$^{d2}$ has (have), independently from each other, the same meanings as defined above in said first position in the molecule and in said second or further positions in the molecule, it being possible for the two or more occurrences of R$^a$, R$^b$, R$^c$, R$^{d1}$ or R$^{d2}$ within a single molecule to be identical or different. For example, when R$^a$ is present twice in the molecule, then the meaning of the first R$^a$ may be H, for example, and the meaning of the second R$^a$ may be methyl, for example.

DEFINITIONS

The terms as mentioned herein below and in the claims have preferably the following meanings:

The term "alkyl" is to be understood as preferably meaning branched and unbranched alkyl, meaning e.g. methyl, ethyl, n-propyl, iso-propyl, n-butyl, iso-butyl, tert-butyl, sec-butyl, pentyl, iso-pentyl, hexyl, heptyl, octyl, nonyl and decyl and the isomers thereof.

The term "haloalkyl" is to be understood as preferably meaning branched and unbranched alkyl, as defined supra, in which one or more of the hydrogen substituents is replaced in the same way or differently with halogen. Particularly preferably, said haloalkyl is, e.g. chloromethyl, fluoropropyl, fluoromethyl, difluoromethyl, trichloromethyl, 2,2,2-trifluoroethyl, pentafluoroethyl, bromobutyl, trifluoromethyl, iodoethyl, and isomers thereof.

The term "alkoxy" is to be understood as preferably meaning branched and unbranched alkoxy, meaning e.g. methoxy, ethoxy, propyloxy, iso-propyloxy, butyloxy, iso-butyloxy, tert-butyloxy, sec-butyloxy, pentyloxy, iso-pentyloxy, hexyloxy, heptyloxy, octyloxy, nonyloxy, decyloxy, undecyloxy and dodecyloxy and the isomers thereof.

The term "haloalkoxy" is to be understood as preferably meaning branched and unbranched alkoxy, as defined supra, in which one or more of the hydrogen substituents is replaced in the same way or differently with halogen, e.g. chloromethoxy, fluoromethoxy, pentafluoroethoxy, fluoropropyloxy, difluoromethyloxy, trichloromethoxy, 2,2,2-trifluoroethoxy, bromobutyloxy, trifluoromethoxy, iodoethoxy, and isomers thereof.

The term "cycloalkyl" is to be understood as preferably meaning a $C_3$-$C_{10}$ cycloalkyl group, more particularly a saturated cycloalkyl group of the indicated ring size, meaning e.g. a cyclopropyl, cyclobutyl, cyclopentyl, cyclohexyl, cycloheptyl, cyclooctyl, cyclononyl, or cyclodecyl group; and also as meaning an unsaturated cycloalkyl group containing one or more double bonds in the C-backbone, e.g. a $C_3$-$C_{10}$ cycloalkenyl group, such as, for example, a cyclopropenyl, cyclobutenyl, cyclopentenyl, cyclohexenyl, cycloheptenyl, cyclooctenyl, cyclononenyl, or cyclodecenyl group, wherein the linkage of said cyclolaklyl group to the rest of the molecule can be provided to the double or single bond.

The term "heterocycloalkyl" is to be understood as preferably meaning a $C_3$-$C_{10}$ cycloalkyl group, as defined supra, featuring the indicated number of ring atoms, wherein one or more ring atom(s) is (are) (a) heteroatom(s) such as NH, NR$^{d1}$, O, S, or (a) group(s) such as a C(O), S(O), S(O)$_2$, or, otherwise stated, in a $C_n$-cycloalkyl group, (wherein n is an integer of 3, 4, 5, 6, 7, 8, 9, or 10), one or more carbon atom(s) is (are) replaced by said heteroatom(s) or said group(s) to give such a $C_n$ cycloheteroalkyl group. Thus, said $C_n$ cycloheteroalkyl group refers, for example, to a three-membered heterocycloalkyl, expressed as $C_3$-heterocycloalkyl, such as oxiranyl ($C_3$). Other examples of heterocycloalkyls are oxetanyl ($C_4$), aziridinyl ($C_3$), azetidinyl ($C_4$), tetrahydrofuranyl ($C_5$), pyrrolidinyl ($C_5$), morpholinyl ($C_6$), dithianyl ($C_6$), thiomorpholinyl ($C_6$), piperidinyl ($C_6$), tetrahydropyranyl ($C_6$), piperazinyl ($C_6$), trithianyl ($C_6$) and chinuclidinyl ($C_8$).

The term "halogen" or "Hal" is to be understood as preferably meaning fluorine, chlorine, bromine, or iodine.

The term "alkenyl" is to be understood as preferably meaning branched and unbranched alkenyl, e.g. a vinyl, propen-1-yl, propen-2-yl, but-1-en-1-yl, but-1-en-2-yl, but-2-en-1-yl, but-2-en-2-yl, but-1-en-3-yl, 2-methyl-prop-2-en-1-yl, or 2-methyl-prop-1-en-1-yl group.

The term "alkynyl" is to be understood as preferably meaning branched and unbranched alkynyl, e.g. an ethynyl, prop-1-yn-1-yl, but-1-yn-1-yl, but-2-yn-1-yl, or but-3-yn-1-yl group.

As used herein, the term "aryl" is defined in each case as having 3-14 carbon atoms, preferably 6-12 carbon atoms, such as, for example, cyclopropenyl, phenyl, tropyl, indenyl, naphthyl, azulenyl, biphenyl, fluorenyl, anthracenyl etc, phenyl being preferred.

As used herein, the term "heteroaryl" is understood as meaning an aromatic ring system which comprises 3-16 ring atoms, preferably 5 or 6 or 9 or 10 atoms, and which contains at least one heteroatom which may be identical or different, said heteroatom being such as oxygen, nitrogen or sulphur, and can be monocyclic, bicyclic, or tricyclic, and in addition in each case can be benzocondensed. Preferably, heteroaryl is selected from thienyl, furanyl, pyrrolyl, oxazolyl, thiazolyl, imidazolyl, pyrazolyl, isoxazolyl, isothiazolyl, oxadiazolyl, triazolyl, thiadiazolyl, thia-4H-pyrazolyl etc., and benzo derivatives thereof, such as, e.g., benzofuranyl, benzothienyl, benzoxazolyl, benzimidazolyl, benzotriazolyl, indazolyl, indolyl, isoindolyl, etc.; or pyridyl, pyridazinyl, pyrimidinyl, pyrazinyl, triazinyl, etc., and benzo derivatives thereof, such as, for example, quinolinyl, isoquinolinyl, etc.; or azocinyl, indolizinyl, purinyl, etc., and benzo derivatives thereof; or cinnolinyl, phthalazinyl, quinazolinyl, quinoxalinyl, naphthpyridinyl, pteridinyl, carbazolyl, acridinyl, phenazinyl, phenothiazinyl, phenoxazinyl, xanthenyl, or oxepinyl, etc.

The term "alkylene", as used herein in the context of the compounds of general formula (I) is to be understood as meaning an optionally substituted alkyl chain or "tether", having 1, 2, 3, 4, 5, or 6 carbon atoms, i.e. an optionally substituted —CH$_2$—("methylene" or "single membered tether" or e.g. —C(Me)$_2$-, or —CH(Me)—, (R)— or (S)— isomers)), —CH$_2$—CH$_2$— ("ethylene", "dimethylene", or "two-membered tether"), —CH$_2$—CH$_2$—CH$_2$— ("propylene", "trimethylene", or "three-membered tether"), —CH$_2$—CH$_2$—CH$_2$—CH$_2$— ("butylene", "tetramethylene", or "four-membered tether"), —CH$_2$—CH$_2$—CH$_2$—CH$_2$—CH$_2$— ("pentylene", "pentamethylene" or "five-membered ether"), or —CH$_2$—CH$_2$—CH$_2$—CH$_2$—CH$_2$—CH$_2$— ("hexylene", "hexamethylene", or six-membered tether") group. Preferably, said alkylene tether is 1, 2, 3, 4, or 5 carbon atoms, more preferably 1 or 2 carbon atoms.

The term "cycloalkylene", as used herein in the context of the compounds of general formula (I) is to be understood as meaning an optionally substituted cycloalkyl ring, having 3, 4, 5, 6, 7, 8, 9 or 10, preferably 3, 4, 5, or 6, carbon atoms, i.e. an optionally substituted cyclopropyl, cyclobutyl, cyclopentyl, cyclohexyl, cycloheptyl, cyclooctyl, cyclononyl, or cyclodecyl ring, preferably a cyclopropyl, cyclobutyl, cyclopentyl or cyclohexyl ring.

The term "heterocycloalkylene", as used herein in the context of the compounds of general formula (I) is to be understood as meaning a cycloalkylene ring, as defined supra, but which contains at least one heteroatom which may be identical or different, said heteroatom being such as O, N, S, S(O) or $S(O)_2$.

The term "arylene", as used herein in the context of the compounds of general formula (I) which include the groups D and E, is to be understood as meaning an optionally substituted monocyclic or polycyclic arylene aromatic system e.g. arylene, naphthylene and biarylene, preferably an optionally substituted phenyl ring or "tether", having 6 or 10 carbon atoms. More preferably, said arylene tether is a ring having 6 carbon atoms. If the term "arylene" is used it is to be understood that the linking residues can be arranged to each other in ortho-, para- and meta-position, e.g. an optionally substituted moiety of structure

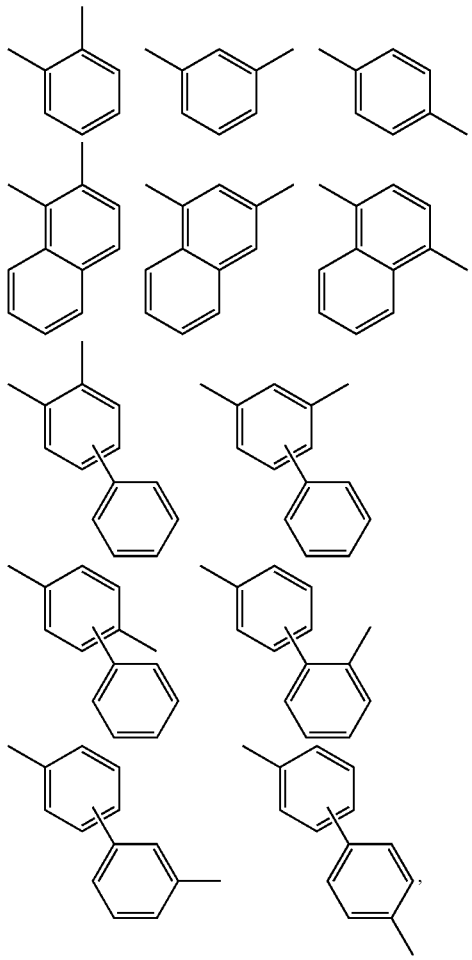

in which linking positions on the rings are shown as non-attached bonds.

The term "heteroarylene", as used herein in the context of the compounds of general formula (I) which include the groups D and E, is to be understood as meaning an optionally substituted monocyclic or polycyclic heteroarylene aromatic system, e.g. heteroarylene, benzoheteroarylene, preferably an optionally substituted 5-membered heterocycle, such as, for example, furan, pyrrole, thiazole, oxazole, isoxazole, or thiophene or "tether", or a 6-membered heterocycle, such as, for example, pyridine, pyrimidine, pyrazine, pyridazine. More preferably, said heteroarylene tether is a ring having 6 carbon atoms, e.g. an optionally substituted structure as shown supra for the arylene moieties, but which contains at least one heteroatom which may be identical or different, said heteroatom being such as oxygen, nitrogen or sulphur. If the term "heteroarylene" is used it is to be understood that the linking residues can be arranged to each other in ortho-, para- and meta-position.

As used herein, the term "$C_1$-$C_6$", as used throughout this text, e.g. in the context of the definition of "$C_1$-$C_6$-alkyl", or "$C_1$-$C_6$-alkoxy", is to be understood as meaning an alkyl group having a finite number of carbon atoms of 1 to 6, i.e. 1, 2, 3, 4, 5, or 6 carbon atoms. It is to be understood further that said term "$C_1$-$C_6$" is to be interpreted as any sub-range comprised therein, e.g. $C_1$-$C_6$, $C_2$-$C_5$, $C_3$-$C_4$, $C_1$-$C_2$, $C_1$-$C_3$, $C_1$-$C_4$, $C_1$-$C_5$ $C_1$-$C_6$; preferably $C_1$-$C_2$, $C_1$-$C_3$, $C_1$-$C_4$, $C_1$-$C_5$, $C_1$-$C_6$; more preferably $C_1$-$C_4$.

Similarly, as used herein, the term "$C_2$-$C_6$", as used throughout this text, e.g. in the context of the definitions of "$C_2$-$C_6$-alkenyl" and "$C_2$-$C_6$-alkynyl", is to be understood as meaning an alkenyl group or an alkynyl group having a finite number of carbon atoms of 2 to 6, i.e. 2, 3, 4, 5, or 6 carbon atoms. It is to be understood further that said term "$C_2$-$C_6$" is to be interpreted as any sub-range comprised therein, e.g. $C_2$-$C_6$, $C_3$-$C_5$, $C_3$-$C_4$, $C_2$-$C_3$, $C_2$-$C_4$, $C_2$-$C_5$; preferably $C_2$-$C_3$.

As used herein, the term "$C_3$-$C_{10}$", as used throughout this text, e.g. in the context of the definitions of "$C_3$-$C_{10}$-cycloalkyl" or "$C_3$-$C_{10}$-heterocycloalkyl", is to be understood as meaning a cycloalkyl group having a finite number of carbon atoms of 3 to 10, i.e. 3, 4, 5, 6, 7, 8, 9 or 10 carbon atoms, preferably 3, 4, 5 or 6 carbon atoms. It is to be understood further that said term "$C_3$-$C_{10}$" is to be interpreted as any sub-range comprised therein, e.g. $C_3$-$C_{10}$, $C_4$-$C_9$, $C_5$-$C_8$, $C_6$-$C_7$; preferably $C_3$-$C_6$.

As used herein, the term "$C_3$-$C_6$", as used throughout this text, e.g. in the context of the definitions of "$C_3$-$C_6$-cycloalkyl" or "$C_3$-$C_6$-heterocycloalkyl", is to be understood as meaning a cycloalkyl group having a finite number of carbon atoms of 3 to 6, i.e. 3, 4, 5, or 6 carbon atoms. It is to be understood further that said term "$C_3$-$C_6$" is to be interpreted as any sub-range comprised therein, e.g. $C_3$-$C_4$, $C_4$-$C_6$, $C_5$-$C_6$.

As used herein, the term "$C_6$-$C_{11}$", as used throughout this text, e.g. in the context of the definitions of "$C_6$-$C_{11}$-aryl", is to be understood as meaning an aryl group having a finite number of carbon atoms of 5 to 11, i.e. 5, 6, 7, 8, 9, 10 or 11 carbon atoms, preferably 5, 6, or 10 carbon atoms. It is to be understood further that said term "$C_6$-$C_{11}$" is to be interpreted as any sub-range comprised therein, e.g. $C_5$-$C_{10}$, $C_6$-$C_9$, $C_7$-$C_8$; preferably $C_5$-$C_6$.

As used herein, the term "$C_5$-$C_{10}$", as used throughout this text, e.g. in the context of the definitions of "$C_5$-$C_{10}$-heteroaryl", is to be understood as meaning a heteroaryl group having a finite number of carbon atoms of 5 to 10, in addition to the one or more heteroatoms present in the ring i.e. 5, 6, 7, 8, 9, or 10 carbon atoms, preferably 5, 6, or 10 carbon atoms. It is to be understood further that said term "$C_5$-$C_{10}$" is to be interpreted as any sub-range comprised therein, e.g. $C_6$-$C_9$, $C_7$-$C_8$, $C_7$-$C_8$; preferably $C_5$-$C_6$.

As used herein, the term "$C_1$-$C_3$", as used throughout this text, e.g. in the context of the definitions of "$C_1$-$C_3$-alkylene", is to be understood as meaning an alkylene group as defined supra having a finite number of carbon atoms of 1 to 3, i.e. 1, 2, or 3. It is to be understood further that said term "$C_1$-$C_3$" is to be interpreted as any sub-range comprised therein, e.g. $C_1$-$C_2$, or $C_2$-$C_3$.

As used herein, the term "one or more times", e.g. in the definition of the substituents of the compounds of the general formulae of the present invention, is understood as meaning "one, two, three, four or five times, particularly one, two, three or four tines, more particularly one, two or three times, more particularly one or two times".

The term "isomers" is to be understood as meaning chemical compounds with the same number and types of atoms as another chemical species. There are two main classes of isomers, constitutional isomers and stereoisomers.

The term "constitutional isomers" is to be understood as meaning chemical compounds with the same number and types of atoms, but they are connected in differing sequences. There are functional isomers, structural isomers, tautomers or valence isomers.

The term "stereoisomers" is to be understood as meaning chemical compounds having atoms which are connected sequentially in the same way, such that condensed formulae for two isomeric molecules are identical. The isomers differ, however, in the way the atoms are arranged in space. There are two major sub-classes of stereoisomers:conformational isomers, which interconvert through rotations around single bonds, and configurational isomers, which are not readily interconvertable.

Configurational isomers are, in turn, can be enantiomers and/or diastereomers. Enantiomers are stereoisomers which are related to each other as mirror images. Enantiomers can contain any number of stereogenic centers, as long as each center is the exact mirror image of the corresponding center in the other molecule. If one or more of these centers differs in configuration, the two molecules are no longer mirror images. Stereoisomers which are not enantiomers are called diastereomers. Diastereomers which still have a different constitution, are another sub-class of diastereomers, the best known of which are simple cis-trans isomers.

In order to limit different types of isomers from each other reference is made to IUPAC Rules Section E (*Pure Appl Chem* 45, 11-30, 1976).

The compound according to Formula (I) can exist in free form or in a salt form. A suitably pharmaceutically acceptable salt of the pyrazolopyridines of the present invention may be, for example, an acid-addition salt of a pyrazolopyridine of the invention which is sufficiently basic, for example, an acid-addition salt with, for example, an inorganic or organic acid, for example hydrochloric, hydrobromic, sulphuric, phosphoric, trifluoroacetic, para-toluenesulphonic, methylsulphonic, citric, tartaric, succinic or maleic acid. In addition, another suitably pharmaceutically acceptable salt of a pyrazolopyridine of the invention which is sufficiently acidic is an alkali metal salt, for example a sodium or potassium salt, an alkaline earth metal salt, for example a calcium or magnesium salt, an ammonium salt or a salt with an organic base which affords a physiologically acceptable cation, for example a salt with N-methyl-glucamine, dimethyl-glucamine, ethyl-glucamine, lysine, 1,6-hexadiamine, ethanolamine, glucosamine, sarcosine, serinol, tris-hydroxy-methyl-aminomethane, aminopropandiol, sovak-base, 1-amino-2,3,4-butantriol.

The compound according to Formula (I) can exist as N-oxides which are defined in that at least one nitrogen of the compounds of the general Formula (I) may be oxidized.

The compound according to Formula (I) can exist as solvates, in particular as hydrate, wherein the compound according to Formula (I) may contain polar solvents, in particular water, as structural element of the crystal lattice of the compounds. The amount of polar solvents, in particular water, may exist in a stoichiometric or unstoichiometric ratio. In case of stoichiometric solvates, e.g. hydrate, are possible hemi-, (semi-), mono-, sesqui-, di-, tri-, tetra-, penta- etc. solvates or hydrates, respectively.

The compounds of the present invention according to Formula (I) can exist as prodrugs, e.g. as in vivo hydrolysable esters. As used herein, the term "in vivo hydrolysable ester" is understood as meaning an in vivo hydrolysable ester of a compound of formula (I) containing a carboxy or hydroxyl group, for example, a pharmaceutically acceptable ester which is hydrolysed in the human or animal body to produce the parent acid or alcohol. Suitable pharmaceutically acceptable esters for carboxy include for example alkyl, cycloalkyl and optionally substituted phenylalkyl, in particular benzyl esters, $C_1$-$C_6$ alkoxymethyl esters, e.g. methoxymethyl, $C_1$-$C_6$ alkanoyloxymethyl esters, e.g. pivaloyloxymethyl, phthalidyl esters, $C_3$-$C_8$ cycloalkoxy-carbonyloxy-$C_1$-$C_6$ alkyl esters, e.g. 1-cyclohexylcarbonyloxyethyl; 1,3-dioxolen-2-onylmethyl esters, e.g. 5-methyl-1,3-dioxolen-2-onylmethyl; and $C_1$-$C_6$-alkoxycarbonyloxyethyl esters, e.g. 1-methoxycarbonyloxyethyl, and may be formed at any carboxy group in the compounds of this invention. An in vivo hydrolysable ester of a compound of formula (I) containing a hydroxyl group includes inorganic esters such as phosphate esters and [alpha]-acyloxyalkyl ethers and related compounds which as a result of the in vivo hydrolysis of the ester breakdown to give the parent hydroxyl group.

Examples of [alpha]-acyloxyalkyl ethers include acetoxymethoxy and 2,2-dimethylpropionyloxymethoxy. A selection of in vivo hydrolysable ester forming groups for hydroxyl include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

The compounds of the present invention according to Formula (I), or salts, N-oxides, or prodrugs thereof, may contain one or more asymmetric centers. Asymmetric carbon atoms may be present in the (R) or (S) configuration or (R,S) configuration. Substituents on a ring may also be present in either cis or trans form. It is intended that all such configurations (including enantiomers and diastereomers), are included within the scope of the present invention. Preferred stereoisomers are those with the configuration which produces the more desirable biological activity. Separated, pure or partially purified configurational isomers or racemic mixtures of the compounds of this invention are also included within the scope of the present invention. The purification of said isomers and the separation of said isomeric mixtures can be accomplished by standard techniques known in the art.

Further another embodiment of the present invention relates to the use of a compound of general formula 1 as mentioned below for the preparation of a compound of general formula (I) as defined supra.

Further another embodiment of the present invention relates to the use of a compound of general formula 7 as mentioned below for the preparation of a compound of general formula (I) as defined supra.

Further another embodiment of the present invention relates to the use of a compound of general formula 8" as mentioned below for the preparation of a compound of general formula (I) as defined supra.

Further another embodiment of the present invention relates to the use of a compound of general formula 11 as mentioned below for the preparation of a compound of general formula (I) as defined supra.

Further another embodiment of the present invention relates to the use of a compound of general formula 15 as mentioned below for the preparation of a compound of general formula (I) as defined supra.

Further another embodiment of the present invention relates to the use of a compound of general formula 16 as mentioned below for the preparation of a compound of general formula (I) as defined supra.

The compounds of the present invention can be used in treating diseases of dysregulated vascular growth or diseases which are accompanied with dysregulated vascular growth. Especially, the compounds effectively interfere with Tie2 signalling. In addition, the compounds of the present invention allow for tunability of the inhibition of an additional kinase target according to the appropriate therapeutic needs.

Therefore, another aspect of the present invention is a use of the compound of general formula (I) described supra for manufacturing a pharmaceutical composition for the treatment of diseases of dysregulated vascular growth or of diseases which are accompanied with dysregulated vascular growth.

Preferably, the use is in the treatment of diseases, wherein the diseases are tumours and/or metastases thereof.

Another preferred use is in the treatment of diseases, wherein the diseases are retinopathy, other angiogenesis dependent diseases of the eye, in particular cornea transplant rejection or age-related macular degeneration, rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

A further use is in the treatment of diseases, wherein the diseases are coronary and peripheral artery disease.

Another use is in the treatment of diseases, wherein the diseases are ascites, oedema such as brain tumour associated oedema, high altitude trauma, hypoxia induced cerebral oedema, pulmonary oedema and macular oedema or oedema following burns and trauma, chronic lung disease, adult respiratory distress syndrome, bone resorption and for benign proliferating diseases such as myoma, benign prostate hyperplasia and wound healing for the reduction of scar formation, reduction of scar formation during regeneration of damaged nerves, endometriosis, pre-eclampsia, postmenopausal bleeding and ovarian hyperstimulation.

Yet another aspect of the invention is a method of treating a disease of dysregulated vascular growth or diseases which are accompanied with dysregulated vascular growth, by administering an effective amount of a compound of general formula (I) described supra.

Preferably, the diseases of said method is tumour and/or metastases thereof.

Also, the diseases of said method are retinopathy, other angiogenesis dependent diseases of the eye, in particular cornea transplant rejection or age-related macular degeneration, e.g. rheumatoid arthritis, and other inflammatory diseases associated with angiogenesis, in particular psoriasis, delayed type hypersensitivity, contact dermatitis, asthma, multiple sclerosis, restenosis, pulmonary hypertension, stroke, and diseases of the bowel.

Further, the disease of the method are coronary and peripheral artery disease.

Other diseases of the method are ascites, oedema such as brain tumour associated oedema, high altitude trauma, hypoxia induced cerebral oedema, pulmonary oedema and macular oedema or oedema following burns and trauma, chronic lung disease, adult respiratory distress syndrome, bone resorption and for benign proliferating diseases such as myoma, benign prostate hyperplasia and wound healing for the reduction of scar formation, reduction of scar formation during regeneration of damaged nerves, endometriosis, pre-eclampsia, postmenopausal bleeding and ovarian hyperstimulation.

The compounds of the present invention can thus be applied for the treatment of diseases accompanied by neoangiogenesis. This holds principally for all solid tumours, e.g. breast, colon, renal, lung and/or brain tumours or metastases thereof and can be extended to a broad range of diseases, where pathologic angiogenesis is persistent. This applies for diseases with inflammatory association, diseases associated with oedema of various forms and diseases associated with stromal proliferation and pathologic stromal reactions broadly. Particularly suited is the treatment for gynaecological diseases where inhibition of angiogenic, inflammatory and stromal processes with pathologic character can be inhibited. The treatment is therefore an addition to the existing armament to treat diseases associated with neoangiogenesis.

The compounds of the present invention can be used in particular in therapy and prevention of tumour growth and metastases, especially in solid tumours of all indications and stages with or without pre-treatment if the tumour growth is accompanied with persistent angiogenesis. However, it is not restricted to tumour therapy but is also of great value for the treatment of other diseases with dysregulated vascular growth. This includes retinopathy and other angiogenesis dependent diseases of the eye (e.g. cornea transplant rejection, age-related macular degeneration), rheumatoid arthritis, and other inflammatory diseases associated with angiogenesis such as psoriasis, delayed type hypersensitivity, contact dermatitis, asthma, multiple sclerosis, restenosis, pulmonary hypertension, stroke and inflammatory diseases of the bowel, such as Crohn's disease. It includes coronary and peripheral artery disease. It can be applied for disease states such as ascites, oedema, such as brain tumour associated oedema, high altitude trauma, hypoxia induced cerebral oedema, pulmonary oedema and macular oedema or oedema following burns and trauma. Furthermore, it is useful for chronic lung disease, adult respiratory distress syndrome. Also for bone resorption and for benign proliferating diseases such as myoma, benign prostate hyperplasia and wound healing for the reduction of scar formation. It is therapeutically valuable for the treatment of diseases, where deposition of fibrin or extracellular matrix is an issue and stroma proliferation is accelerated (e.g. fibrosis, cirrhosis, carpal tunnel syndrome etc). In addition it can be used for the reduction of scar formation during regeneration of damaged nerves, permitting the reconnection of axons. Further uses are endometriosis, pre-eclampsia, postmenopausal bleeding and ovarian hyperstimulation.

Another aspect of the present invention is a pharmaceutical composition which contains a compound of Formula (I), or a pharmaceutically acceptable salt thereof, or an N-oxide thereof, or a pro-drug thereof, in admixture with one or more suitable excipients. This composition is particularly suited for the treatment of diseases of dysregulated vascular growth or of diseases which are accompanied with dysregulated vascular growth as explained above.

In order that the compounds of the present invention be used as pharmaceutical products, the compounds or mixtures thereof may be provided in a pharmaceutical composition, which, as well as the compounds of the present invention for enteral, oral or parenteral application contain suitable pharmaceutically acceptable organic or inorganic inert base material, e.g. purified water, gelatine, gum Arabic, lactate, starch, magnesium stearate, talcum, vegetable oils, polyalkyleneglycol, etc.

The pharmaceutical compositions of the present invention may be provided in a solid form, e.g. as tablets, dragées, suppositories, capsules or in liquid form, e.g. as a solution, suspension or emulsion. The pharmaceutical composition may additionally contain auxiliary substances, e.g. preservatives, stabilisers, wetting agents or emulsifiers, salts for adjusting the osmotic pressure or buffers.

For parenteral applications, (including intravenous, subcutaneous, intramuscular, intravascular or infusion), sterile injection solutions or suspensions are preferred, especially aqueous solutions of the compounds in polyhydroxyethoxy containing castor oil.

The pharmaceutical compositions of the present invention may further contain surface active agents, e.g. salts of gallenic acid, phospholipids of animal or vegetable origin, mixtures thereof and liposomes and parts thereof.

For oral application tablets, dragées or capsules with talcum and/or hydrocarbon-containing carriers and binders, e.g. lactose, maize and potato starch, are preferred. Further application in liquid form is possible, for example as juice, which contains sweetener if necessary.

The dosage will necessarily be varied depending upon the route of administration, age, weight of the patient, the kind and severity of the illness being treated and similar factors. The daily dose is in the range of 0.5 to 1,500 mg. A dose can be administered as unit dose or in part thereof and distributed over the day. Accordingly the optimum dosage may be determined by the practitioner who is treating any particular patient.

It is possible for compounds of general formula (I) of the present invention to be used alone or, indeed in combination with one or more further drugs, particularly anti-cancer drugs or compositions thereof. Particularly, it is possible for said combination to be a single pharmaceutical composition entity, e.g. a single pharmaceutical formulation containing one or more compounds according to general formula (I) together with one or more further drugs, particularly anti-cancer drugs, or in a form, e.g. a "kit of parts", which comprises, for example, a first distinct part which contains one or more compounds according to general formula I, and one or more further distinct parts each containing one or more further drugs, particularly anti-cancer drugs. More particularly, said first distinct part may be used concomitantly with said one or more further distinct parts, or sequentially.

Another aspect of the present invention is a method which may be used for preparing the compounds according to the present invention.

EXPERIMENTAL DETAILS AND GENERAL PROCESSES

The following table lists the abbreviations used in this paragraph and in the Examples section as far as they are not explained within the text body. NMR peak forms are stated as they appear in the spectra, possible higher order effects have not been considered. Chemical names were generated using AutoNom2000 as implemented in MDL ISIS Draw. The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. from Separtis such as Isolute® Flash silica gel or Isolute® Flash NH$_2$ silica gel in combination with a Flashmaster II autopurifier (Argonaut/Biotage) and eluents such as gradients of hexane/EtOAc or DCM/ethanol. In some cases, the compounds may be purified by preparative HPLC using for example a Waters autopurifier equipped with a diode array detector and/or on-line electrospray ionization mass spectrometer in combination with a suitable prepacked reverse phase column and eluants such as gradients of water and acetonitrile which may contain additives such as trifluoroacetic acid or aqueous ammonia.

Reactions may be monitored and product purity may be analyzed by LC-MS analysis employing conditions such as, for example, the following specifications:

| | |
|---|---|
| Apparatus: | WATERS ACQUITY UPLC/SQD |
| Column: | Acquity BEH C18 1.7 µm 50 × 2.1 mm |
| Solvent: | A:H2O B:Acetonitril |
| Buffer: | A/0.05% TFA |
| Gradient: | 99% A + 1% B__1−>99% B(1.7') |
| Flow: | 0.8 mL/min |
| Solution: | 1 mg/mL ACN/H2O 7:3 |
| Injection Volume: | 2 µl |
| Detection: | DAD (200-400 nm) TAC; MS-ESI+ (125-1000 m/z) TIC |
| Temperature: | 60° C. |

Alternatively, 0.05% TFA can be replaced by, for example, 0.2% NH$_3$.

| Abbreviation | Meaning |
|---|---|
| Ac | Acetyl |
| Boc | tert-butytoxycarbonyl |
| br | Broad |
| c- | cyclo- |
| CI | chemical ionisation |
| d | Doublet |
| dd | doublet of doublet |
| DCM | Dichloromethane |
| DIPEA | N,N-diisopropylethyl amine |
| DMAP | N,N-dimethylaminopyridine |
| DMF | N,N-dimethylformamide |
| DMSO | dimethyl sulfoxide |
| eq. | Equivalent |
| ESI | electrospray ionisation |
| GP | general procedure |
| HPLC | high performance liquid chromatography |
| LC-MS | liquid chromatography mass spectrometry |
| m | Multiplet |
| mc | centred multiplet |
| MS | mass spectrometry |
| NMR | nuclear magnetic resonance spectroscopy: chemical shifts (δ) are given in ppm. |
| OTf | Trifluoromethanesulphonyl |
| Pg | protecting group |
| POPd | dihydrogen dichlorobis(di-tert-butyl phosphinito-κP)palladate(2); CombiPhos Catalysts, Inc. |
| q | Quartet |
| rf | at reflux |
| r.t. or rt | room temperature |
| s | Singlet |
| sept. | Septet |

| Abbreviation | Meaning |
| --- | --- |
| T3P | 1-propanephosphoric acid cyclic anhydride; 2,4,6-tripropyl-[1,3,5,2,4,6]trioxatriphosphinane 2,4,6-trioxide |
| t | Triplet |
| TEA | Triethylamine |
| TFA | trifluoroacetic acid |
| THF | Tetrahydrofuran |

The following schemes and general procedures illustrate general synthetic routes to the compounds of general formula I of the invention and are not intended to be limiting. Specific examples are described in the subsequent paragraph.

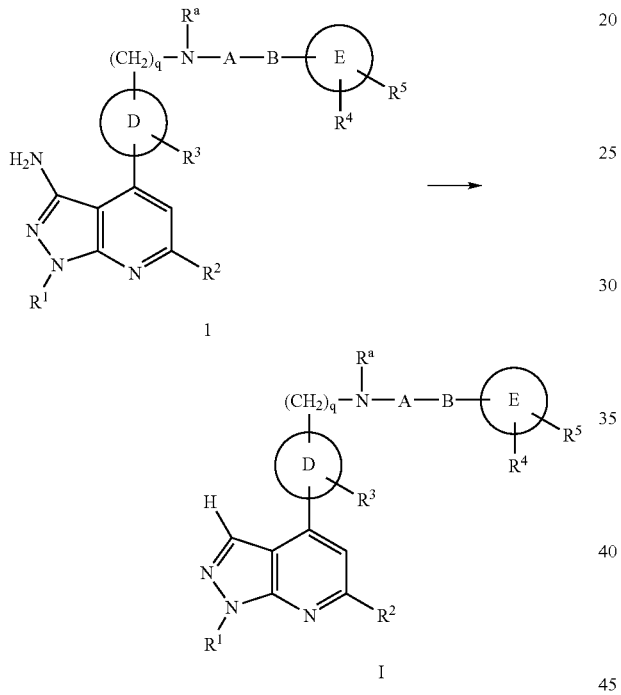

Scheme 1 General procedure for the preparation of compounds of the general formula (I) by deamination of intermediates of general formula 1, wherein A, B, D, E, $R^a$, $R^1$, $R^2$, $R^3$, $R^4$, $R^5$ and q are as defined in the description and claims of this invention.

Compounds of general formula (I) can be synthesized according to the procedure depicted in Scheme 1 by deamination of the corresponding 3-aminopyrazolopyridines of general formula 1.

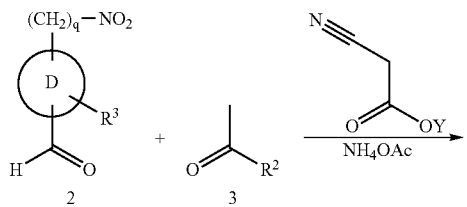

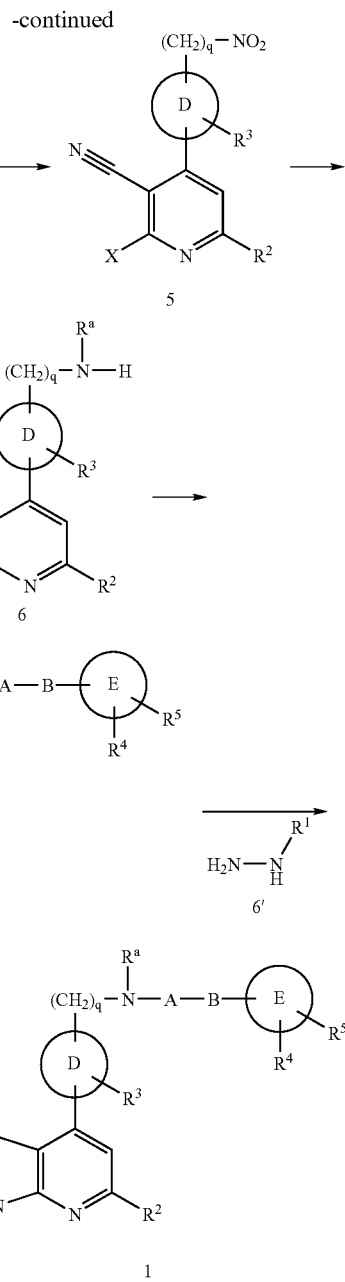

Scheme 2 General procedure for the preparation of intermediates of the general formula 1, wherein X stands for OTf, Cl, F, OAc, OMe, Y stands for Me, Et, and A, B, D, E, $R^a$, $R^1$, $R^2$, $R^3$, $R^4$, $R^5$ and q are as defined in the description and claims of this invention.

Intermediates of general formula 1 can be synthesized according to the procedure depicted in Scheme 2. Pyridones of general formula 4 are accessible by multi-component coupling of a (hetero)aryl carbaldehyde 2, a methylketone 3, an alkyl cyanoacetate (e.g. methyl cyano acetate or ethyl cyano acetate) and an ammonium salt, preferably ammonium acetate, in a suitable solvent, preferably ethanol, at temperatures up to the boiling point of the solvent, whereby in the case of ethanol 80° C. is preferred.

The so formed pyridones 4 are transformed into pyridines of general formula 5 carrying a leaving group X at the C2 position, wherein X stands for, but is not limited to, trifluoromethanesulfonyl (OTf), acetate (OAc), methoxy (OMe), Cl or F. Preferably, X stands for Cl, even more preferably X stands for OTf. Conversion of intermediate compounds of general formula 4 into intermediates of general formula 5 may be achieved by a variety of methods, e.g. when X=Cl, by reaction with phosphorus oxychloride, optionally in the presence of DMF; or, for example, when X=OTf by reaction with trifluoromethanesulfonic acid anhydride, in the presence of a suitable base, e.g. pyridine, which may also be used as solvent, optionally in the presence of an inert solvent, e.g. dichloromethane, at temperatures ranging from −20° C. to room temperature, whereby 0° C. up to room temperature is preferred.

Reduction of the nitro group in intermediate compounds of general formula 5 gives rise to intermediate compounds of general formula 6. The person skilled in the art is well aware of many methods for nitro group reduction, whereby preferred is the reduction of intermediate compounds of general formula 5 with tin(II)chloride dihydrate in a suitable solvent, e.g. ethanol, at temperatures ranging from room temperature to the boiling point of the solvent, whereby in the case of ethanol 80° C. is preferred.

Intermediate compounds of general formula 7 are formed from intermediate compounds of general formula 6 by reaction with, for example, a suitably functionalized isocyanate (leading to ureas), a suitably functionalized sulfonyl chloride (leading to sulfonyl amides) or a suitably functionalized acid chloride (leading to carboxylic amides), in the presence of a suitable base as necessary, e.g. pyridine, which may also be used as solvent, optionally in the presence of an inert solvent, e.g. dichloromethane, acetonitrile, DMF or THF, at temperatures ranging from −20° C. to the boiling point of the solvent, whereby room temperature is preferred. Reaction of intermediate compounds of general formula 7 with hydrazine (or hydrazine hydrate) or substituted hydrazines of general formula 6' in a suitable solvent, e.g. 1-propanol, at temperatures from room temperature up to the boiling point of the solvent, whereby in the case of 1-PrOH 100° C. is preferred, leads to intermediates of general formula 1.

A variety of substituted hydrazine building blocks required for the conversion of pyridine 7 into intermediates 1 is commercially available, either in form of their free base or as various types of salts (e.g. hydrochlorides, oxalates), which can be transformed into their respective free bases by alkaline treatment either before the cyclization or in situ. Additionally, substituted alkyl-, allyl-, and benzylhydrazines (or their respective hydrochloride salts) are accessible from the respective alkyl-, allyl- and benzylhalides, preferably the respective alkyl-, allyl- and benzylbromides, by nucleophilic substitution reaction with a protected hydrazine, such as Boc-NHNH$_2$, in an inert solvent, preferably MeOH, in the presence of an amine promoter, e.g. Et$_3$N, at temperatures ranging from room temperature up to the boiling point of the solvent, followed by Boc-deprotection employing conditions known to the person skilled in the art, preferably by treatment with HCl in a mixture of diethyl ether and methanol (for a representative procedure, see *J. Med. Chem.* 2006, 49, 2170).

The substituents $R^a$, $R^1$, $R^2$, $R^3$, $R^4$, $R^5$ may be further modified on each step (general formula 1 to general formula 14) or in the last step (general formula I). These modifications can be such as the introduction of protecting groups, cleavage of protecting groups, reduction or oxidation of functional groups, substitution or other reactions. Appropriate protecting groups and their introduction and cleavage are well-known to the person skilled in the art (see for example T. W. Greene and P. G. M. Wuts in *Protective Groups in Organic Synthesis*, 3$^{rd}$ edition, Wiley 1999).

The person skilled in the art is well aware of alternative methods of forming ureas, which may be of special importance in cases were the respective isocyanates are not readily available.

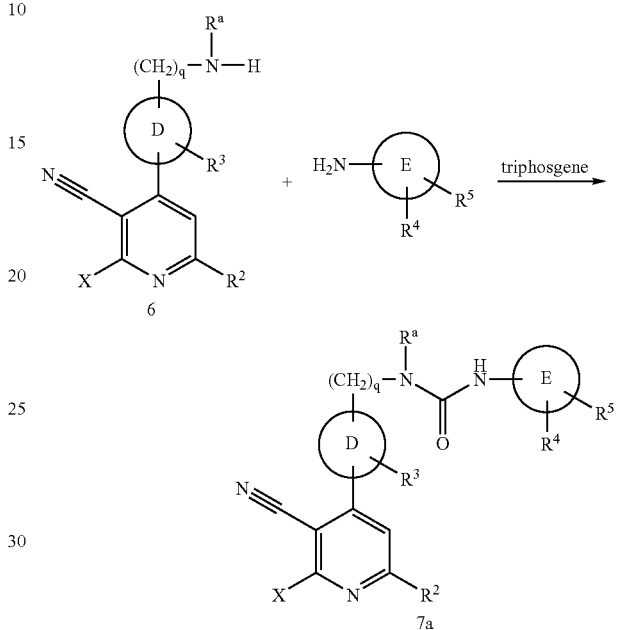

Scheme 3 Urea formation by in situ activation of one of two amines with triphosgene and subsequent reaction with the second amine, wherein X, stands for OTf, Cl, F, OAc, OMe, and A, B, D, E, $R^a$, $R^1$, $R^2$, $R^3$, $R^4$, $R^5$ and q are as defined in the description and claims of this invention.

An alternative process of generating ureas of general formula 7a is depicted in Scheme 3. In this case, urea formation starting from amines of general formula 6 may be achieved by coupling with a second functionalized amine via in situ transformation of one of the reacting amines into the respective carbamoyl chloride, aryl- or alkenylcarbamate (see for example *J. Org. Chem.* 2005, 70, 6960 and references cited therein). This process may provide an alternative to the formation and isolation of the respective isocyanate derived from one of the starting amines (see for example *Tetrahedron Lett.* 2004, 45, 4769). More particularly, ureas of formula 7a may be formed from two suitably functionalized amines and a suitable phosgene equivalent, preferably triphosgene, in an inert solvent, preferably acetonitrile, at temperatures ranging from −20° C. to room temperature, whereby room temperature is preferred.

Processes for the preparation of functionalized (hetero)aryl amines are well known to the person skilled in the art. Starting from commercially available (hetero)aryl amines or nitro (hetero)arylenes, well known transformations, including, but not limited to, alkylations, nucleophilic or electrophilic substitutions, acylations, halogenations, nitrations, sulfonylations, (transition) metal catalyzed couplings, metallations, rearrangements, reductions, and/or oxidations may be applied to prepare functionalized amines to be used in the urea formation step. In addition to specific procedures given in the following experimental section, detailed procedures may be found in the scientific and patent literature (see for example WO2005051366, WO2005110410, WO2005113494, and WO2006044823).

In the case of the transformation of amines of general formula 6 into amides, it is also possible to react amines of general formula 6 with an appropriate ester according to a method described in *J. Org. Chem.* 1995, 8414 in the presence of trimethylaluminium and in suitable solvents such as toluene, at temperatures of 0° C. to the boiling point of the solvent. For amide formation, however, all processes that are known from peptide chemistry to the person skilled in the art are also available. For example, the corresponding acid, which may be obtained from the corresponding ester by saponification, can be reacted with amines of general formula 6 in aprotic polar solvents, such as, for example, DMF, via an activated acid derivative, which is obtainable, for example, with hydroxybenzotriazole and a carbodiimide, such as, for example, diisopropylcarbodiimide (DIC), at temperatures of between 0° C. and the boiling point of the solvent, preferably at 80° C., or else with preformed reagents, such as, for example, O-(7-azabenzotriazol-1-yl)-1,1,3,3-tetramethyluronium hexafluorophosphate (HATU) (see for example *Chem. Comm.* 1994, 201), at temperatures of between 0° C. and the boiling point of the solvent, preferably at room temperature, or else with activating agents such as dicyclohexylcarbodiimide (DCC)/dimethylaminopyridine (DMAP) or N-ethyl-N'-dimethylaminopropylcarbodiimide (EDCI)/dimethylaminopyridine (DMAP) or T3P. The addition of a suitable base such as N-methylmorpholine, for example, may be necessary. Amide formation may also be accomplished via the acid halide, mixed acid anhydride, imidazolide or azide.

The carboxylic acids required for the above described amide coupling reactions are either commercially available or are accessible from commercially available carboxylic esters or nitriles. Alternatively, (hetero)aryls bearing a methylenenitrile substituent are easily accessible from the respective halides via a nucleophilic substitution reaction (e.g. KCN, cat. KI, EtOH/$H_2O$). Incorporation of additional functionality into commercially available starting materials can be accomplished by a multitude of aromatic transformation reactions known to the person skilled in the art, including, but not limited to, electrophilic halogenations, electrophilic nitrations, Friedel-Crafts acylations, nucleophilic displacement of fluorine by oxygen nucleophiles and transformation of (hetero)aryl carboxylic acids into amides and subsequent reduction into benzylic amines, whereby the latter two methods are of particular relevance for the introduction of ether and/or aminomethylene side chains.

Benzylic nitrites and esters (and heteroaryl analogs thereof) can be efficiently alkylated at the benzylic position under basic conditions and subsequently hydrolyzed to the corresponding alkylated acids. Conditions for α-alkylations of nitrites and esters include, but are not limited to, the use of alkyl bromides or alkyl iodides as electrophiles under basic conditions in the presence or absence of a phase-transfer catalyst in a mono- or biphasic solvent system. Particularly, by using excess alkyl iodides as electrophilic species α,α-dialkylated nitrites are accessible. More particularly, by using 1,ω-dihaloalkyls as electrophiles cycloalkyl moieties can be installed at the benzylic position of nitrites and esters (*J. Med. Chem.* 1975, 18, 144; WO2003022852). Even more particularly, by using a 1,2-dihaloethane, such as, for example, 1,2-dibromoethane or 1-bromo-2-chloroethane, a cyclopropane ring can be installed at the benzylic position of a nitrite or ester. The hydrolysis of nitrites to yield carboxylic acids can be accomplished, as known to the person skilled in the art, under acid or base-mediated conditions.

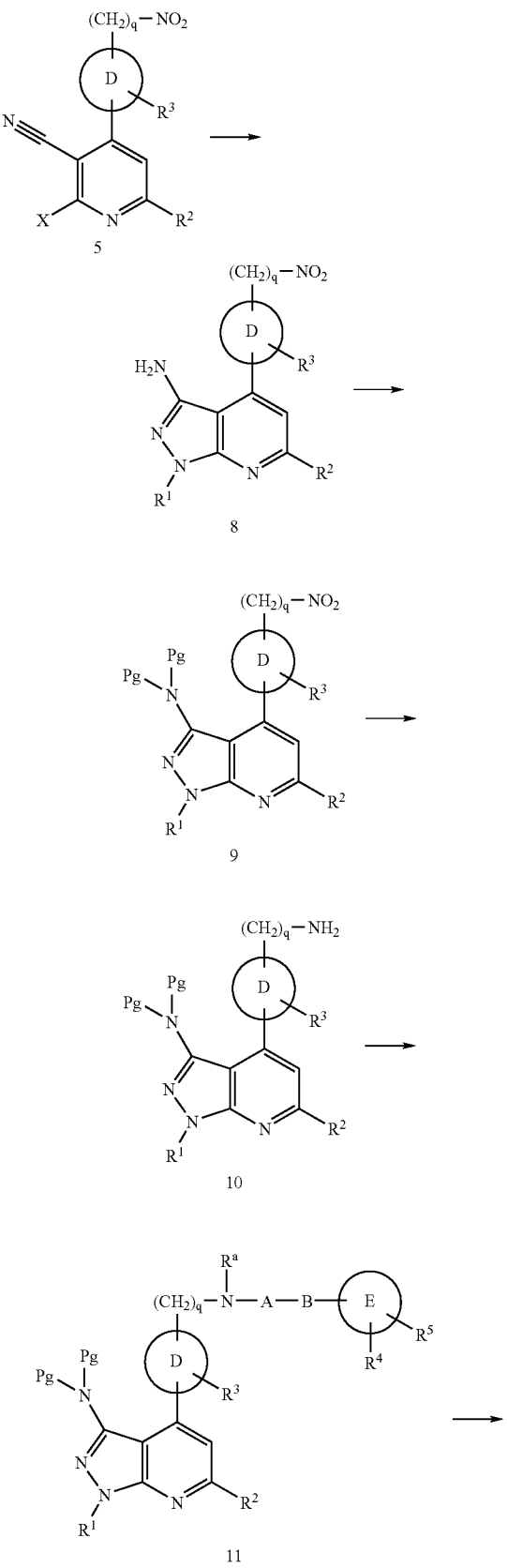

Scheme 4

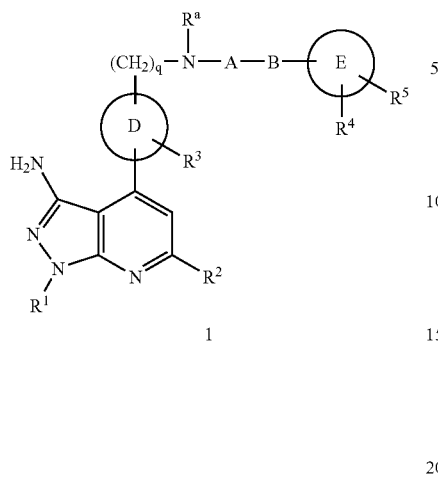

Scheme 4 Alternative general procedure for the preparation of Intermediates of the general formula 1, wherein X stands for OTf, Cl, F, OAc, OMe, and A, B, D, E, $R^a$, $R^d$, $R^2$, $R^3$, $R^4$, $R^5$ and q are as defined in the description and claims of this invention. The 3-Amino group at the pyrazolo ring of compounds of the general formula 9, 10, and 11 may be substituted with one or two protecting groups, preferably one or two Boc groups or even more preferably said amino group may be protected in form of a phthalimide.

An alternative synthetic route toward intermediates of general formula 1 is depicted in Scheme 4. Pyridines of the general formula 5, which can be prepared as described above, can be transformed into the respective pyrazolopyridines of general formula 8 by cyclization with hydrazine (or its hydrate) or substituted hydrazines in a suitable solvent, e.g. 1-propanol, at temperatures from room temperature up to the boiling point of the solvent, whereby in the case of 1-PrOH 100° C. is preferred.

Protection of the 3-amino group of the pyrazole nucleus leads to compounds of the general formula 8. Suitable protecting groups for amino functions are well known to the person skilled in the art (see for example T. W. Greene and P. G. M. Wuts in *Protective Groups in Organic Synthesis*, 3$^{rd}$ edition, Wiley 1999). Preferably, the 3-amino group is protected by formation of the respective phthalimide. In particular, phthalimido protection of 3-aminopyrazoles can be achieved by reaction of the amine with phthalic anhydride in a suitable inert solvent, e.g. acetonitrile or dioxane, optionally in the presence of a basic mediator, e.g. $Et_3N$, DIPEA or DMAP, at temperatures from room temperature up to the boiling point of the respective solvent.

Nitro reduction yielding amino compounds of the general formula 10 and e.g. urea, sulfonamide, and amide formation to give compounds of general formula 11 are feasible as described above. Finally, the intermediates of formula 1 are accessible by deprotection of the amino group in compounds of the general formula 11. Preferably, cleavage of the phthalimido group can be achieved, as known to the person skilled in the art, by reaction with hydrazine or hydrazine hydrate in solvents such as EtOH at temperatures from room temperature up to the boiling point of the respective solvent.

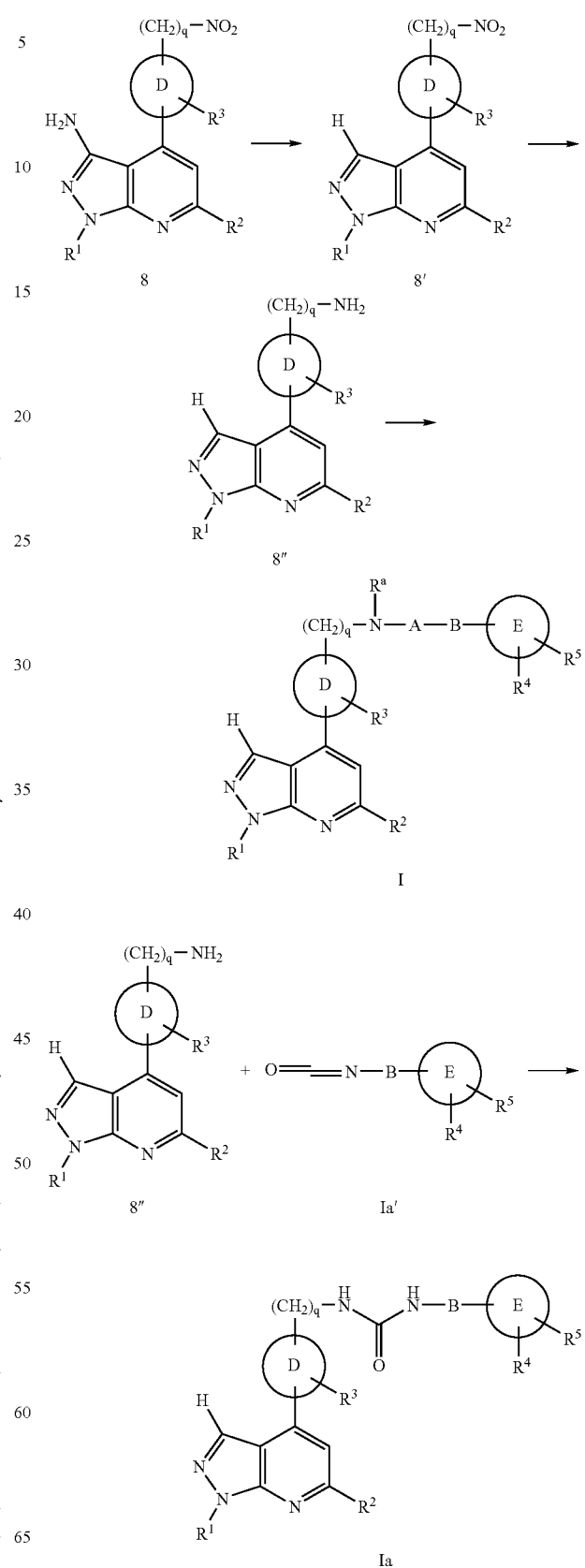

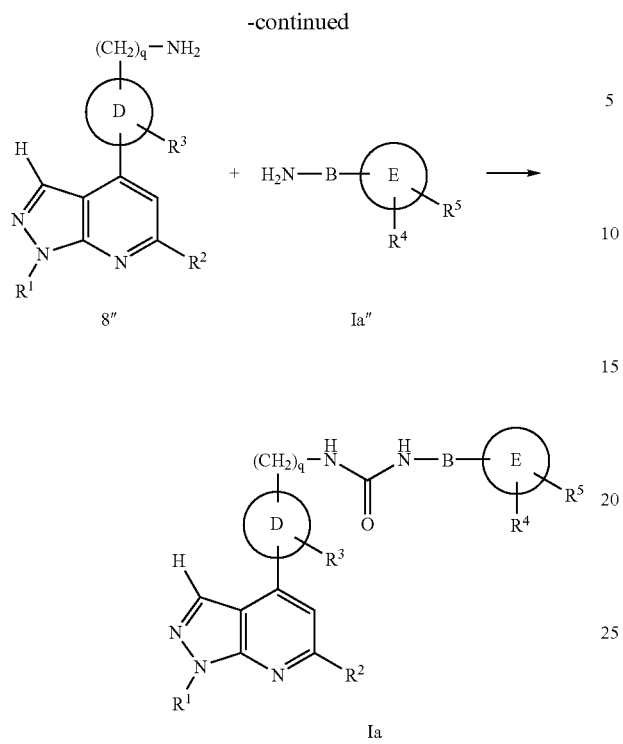

Scheme 5 Alternative general procedure for the preparation of compounds of the general formula (I) starting from intermediates of general formula 8, wherein A, B, D, E, $R^a$, $R^1$, $R^2$, $R^3$, $R^4$, $R^5$ and q are as defined in the description and claims herein.

Alternatively, use of amine protecting groups can be avoided by switching the order of steps (as exemplified in Scheme 5). Deamination of intermediates of general formula 8 and subsequent nitro group reduction of intermediates of general formula 8' gives rise to anilines of general formula 8'', which can be transformed into ureas or sulfonamides or amides of general formula I as described above. For example, anilines of formula 8'' can be reacted with isocyanates of formula Ia' or anilines of formula Ia'' in accordance to the before mentioned transformations to yield ureas of formula Ia.

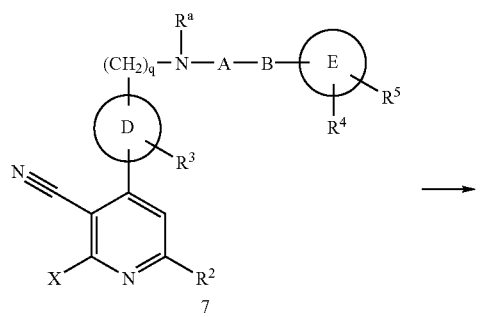

Scheme 6 Additional general procedure for the preparation of intermediates of the general formula 1 employing a late-stage N1-functionalization, wherein X stands for OTf, Cl, F, OAc, OMe, and X' represents OTf, Cl, Br, I, OMs (methanesulfonyl), OAc, and A, B, D, E, $R^a$, $R^1$, $R^2$, $R^3$, $R^4$, $R^5$ and q are as defined in the description and claims of this invention.

As a further optional process leading to compounds of the present invention, introduction of $R^1$-substituents as present in intermediates of general formula 1 can be accomplished after formation of 1H-pyrazolopyridines 12 by subsequent acylation or alkylation (Scheme 6). This process is of particular importance if appropriately substituted hydrazines are not readily available. 1H-Pyrazolopyridines of general formula 12 are accessible from synthetic intermediates of formula 7 (which can be prepared as described above) by cyclization with hydrazine or more preferably with hydrazine hydrate in a suitable solvent, preferably 1-propanol, at temperatures from room temperature up to the boiling point of the solvent, whereby in the case of 1-PrOH 100° C. is preferred. Introduction of $R^1$- groups to yield intermediates of general formula 1 can be achieved employing various conditions for introducing substituents to nitrogen atoms as known to the person skilled in the art. These conditions include, but are not limited to, alkylations under basic conditions employing alkyl-, allyl-, benzylhalides or α-halocarbonyl compounds as electrophiles (e.g. WO2005056532; *Chem. Pharm. Bull.* 1987, 35, 2292; *J. Med. Chem.* 2005, 48, 6843), alkylations under reductive conditions employing aldehydes as electrophiles and an appropriate reducing agent (e.g. $BH_3$.pyr, NaBH(OAc)$_3$, NaBH$_3$CN, NaBH$_4$), Mitsunobu-type alkylations employing primary or secondary alcohols as electrophiles (e.g. *Tetrahedron* 2006, 62, 1295; *Bioorg. Med. Chem. Lett.* 2002, 12, 1687), or N-acylations (see for example *J. Med. Chem.* 2005, 48, 6843) optionally followed by amide reduction. The presence of the 3-amino group may give rise to regioisomeric product mixtures under some of these conditions requiring separation of regioisomeric products by methods known to the person skilled in the art. Intermittent protection of the 3-amino group, e.g. by formation of a phthalimido group under conditions as described above, followed by N1 substitution and protecting group cleavage may instead allow regioselective introduction of substituents at N1 (see for example US20040235892). Conditions for N1-alkylation of 3-aminopyrazoles of the general formula 12 include, but are not limited to, treatment with an excess of the respective electrophile (e.g. alkyl-, allyl-, benzylhalides or α-halocarbonyl compounds) in the presence of a base, e.g. potassium carbonate or cesium carbonate, in DMF at temperatures from room temperature up to the boiling point of the solvent. Even more preferably, 1H-pyrazoles of general formula 12 are deprotonated with sodium hydride in DMF at temperatures from 0° C. up to 80° C. followed by reaction with the respective electrophile (e.g. alkyl-, allyl-, benzylhalides or α-halocarbonyl compounds) in DMF at temperatures from room temperature up to the boiling point of the solvent.

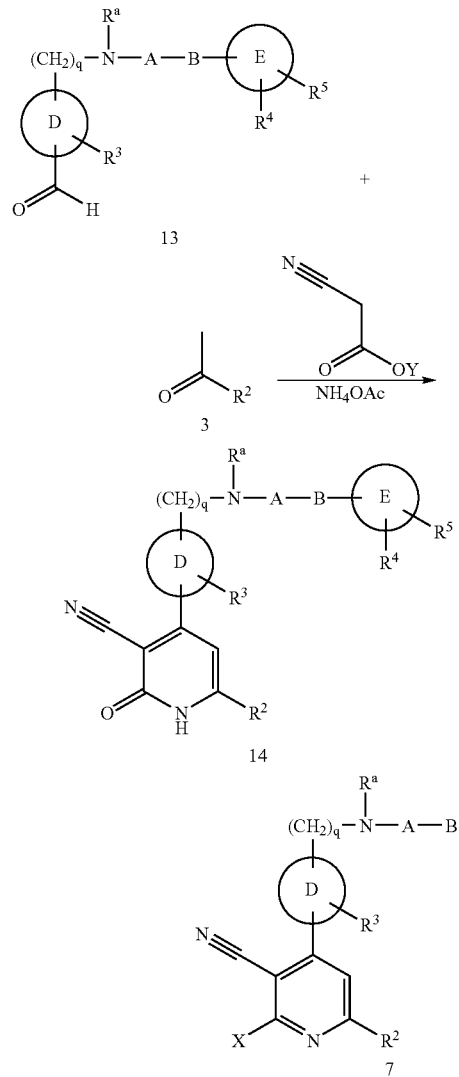

Scheme 7 Alternative order of transformations for the preparation of compounds of the general formula (I), wherein X, stands for OTf, Cl, F, OAc, OMe, Y stands for Me, Et and A, B, D, E, $R^a$, $R^1$, $R^2$, $R^3$, $R^4$, $R^5$ and q are as defined in the description and claims of this invention.

Alternatively to the process shown in Scheme 2, the order of transformations for the preparation of intermediates of formula 1 may be changed as exemplified in Scheme 7. A fully functionalized northern part of compounds of the present invention may already be present in aldehydes of general formula 13, which lead upon multicomponent coupling as described above to pyridones of general formula 14. Transformation of pyridones of general formula 14 into pyridines of general formula 7 can be accomplished as described above.

An alternative process for the preparation of compounds of the present invention is depicted in Scheme 8.

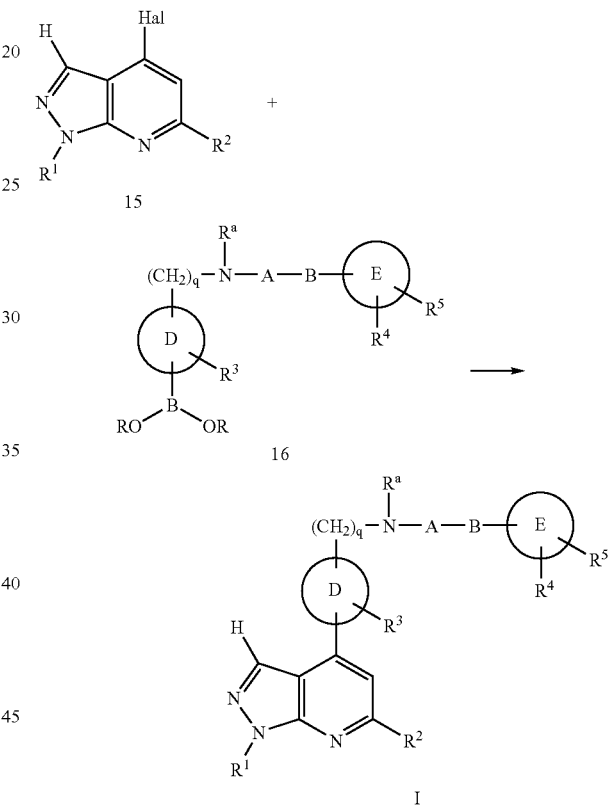

Scheme 8 Additional general procedure for the preparation of compounds of the general formula (I) employing a late-stage transition metal-catalyzed coupling reaction, wherein A, B, D, E, $R^a$, $R^1$, $R^2$, $R^3$, $R^4$, $R^5$ and q are as defined in the description and claims of this invention and Hal stands for Cl, Br or I and R stands for H or alkyl or wherein the two OR groups form a pinacolate.

In this convergent process, compounds of the present invention of general formula I are prepared by a transition metal catalyzed coupling of an appropriate halo precursor of general formula 15 and an appropriately substituted boronic acid or boronate esters. More particularly, compounds of the present invention can be prepared starting from a halogenated pyrazolopyridine (15) by Pd-catalyzed Suzuki-type coupling reactions with (hetero)aryl boronic acids (16) or even more particularly with their respective boronate esters (e.g. a pinacolate ester). Transition metal-catalyzed couplings of heteroaryl halides with (hetero)aryl boronic acids or aryl boronate esters are well known to the person skilled in the art. Various catalyst/ligand/base/solvent combinations have been published in the scientific literature (*Tetrahedron* 2005, 61, 5131 and references cited therein; *Eur. J. Org. Chem.* 2006, 1917 and references cited therein; *Eur. J. Org. Chem.* 2006, 2063 and references cited therein), which allow a fine-tuning of the required reaction conditions in order to allow for a broad set of additional functional groups on both coupling partners. Alternatively, the boronic acids of general formula 16 may be replaced by, for example, a suitably substituted stannane. Conditions for Stille-type couplings of aryl- or heteroaryl stannanes to aryl or heteroaryl halides employing a Pd catalyst and optionally a mediator are well known to the person skilled in the art.

The respective halogenated pyrazolopyridines of general formula 15 can be synthesized according to literature procedures e.g. from 3-aminopyrazole (see for example *J. Prakt. Chem.* 1982, 324, 557) or from 5-carboxy-4-hydroxypyrazolopyridines (see for example *J. Med. Chem.* 1975, 18, 161) by decarboxylation followed by halogenation or from 2,4-dihalopyridine-3-carboxaldehydes (commercially available or synthesized e.g. according to US20040044040) by hydrazine cyclization. The boronic acids and their respective pinacolate esters (16) needed for the above mentioned coupling reactions can be prepared e.g. by urea formation or sulphonamide formation or amide coupling of accordingly substituted anilines (or benzylic amines or higher homologs). In addition, boronic acids or boronate esters can be introduced into aryl or heteroaryl compounds inter alia by substituting halogen atoms. This substitution can be accomplished by metalation followed by electrophilic borylation (*Org. Biomol. Chem.* 2004, 2, 852) or by direct Pd- or Cu-catalyzed borylation (*Synlett* 2003, 1204 and references cited therein; *Org. Lett.* 2006, 8, 261). Interconversion of boronic acids into the respective esters (e.g. their pinacolate esters) can be accomplished under standard conditions (for example by treatment with pinacol in EtOH at r.t.).

EXAMPLES

In the subsequent paragraphs general procedures for the synthesis of the below mentioned specific example compounds are summarized.

General Procedure 1 (GP1): Pyridone Multi-Component Coupling

To a suspension of ammonium acetate (8 eq.) in EtOH (60 mL per mmol NH$_4$OAc) were added successively the respective methylketone component (1 eq.), methyl cyanoacetate (1 eq.), and 4-nitrobenzaldehyde (1 eq.). The resulting mixture was stirred at reflux for 1-5 h and subsequently for 16 h at r.t. The precipitate was filtered off, washed with EtOH and hexane and dried to yield the pyridone in sufficient purity for use in subsequent transformations without additional purification steps. Concentration of the filtrate gave rise to additional pyridone precipitation improving the overall yield of the multi-component coupling.

General Procedure 2 (GP 2): Triflate Formation

To a solution of the respective pyridone (1 eq.) in DCM (8 mL per mmol pyridone) was added pyridine (1.5 eq.) and subsequently at 0° C. dropwise trifluoromethanesulfonic acid anhydride (1.5 eq.). The resulting mixture was gradually warmed to room temperature and stirring was continued for 2 h. The reaction mixture was diluted with DCM and quenched with water. The aqueous layer was extracted with DCM and the combined organic layers were dried and concentrated in vacuo. Flash column chromatography provided the 2-pyridyl triflates.

General Procedure 3 (GP 3): Nitro Reduction

The respective nitro compound (1 eq.) was dissolved in EtOH (7 mL per mmol nitro compound) and treated in a counterflow of argon portionwise with SnCl$_2$.2H$_2$O (5 eq.). The resulting slurry was vigorously stirred and heated to 70° C. for 30 to 120 min. The reaction mixture was poured into 25% NH$_3$ solution (25 mL per mmol nitro compound), extracted with EtOAc, the combined organic layers were washed with brine twice, dried and concentrated in vacuo. The resulting aniline was usually used for subsequent reactions without additional purification steps.

General Procedure 4a (GP 4a): Formation of N1-Substituted Pyrazolopyridines (Conditions a)

Step 1

The respective aniline (1 eq.) was dissolved in DCM (4 mL per mmol aniline) and treated with the respective commercially available isocyanate (1-1.2 eq.). The reaction mixture was stirred at room temperature until TLC indicated complete consumption of the starting aniline (usually 16 h). The reaction mixture was concentrated in vacuo. In most cases, the crude urea was used in the subsequent cyclization without further purification, however, in cases with incomplete urea formation (as judged by TLC) flash column chromatography was applied for purification.

Step 2

The crude or purified urea from step 1 (1 eq.) was dissolved in 1-PrOH (12-15 mL per mmol urea) and treated optionally with Et$_3$N (1.5 eq) and subsequently with the respective commercially available substituted hydrazine (1-3 eq.). The resulting mixture was stirred at 100° C. for 3 h, concentrated in vacuo and the pyrazolopyridine product was isolated by flash column chromatography followed by re-crystallization and/or preparative HPLC purification.

General Procedure 4b (GP 4b): Formation of N1-Substituted Pyrazolopyridines (Conditions B)

Step 1

The aniline (1.2 eq.) was dissolved in 10 mL acetonitrile and treated with triphosgene (0.2 mmol, 0.4 eq.) and stirred at room temperature for 1 h upon which the 2-pyridyltriflate was added and stirring was continued at r.t. for 16 h. The reaction mixture was concentrated and the crude urea used in the subsequent cyclization without additional purification.

Step 2

The crude urea from step 1 (1 eq.) was dissolved in 1-PrOH (12-15 mL per mmol urea) and treated optionally with Et$_3$N (1.5 eq) and subsequently with the respective commercially available substituted hydrazine (1-3 eq.). The resulting mixture was stirred at 100° C. for 3 h, concentrated in vacuo and the pyrazolopyridine product was isolated by flash column chromatography followed by re-crystallization and/or preparative HPLC purification.

General Procedure 4c (GP 4c): Preparation of 1H-pyrazolopyridines (Conditions A)

Step 1

The respective aniline (1 eq.) was dissolved in DCM (4 mL per mmol aniline) and treated with the respective commercially available isocyanate (1-1.2 eq.). The reaction mixture was stirred at room temperature until TLC indicated complete consumption of the starting aniline (usually 16 h). The reaction mixture was concentrated in vacuo. In most cases, the crude urea was used in the subsequent cyclization without further purification, however, in cases with incomplete urea formation (as judged by TLC) flash column chromatography was applied for purification.

Step 2

The crude or purified urea from step 1 (1 eq.) was dissolved in 1-PrOH (12-15 mL per mmol urea) and treated optionally with Et$_3$N (1.5 eq) and subsequently with 80% hydrazine hydrate (1-3 eq.). The resulting mixture was stirred at 100° C. for 3 h, concentrated in vacuo and the pyrazolopyridine product was isolated by flash column chromatography followed by re-crystallization and/or preparative HPLC purification.

General Procedure 4d (GP 4d): Preparation of 1H-pyrazolopyridines (Conditions B)

Step 1

The aniline (1.2 eq.) was dissolved in 10 mL acetonitrile and treated with triphosgene (0.2 mmol, 0.4 eq.) and stirred at room temperature for 1 h upon which the 2-pyridyltriflate was added and stirring was continued at r.t. for 16 h. The reaction mixture was concentrated and the crude urea used in the subsequent cyclization without additional purification.

Step 2

The crude or purified urea from step 1 (1 eq.) was dissolved in 1-PrOH (12-15 mL per mmol urea) and treated optionally with Et$_3$N (1.5 eq) and subsequently with 80% hydrazine hydrate (1-3 eq.). The resulting mixture was stirred at 100° C. for 3 h, concentrated in vacuo and the pyrazolopyridine product was isolated by flash column chromatography followed by re-crystallization and/or preparative HPLC purification.

General Procedure 5 (GP 5): N1-Alkylation of 1H-pyrazolopyridines

The respective 1H-pyrazolopyridine was dissolved in dry DMF under an atmosphere of argon and treated with sodium hydride and subsequently stirred at 50° C. for 1 h. A solution of the respective alkyl halide in DMF was added dropwise and stirring was continued at 50° C. for 1 h. [In cases were the respective halide is only available as a salt (e.g. hydrochloride or hydrobromide salt), this salt was dissolved in DMF and treated with Et$_3$N, and the resulting slurry was added to the deprotonated 1H-pyrazolopyridine upon filtration through a Millipore filter.] The reaction mixture was diluted with EtOAc, quenched with water, the aqueous layer was extracted with EtOAc and the combined organic layers were dried and concentrated in vacuo. Flash column chromatography optionally followed by recrystallization or preparative HPLC purification yielded the desired alkylated pyrazolopyridines.

General Procedure 6 (GP 6): Desamination of Aminopyrazolopyridines

The respective aminopyrazole compound (1 eq.) was dissolved in EtOH (1.8 mL per mmol) and treated with concentrated sulphuric acid and heated to 80° C. At this temperature sodium nitrite (2.5 eq.) was added portionwise and stirring at reflux was continued until TLC indicated complete consumption of the starting material (usually within 1 h after completion of sodium nitrite addition). The reaction mixture was cooled to room temperature and poured onto ice. The precipitate was filtered off and washed with ice-water. Optionally, the crude product was taken up in ethyl acetate, washed with sodium bicarbonate solution and brine, dried and concentrated in vacuo. In some cases additional purification steps (flash column chromatography and/or preparative HPLC) were necessary.

General Procedure 7 (GP 7): Amide Formation and Cyclization

Step 1

The respective aniline (1 eq.) was dissolved in DCM (12 mL per mmol aniline) and treated with pyridine (1.5 eq.) and the respective carboxylic acid chloride (1.2 eq.). The reaction mixture was stirred at room temperature until TLC indicated complete consumption of the starting aniline (usually 16 h). The reaction mixture was quenched with NaHCO$_3$ and extracted with ethyl acetate. The organic layers were dried and concentrated in vacuo. In most cases, the crude amide was used in the subsequent cyclization without further purification, however, in cases with incomplete amide formation (as judged by TLC) flash column chromatography was applied for purification.

Step 2

The crude or purified amide from step 1 (1 eq.) was dissolved in 1-PrOH (12-15 mL per mmol amide) and treated optionally with Et$_3$N (1.5 eq) and subsequently with 80% hydrazine hydrate or a substituted hydrazine (1-3 eq.). The resulting mixture was stirred at 100° C. for 3 h, concentrated in vacuo and the pyrazolopyridine product was isolated by flash column chromatography followed by re-crystallization and/or preparative HPLC purification.

General Procedure 8 (GP 8): Sulfonamide Formation and Cyclization

Step 1

The respective aniline (1 eq.) was dissolved in DCM (12 mL per mmol aniline) and treated with pyridine (1.5 eq.) and the respective sulfonyl chloride (1.2 eq.). The reaction mixture was stirred at room temperature until TLC indicated complete consumption of the starting aniline (usually 16 h). The reaction mixture was quenched with NaHCO$_3$ and extracted with ethyl acetate. The organic layers were dried and concentrated in vacuo. In most cases, the crude sulfonamide was used in the subsequent cyclization without further purification, however, in cases with incomplete sulfonamide formation (as judged by TLC) flash column chromatography was applied for purification.

Step 2

The crude or purified sulfonamide from step 1 (1 eq.) was dissolved in 1-PrOH (12-15 mL per mmol sulfonamide) and treated optionally with Et$_3$N (1.5 eq) and subsequently with 80% hydrazine hydrate or a substituted hydrazine (1-3 eq.). The resulting mixture was stirred at 100° C. for 3 h, concentrated in vacuo and the pyrazolopyridine product was isolated by flash column chromatography followed by re-crystallization and/or preparative HPLC purification.

General Procedure 9 (GP 9): Ester Saponification

The carboxylic acid ester was treated with EtOH and aqueous sodium hydroxide solution (1 M) and stirred for 3 hours at 80° C. To the cold solution was added the same volume of water. The mixture was acidified with a 20% solution of citric acid. The precipitate was filtered off, washed with water and dried to yield the carboxylic acid.

General Procedure 10 (GP 10) Amide Formation

The carboxylic acid (1 eq.) was suspended in DCM and treated with the amine (1.3 eq.) and 4-methylmorpholine (5 eq.). The suspension was stirred for 10 minutes at room temperature and then cooled with ice. 2,4,6-tripropyl-[1,3,5, 2,4,6]trioxatriphosphinane 2,4,6-trioxide (T3P; 2 eq.) was added and the solution stirred over night at room temperature. The mixture was concentrated in vacuo, taken up in sodium bicarbonate solution and stirred. The precipitate was filtered off, washed with water and dried to yield the amide. In some cases additional purification steps (flash column chromatography and/or preparative HPLC) were necessary.

SYNTHETIC INTERMEDIATES

Intermediate 1.1

Preparation of 6-tert-Butyl-4-(4-nitro-phenyl)-2-oxo-1,2-dihydro-pyridine-3-carbonitrile

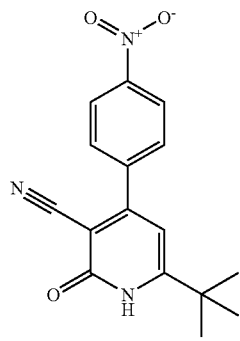

In analogy to GP 1, reaction of 61.7 g ammonium acetate (800 mmol, 8 eq.), 10.73 ml ethyl cyanoacetate (100 mmol, 1 eq.), 12.55 ml 3,3-dimethylbutan-2-one (100 mmol, 1 eq.), and 15.12 g 4-nitrobenzaldehyde (100 mmol, 1 eq.) yielded 10.02 g product (34% yield).

$^1$H-NMR (d$_6$-DMSO; 300 MHz): 12.38 (br. s, 1H); 8.34 (d, 2H); 7.89 (d, 2H); 6.28 (s, 1H); 1.28 (s, 9H).

MS (ESI): [M+H]$^+$=298.

Intermediate 1.2

Preparation of 6-Isopropyl-4-(4-nitro-phenyl)-2-oxo-1,2-dihydro-pyridine-3-carbonitrile

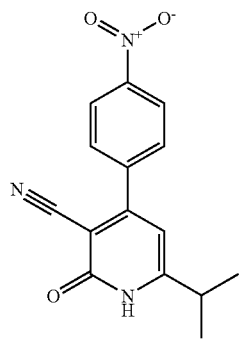

In analogy to GP 1, reaction of 61.7 g ammonium acetate (800 mmol, 8 eq.), 10.67 ml ethyl cyanoacetate (100 mmol, 1 eq.), 10.71 ml 3-methyl-butan-2-one (100 mmol, 1 eq.), and 15.12 g 4-nitrobenzaldehyde (100 mmol, 1 eq.) yielded 4.24 g product (15% yield).

$^1$H-NMR (d$_6$-DMSO; 300 MHz): 12.62 (br. s, 1H); 8.34 (d, 2H); 7.87 (d, 2H); 6.35 (s, 1H); 2.87 (sept, 1H); 1.20 (d, 6H).

MS (ESI): [M+H]$^+$=284.

Intermediate 1.3

Preparation of 6-Methyl-4-(4-nitro-phenyl)-2-oxo-1,2-dihydro-pyridine-3-carbonitrile

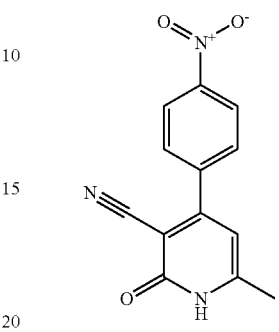

In analogy to GP 1, reaction of 8.16 g ammonium acetate (106 mmol, 8 eq.), 1.41 ml ethyl cyanoacetate (13.23 mmol, 1 eq.), 0.98 ml dry acetone (13.23 mmol, 1 eq.), and 2 g 4-nitrobenzaldehyde (13.23 mmol, 1 eq.) yielded 1.56 g product (46% yield).

$^1$H-NMR (d$_6$-DMSO; 400 MHz): 12.76 (br. s, 1H); 8.34 (d, 2H); 7.84 (d, 2H); 6.36 (s, 1H); 2.30 (s, 3H).

Intermediate 1.4

Preparation of 6-Cyclopropyl-4-(4-nitro-phenyl)-2-oxo-1,2-dihydro-pyridine-3-carbonitrile

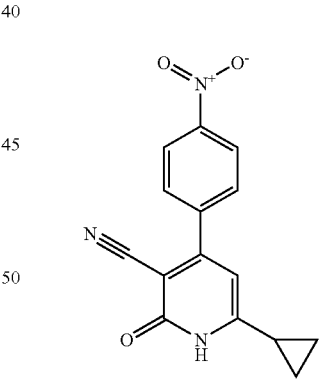

In a modification of GP 1, reaction of 17.9 g ammonium acetate (233 mmol, 7 eq.), 3.5 ml methyl cyanoacetate (40 mmol, 1.2 eq.), 3.8 ml 1-cyclopropyl-ethanone (38 mmol, 1.15 eq.), and 5 g 4-nitrobenzaldehyde (33 mmol, 1 eq.) yielded 3.23 g product (11.5 mmol, 35% yield).

$^1$H-NMR (d6-DMSO; 300 MHz): 12.82 (br. s, 1H); 8.37 (d, 2H); 7.88 (d, 2H); 6.10 (s, 1H); 2.00 (m, 1H); 1.00-1.25 (m, 4H).

Intermediate 1.5

Preparation of 2-[5-Cyano-4-(4-nitro-phenyl)-6-oxo-1,6-dihydro-pyridin-2-yl]-2-methyl-propionic acid ethyl ester

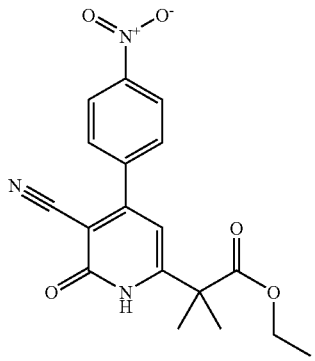

In analogy to GP 1, reaction of 1.85 g ammonium acetate (24 mmol, 8 eq.), 0.28 ml ethyl cyanoacetate (3 mmol, 1 eq.), 475 mg 2,2-dimethyl-3-oxo-butyric acid ethyl ester (3 mmol, 1 eq.), and 453 mg 4-nitrobenzaldehyde (3 mmol, 1 eq.) yielded 125 mg product (11% yield).

$^1$H-NMR (d$_6$-DMSO; 300 MHz): 8.30 (d, 2H); 7.79 (d, 2H); 6.16 (s, 1H); 4.04 (q, 2H); 1.41 (s, 6H); 1.11 (t, 3H) (isolated as acetate salt).

Intermediate 1.6

Preparation of 1-[5-Cyano-4-(4-nitro-phenyl)-6-oxo-1,6-dihydro-pyridin-2-yl]-cyclopropanecarboxylic acid ethyl ester

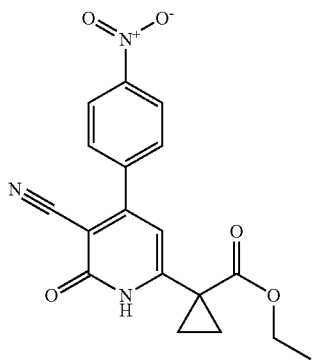

In analogy to GP 1, reaction of 28.9 g ammonium acetate (375 mmol, 8 eq.), 5 ml ethyl cyanoacetate (47.3 mmol, 1 eq.), 7.32 g 1-acetyl-cyclopropanecarboxylic acid ethyl ester (47 mmol, 1 eq.), and 7.08 g 4-nitrobenzaldehyde (47 mmol, 1 eq.) yielded 7.2 g product (43% yield).

$^1$H-NMR (d$_6$-DMSO; 300 MHz): 13.12 (br. s, 1H); 8.38 (d, 2H); 7.94 (d, 2H); 6.51 (br. s, 1H); 4.10 (q, 2H); 1.49 (br. s, 4H); 1.16 (t, 3H).

Intermediate 1.7

Preparation of 6-Furan-2-yl-4-(4-nitro-phenyl)-2-oxo-1,2-dihydro-pyridine-3-carbonitrile

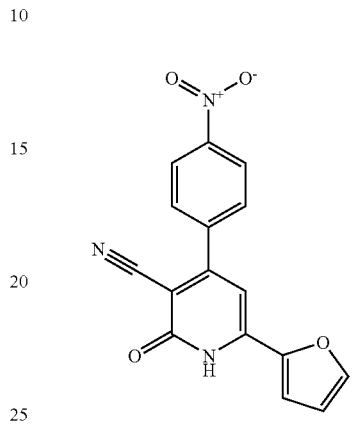

In analogy to GP 1, reaction of 1.85 g ammonium acetate (24 mmol, 8 eq.), 0.28 ml ethyl cyanoacetate (3 mmol, 1 eq.), 330 mg furan-2-carbaldehyde (3 mmol, 1 eq.), and 453 mg 4-nitrobenzaldehyde (3 mmol, 1 eq.) yielded 362 mg product (39% yield).

$^1$H-NMR (d$_6$-DMSO; 300 MHz): 8.29 (d, 2H); 7.79 (d, 2H); 7.73 (m, 1H); 7.01 (d, 1H); 6.57 (dd, 1H); 6.50 (s, 1H) (isolated as acetate salt).

Intermediate 1.8

Preparation of 4-(4-Nitro-phenyl)-2-oxo-1,2-dihydro-pyridine-3-carbonitrile

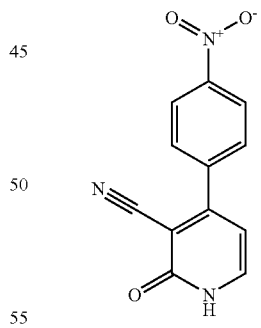

Step 1

In a flask fitted with a Dean-Stark water separator glacial AcOH (6 ml, 0.100 mot) and ammonium acetate (3.85 g, 0.050 mot) were placed. The flask was gently heated to dissolve ammonium acetate. Then a solution of 4-nitroacetophenone (20.6 g, 0.125 mot) in benzene (150 ml) and malononitrile (8.25 g, 0.125 mot) were added. The solution was heated to vigorous reflux during 4 h, cooled, washed with water (3×100 ml), and dried over Na$_2$SO$_4$. Benzene was removed under reduced pressure to give a thick, brown oil. The oil was dissolved in hot ethanol (100 ml), chilled to 0° C., the precipitate was filtered off and dried. Yield 20.9 g (98 mmol, 79%).

$^1$H-NMR (d6-DMSO; 300 MHz): 8.38 (d, 2H); 7.71 (d, 2H); 2.40 (S, 3H).

Step 2

Dimethylformamide dimethyl acetal (10 ml, 72.8 mmol) was added to the suspension of the product from step 1 (13.0 g, 61 mmol) and AcOH (4.4 ml, 72.8 mmol). The mixture was heated until it began to boil. After cooling, 25 ml of isopropanol was added to the mixture, it was filtered, washed with isopropanol and dried. 13.0 g of crude product containing 85% of the desired enamine was obtained.

$^1$H-NMR (CDCl$_3$; 300 MHz): 8.35 (d, 2H); 7.50 (d, 2H); 6.50 (d, 1H); 5.85 (d, 1H); 3.05 (s, 6H).

Step 3

The crude enamine from step 2 (13.0 g, 41.2 mmol) was dissolved in acetic acid (130 ml) containing 98% sulfuric acid (26 ml) and water (39 ml). The solution was refluxed for 2 h. After cooling, the precipitate was filtered and washed with water. Yield 6.8 g (28 mmol, 58%).

$^1$H-NMR (DMSO; 300 MHz): 12.80 (br. s, 1H); 8.40 (d, 2H); 7.85-7.95 (m, 3H); 6.5 (d, 1H);

MS (LCMS): [M+H]$^+$=242.

Intermediate 2.1

Preparation of Trifluoromethanesulfonic acid 6-tert-butyl-3-cyano-4-(4-nitrophenyl)-pyridin-2-yl ester

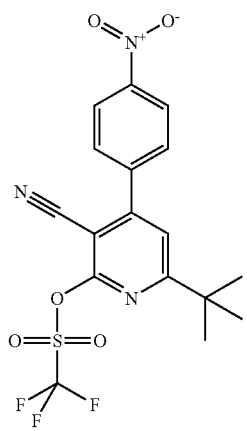

In analogy to GP 2, reaction of 3.51 g Intermediate 1.1 (11.8 mmol, 1 eq.), 1.43 mL dry pyridine (17.7 mmol, 1.5 eq.), 2.98 ml trifluoromethanesulfonic acid anhydride (17.7 mmol, 1.5 eq.) in 95 mL DCM yielded 4.42 g 2-pyridyl triflate (10.4 mmol, 88% yield).

$^1$H-NMR (d$_6$-DMSO; 300 MHz): 8.47 (d, 2H); 8.08 (d, 2H); 7.93 (s, 1H); 1.38 (s, 9H).

Intermediate 2.2

Preparation of Trifluoromethanesulfonic acid 3-cyano-6-isopropyl-4-(4-nitrophenyl)-pyridin-2-yl ester

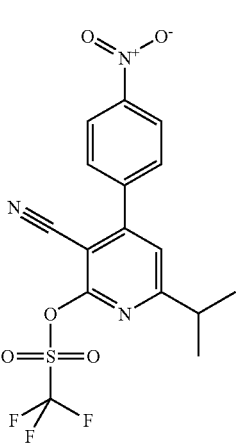

In analogy to GP 2, reaction of 4.19 g Intermediate 1.2 (14.8 mmol, 1 eq.), 1.79 mL dry pyridine (22.2 mmol, 1.5 eq.), 3.73 ml trifluoromethanesulfonic acid anhydride (22.2 mmol, 1.5 eq.) in 110 mL DCM yielded 5.6 g 2-pyridyl triflate (13.5 mmol, 91% yield).

$^1$H-NMR (d$_6$-DMSO; 300 MHz): 8.42 (d, 2H); 8.01 (d, 2H); 7.87 (s, 1H); 3.20 (sept, 1H); 1.24 (d, 6H).

MS (ESI): [M+H]$^+$=416.

Intermediate 2.3

Preparation of Trifluoromethanesulfonic acid 3-cyano-6-methyl-4-(4-nitro-phenyl)-pyridin-2-yl ester

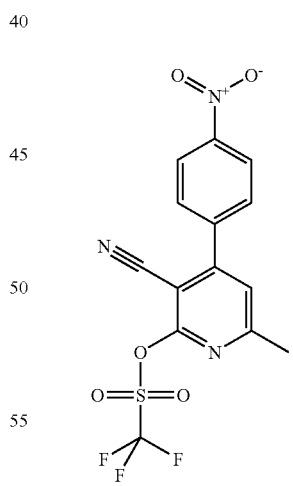

In analogy to GP 2, reaction of 4.5 g Intermediate 1.3 (17.6 mmol, 1 eq.), 2.13 mL dry pyridine (26.4 mmol, 1.5 eq.), 4.45 ml trifluoromethanesulfonic acid anhydride (26.4 mmol, 1.5 eq.) in 140 mL DCM yielded 2.9 g 2-pyridyl triflate (7.4 mmol, 42% yield).

$^1$H-NMR (d$_6$-DMSO; 300 MHz): 8.42 (d, 2H); 7.98 (d, 2H); 7.88 (s, 1H); 2.62 (s, 3H).

Intermediate 2.4

Preparation of Trifluoromethanesulfonic acid 3-cyano-6-cyclopropyl-4-(4-nitrophenyl)-pyridin-2-yl ester

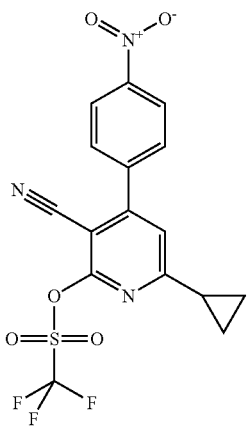

In a modification to GP 2, reaction of 1.5 g Intermediate 1.4 (5.3 mmol, 1 eq.), and 2.69 ml trifluoromethanesulfonic acid anhydride (16 mmol, 3 eq.) in pure pyridine yielded 1.49 g 2-pyridyl triflate (3.6 mmol, 68% yield).

$^1$H-NMR (CDCl$_3$; 300 MHz): 8.41 (d, 2H); 7.78 (d, 2H); 7.40 (s, 1H); 2.15 (m, 1H); 1.20-1.30 (m, 4H).

Intermediate 2.5

Preparation of 1-[5-Cyano-4-(4-nitro-phenyl)-6-trifluoromethanesulfonyloxy-pyridin-2-yl]-cyclopropanecarboxylic acid ethyl ester

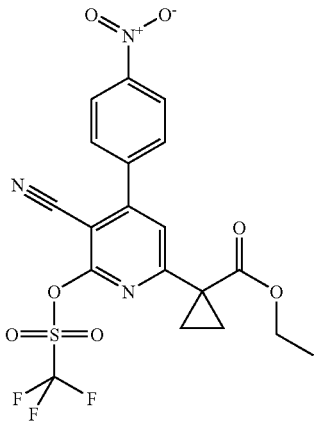

In analogy to GP 2, reaction of 7.2 g Intermediate 1.6 (20.4 mmol, 1 eq.), 2.5 mL dry pyridine (30.6 mmol, 1.5 eq.), 5.14 ml trifluoromethanesulfonic acid anhydride (30.6 mmol, 1.5 eq.) in 320 mL DCM yielded 4.2 g 2-pyridyl triflate (8.65 mmol, 43% yield).

$^1$H-NMR (d$_6$-DMSO; 300 MHz): 8.47 (d, 2H); 8.25 (s, 1H); 8.05 (d, 2H); 4.14 (q, 2H); 1.75 (m, 2H); 1.62 (m, 2H); 1.17 (t, 3H).

Intermediate 2.6

Preparation of Trifluoromethanesulfonic acid 3-cyano-4-(4-nitro-phenyl)-pyridin-2-yl ester

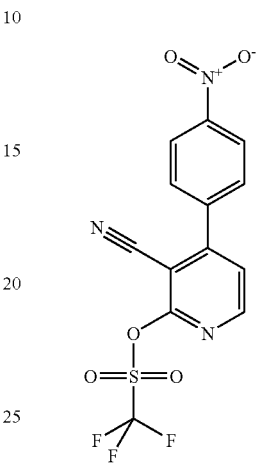

In analogy to GP 2, reaction of 11.3 g Intermediate 1.8 (47 mmol, 1 eq.), 5.6 mL dry pyridine (70 mmol, 1.5 eq.), 12 ml trifluoromethanesulfonic acid anhydride (70 mmol, 1.5 eq.) in 450 mL DCM yielded 12.2 g 2-pyridyl triflate (33 mmol, 70% yield).

$^1$H-NMR (d$_6$-DMSO; 300 MHz): 8.85 (d, 1H); 8.50 (d, 2H); 8.00-8.20 (m, 3H).

MS (LCMS): [M+H]$^+$=374.

Intermediate 3.1

Preparation of Trifluoromethanesulfonic acid 4-(4-amino-phenyl)-6-tert-butyl-3-cyano-pyridin-2-yl ester

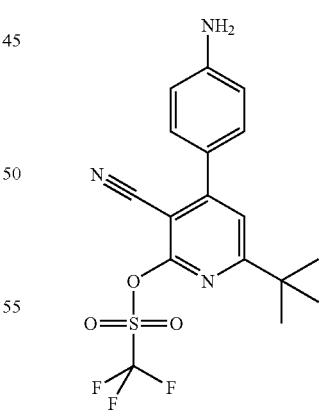

In analogy to GP 3, reaction of 4.7 g Intermediate 2.1 (11.3 mmol, 1 eq.) with 12.8 g tin(II)chloride dihydrate (56.6 mmol, 5 eq.) in 80 mL EtOH yielded 4 g of the aniline (10 mmol, 88% yield), which was used without further purification.

$^1$H-NMR (d$_6$-DMSO; 400 MHz): 7.61 (s, 1H); 7.51 (d, 2H); 6.68 (d, 2H); 5.91 (br. s, 2H); 1.29 (s, 9H).

Intermediate 3.2

Preparation of Trifluoromethanesulfonic acid 4-(4-amino-phenyl)-3-cyano-6-isopropyl-pyridin-2-yl ester

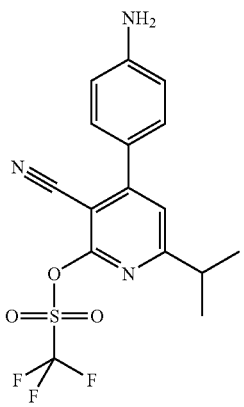

In analogy to GP 3, reaction of 5.6 g Intermediate 2.2 (13.5 mmol, 1 eq.) with 15.6 g tin(II)chloride dihydrate (69.1 mmol, 5 eq.) in 100 mL EtOH yielded the desired amine in a quantitative yield.

$^1$H-NMR (d$_6$-DMSO; 400 MHz): 7.63 (s, 1H); 7.50 (d, 2H); 6.67 (d, 2H); 5.91 (br. s, 2H); 3.10 (sept, 1H); 1.20 (d, 6H).

MS (ESI): [M+H]$^+$=386.

Intermediate 3.3

Preparation of Trifluoromethanesulfonic acid 4-(4-amino-phenyl)-3-cyano-6-methylpyridin-2-yl ester

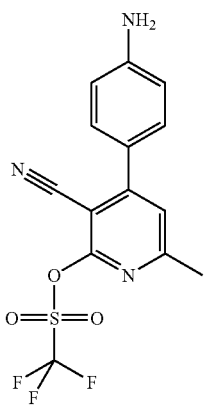

In analogy to GP 3, reaction of 866 mg Intermediate 2.3 (2.24 mmol, 1 eq.) with 2.52 g tin(II)chloride dihydrate (11.18 mmol, 5 eq.) in 11 mL EtOH yielded the desired amine in a quantitative yield.

$^1$H-NMR (d$_6$-DMSO; 300 MHz): 7.66 (s, 1H); 7.48 (d, 2H); 6.67 (d, 2H); 5.91 (br. s, 2H); 2.52 (s, 3H).

MS (ESI): [M+H]$^+$=358.

Intermediate 3.4

Preparation of Trifluoromethanesulfonic acid 4-(4-amino-phenyl)-3-cyano-6-cyclopropyl-pyridin-2-yl ester

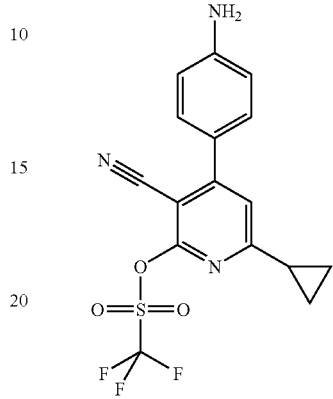

In analogy to GP 3, reaction of 1.49 g Intermediate 2.4 (3.6 mmol, 1 eq.) with 4.1 g tin(II)chloride dihydrate (18.19 mmol, 5 eq.) in 20 mL EtOH yielded 1.2 g of the desired aniline (3.1 mmol, 86% yield).

$^1$H-NMR (d$_6$-DMSO; 300 MHz): 7.76 (s, 1H); 7.51 (d, 2H); 6.70 (d, 2H); 5.92 (br. s, 2H); 2.31 (m, 1H); 1.15-1.20 (m, 2H); 0.96-1.00 (m, 2H).

Intermediate 3.5

Preparation of 1-[4-(4-Amino-phenyl)-5-cyano-6-trifluoromethanesulfonyloxy-pyridin-2-yl]-cyclopropanecarboxylic acid ethyl ester

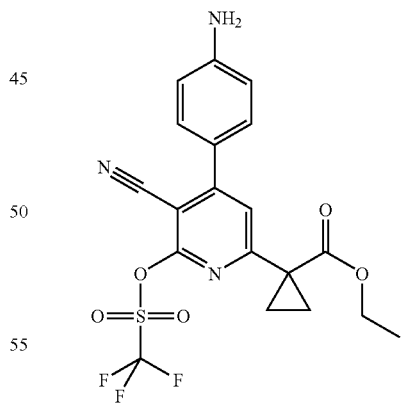

In analogy to GP 3, reaction of 3.8 g Intermediate 2.5 (7.8 mmol, 1 eq.) with 8.83 g tin(II)chloride dihydrate (39.1 mmol, 5 eq.) in 200 mL EtOH yielded 3.57 g of the aniline (7.38 mmol, 94% yield), which was used without further purification.

$^1$H-NMR (d$_6$-DMSO; 300 MHz): 8.01 (s, 1H); 7.55 (d, 2H); 6.72 (d, 2H); 6.00 (br. s, 2H); 4.13 (q, 2H); 1.66 (m, 2H); 1.56 (m, 2H); 1.16 (t, 3H).

Intermediate 3.6

Preparation of Trifluoromethanesulfonic acid 4-(4-amino-phenyl)-3-cyano-pyridin-2-yl ester

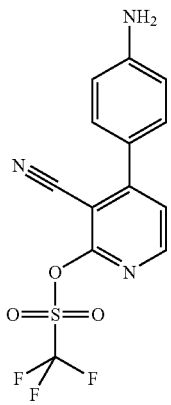

In analogy to GP 3, reaction of 5.6 g Intermediate 1.12 (15 mmol, 1 eq.) with 16.92 g tin(II)chloride dihydrate (75 mmol, 5 eq.) in 75 mL EtOH yielded 4.41 g of the desired product (86% yield).

$^1$H-NMR ($d_6$-DMSO; 300 MHz): 8.52 (d, 1H); 7.75 (d, 1H); 7.51 (d, 2H); 6.68 (d, 2H); 5.98 (br. s, 2H).

Intermediate 4.1

Preparation of Trifluoromethanesulfonic acid 6-tert-butyl-3-cyano-4-{4-[3-(3-trifluoromethyl-phenyl)-ureido]-phenyl}-pyridin-2-yl ester

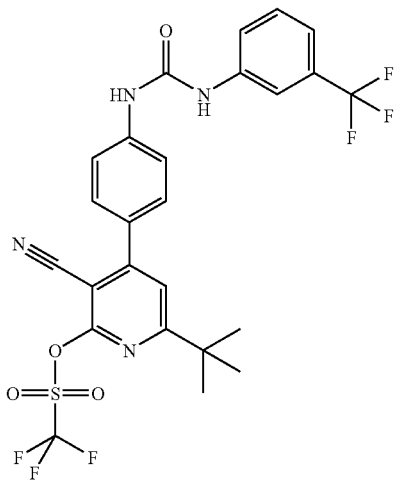

In analogy to GP 4a (step 1), reaction of 500 mg Intermediate 3.1 (1.25 mmol, 1 eq.) with 0.18 mL 1-isocyanato-3-trifluoromethyl-benzene (1.25 mmol, 1 eq.) in 4.5 mL DCM yielded the crude urea, which was not further purified but used directly in subsequent cyclization steps.

$^1$H-NMR ($d_6$-DMSO; 300 MHz): 9.17 (s, 1H); 9.13 (S, 1H); 7.99 (br. s, 1H); 7.76 (s, 1H); 7.66-7.74 (m, 4H); 7.57 (br. d, 1H); 7.49 (t, 1H); 7.30 (br. d, 1H); 1.32 (s, 9H).
MS (ESI): [M+H]$^+$=587.

Intermediate 4.2

Preparation of Trifluoromethanesulfonic acid 3-cyano-6-isopropyl-4-{4-[3-(3-trifluoromethyl-phenyl)-ureido]-phenyl}-pyridin-2-yl ester

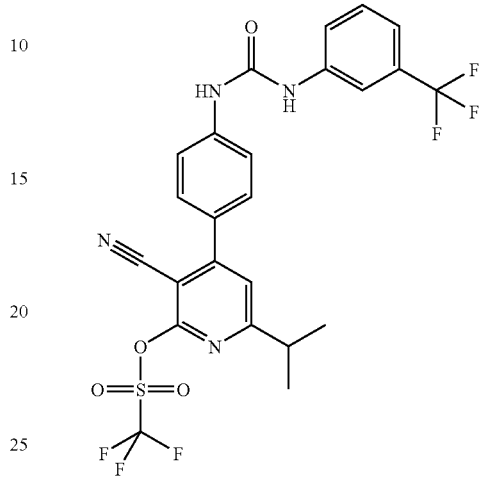

In analogy to GP 4a (step 1), reaction of 5.4 g Intermediate 3.2 (14 mmol, 1 eq.) with 3.15 g 1-isocyanato-3-trifluoromethyl-benzene (16.82 mmol, 1.2 eq.) in 50 mL DCM yielded the crude urea in quantitative yield, which was used for subsequent cyclizations without further purification.

$^1$H-NMR ($d_6$-DMSO; 300 MHz): 9.17 (s, 2H); 8.00 (br. s, 1H); 7.76 (s, 1H); 7.66-7.73 (m, 4H); 7.58 (br. d, 1H); 7.50 (t, 1H); 7.30 (br. d, 1H); 3.17 (sept., 1H); 1.23 (d, 6H).
MS (ESI): [M+H]$^+$=573.

Intermediate 4.3

Preparation of Trifluoromethanesulfonic acid 3-cyano-6-methyl-4-{4-[3-(3-trifluoromethyl-phenyl)-ureido]-phenyl}-pyridin-2-yl ester

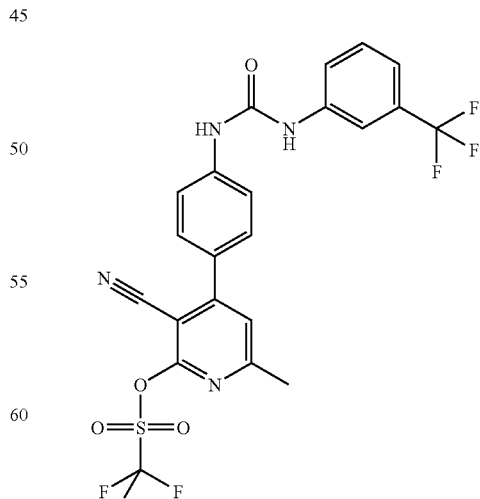

In analogy to GP 4a (step 1), reaction of 357.3 mg Intermediate 3.3 (1 mmol, 1 eq.) with 0.16 mL 1-isocyanato-3- trifluoromethyl-benzene (1.2 mmol, 1.2 eq.) in 10 mL DCM yielded the crude urea, which was used for subsequent cyclizations without further purification.

$^1$H-NMR (d$_6$-DMSO; 400 MHz): 9.54 (s, 1H); 9.52 (s, 1H); 7.99 (br. s, 1H); 7.79 (s, 1H); 7.66-7.71 (m, 4H); 7.57 (br. d, 1H); 7.50 (t, 1H); 7.30 (br. d, 1H); 2.58 (s, 3H).

Intermediate 4.4

Preparation of 1-{5-Cyano-4-[4-(3-phenyl-ureido)-phenyl]-6-trifluoromethanesulfonyloxy-pyridin-2-yl}-cyclopropanecarboxylic acid ethyl ester

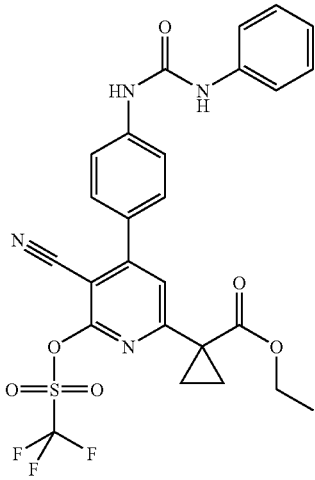

In analogy to GP 4a (step 1), reaction of 890 mg Intermediate 3.5 (1.95 mmol, 1 eq.) with 0.25 mL isocyanatobenzene (2.35 mmol, 1.2 eq.) in 15 mL DCM yielded 820 mg of the urea (1.43 mmol, 73% yield), which was used without further purification.

$^1$H-NMR (d$_6$-DMSO; 300 MHz): 9.08 (s, 1H); 8.83 (s, 1H); 8.14 (s, 1H); 7.72 (m, 4 H); 7.48 (d, 2H); 7.30 (m, 2H); 7.00 (m, 1H); 4.15 (q, 2H); 1.71 (m, 2H); 1.60 (m, 2H); 1.18 (t, 3H).

MS (ESI): [M+H]$^+$=575 (100%).

Intermediate 4.5

Preparation of 1-(5-Cyano-6-trifluoromethanesulfonyloxy-4-{4-[3-(3-trifluoromethyl-phenyl)-ureido]-phenyl}-pyridin-2-yl)-cyclopropanecarboxylic acid ethyl ester

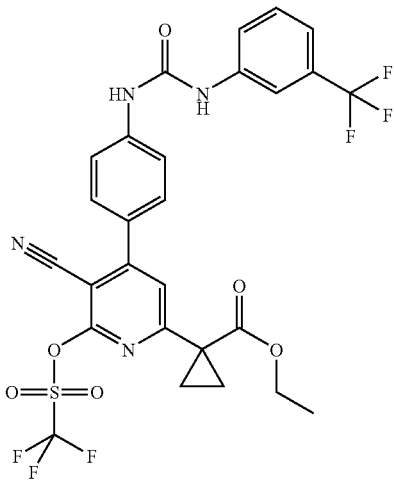

In analogy to GP 4a (step 1), reaction of 3.3 g Intermediate 3.5 (7.25 mmol, 1 eq.) with 1.63 g 1-isocyanato-3-trifluoromethyl-benzene (8.7 mmol, 1.2 eq.) in 150 mL DCM yielded 3.78 g of the urea (5.9 mmol, 81% yield), after purification by flash column chromatography.

$^1$H-NMR (d$_6$-DMSO; 300 MHz): 9.22 (s, 1H); 9.21 (s, 1H); 8.15 (s, 1H); 8.04 (s, 1H); 7.73 (m, 4H); 7.60 (m, 1H); 7.54 (m, 1H); 7.34 (m, 1H); 4.15 (q, 2H); 1.71 (m, 2H); 1.60 (m, 2H); 1.18 (t, 3H).

Intermediate 4.6

Preparation of 1-(5-Cyano-4-{4-[3-(2-fluoro-5-methyl-phenyl)-ureido]-phenyl}-6-trifluoromethanesulfonyloxy-pyridin-2-yl)-cyclopropanecarboxylic acid ethyl ester

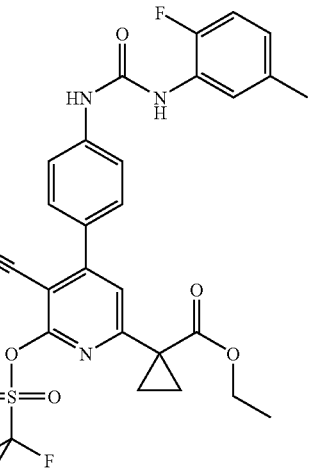

In analogy to GP 4a (step 1), reaction of 0.95 g Intermediate 3.5 (2.1 mmol, 1 eq.) with 0.38 g 2-fluoro-5-methyl-1-isocyanatobenzene (2.5 mmol, 1.2 eq.) in 25 mL DCM yielded 1.0 g of the urea (66% yield), which was used without further purification.

$^1$H-NMR (d$_6$-DMSO; 400 MHz): 9.45 (s, 1H); 8.64 (s, 1H); 8.15 (s, 1H); 7.99 (d, 1H); 7.76 (d, 2H); 7.70 (d, 2H); 7.13 (dd, 1H); 6.83 (m, 1H); 4.14 (q, 2H); 2.28 (s, 3H); 1.71 (m, 2H); 1.60 (m, 2H); 1.18 (t, 3H).

MS (ESI): [M+H]$^+$=607.

Intermediate 5.1

Preparation of 1-[4-(3-Amino-6-tert-butyl-1H-pyrazolo[3,4-b]pyridin-4-yl)-phenyl]-3-(3-trifluoromethyl-phenyl)-urea

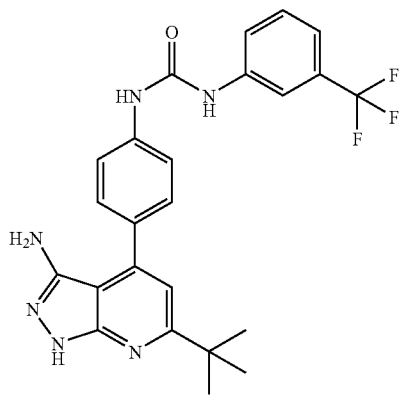

In analogy to GP 4c, reaction of Intermediate 3.1 (500 mg, 1.25 mmol, 1 eq.) with 1-isocyanato-3-trifluoromethyl-benzene (0.18 mL, 1.25 mmol, 1.1 eq.) in 4.5 mL DCM followed by treatment of the isolated crude urea with 180 μL 80% hydrazine hydrate (3.75 mmol, 3 eq.) in 15.6 mL 1-PrOH yielded 127 mg of the 1H-pyrazolopyridine (0.272 mmol, 22% yield over 2 steps).

$^1$H-NMR (d$_6$-DMSO; 400 MHz): 12.09 (s, 1H); 9.11 (s, 1H); 9.01 (s, 1H); 8.00 (s, 1H); 7.61 (d, 2H); 7.57 (d, 1H); 7.50 (m, 3H); 7.29 (d, 1H); 6.92 (s, 1H); 4.99 (s, 2H); 1.33 (s, 9H).
MS (ESI): [M+H]$^+$=469.

Intermediate 5.2

Preparation of 1-[4-(3-Amino-6-isopropyl-1H-pyrazolo[3,4-b]pyridin-4-yl)-phenyl]-3-(3-trifluoromethyl-phenyl)-urea

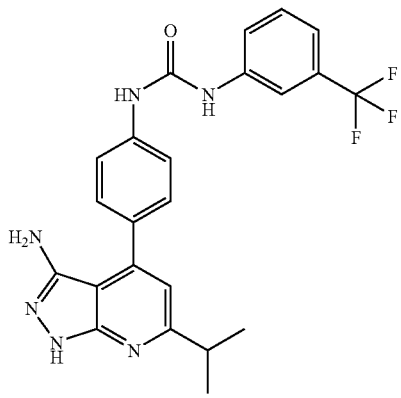

In analogy to GP 4c (step 2), reaction of Intermediate 4.2 (286.2 mg, 0.5 mmol) with 91 μl hydrazine hydrate (1.9 mmol, 3.8 eq.) in 7.5 mL 1-PrOH yielded 70 mg of the 1H-pyrazolopyridine (0.154 mmol, 31% yield).

$^1$H-NMR (d$_6$-DMSO; 400 MHz): 12.07 (br. s, 1H); 9.10 (s, 1H); 9.00 (s, 1H); 8.01 (s, 1H); 7.62 (d, 2H); 7.57 (d, 1H); 7.50 (d, 2H); 7.49 (t, 1H); 7.29 (d, 1H); 6.78 (s, 1H); 4.48 (br. s, 2H); 3.07 (sept, 1H); 1.25 (d, 6H).
MS (ESI): [M+H]$^+$=455.

Intermediate 5.3

Preparation of 1-[4-(3-Amino-6-methyl-1H-pyrazolo[3,4-b]pyridin-4-yl)-phenyl]-3-(3-trifluoromethyl-phenyl)-urea

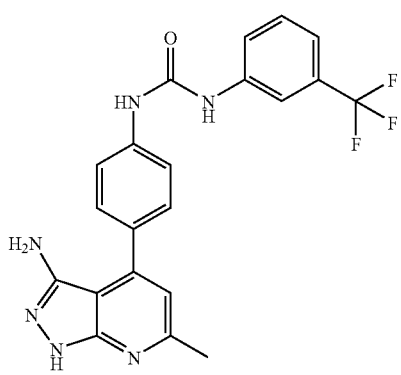

In analogy to GP 4c, reaction of Intermediate 3.3 (357 mg, 1 mmol, 1 eq.) with 1-isocyanato-3-trifluoromethyl-benzene (0.16 mL, 1.21 mmol, 1.2 eq.) in 10 mL DCM followed by treatment of the isolated crude urea with 150 μL 80% hydrazine hydrate (3 mmol, 3 eq.) in 15 mL 1-PrOH yielded 149 mg of the 1H-pyrazolopyridine (0.35 mmol, 35% yield over 2 steps).

$^1$H-NMR (d$_6$-DMSO; MHz): 12.02 (br. s, 1H); 9.18 (br. s, 1H); 9.12 (br. s, 1H); 8.01 (s, 1H); 7.62 (d, 2H); 7.57 (d, 1H); 7.49 (t, 1H); 7.50 (d, 2H); 7.29 (d, 1H); 6.76 (s, 1H); 4.48 (br. s, 2H); 2.49 (s, 3H).

Intermediate 5.4

Preparation of 1-{3-Amino-4-[4-(3-phenyl-ureido)-phenyl]-1H-pyrazolo[3,4-b]pyridin-6-yl}-cyclopropanecarboxylic acid ethyl ester

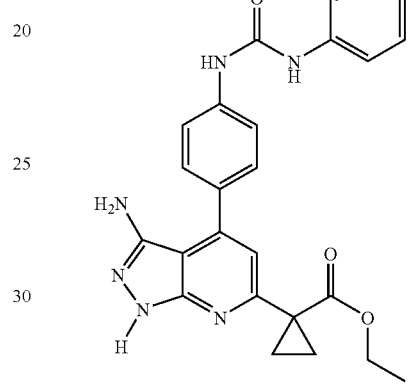

In analogy to GP 4c (step 2), reaction of Intermediate 4.4 (420 mg, 0.73 mmol, 1 eq.) with 110 μL 80% hydrazine hydrate (2.19 mmol, 3 eq.) in 20 mL 1-PrOH yielded 242 mg of the 1H-pyrazolopyridine (0.53 mmol, 72% yield).

$^1$H-NMR (d$_6$-DMSO; 300 MHz): 12.19 (br. s, 1H); 8.92 (br. s, 1H); 8.76 (br. s, 1H); 7.65 (d, 2H); 7.53 (m, 2H); 7.48 (m, 2H); 7.30 (m, 2H); 7.02 (s, 1H); 6.99.

Intermediate 5.5

Preparation of 1-[4-(3-Amino-1H-pyrazolo[3,4-b]pyridin-4-yl)-phenyl]-3-(3-trifluoromethyl-phenyl)-urea

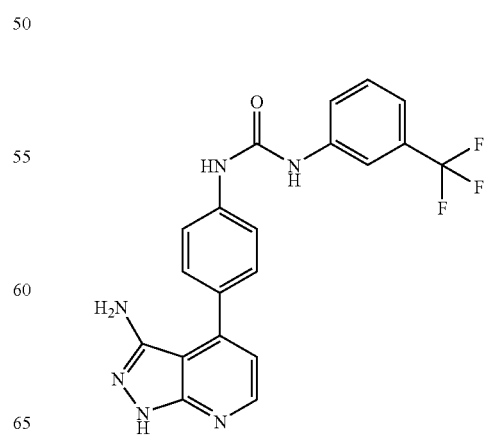

In analogy to GP 4c, reaction of Intermediate 3.6 (1 eq.) with 1-isocyanato-3-trifluoromethyl-benzene (1.1 eq.) in DCM (0.01 M) followed by treatment of the isolated crude urea with 80% hydrazine hydrate (3 eq.) in 1-PrOH (0.07 M) yielded the desired pyrazolopyridine which was further purified by preparative HPLC.

$^1$H-NMR (d$_6$-DMSO; 300 MHz): 9.20 (s, 1H); 9.12 (s, 1H); 8.37 (d, 1H); 8.01 (s, 1H); 7.65 (d, 2H); 7.58 (d, 1H); 7.53 (d, 2H); 7.49 (t, 1H); 7.29 (d, 1H); 6.91 (d, 1H) (TFA salt).

MS (ESI): [M+H]$^+$=413.

The following intermediates 5.6 to 5.45 were prepared in analogy to Intermediates 5.1 to 5.5 from the respective aniline intermediates and the respective isocyanates and subsequent cyclization with hydrazine hydrate by applying general procedure GP 4c.

| Intermediate | Structure | Name | Analytical data |
|---|---|---|---|
| 5.6 | 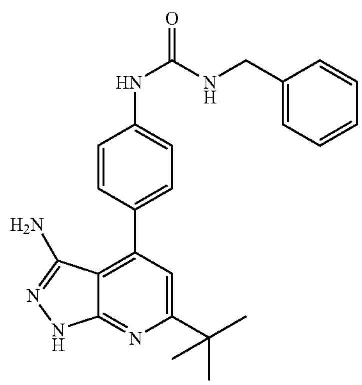 | 1-[4-(3-amino-6-tert-butyl-1H-pyrazolo[3,4-b]pyridin-4-yl)-phenyl]-3-benzyl-urea | $^1$H-NMR: (d6-DMSO, 300 MHz) 1.34 (9 H, s), 4.30 (2 H, d), 4.46 (2 H, s), 6.68 (1 H, t), 6.91 (1 H, s), 7.19-7.34 (5 H, m), 7.45 (2 H, d), 7.57 (2 H, d), 8.79 (1 H, s), 12.07 (1 H, s). |
| 5.7 | 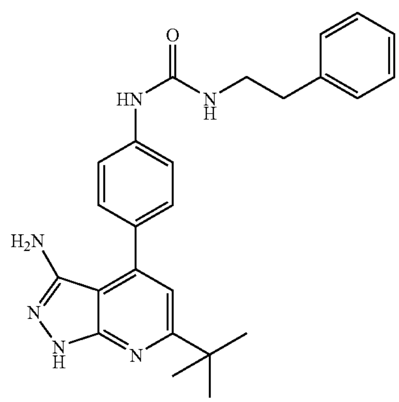 | 1-[4-(3-amino-6-tert-butyl-1H-pyrazolo[3,4-b]pyridin-4-yl)-phenyl]-3-phenethyl-urea | $^1$H-NMR: (d6-DMSO, 300 MHz) 1.38 (9 H, s), 2.78 (2 H, t), 3.38 (2 H, signal obscured by residual H$_2$O), 4.51 (2 H, s), 6.22 (1 H, t), 6.93 (1 H, s), 7.20-7.35 (5 H, m), 7.48 (2 H, d), 7.58 (2 H, d), 8.75 (1 H, s), 12.12 (1 H, s). |
| 5.8 | 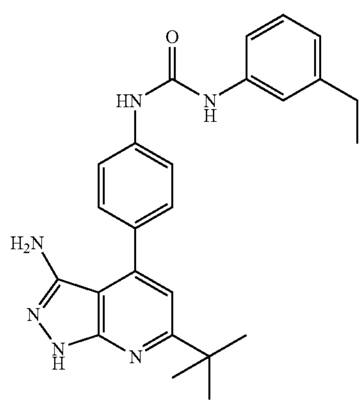 | 1-[4-(3-amino-6-tert-butyl-1H-pyrazolo-[3,4-b]pyridin-4-yl)-phenyl]-3-(3-ethyl-phenyl)-urea | $^1$H-NMR: (d6-DMSO, 300 MHz) 1.14 (3 H, t), 1.43 (9 H, s), 2.53 (2 H, q), 4.45 (2 H, s), 6.80 (1 H, d), 6.93 (1 H, s), 7.16 (1 H, t), 7.23 (1 H, dbr), 7.30 (1 H, sbr) 7.49 (2 H, d), 7.60 (2 H, d), 8.62 (1 H, s), 8.84 (1 H, s), 12.06 (1 H, s). |

-continued

| Intermediate | Structure | Name | Analytical data |
|---|---|---|---|
| 5.9 | 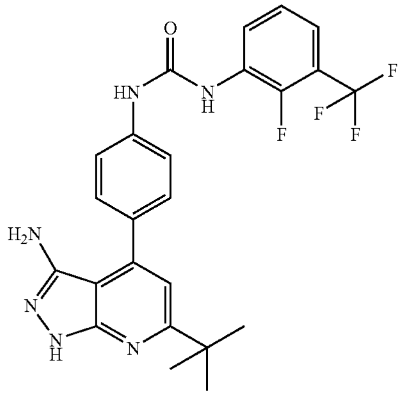 | 1-[4-(3-amino-6-tert-butyl-1H-pyrazolo[3,4-b]pyridin-4-yl)-phenyl]-3-(2-fluoro-3-trifluoromethyl-phenyl)-urea | ¹H-NMR: (d6-DMSO, 300 MHz) 1.35 (9 H, s), 4.50 (2 H, s), 6.93 (1 H, s), 7.30-7.39 (2 H, m), 7.53 (2 H, d), 7.63 (2 H, d), 8.39-8.49 (1 H, m), 8.87 (1 H, s), 9.33 (1 H, s), 12.10 (1 H, s). |
| 5.10 | 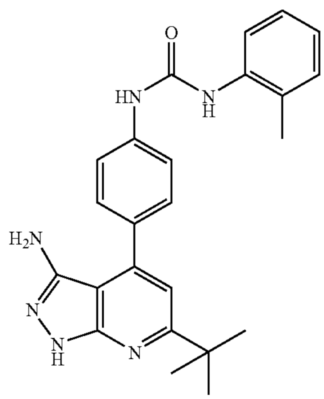 | 1-[4-(3-amino-6-tert-butyl-1H-pyrazolo-[3,4-b]pyridin-4-yl)-phenyl]-3-o-tolyl-urea | ¹H-NMR: (d6-DMSO, 400 MHz) 1.40 (9 H, s), 2.27 (3 H, s), 4.52 (2 H, s), 6.96 (2 H, m), 7.17 (2 H, m), 7.53 (2 H, d), 7.65 (2 H, d), 7.86 (1 H, d), 8.02 (1 H, s), 9.28 (1 H, s), 12.11 (1 H, s). |
| 5.11 | 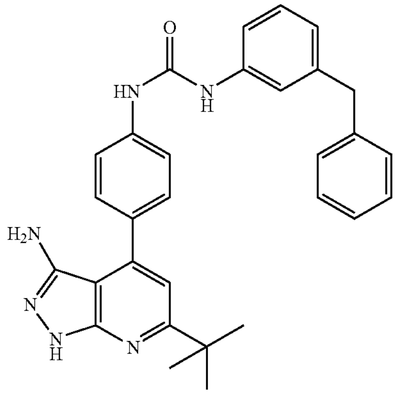 | 1-[4-(3-amino-6-tert-butyl-1H-pyrazolo-[3,4-b]pyridin-4-yl)-phenyl]-3-(3-benzyl-phenyl)-urea | ¹H-NMR: (d6-DMSO, 400 MHz) 1.38 (9 H, s), 3.91 (2 H, s), 4.50 (2 H, s), 6.86 (1 H, d), 6.96 (1 H, s), 7.20 (4 H, m), 7.30 (4 H, m), 7.52 (2 H, d), 7.61 (2 H, d), 8.75 (1 H, s), 8.90 (1 H, s), 12.11 (1 H, s). |

| Intermediate | Structure | Name | Analytical data |
|---|---|---|---|
| 5.12 | 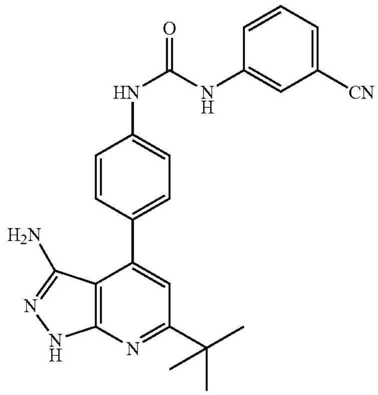 | 1-[4-(3-amino-6-tert-butyl-1H-pyrazolo-[3,4-b]pyridin-4-yl)-phenyl]-3-(3-cyano-phenyl)-urea | $^1$H-NMR: (d6-DMSO, 400 MHz) 1.32 (9 H, s), 4.48 (2 H, s), 6.91 (1 H, s), 7.40 (1 H, d), 7.47 (1 H, t), 7.51 (2 H, d), 7.61 (2 H, d), 7.96 (1 H, s), 9.05 (1 H, s), 9.08 (1 H, s), 12.10 (1 H, s). |
| 5.13 | 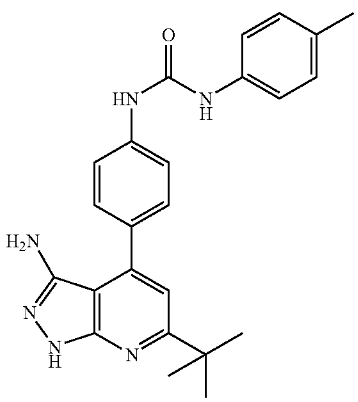 | 1-[4-(3-amino-6-tert-butyl-1H-pyrazolo-[3,4-b]pyridin-4-yl)-phenyl]-3-p-tolyl-urea | $^1$H-NMR: (d6-DMSO, 300 MHz) 1.35 (9 H, s), 2.22 (3 H, s), 4.47 (2 H, s), 6.91 (1 H, s), 7.05 (2 H, d), 7.30 (2 H, d), 7.48 (2 H, d), 7.60 (2 H, d), 8.59 (1 H, s), 8.81 (1 H, s), 12.07 (1 H, s). |
| 5.14 | 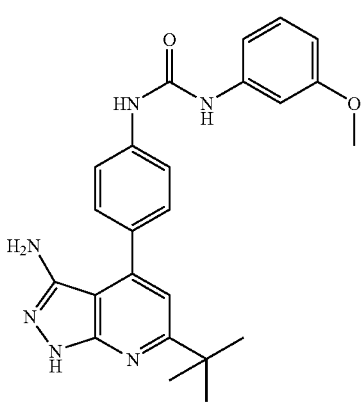 | 1-[4-(3-amino-6-tert-butyl-1H-pyrazolo-[3,4-b]pyridin-4-yl)-phenyl]-3-(3-methoxy-phenyl)-urea | $^1$H-NMR: (d6-DMSO, 300 MHz) 1.33 (9 H, s), 3.70 (3 H, s), 4.47 (2 H, s), 6.53 (1 H, dd), 6.92 (2 H, m), 7.15 (2 H, m), 7.49 (2 H, d), 7.60 (2 H, d), 8.74 (1 H, s), 8.89 (1 H, s), 12.08 (1 H, s). |

-continued

| Intermediate | Structure | Name | Analytical data |
|---|---|---|---|
| 5.15 | 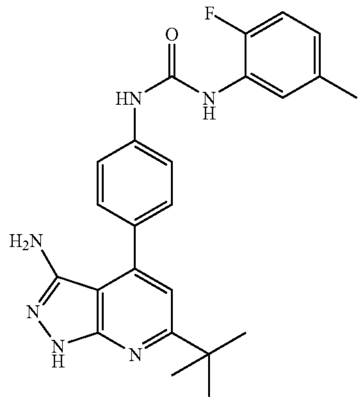 | 1-[4-(3-amino-6-tert-butyl-1H-pyrazolo[3,4-b]pyridin-4-yl)-phenyl]-3-(2-fluoro-5-methyl-phenyl)-urea | $^1$H-NMR: (d6-DMSO, 300 MHz) 12.09 (s, 1 H); 9.25 (s, 1 H); 8.52 (s, 1 H); 7.97 (d, 1 H); 7.61 (d, 2 H); 7.51 (d, 2 H); 7.08 (dd, 1 H); 6.93 (s, 1 H); 6.75-6.80 (m, 1 H); 4.48 (br. s, 2 H); 2.24 (s, 3 H); 1.34 (s, 9 H). |
| 5.16 | 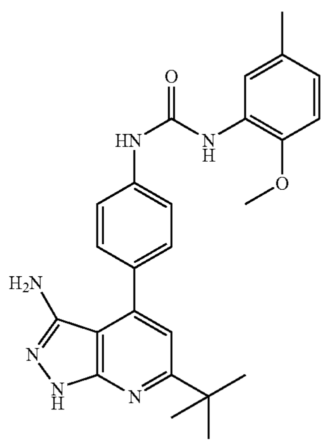 | 1-[4-(3-amino-6-tert-butyl-1H-pyrazolo-[3,4-b]pyridin-4-yl)-phenyl]-3-(2-methoxy-5-methyl-phenyl)-urea | $^1$H-NMR: (d6-DMSO, 300 MHz) 1.33 (9 H, s), 2.20 (3 H, s), 3.81 (3 H, s), 4.48 (2 H, s), 6.71 (1 H, dbr), 6.86 81 h, d), 6.91 (1 H, s), 7.50 (2 H, d), 7.60 (2 H, d), 7.98 (1 H, s), 8.20 (1 H, s), 9.49 (1 H, s), 12.08 (1 H, s). |
| 5.17 | 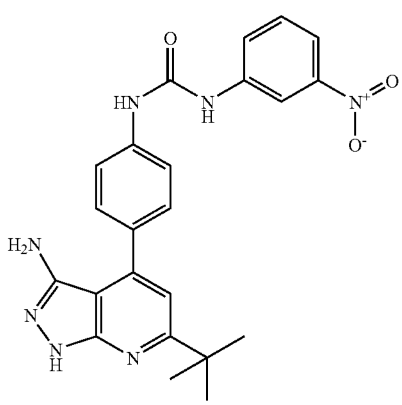 | 1-[4-(3-amino-6-tert-butyl-1H-pyrazolo-[3,4-b]pyridin-4-yl)-phenyl]-3-(3-nitro-phenyl)-urea | $^1$H-NMR: (d6-DMSO, 400 MHz) 1.36 (9 H, s), 4.49 (2 H, s), 6.91 (1 H, s), 7.53 (3 H, m), 7.63 (2 H, d), 7.70 (1 H, dbr), 7.80 (1 H, dbr), 8.54 (1 H, sbr), 9.07 (1 H, s), 9.28 (1 H, s), 12.09 (1 H, s). |

-continued

| Intermediate | Structure | Name | Analytical data |
|---|---|---|---|
| 5.18 | 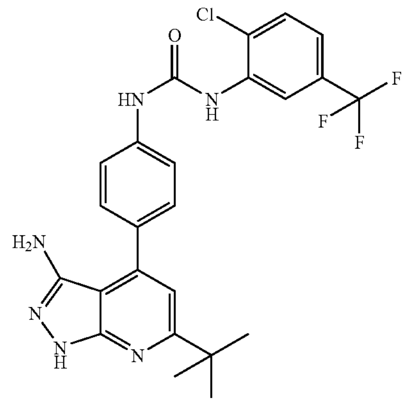 | 1-[4-(3-amino-6-tert-butyl-1H-pyrazolo[3,4-b]pyridin-4-yl)-phenyl]-3-(2-chloro-5-trifluoromethyl-phenyl)-urea | $^1$H-NMR: (d6-DMSO, 300 MHz) 1.33 (9 H, s), 4.49 (2 H, s), 6.93 (1 H, s), 7.37 (1 H, d), 7.53 (2 H, d), 7.63 (2 H, d), 7.70 (1 H, d), 8.62 (1 H, s), 8.67 (1 H, s), 9.76 (1 H, s), 12.10 (1 H, s). |
| 5.19 | 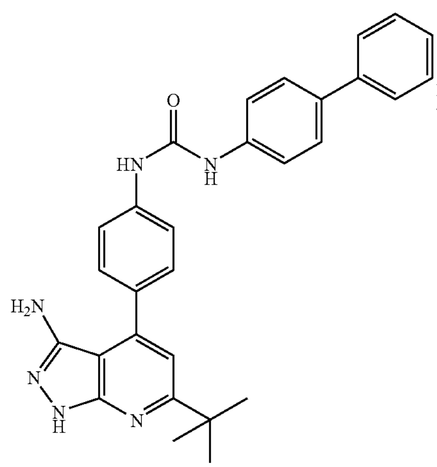 | 1-[4-(3-amino-6-tert-butyl-1H-pyrazolo-[3,4-b]pyridin-4-yl)-phenyl]-3-biphenyl-4-yl-urea | $^1$H-NMR: (d6-DMSO, 400 MHz) 1.32 (9 H, s), 4.49 (2 H, s), 6.91 (1 H, s), 7.27 (1 H, t), 7.40 (2 H, t), 7.48-7.67 (10 H, m), 8.83 (1 H, s), 8.92 (1 H, s), 12.08 (1 H, s). |
| 5.20 | 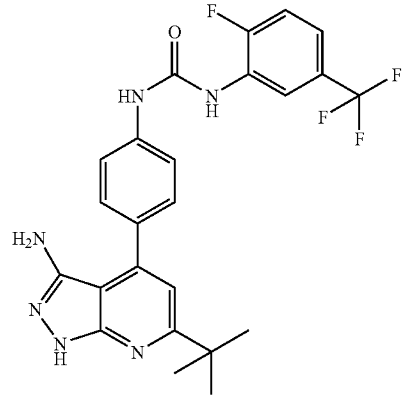 | 1-[4-(3-amino-6-tert-butyl-1H-pyrazolo[3,4-b]pyridin-4-yl)-phenyl]-3-(2-fluoro-5-trifluoromethyl-phenyl)-urea | $^1$H-NMR: (d6-DMSO, 300 MHz) 1.35 (9 H, s), 4.47 (2 H, s), 6.93 (1 H, s), 7.34-7.40 (1 H, m), 7.47 (1 H, d), 7.53 (2 H, d), 7.63 (2 H, d), 8.59-8.63 (1 H, m), 8.94 (1 H, s), 9.37 (1 H, s), 12.10 (1 H, s). |

-continued

| Intermediate | Structure | Name | Analytical data |
|---|---|---|---|
| 5.21 | 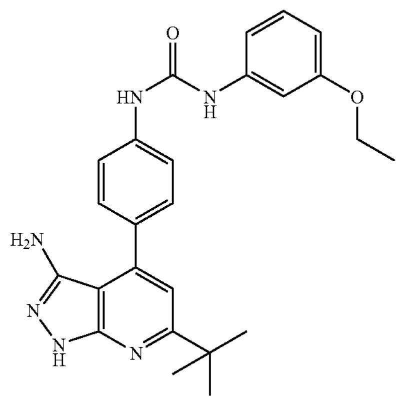 | 1-[4-(3-amino-6-tert-butyl-1H-pyrazolo-[3,4-b]pyridin-4-yl)-phenyl]-3-(3-ethoxy-phenyl)-urea | $^1$H-NMR: (d6-DMSO, 300 MHz) 1.29 (3 H, t), 1.34 (9 H, s), 3.97 (2 H, q), 4.47 (2 H, s), 6.50 (1 H, dbr), 6.90 (1 H, dbr), 6.92 (1 H, s), 7.14 (2 H, m), 7.49 (2 H, d), 7.61 (2 H, d), 8.71 (1 H, s), 8.88 (1 H, s), 12.06 (1 H, s). |
| 5.22 | 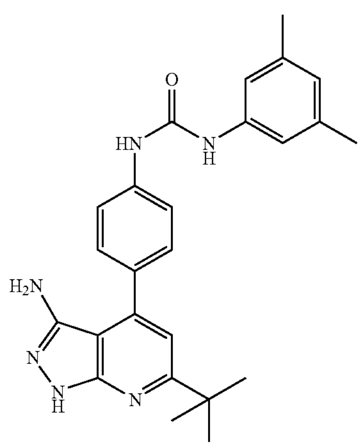 | 1-[4-(3-amino-6-tert-butyl-1H-pyrazolo-[3,4-b]pyridin-4-yl)-phenyl]-3-(3,5-dimethyl-phenyl)-urea | $^1$H-NMR: (d6-DMSO, 300 MHz) 1.34 (9 H, s), 2.20 (6 H, s), 4.47 (2 H, s), 6.59 (1 H, sbr), 6.91 (1 H, s), 7.05 (2 H, sbr), 7.48 (2 H, d), 7.60 (2 H, d), 8.52 (1 H, s), 8.81 (1 H, s), 12.06 (1 H, s). |
| 5.23 | 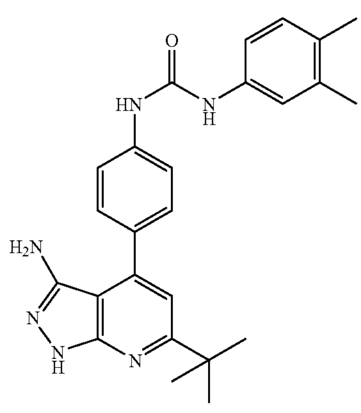 | 1-[4-(3-amino-6-tert-butyl-1H-pyrazolo-[3,4-b]pyridin-4-yl)-phenyl]-3-(3,4-dimethyl-phenyl)-urea | $^1$H-NMR: (d6-DMSO, 300 MHz) 1.33 (9 H, s), 2.11 (3 H, s), 2.15 (3 H, s), 4.48 (2 H, s), 6.90 (1 H, s), 7.00 (1 H, d), 7.14 (1 H, dbr), 7.22 (1 H, sbr), 7.48 (2 H, d), 7.59 (2 H, d), 8.50 (1 H, s), 8.80 (1 H, s), 12.04 (1 H, s). |

-continued

| Intermediate | Structure | Name | Analytical data |
|---|---|---|---|
| 5.24 | 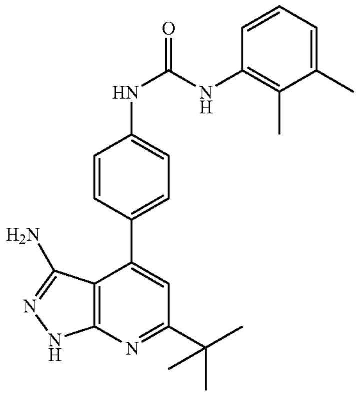 | 1-[4-(3-amino-6-tert-butyl-1H-pyrazolo-[3,4-b]pyridin-4-yl)-phenyl]-3-(2,3-dimethyl-phenyl)-urea | ¹H-NMR: (d6-DMSO, 400 MHz) 1.32 (9 H, s), 2.11 (3 H, s), 2.21 (3 H, s), 4.48 (2 H, s), 6.88 (1 H, d), 6.92 (1 H, s), 7.01 (1 H, t), 7.50 (3 H, m), 7.61 (2 H, d), 7.99 (1 H, s), 9.12 (1 H, s), 12.07 (1 H, s). |
| 5.25 | 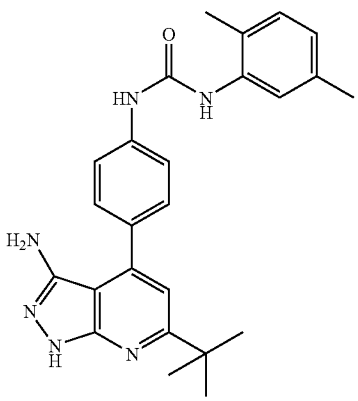 | 1-[4-(3-amino-6-tert-butyl-1H-pyrazolo-[3,4-b]pyridin-4-yl)-phenyl]-3-(2,5-dimethyl-phenyl)-urea | ¹H-NMR: (d6-DMSO, 300 MHz) 1.32 (9 H, s), 2.17 (3 H, s), 2.23 (3 H, s), 4.48 (2 H, s), 6.74 (1 H, dbr), 6.92 (1 H, s), 7.02 (1 H, d), 7.49 (2 H, d), 7.62 (3 H, m), 7.88 (1 H, s), 9.18 (1 H, s), 12.06 (1 H, s). |
| 5.26 | 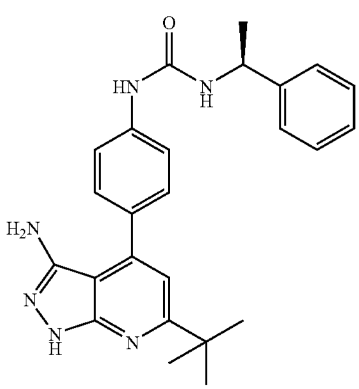 | 1-[4-(3-amino-6-tert-butyl-1H-pyrazolo[3,4-b]pyridin-4-yl)-phenyl]-3-((S)-1-phenyl-ethyl)-urea | $\alpha_D^{20}$ (c = 0.52 in DMF) = −43.4° ± 0.4° |
| 5.27 | 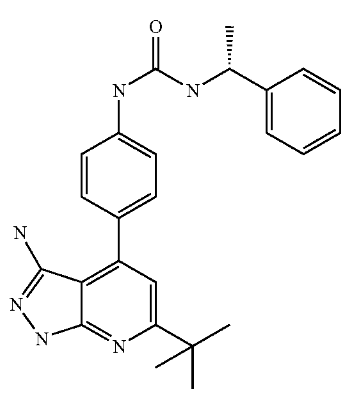 | 1-[4-(3-amino-6-tert-butyl-1H-pyrazolo[3,4-b]pyridin-4-yl)-phenyl]-3-((R)-1-phenyl-ethyl)-urea | $\alpha_D^{20}$ (c = 0.64 in DMF) = +39.9° ± 0.4° |

| Intermediate | Name | Analytical data |
|---|---|---|
| 5.28 | 1-[4-(3-amino-6-tert-butyl-1H-pyrazolo[3,4-b]pyridin-4-yl)-phenyl]-3-(4-cyano-phenyl)-urea | $^1$H-NMR: (d6-DMSO) 1.32 (s, 9 H); 4.48 (br. s, 2 H); 6.91 (s, 1 H); 7.51 (m, 2 H); 7.61 (m, 4 H); 7.70 (m, 2 H); 9.07 (s, 1 H); 9.24 (s, 1 H); 12.10 (s, 1 H). |
| 5.29 | 1-[4-(3-amino-6-tert-butyl-1H-pyrazolo[3,4-b]pyridin-4-yl)-phenyl]-3-(4-fluoro-phenyl)-urea | $^1$H-NMR: (d6-DMSO) 1.36 (s, 9 H); 4.46 (br. d, 2 H); 6.91 (s, 1 H); 7.10 (m, 2 H); 7.40-7.53 (m, 4 H); 7.60 (m, 2 H); 8.74 (s, 1 H); 8.86 (s, 1 H); 12.08 (s, 1 H). |
| 5.30 | 1-[4-(3-amino-6-tert-butyl-1H-pyrazolo[3,4-b]pyridin-4-yl)-phenyl]-3-(2,4-difluoro-phenyl)-urea | $^1$H-NMR: (d6-DMSO) 1.37 (s, 9 H); 4.50 (br.s, 2 H); 6.96 (s, 1 H); 7.07 (1 H); 7.32 (1 H); 7.55 (2 H); 7.63 (2 H); 8.10 (s, 1 H); 8.57 (s, 1 H); 9.22 (s, 1 H); 12.10 (s, 1 H). |

| Intermediate | Structure | Name | Analytical data |
|---|---|---|---|
| 5.31 | 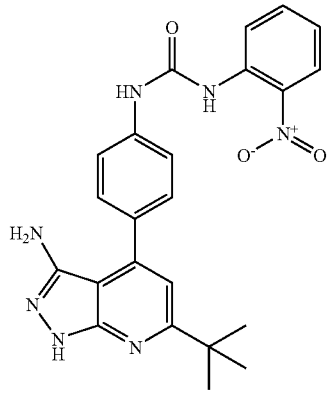 | 1-[4-(3-amino-6-tert-butyl-1H-pyrazolo[3,4-b]pyridin-4-yl)-phenyl]-3-(2-nitro-phenyl)-urea | $^1$H-NMR: (d6-DMSO) 1.38 (9 H); 4.50 (2 H); 6.97 (1 H); 7.22 (1 H); 7.56 (2 H); 7.66-7.78 (3 H); 8.11 (1 H); 8.31 (1 H); 9.65 (1 H); 10.06 (1 H); 12.10 (1 H). |
| 5.32 | 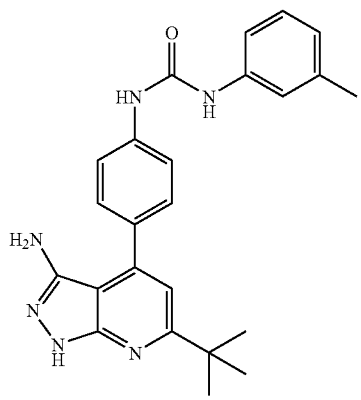 | 1-[4-(3-amino-6-tert-butyl-1H-pyrazolo[3,4-b]pyridin-4-yl)-phenyl]-3-m-tolyl-urea | $^1$H-NMR: d6-DMSO) 1.32 (9 H); 2.23 (3 H); 4.48 (2 H); 6.77 (1 H); 6.91 (1 H); 7.12 (1 H); 7.22 (1 H); 7.28 (1 H); 7.50 (2 H); 7.60 (2 H); 8.64 (1 H); 8.89 (1 H); 12.08 (1 H). |
| 5.33 | 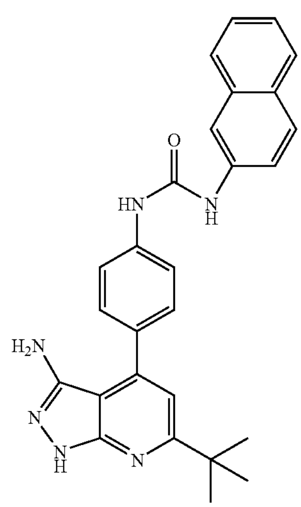 | 1-[4-(3-amino-6-tert-butyl-1H-pyrazolo[3,4-b]pyridin-4-yl)-phenyl]-3-naphthalen-2-yl-urea | $^1$H-NMR: (d6-DMSO) 1.40 (9 H); 4.52 (2 H); 6.98 (1 H); 7.38 (1 H); 7.48 (1 H); 7.56 (3 H); 7.70 (2 H); 7.78-7.90 (3 H); 8.13 (1 H); 9.00 (1 H); 9.05 (1 H); 12.12 (1 H). |

-continued

| Intermediate | Structure | Name | Analytical data |
|---|---|---|---|
| 5.34 | 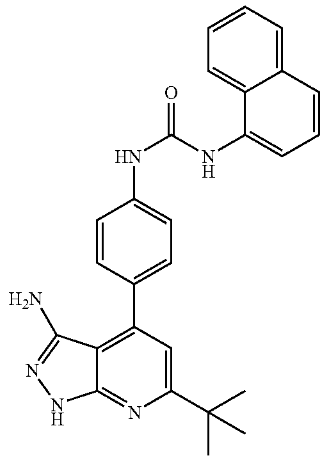 | 1-[4-(3-amino-6-tert-butyl-1H-pyrazolo[3,4-b]pyridin-4-yl)-phenyl]-3-naphthalen-1-yl-urea | $^1$H-NMR: (d6-DMSO) δ = 1.39 (9 H); 4.51 (2 H); 6.98 (1 H); 7.45-7.78 (8 H); 7.95 (1 H); 8.02 (1 H); 8.16 (1 H); 8.84 (1 H); 9.30 (1 H); 12.12 (1 H). |
| 5.35 | 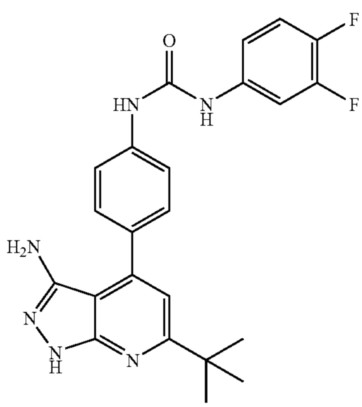 | 1-[4-(3-amino-6-tert-butyl-1H-pyrazolo[3,4-b]pyridin-4-yl)-phenyl]-3-(3,4-difluoro-phenyl)-urea | $^1$H-NMR: (d6-DMSO) 1.32 (9 H); 4.46 (2 H); 6.91 (1 H); 7.11 (1 H); 7.31 (1 H); 7.50 (2 H); 7.58-7.70 (3 H) 8.95 (2 H). |
| 5.36 | 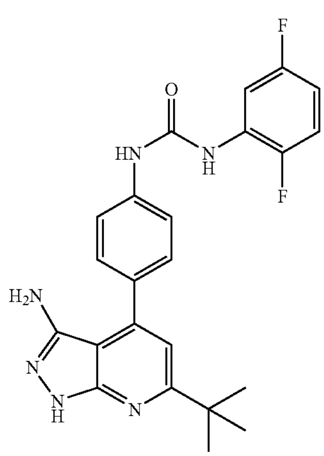 | 1-[4-(3-amino-6-tert-butyl-1H-pyrazolo[3,4-b]pyridin-4-yl)-phenyl]-3-(2,5-difluoro-phenyl)-urea | $^1$H-NMR: (d6-DMSO) 1.39 (9 H); 4.51 (2 H); 6.84 (1 H); 6.96 (1 H); 7.31 (1 H); 7.58 (2 H); 7.66 (2 H); 8.06 (1 H); 8.84 (1 H); 9.38 (1 H); 12.10 (1 H). |

| Intermediate | Structure | Name | Analytical data |
|---|---|---|---|
| 5.37 | 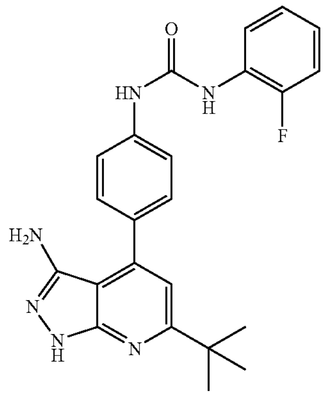 | 1-[4-(3-amino-6-tert-butyl-1H-pyrazolo[3,4-b]pyridin-4-yl)-phenyl]-3-(2-fluoro-phenyl)-urea | ¹H-NMR: (d6-DMSO) 1.38 (9 H); 4.50 (2 H); 6.95 (1 H); 7.04 (1 H); 7.16 (1 H); 7.26 (1 H); 7.55 (2 H); 7.66 (2 H); 8.18 (1 H); 8.62 (1 H); 9.31 (1 H); 12.10 (1 H). |
| 5.38 | 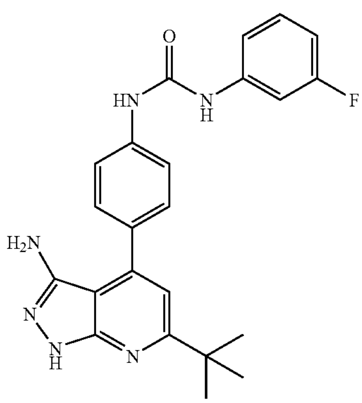 | 1-[4-(3-amino-6-tert-butyl-1H-pyrazolo[3,4-b]pyridin-4-yl)-phenyl]-3-(3-fluoro-phenyl)-urea | ¹H-NMR: (d6-DMSO) 1.38 (9 H); 4.50 (2 H); 6.79 (1 H); 6.96 (1 H); 7.15 (1 H); 7.31 (1 H); 7.49-7.60 (3 H); 7.65 (2 H); 8.98 (2 H); 12.11 (1 H). |
| 5.39 | 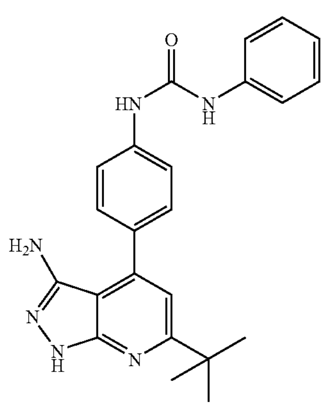 | 1-[4-(3-Amino-6-tert-butyl-1H-pyrazolo[3,4-b]pyridin-4-yl)-phenyl]-3-phenyl-urea | ¹H-NMR: (d6-DMSO) 1.39 (9 H); 4.52 (2 H); 6.93-7.03 (2 H); 7.29 (2 H); 7.44-7.58 (4 H); 7.65 (2 H); 8.81 (1 H); 8.99 (1 H); 12.12 (1 H). |

-continued

| Intermediate | Structure | Name | Analytical data |
|---|---|---|---|
| 5.40 | 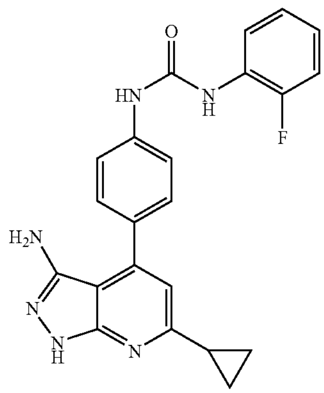 | 1-[4-(3-amino-6-cyclopropyl-1H-pyrazolo[3,4-b]pyridin-4-yl)-phenyl]-3-(2-fluoro-phenyl)-urea | $^1$H-NMR: d6-DMSO) 0.94 (4 H); 2.15 (1 H); 4.45 (2 H); 6.80 (1 H); 6.99 (1 H); 7.10 (1 H); 7.20 (1 H); 7.50 (2 H); 7.59 (2 H); 8.12 (1 H); 8.60 (1 H); 9.26 (1 H); 11.95 (1 H). |
| 5.41 | 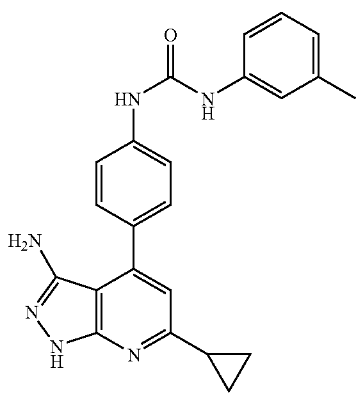 | 1-[4-(3-amino-6-cyclo-propyl-1H-pyrazolo-[3,4-b]pyridin-4-yl)-phenyl]-4-yl)-phenyl]-3-m-tolyl-urea | $^1$H-NMR: (d6-DMSO, 400 MHz) 0.96 (4 H, m), 2.15 (1 H, m), 2.25 (3 H, s), 4.46 (2 H, s), 6.77 (1 H, dbr), 6.81 (1 H, s), 7.12 (1 H, t), 7.20 (1 H, m), 7.26 (1 H, sbr), 7.48 (2 H, d), 7.60 (2 H, d), 8.61 (1 H, s), 8.83 (1 H, s), 11.96 (1 H, s). |
| 5.42 | 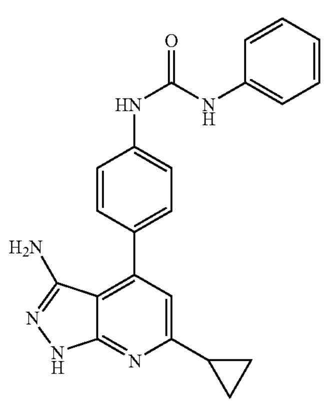 | 1-[4-(3-amino-6-cyclopropyl-1H-pyrazolo[3,4-b]pyridin-4-yl)-phenyl]-3-phenyl-urea | $^1$H-NMR: (d6-DMSO) 1.00 (4 H); 2.19 (1 H); 4.48 (2 H); 6.86 (1 H); 6.99 (1 H); 7.30 (2 H); 7.45-7.59 (4 H); 7.63 (2 H); 8.78 (1 H); 8.91 (1 H); 11.97 (1 H). |

-continued

| Intermediate | Structure | Name | Analytical data |
|---|---|---|---|
| 5.43 | 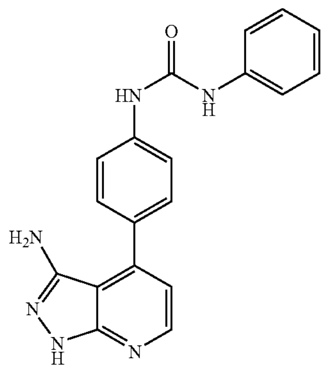 | 1-[4-(3-Amino-1H-pyrazolo[3,4-b]-pyridin-4-yl)-phenyl]-3-phenyl-urea | $^1$H-NMR: (d6-DMSO, 400 MHz) 12.24 (s, 1 H); 8.92 (s, 1 H); 8.76 (s, 1 H); 8.33 (d, 1 H); 7.62 (d, 2 H); 7.50 (d, 2 H); 7.45 (d, 2 H); 7.26 (t, 2 H); 6.95 (t, 1 H); 6.87 (d, 1 H); 4.52 (s, 2 H). MS (ESI): [M + H]$^+$ = 345. |
| 5.44 | 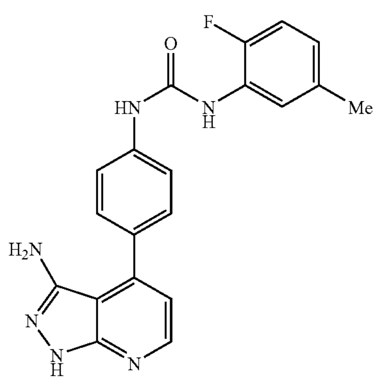 | 1-[4-(3-Amino-1H-pyrazolo[3,4-b]-pyridin-4-yl)-phenyl]-3-(2-fluoro-5-methyl-phenyl)-urea | $^1$H-NMR: (d6-DMSO, 400 MHz) 12.24 (s, 1 H); 9.29 (s, 1 H); 8.56 (s, 1 H); 8.33 (d, 1 H); 7.97 (dd, 1 H); 7.61 (d, 2 H); 7.51 (d, 2 H); 7.08 (dd, 1 H); 6.87 (dd, 1 H); 6.76-6.80 (m, 1 H); 4.57 (s, 2 H); 2.24 (s, 3 H). MS (ESI): [M + H]$^+$ = 377. |
| 5.45 | 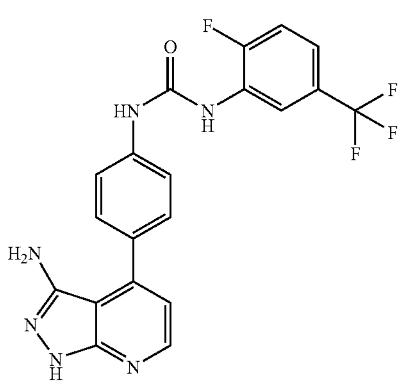 | 1-[4-(3-Amino-1H-pyrazolo[3,4-b]-pyridin-4-yl)-phenyl]-3-(2-fluoro-5-trifluoromethyl-phenyl)-urea | $^1$H-NMR: (d6-DMSO, 300 MHz) 12.25 (br. s, 1 H); 9.22 (br. s, 2 H); 8.60 (dd, 1 H); 8.33 (d, 1 H); 7.63 (d, 2 H); 7.52 (d, 2 H); 7.46 (d, 1 H); 7.33 7.39 (m, 1 H); 6.87 (d, 1 H); 4.57 (s, 2 H). MS (ESI): [M + H]$^+$ = 431. |

The following intermediates 6.1 to 6.4 were prepared from the respective anilines by applying general procedure GP 4d.

| Intermediate | Structure | Name | Analytical data |
|---|---|---|---|
| 6.1 | 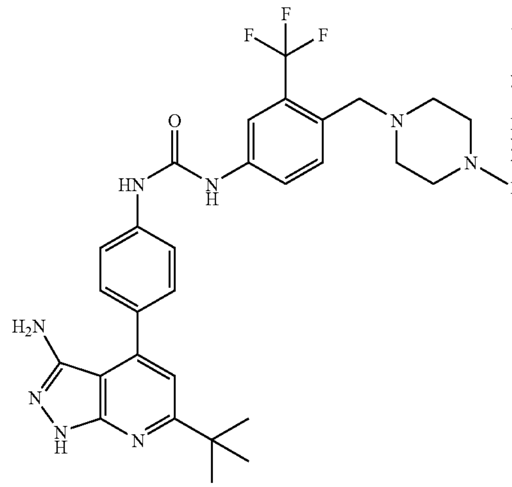 | 1-[4-(3-Amino-6-tert-butyl-1H-pyrazolo[3,4-b]pyridin-4-yl)-phenyl]-3-[4-(4-methyl-piperazin-1-ylmethyl)-3-trifluoromethyl-phenyl]-urea | $^1$H-NMR: (d6-DMSO, 300 MHz) 12.09 (s, 1 H); 9.07 (s, 1 H); 8.99 (s, 1 H); 7.95 (s, 1 H); 7.56-7.63 (m, 4 H); 7.50 (d, 2 H); 6.93 (s, 1 H); 4.46 (D, 2 H); 3.49 (s, 2 H); 2.22-2.39 (m, 8 H); 2.11 (s, 3 H); 1.34 (s, 9 H). MS (ESI): [M + H]$^+$ = 581. |
| 6.2 | 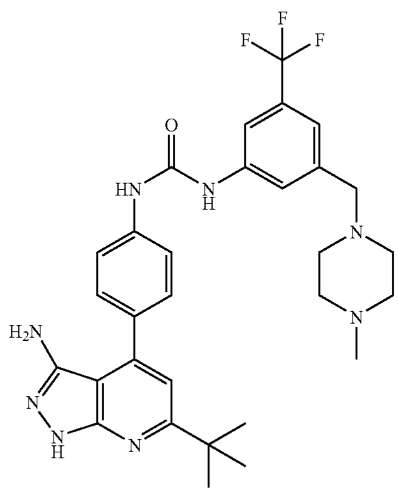 | 1-[4-(3-Amino-6-tert-butyl-1H-pyrazolo[3,4-b]pyridin-4-yl)-phenyl]-3-[3-(4-methyl-piperazin-1-ylmethyl)-5-trifluoromethyl-phenyl]-urea | $^1$H-NMR: (d6-DMSO, 400 MHz) 12.10 (s, 1 H); 9.12 (s, 1 H); 8.97 (s, 1 H); 7.89 (s, 1 H); 7.62 (d, 2 H); 7.52 (s, 1 H); 7.51 (d, 2 H); 7.19 (s, 1 H); 6.93 (s, 1 H); 4.47 (d, 2 H); 3.48 (s, 2 H); 2.23-2.40 (m, 8 H); 2.12 (s, 3 H); 1.34 (s, 9 H). MS (ESI): [M + H]$^+$ = 581. |
| 6.3 | 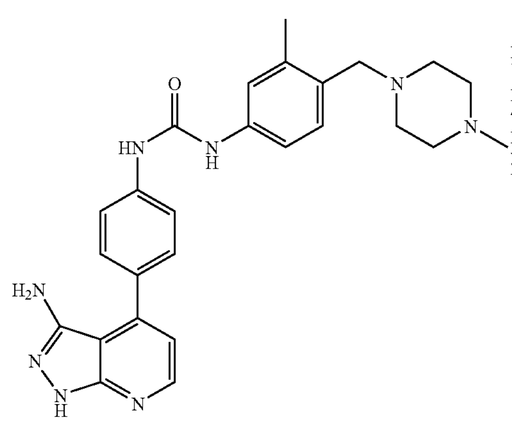 | 1-[4-(3-Amino-1H-pyrazolo[3,4-b]pyridin-4-yl)-phenyl]-3-[3-methyl-4-(4-methyl-piperazin-1-ylmethyl)-phenyl]-urea | MS (LC-MS-ESI): [M + H]$^+$ = 471 (89% purity). |

-continued

| Intermediate | Structure | Name | Analytical data |
|---|---|---|---|
| 6.4 | 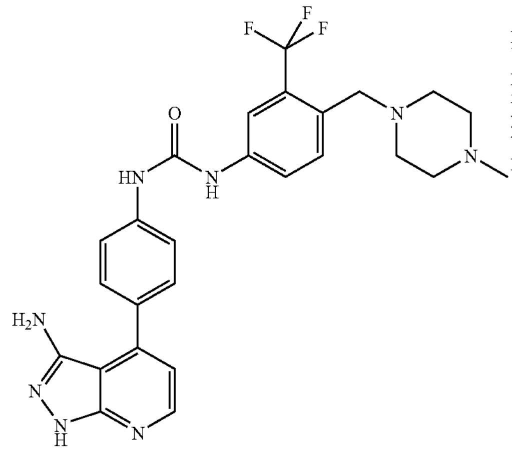 | 1-[4-(3-Amino-1H-pyrazolo[3,4-b]pyridin-4-yl)-phenyl]-3-[4-(4-methyl-piperazin-1-ylmethyl)-3-trifluoromethyl-phenyl]-urea | $^1$H-NMR: (d6-DMSO, 400 MHz) 12.24 (s, 1 H); 9.07 (s, 1 H); 8.99 (s, 1 H); 8.33 (d, 1 H); 7.96 (s, 1 H); 7.49-7.63 (m, 6 H); 6.86 (d, 1 H); 4.56 (s, 2 H); 3.50 (s, 2 H); 2.21-2.42 (m, 8 H); 2.13 (s, 3 H); MS (LC-MS-ESI): [M + H]$^+$ = 524. |

Intermediate 7.1

Preparation of 1-[4-(3-Amino-6-tert-butyl-1-methyl-1H-pyrazolo[3,4-b]pyridin-4-yl)-phenyl]-3-(3-trifluoromethyl-phenyl)-urea

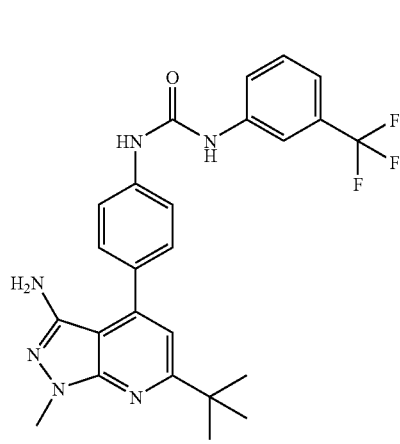

In analogy to GP 4a (step 2), reaction of Intermediate 4.1 (0.41 mmol) with 67 µl methyl hydrazine (1.26 mmol, 3 eq.) in 7 mL 1-PrOH yielded 25 mg of the pyrazolopyridine (0.052 mmol, 13% yield over 2 steps).

$^1$H-NMR (d$_6$-DMSO; 300 MHz): 9.10 (s, 1H); 9.02 (s, 1H); 8.00 (s, 1H); 7.50-7.64 (m, 6H); 7.30 (d, 1H); 6.93 (s, 1H); 4.59 (br. s, 2H); 3.78 (s, 3H); 1.37 (s, 9H).

MS (ESI): [M+H]$^+$=483.

Intermediate 7.2

Preparation of 1-{4-[3-Amino-6-tert-butyl-1-(2-hydroxy-ethyl)-1H-pyrazolo[3,4-b]pyridin-4-yl]-phenyl}-3-(3-trifluoromethyl-phenyl)-urea

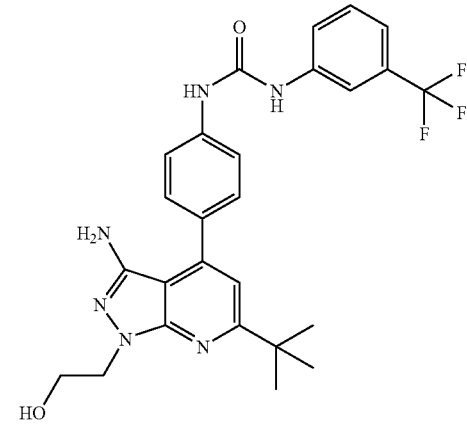

In analogy to GP 4a (step 2), reaction of Intermediate 4.1 (0.42 mmol) with 85 µl 2-hydrazino ethanol (1.26 mmol, 3 eq.) in 7 mL 1-PrOH yielded 39 mg of the pyrazolopyridine (0.076 mmol, 18% yield over 2 steps).

$^1$H-NMR (d$_6$-DMSO; 400 MHz): 9.42 (s, 1H); 9.32 (s, 1H); 8.01 (s, 1H); 7.65 (d, 2H); 7.59 (d, 1H); 7.47-7.52 (m, 3H); 7.29 (d, 1H); 6.93 (s, 1H); 4.83 (t, 1H); 4.60 (br.s, 2H); 4.24 (t, 2H); 3.73-3.80 (m, 2H); 1.36 (s, 9H).

MS (ESI): [M+H]$^+$=513.

Intermediate 7.3

Preparation of (3-Amino-6-tert-butyl-4-{4-[3-(3-trifluoromethyl-phenyl)-ureido]-phenyl}-pyrazolo[3,4-b]pyridin-1-yl)-acetic acid ethyl ester

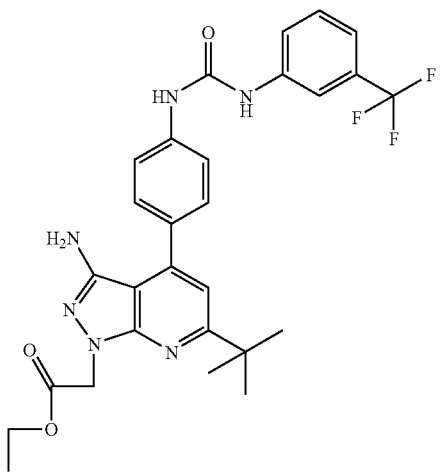

In a modification to GP 4a (step 2), Intermediate 4.1 (0.42 mmol) was dissolved in 7 mL 1-PrOH and treated with 195.8 mg hydrazino-acetic acid methyl ester hydrochloride (1.26 mmol, 3 eq.) and 0.17 mL Et$_3$N (1.26 mmol, 3 eq.) yielding after typical work-up and product isolation 26 mg of the pyrazolopyridine (0.047 mmol, 11% yield over 2 steps).

$^1$H-NMR (d$_6$-DMSO; 400 MHz): 9.11 (s, 1H); 9.04 (s, 1H); 8.01 (s, 1H); 7.46-7.64 (m, 6H); 7.29 (d, 1H); 7.00 (s, 1H); 4.98 (s, 2H); 4.70 (s, 2H); 4.10 (q, 2H); 1.33 (S, 9H); 1.15 (t, 3H).

MS (ESI): [M+H]$^+$=555.

Intermediate 7.4

Preparation of 1-[4-(3-Amino-6-isopropyl-1-methyl-1H-pyrazolo[3,4-b]pyridin-4-yl)-phenyl]-3-(3-trifluoromethyl-phenyl)-urea

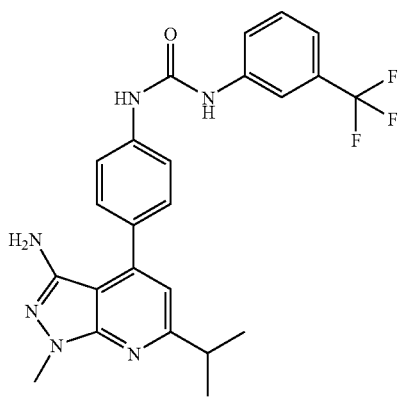

In analogy to GP 4a (step 2), reaction of Intermediate 4.2 (286.2 mg, 0.5 mmol) with 80 μl methyl hydrazine (1.5 mmol, 3 eq.) in 7.5 mL 1-PrOH yielded 183.1 mg of the pyrazolopyridine (0.39 mmol, 78% yield).

$^1$H-NMR (d$_6$-DMSO; 300 MHz): 9.10 (s, 1H); 9.01 (s, 1H); 8.01 (s, 1H); 7.62 (d, 2H); 7.57 (d, 1H); 7.51 (d, 2H); 7.49 (t, 1H); 7.29 (d, 1H); 6.79 (s, 1H); 4.58 (br. s, 2H) 3.76 (s, 3H); 3.08 (sept., 1H); 1.27 (d, 6H).

Intermediate 7.5

Preparation of 1-{4-[3-Amino-1-(2-hydroxy-ethyl)-6-isopropyl-1H-pyrazolo[3,4-b]pyridin-4-yl]-phenyl}-3-(3-trifluoromethyl-phenyl)-urea

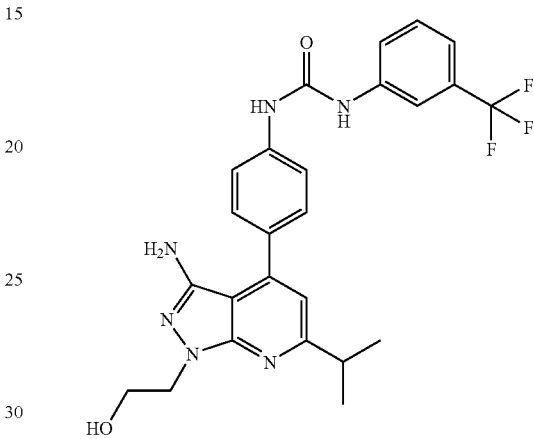

In analogy to GP 4a (step 2), reaction of Intermediate 4.2 (286.2 mg, 0.5 mmol) with 100 μl 2-hydrazino ethanol (1.5 mmol, 3 eq.) in 7.5 mL 1-PrOH yielded 82.4 mg of the pyrazolopyridine (0.17 mmol, 33% yield).

$^1$H-NMR (d$_6$-DMSO; 400 MHz): 9.10 (s, 1H); 9.01 (s, 1H); 8.01 (s, 1H); 7.63 (d, 2H); 7.57 (d, 1H); 7.50 (d, 2H); 7.49 (t, 1H); 7.29 (d, 1H); 6.79 (s, 1H); 4.83 (t, 1H); 4.39 (br. s, 2H); 4.22 (t, 2H); 3.75 (q, 2H); 3.07 (sept., 1H); 1.27 (d, 6H).

MS (ESI): [M+H]$^+$=499.

Intermediate 7.6

Preparation of 1-[4-(3-Amino-1,6-dimethyl-1H-pyrazolo[3,4-b]pyridin-4-yl)-phenyl]-3-(2-fluoro-5-trifluoromethyl-phenyl)-urea

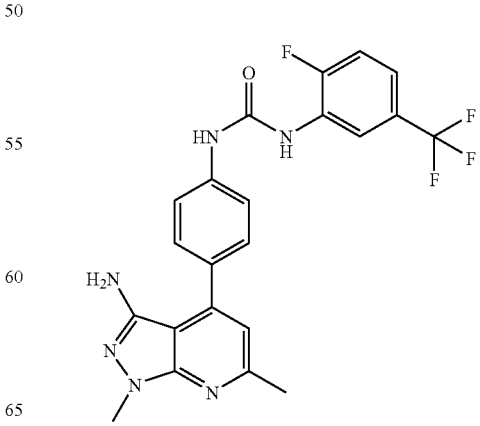

In analogy to GP 4a, reaction of Intermediate 3.3 (428.9 mg, 1.2 mmol) with 1-isocyanato-2-fluoro-5-trifluoromethyl-benzene (0.19 mL, 1.32 mmol, 1.1 eq.) in 12 mL DCM followed by treatment of one half of the so formed crude urea with 96 μL methylhydrazine (1.8 mmol, 3 eq.) in 9 mL 1-PrOH yielded 80 mg of the pyrazolopyridine (0.175 mmol, 29% yield).

$^1$H-NMR (d$_6$-DMSO; 400 MHz): 9.40 (d, 1H); 8.98 (s, 1H); 8.60 (d, 1H); 7.62 (d, 2H); 7.51 (d, 2H); 7.46-7.50 (m, 1H); 7.35-7.40 (m, 1H); 6.78 (s, 1H); 4.58 (br. s, 2H); 3.75 (s, 3H); 2.52 (s, 3H);

MS (ESI): [M+H]$^+$=459.

Intermediate 7.7

Preparation of 1-{3-Amino-1-methyl-4-[4-(3-phenyl-ureido)-phenyl]-1H-pyrazolo[3,4-b]pyridin-6-yl}-cyclopropanecarboxylic acid ethyl ester

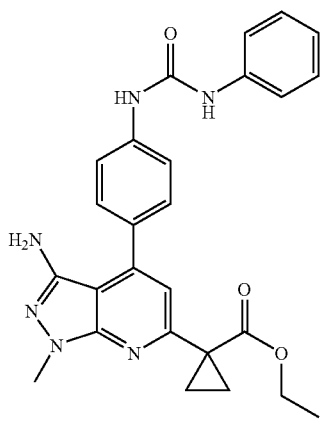

In analogy to GP 4a (step 2), reaction of 420 mg Intermediate 4.4 (0.73 mmol) with 120 μl methyl hydrazine (2.2 mmol, 3 eq.) in 20 mL 1-PrOH yielded 219 mg of the pyrazolopyridine (0.46 mmol, 64% yield).

$^1$H-NMR (d$_6$-DMSO; 300 MHz): 8.94 (br. s, 1H); 8.77 (br. s, 1H); 7.65 (d, 2H); 7.55 (m, 2H); 7.47 (m, 2H); 7.30 (m, 2H); 7.03 (s, 1H); 6.99 (m, 1H); 4.68 (br. s, 2H); 4.10 (q, 2H); 3.78 (s, 3H); 1.54 (s, 4H); 1.14 (t, 3H).

Intermediate 7.8

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethyl ester

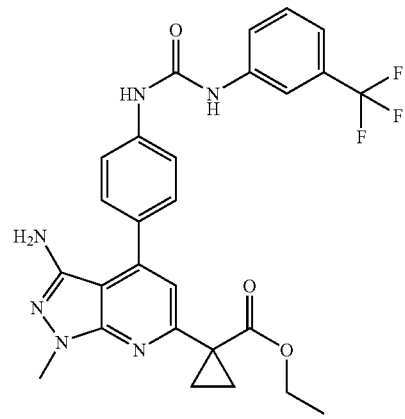

In analogy to GP 4a (step 2), reaction of 3.78 g Intermediate 4.5 (5.9 mmol) with 940 μl methyl hydrazine (17.7 mmol, 3 eq.) in 150 mL 1-PrOH yielded 2.5 g of the pyrazolopyridine (4.7 mmol, 79% yield).

$^1$H-NMR (d$_6$-DMSO; 400 MHz): 9.14 (br. s, 1H); 9.07 (br. s, 1H); 8.04 (s, 1H); 7.68 (d, 2H); 7.60 (m, 1H); 7.54 (m, 3H); 7.33 (m, 1H); 7.04 (s, 1H); 4.68 (br. s, 2H); 4.10 (q, 2H); 3.78 (s, 3H); 1.54 (s, 4H); 1.14 (t, 3H).

Intermediate 7.9

Preparation of 1-[4-(3-Amino-1-methyl-1H-pyrazolo[3,4-b]pyridin-4-yl)-phenyl]-3-(3-trifluoromethyl-phenyl)-urea

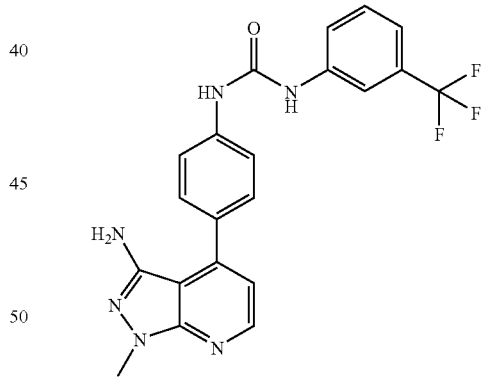

In analogy to GP 4a, reaction of Intermediate 3.6 (1.03 g, 3 mmol, 1 eq.) with 1-isocyanato-3-trifluoromethyl-benzene (0.44 mL, 3.3 mmol, 1.1 eq.) in 30 mL DCM yielded 1.4 g of the crude urea (88%). 663 mg of this crude urea were treated with 100 μL methylhydrazine (1.8 mmol, 3 eq.) in 21 mL 1-PrOH yielding 326 mg of the pyrazolopyridine (61% yield).

$^1$H-NMR (d$_6$-DMSO; 400 MHz): 9.11 (s, 1H); 9.02 (s, 1H); 8.37 (d, 1H); 8.01 (br. s, 1H); 7.63 (d, 2H); 7.57 (d, 1H); 7.48-7.52 (m, 3H); 7.29 (d, 1H); 6.89 (d, 1H); 4.67 (br. s, 2H); 3.79 (s, 3H).

MS (ESI): [M+H]$^+$=427.

The following intermediates 7.10 to 7.12 were prepared from the respective anilines by applying general procedure GP 4a.

| Intermediate | Structure | Name | Analytical data |
|---|---|---|---|
| 7.10 | 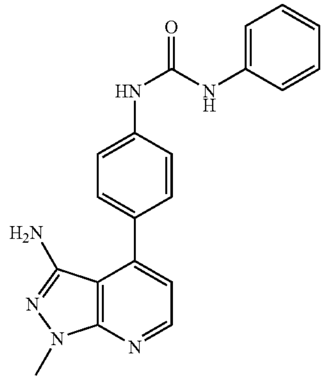 | 1-[4-(3-Amino-1-methyl-1H-pyrazolo[3,4-b]pyridin-4-yl)-phenyl]-3-phenyl-urea | $^1$H-NMR: (d6-DMSO, 300 MHz) 8.90 (s, 1 H), 8.74 (s, 1 H), 8.36 (d, 1 H); 7.62 (d, 2 H); 7.50 (d, 2 H); 7.44 (d, 2 H); 7.26 (t, 2 H); 6.94 (t, 1 H); 6.88 (d, 1 H); 4.67 (s, 2 H); 3.79 (s, 3 H). MS (ESI): [M + H]$^+$ = 359 |
| 7.11 | 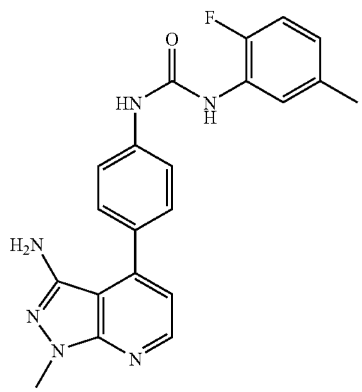 | 1-[4-(3-Amino-1-methyl-1H-pyrazolo[3,4-b]pyridin-4-yl)-phenyl]-3-(2-fluoro-5-methyl-phenyl)-urea | $^1$H-NMR: (d6-DMSO, 300 MHz) 9.27 (s, 1 H); 8.54 (d, 1 H); 8.37 (d, 1 H); 7.97 (dd, 1 H); 7.61 (d, 2 H); 7.51 (d, 2 H); 7.08 (dd, 1 H); 6.88 (d, 1 H); 6.76-6.80 (m, 1 H); 4.67 (s, 2 H); 3.79 (s, 3 H), 2.24 (s, 3 H). MS (ESI): [M + H]$^+$ = 391 |
| 7.12 | 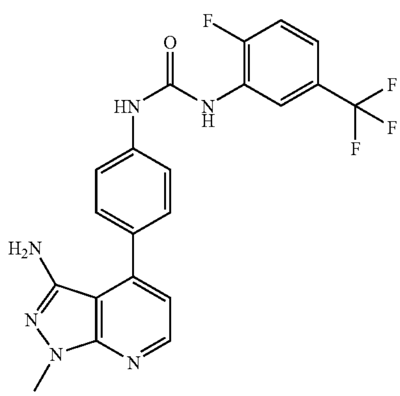 | 1-[4-(3-Amino-1-methyl-1H-pyrazolo[3,4-b]pyridin-4-yl)-phenyl]-3-(2-fluoro-5-trifluoromethyl-phenyl)-urea | $^1$H-NMR: (d6-DMSO, 300 MHz) 9.38 (s, 1 H); 8.95 (d, 1 H); 8.60 (dd, 1 H); 8.37 (d, 1 H); 7.63 (d, 2 H); 7.53 (d, 2 H); 7.46 (d, 1 H); 7.34-7.39 (m, 1 H); 6.89 (d, 1 H); 4.67 (s, 2 H); 3.79 (s, 3 H). MS (ESI): [M + H]$^+$ = 445. |

Intermediate 7.13

Preparation of 1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid ethyl ester

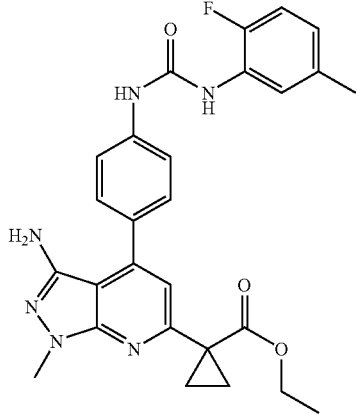

In analogy to GP 4a (step 2), reaction of 1 g Intermediate 4.6 (1.65 mmol) with 0.26 ml methyl hydrazine (4.95 mmol, 3 eq.) in 50 mL 1-PrOH yielded 0.7 g of the pyrazolopyridine (84% yield).

$^1$H-NMR (d$_6$-DMSO; 400 MHz): 9.30 (s, 1H); 8.57 (m, 1H); 8.00 (dd, 1H); 7.65 (d, 2H); 7.55 (d, 2H); 7.12 (dd, 1H); 7.04 (s, 1H); 6.82 (m, 1H); 4.68 (br. s, 2H); 4.10 (q, 2H); 3.78 (s, 3H); 2.28 (s, 3H); 1.54 (s, 4H); 1.14 (t, 3H).

Intermediate 8.1

Preparation of 1-[4-(3-Amino-6-tert-butyl-1-methyl-1H-pyrazolo[3,4-b]pyridin-4-yl)-phenyl]-3-(5-tert-butyl-isoxazol-3-yl)-urea

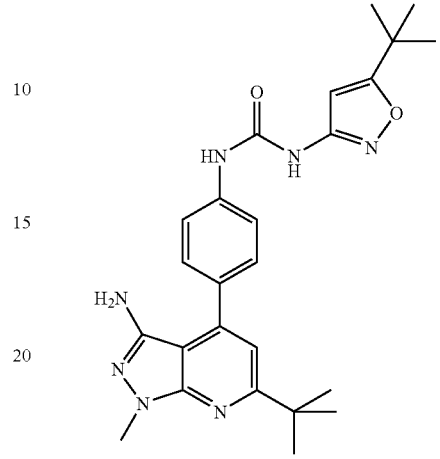

In analogy to GP 4b, 3-amino-5-tert-butylisoxazole (88.45 mg, 0.63 mmol, 1.23 eq.) was treated with triphosgene (59.44 mg, 0.2 mmol, 0.4 eq.) and Intermediate 3.1 (200 mg, 0.5 mmol, 1 eq.) in 10 mL acetonitril. The crude urea was subsequently cyclized with 48 μL methylhydrazine (0.91 mmol, 1.8 eq.) in 10 mL 1-PrOH to yield 80 mg of the N1-methyl-pyrazolopyridine (0.15 mmol, 30% yield over 2 steps).

$^1$H-NMR (d$_6$-DMSO; 400 MHz): 9.55 (br. s, 1H); 9.02 (br. s, 1H); 7.60 (d, 2H); 7.51 (d, 2H); 6.92 (s, 1H); 6.50 (s, 1H); 4.57 (br. s, 2H); 3.77 (s, 3H); 1.36 (s, 9H); 1.27 (s, 9H).

MS (ESI): [M+H]$^+$=462.

The following intermediates 8.2 to 8.16 were prepared from the respective anilines by applying general procedure GP 4b.

| Intermediate | Structure | Name | Analytical data |
|---|---|---|---|
| 8.2 | 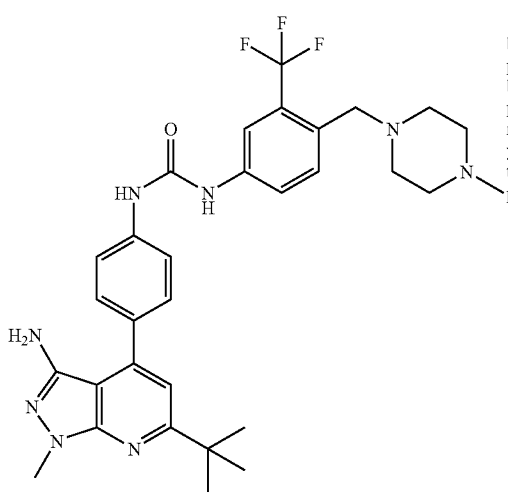 | 1-[4-(3-Amino-6-tert-butyl-1-methyl-1H-pyrazolo[3,4-b]pyridin-4-yl)-phenyl]-3-[4-(4-methyl-piperazin-1-yl-methyl)-3-trifluoromethyl-phenyl]-urea | $^1$H-NMR: (d6-DMSO, 300 MHz) 9.06 (s, 1 H); 8.99 (s, 1 H); 7.95 (d, 1 H); 7.49-7.63 (m, 6 H); 6.93 (s, 1 H); 4.58 (br. s, 2 H); 3.76 (s, 3 H); 3.49 (s, 2 H); 2.20-2.45 (m, 8 H); 2.12 (s, 3 H); 1.36 (s, 9 H). MS (ESI): [M + H]$^+$ = 595 |

| Intermediate | Structure | Name | Analytical data |
|---|---|---|---|
| 8.3 | 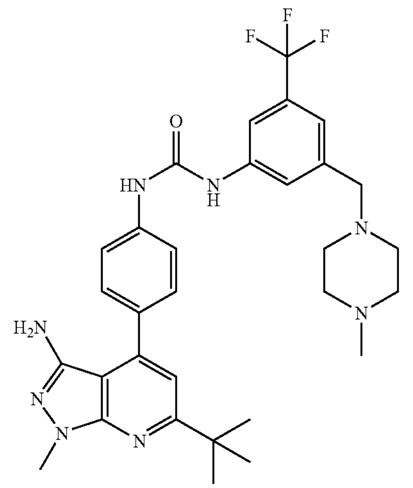 | 1-[4-(3-Amino-6-tert-butyl-1-methyl-1H-pyrazolo[3,4-b]pyridin-4-yl)-phenyl]-3-[3-(4-methyl-piperazin-1-yl-methyl)-5-trifluoromethyl-phenyl]-urea | $^1$H-NMR: (d6-DMSO, 40 MHz) 9.15 (s, 1 H); 9.00 (s, 1 H); 7.89 (s, 1 H); 7.50-7.65 (m, 5 H); 7.19 (s, 1 H); 6.93 (s, 1 H); 4.58 (br. s, 2 H); 3.76 (s, 3 H); 3.48 (s, 2 H); 2.20-2.45 (m, 8 H); 2.11 (s, 3 H); 1.37 (s, 9 H). MS (ESI): [M + H]$^+$ = 595. |
| 8.4 | 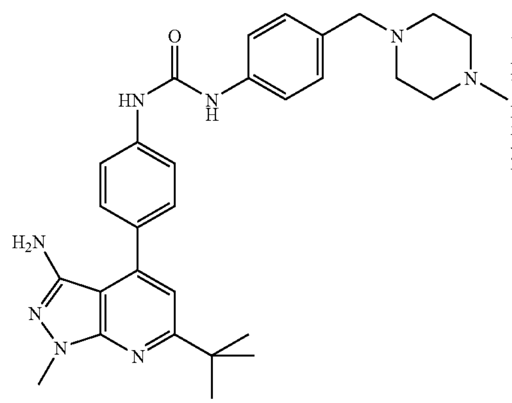 | 1-[4-(3-Amino-6-tert-butyl-1-methyl-1H-pyrazolo[3,4-b]pyridin-4-yl)-phenyl]-3-[4-(4-methyl-piperazin-1-ylmethyl)-phenyl]-urea | $^1$H-NMR: (CDCl$_3$, 300 MHz) 7.74 (br. s, 1 H); 7.57 (br. s, 1 H); 7.46-7.55 (m, 4 H); 7.22-7.34 (m, 4 H); 6.91 (s, 1 H); 3.93 (s, 3 H); 3.45 (s, 2 H); 2.39-2.56 (m, 8 H); 2.29 (s, 3 H); 1.41 (s, 9 H). |
| 8.5 | 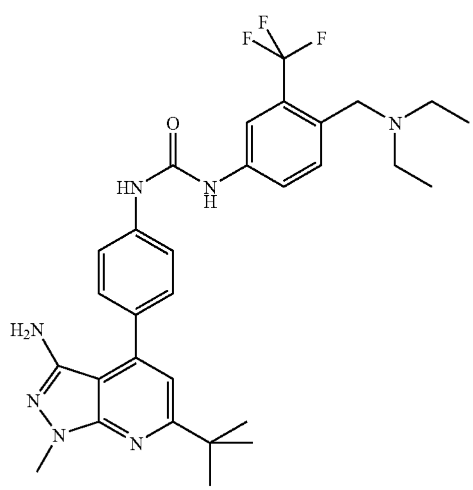 | 1-[4-(3-Amino-6-tert-butyl-1-methyl-1H-pyrazolo[3,4-b]pyridin-4-yl)-phenyl]-3-(4-diethylaminomethyl-3-trifluoromethyl-phenyl)-urea | $^1$H-NMR: (DMSO, 300 MHz) 9.04 (s, 1 H); 8.99 (s, 1 H); 7.94 (d, 1 H); 7.69 (d, 1 H); 7.62 (d, 2 H); 7.52-7.56 (m, 1 H); 7.50 (d, 2 H); 4,58 (br. s, 2 H); 3.77 (s, 3 H); 3.56 (s, 2 H); 2.44 (q, 4 H); 1.36 (s, 9 H); 0.93 (t, 6 H). |

| Intermediate | Structure | Name | Analytical data |
|---|---|---|---|
| 8.6 | 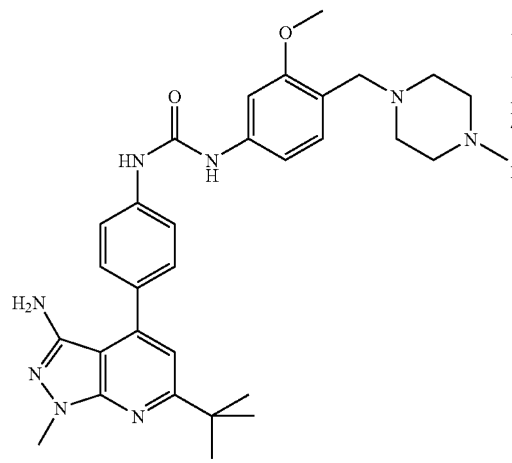 | 1-[4-(3-Amino-6-tert-butyl-1-methyl-1H-pyrazolo[3,4-b]pyridin-4-yl)-phenyl]-3-[3-methoxy-4-(4-methyl-piperazin-1-ylmethyl)-phenyl]-urea | $^1$H-NMR: (DMSO, 300 MHz) 8.88 (s, 1 H); 8.74 (s, 1 H); 7.61 (d, 2 H); 7.49 (d, 2 H); 7.23 (d, 1 H); 7.12 (d, 1 H); 6.92 (s, 1 H); 6.88 (dd, 1 H); 4.58 (br. s, 2 H); 3.75 (s, 3 H); 3.72 (s, 3 H); 3.35 (s, 2 H); 2.18-2.40 (m, 8 H); 2.10 (s, 3 H); 1.36 (s, 9 H). |
| 8.7 | 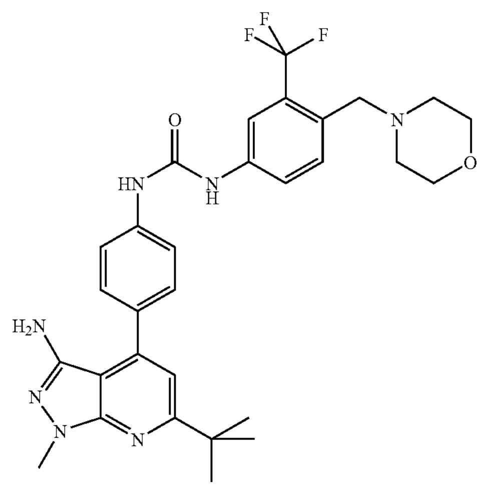 | 1-[4-(3-Amino-6-tert-butyl-1-methyl-1H-pyrazolo[3,4-b]pyridin-4-yl)-phenyl]-3-(4-morpholin-4-ylmethyl-3-trifluoromethyl-phenyl)-urea | $^1$H-NMR: (DMSO, 300 MHz) 9.06 (s, 1 H); 8.98 (s, 1 H); 7.96 (d, 1 H); 7.49-7.64 (m, 6 H); 6.93 (s, 1 H); 4.58 (br. s, 2 H); 3.77 (s, 3 H); 3.54-3.57 (m, 4 H); 3.51 (s, 2 H); 2.32-2.35 (m, 4 H); 1.36 (s, 9 H). MS (ESI): [M + H]$^+$ = 582. |
| 8.8 | 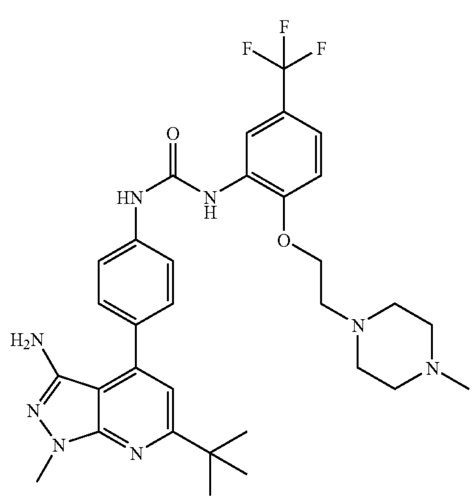 | 1-[4-(3-Amino-6-tert-butyl-1-methyl-1H-pyrazolo[3,4-b]pyridin-4-yl)-phenyl]-3-{2-[2-(4-methyl-piperazin-1-yl)-ethoxy]-5-trifluoromethyl-phenyl}-urea | $^1$H-NMR: (DMSO, 300 MHz) 9.71 (s, 1 H); 8.53 (s, 1 H); 8.35 (s, 1 H); 7.63 (d, 2 H); 7.51 (d, 2 H); 7.27 (dd, 1 H); 7.23 (d, 1 H); 6.93 (s, 1 H); 4.58 (s, 2 H); 4.27 (t, 2 H); 3.77 (s, 3 H); 2.77 (t, 2 H); 2.43-2.52 (m, 4 H); 2.19-2.32 (m, 4 H); 2.08 (s, 3 H); 1.36 (s, 9 H). MS (ESI): [M + H]$^+$ = 625. |

| Intermediate | Structure | Name | Analytical data |
|---|---|---|---|
| 8.9 | 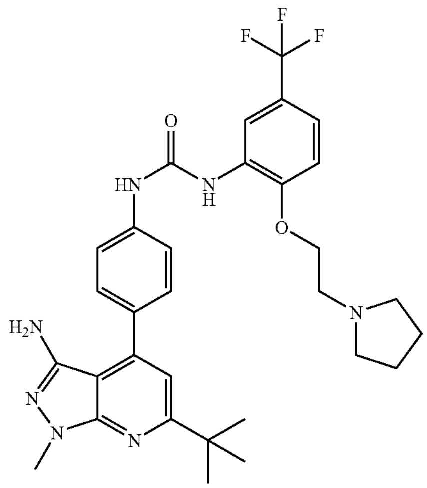 | 1-[4-(3-Amino-6-tert-butyl-1-methyl-1H-pyrazolo[3,4-b]pyridin-4-yl)-phenyl]-3-[2-(2-pyrrolidin-1-yl-ethoxy)-5-trifluoromethyl-phenyl]-urea | ¹H-NMR: (DMSO, 300 MHz) 9.73 (s, 1 H); 8.53 (s, 1 H); 8.38 (s, 1 H); 7.63 (d, 2 H); 7.52 (d, 2 H); 7.28 (dd, 1 H); 7.22 (d, 1 H); 6.93 (s, 1 H); 4.58 (br. s, 2 H); 4.27 (t, 2 H); 3.77 (s, 3 H); 2.88 (t, 2 H); 2.49-2.55 (m, 4 H); 1.64-1.68 (m, 4 H); 1.36 (s, 9 H). |
| 8.10 | 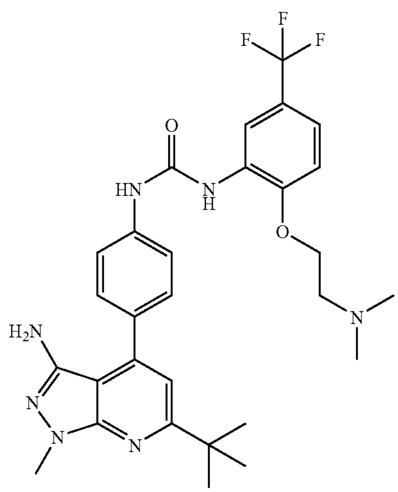 | 1-[4-(3-Amino-6-tert-butyl-1-methyl-1H-pyrazolo[3,4-b]pyridin-4-yl)-phenyl]-3-[2-(2-dimethylamino-ethoxy)-5-trifluoromethyl-phenyl]-urea | ¹H-NMR: (DMSO, 300 MHz) 10.53 (s, 1 H); 9.20 (s, 1 H); 8.62 (d, 1 H); 7.66 (d, 2 H); 7.51 (d, 2 H); 7.32 (dd, 1 H); 7.20 (d, 1 H); 6.93 (s, 1 H); 4.58 (s, 2 H); 4.44 (t, 2 H); 3.77 (s, 3 H); 3.60-3.61 (m, 2 H); 2.87 (s, 6 H); 1.36 (s, 9 H). MS (ESI): [M + H]⁺ = 570. |
| 8.11 | 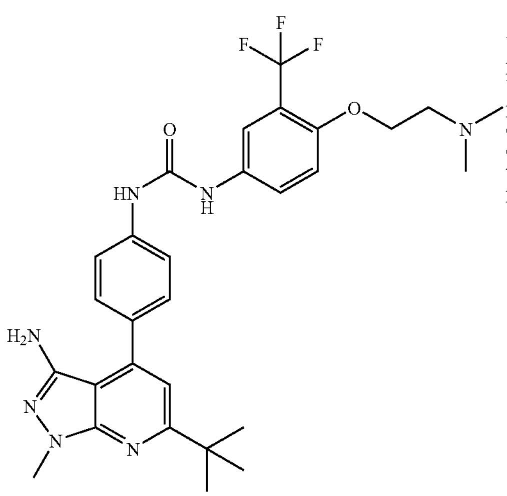 | 1-[4-(3-Amino-6-tert-butyl-1-methyl-1H-pyrazolo[3,4-b]pyridin-4-yl)-phenyl]-3-[4-(2-dimethylamino-ethoxy)-3-trifluoromethyl-phenyl]-urea | ¹H-NMR: (DMSO, 300 MHz) 8.92 (s, 1 H); 8.81 (s, 1 H); 7.82 (d, 1 H); 7.60 (d, 2 H); 7.54 (dd, 1 H); 7.49 (d, 2 H); 7.20 (d, 1 H); 6.93 (s, 1 H); 4.57 (s, 2 H); 4.11 (t, 2 H); 3.77 (s, 3 H); 2.60 (t, 2 H); 2.18 (s, 6 H); 1.36 (s, 9 H). MS (ESI): [M + H]⁺ = 570. |

| Intermediate | Structure | Name | Analytical data |
|---|---|---|---|
| 8.12 | 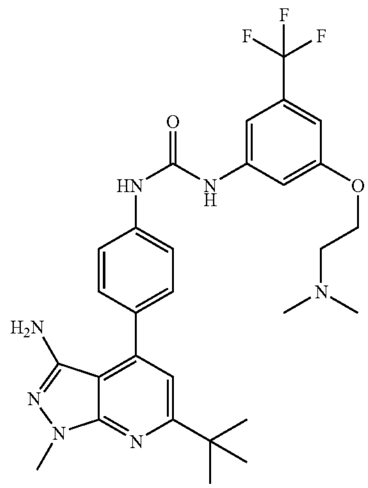 | 1-[4-(3-Amino-6-tert-butyl-1-methyl-1H-pyrazolo[3,4-b]pyridin-4-yl)-phenyl]-3-[3-(2-dimethylamino-ethoxy)-5-trifluoromethyl-phenyl]-urea | $^1$H-NMR: (DMSO, 400 MHz) 9.10 (s, 1 H); 9.06 (s, 1 H); 7.62 (d, 2 H); 7.51 (d, 2 H); 7.45 (s, 1 H); 7.27 (s, 1 H); 6.93 (s, 1 H); 6.84 (s, 1 H); 4.58 (s, 2 H); 4.08 (t, 2 H); 3.76 (s, 3 H); 2.60 (t, 2 H); 2.19 (s, 6 H); 1.36 (s, 9 H). MS (ESI): [M + H]$^+$ = 570. |
| 8.13 | 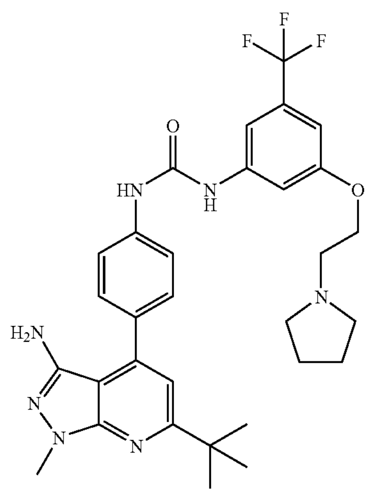 | 1-[4-(3-Amino-6-tert-butyl-1-methyl-1H-pyrazolo[3,4-b]pyridin-4-yl)-phenyl]-3-[3-(2-pyrrolidin-1-yl-ethoxy)-5-trifluoromethyl-phenyl]-urea | $^1$H-NMR: (DMSO, 400 MHz) 9.08 (s, 1 H); 9.04 (s, 1 H); 7.62 (d, 2 H); 7.51 (d, 2 H); 7.45 (s, 1 H); 7.27 (s, 1 H); 6.93 (s, 1 H); 6.84 (s, 1 H); 4.58 (s, 2 H); 4.10 (t, 2 H); 3.76 (s, 3 H); 2.76 (t, 2 H); 2.48-2.51 (m, 4 H); 1.64-1.67 (m, 4 H); 1.35 (s, 9 H). MS (ESI): [M + H]$^+$ = 596. |
| 8.14 | 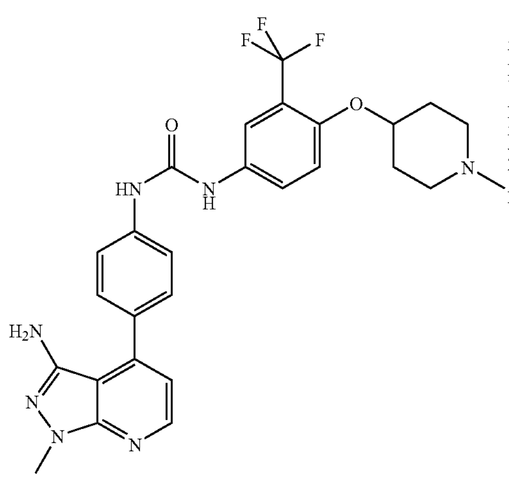 | 1-[4-(3-Amino-1-methyl-1H-pyrazolo[3,4-b]pyridin-4-yl)-phenyl]-3-[4-(1-methyl-piperidin-4-yloxy)-3-trifluoromethyl-phenyl]-urea | MS (ESI): [M + H]$^+$ = 540. |

| Intermediate | Structure | Name | Analytical data |
|---|---|---|---|
| 8.15 | 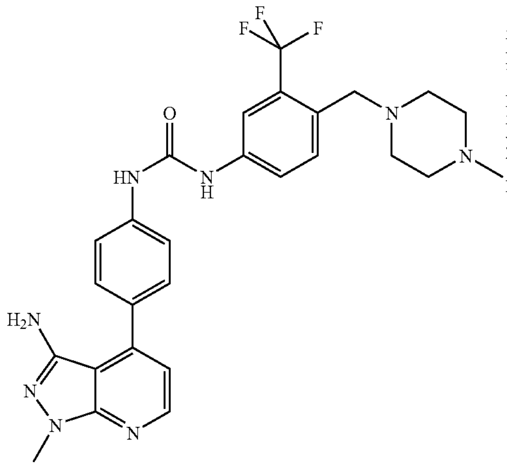 | 1-[4-(3-Amino-1-methyl-1H-pyrazolo[3,4-b]pyridin-4-yl)-phenyl]-3-[4-(4-methyl-piperazin-1-ylmethyl)-3-trifluoromethyl-phenyl]-urea | MS (ESI): $[M + H]^+ = 539$; $[M + 2H]^{++} = 270$. |
| 8.16 | 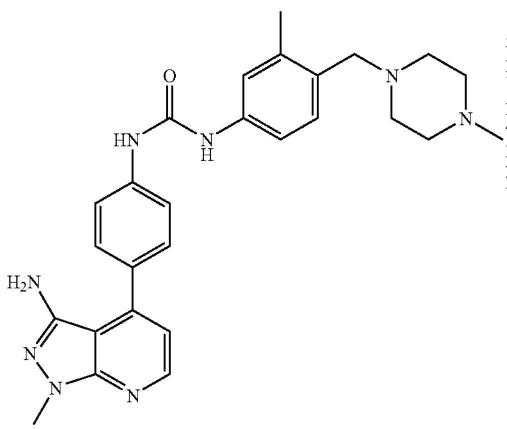 | 1-[4-(3-Amino-1-methyl-1H-pyrazolo[3,4-b]pyridin-4-yl)-phenyl]-3-[3-methyl-4-(4-methyl-piperazin-1-ylmethyl)-phenyl]-urea | MS (LC-MS-ESI): $[M + H]^+ = 485$ (93% purity); |

Intermediate 9.1

1-{4-[3-Amino-6-isopropyl-1-(2-morpholin-4-yl-ethyl)-1H-pyrazolo[3,4-b]pyridin-4-yl]-phenyl}-3-(3-trifluoromethyl-phenyl)-urea

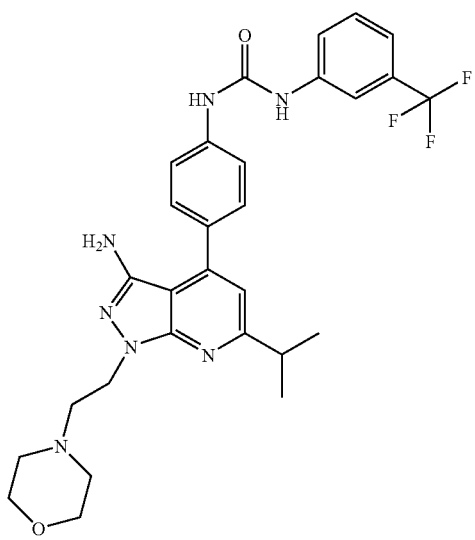

In analogy to GP 5, reaction of 1-[4-(3-Amino-6-isopropyl-1H-pyrazolo[3,4-b]pyridin-4-yl)-phenyl]-3-(3-trifluoromethyl-phenyl)-urea (136 mg, 0.3 mmol, 1 eq.) with 39.3 mg NaH, 167 mg 4-(2-Chloro-ethyl)-morpholine hydrochloride (0.9 mmol, 3 eq.), 0.12 mL triethylamine (0.9 mmol, 3 eq.) in 3+3 mL DMF yielded after HPLC purification 16.6 mg of the desired product (10% yield).

$^1$H-NMR (d$_6$-DMSO; 300 MHz): 9.15 (s, 1H); 9.06 (s, 1H); 8.05 (s, 1H); 7.67 (d, 2H); 7.62 (d, 1H); 7.52-7.58 (m, 3H); 7.34 (d, 1H); 6.83 (s, 1H); 4.65 (br. s, 2H); 4.35 (t, 2H); 3.48-3.51 (m, 4H); 3.12 (sept, 1H); 2.73 (t, 2H); 2.46-2.49 (m, 4H); 1.30 (d, 6H).

MS (ESI): [M+H]$^+$=568.

The following intermediates 9.2 to 9.7 were prepared from the 1H-pyrazolopyridines by applying general procedure GP 5 followed by preparative HPLC purification.

| Intermediate | Structure | Name | Analytical data |
|---|---|---|---|
| 9.2 | 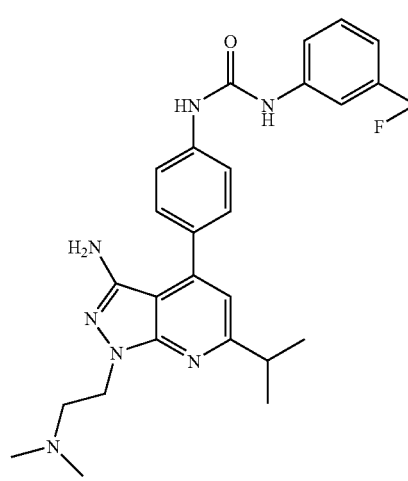 | 1-{4-[3-Amino-1-(2-dimethylamino-ethyl)-6-isopropyl-1H-pyrazolo[3,4-b]pyridin-4-yl]-phenyl}-3-(3-trifluoromethyl-phenyl)-urea | $^1$H-NMR: (d6-DMSO, 300 MHz) 9.15 (s, 1 H); 9.06 (s, 1 H); 8.01 (s, 1 H); 7.62 (d, 2 H); 7.57 (d, 1 H); 7.50 (d, 2 H); 7.49 (t, 1 H); 7.29 (d, 1 H); 6.78 (s, 1 H); 4.58 (s, 2 H); 4.27 (t, 2 H); 3.08 (sept., 1 H); 2.63 (t, 2 H); 2.14 (s, 6 H); 1.26 (d, 6 H). |
| 9.3 | 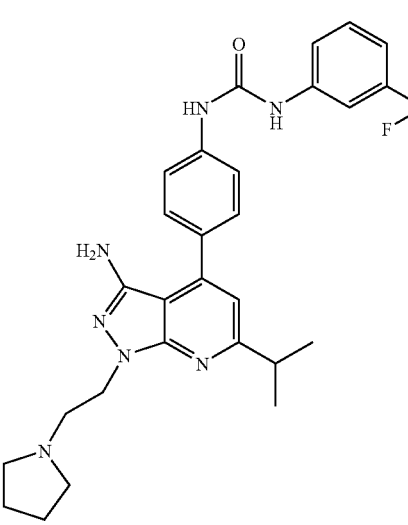 | 1-{4-[3-Amino-6-isopropyl-1-(2-pyrrolidin-1-yl-ethyl)-1H-pyrazolo[3,4-b]pyridin-4-yl]-phenyl}-3-(3-trifluoromethyl-phenyl)-urea | $^1$H-NMR: (d6-DMSO, 300 MHz) 9.16 (s, 1 H); 9.07 (s, 1 H); 8.01 (s, 1 H); 7.62 (d, 2 H); 7.57 (d, 1 H); 7.50 (d, 2 H); 7.49 (t, 1 H); 7.29 (d, 1 H); 6.78 (s, 1 H); 4.59 (s, 2 H); 4.29 (t, 2 H); 3.07 (sept. 1 H); 2.78 (t, 2 H); 2.47-2.50 (m, 4 H); 1.55-1.62 (m, 4 H); 1.26 (d, 6 H). |

| Inter-mediate | Structure | Name | Analytical data |
|---|---|---|---|
| 9.4 | 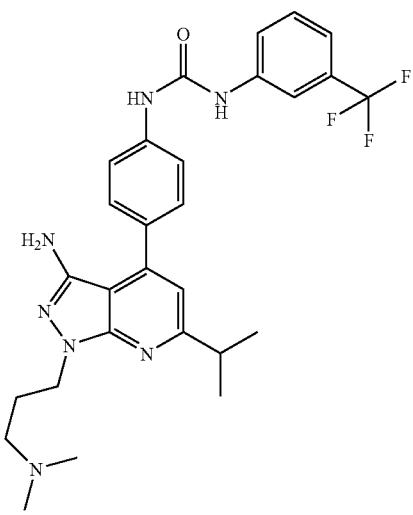 | 1-{4-[3-Amino-1-(3-dimethylamino-propyl)-6-isopropyl-1H-pyrazolo[3,4-b]pyridin-4-yl]-phenyl}-3-(3-trifluoromethyl-phenyl)-urea | $^1$H-NMR: (d6-DMSO, 300 MHz) 9.35 (br. s, 1 H); 9.27 (s, 1 H); 8.01 (s, 1 H); 7.63 (d, 2 H); 7.59 (d, 1 H); 7.50 (d, 2 H); 7.48 (t, 1 H); 7.28 (d, 1 H); 6.78 (s, 1 H); 4.58 (s, 2 H); 4.20 (t, 2 H); 3.07 (sept. 1 H); 2.19 (t, 2 H); 2.08 (s, 6 H); 1.85 (quint. 2 H); 1.26 (d, 6 H). |
| 9.5 | 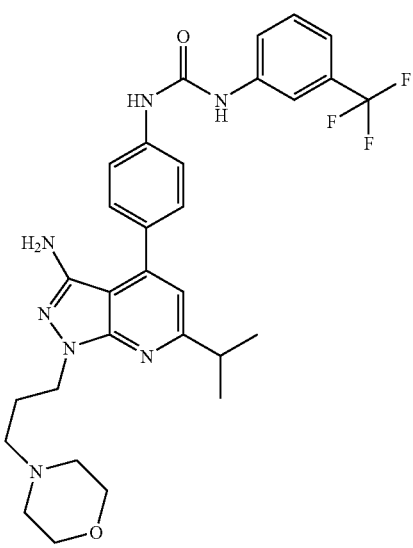 | 1-{4-[3-Amino-6-isopropyl-1-(3-morpholin-4-yl-propyl)-1H-pyrazolo[3,4-b]pyridin-4-yl]-phenyl}-3-(3-trifluoromethyl-phenyl)-urea | $^1$H-NMR: (d6-DMSO, 300 MHz) 9.44 (br, 2 H); 8.02 (s, 1 H); 7.63 (d, 2 H); 7.60 (d, 1 H); 7.49 (d, 2 H); 7.48 (t, 1 H); 7.27 (d, 1 H); 6.77 (s, 1 H); 4.58 (s, 2 H); 4.23 (t, 2 H); 3.48-4.52 (m, 4 H); 3.06 (sept. 1 H); 2.20-2.30 (m, 6 H); 1.88 (quint. 2 H); 1.26 (d, 6 H). |

| Intermediate | Structure | Name | Analytical data |
|---|---|---|---|
| 9.6 | 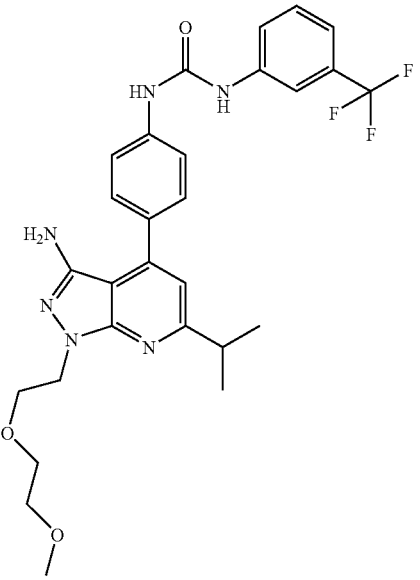 | 1-(4-{3-Amino-6-isopropyl-1-[2-(2-methoxy-ethoxy)-ethyl]-1H-pyrazolo[3,4-b]pyridin-4-yl}-phenyl)-3-(3-trifluoromethyl-phenyl)-urea | $^1$H-NMR: (d6-DMSO, 300 MHz) 9.10 (s, 1 H); 9.01 (s, 1 H); 8.00 (s, 1 H); 7.62 (d, 2 H); 7.57 (D, 1 H); 7.51 (d, 2 H); 7.49 (t, 1 H); 7.29 (d, 1 H); 6.79 (s, 1 H); 4.61 (s, 2 H); 4.32 (t, 2 H); 3.78 (t, 2 H); 3.50 (dd, 2 H); 3.31-3.36 (m, 2 H); 3.14 (s, 3 H); 3.07 (sept., 1 H); 1.26 (d, 6 H). |
| 9.7 | 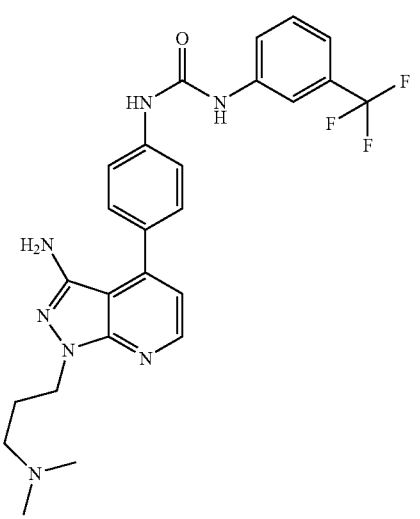 | 1-{4-[3-Amino-1-(3-dimethylamino-propyl)-1H-pyrazolo[3,4-b]pyridin-4-yl]-phenyl}-3-(3-trifluoromethyl-phenyl)-urea | $^1$H-NMR: (d6-DMSO, 400 MHz) 9.26-9.52 (br, 2 H); 8.36 (d, 1 H); 8.01 (s, 1 H); 7.64 (d, 2 H); 7.59 (d, 1 H); 7.50 (d, 2 H); 7.48 (t, 1 H); 7.28 (d, 1 H); 6.87 (d, 1 H); 4.67 (s, 2 H); 4.22 (t, 2 H); 2.18 (t, 2 H); 2.07 (s, 6 H); 1.87 (quint, 2 H). |

The following intermediates 10.1 to 10.15 were prepared by applying GP 7 or GP 8 using the respective aniline intermediates, the respective carboxylic acid chlorides or sulfonyl chlorides and subsequently hydrazine hydrate or substituted hydrazines.

| Intermediate | Structure | Name | Analytical data |
|---|---|---|---|
| 10.1 | 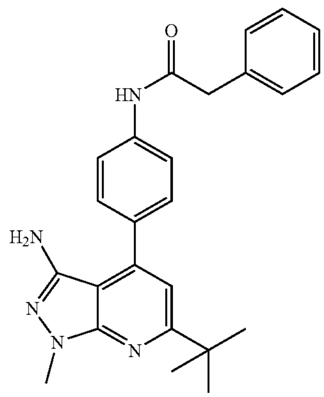 | N-[4-(3-Amino-6-tert-butyl-1-methyl-1H-pyrazolo[3,4-b]pyridin-4-yl)-phenyl]-2-phenyl-acetamide | $^1$H-NMR: (DMSO, 400 MHz) 10.36 (1 H, s); 7.75 (2 H, d); 7.51 (2 H, d); 7.28-7.33 (4 H, m); 7.20-7.24 (1 H, m); 6.91 (1 H, s); 4.53-4.55 (2 H, m); 3.76 (3 H, s); 3.65 (2 H, s); 1.35 (9 H, s). |
| 10.2 | 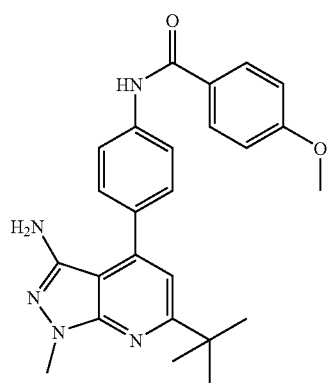 | N-[4-(3-Amino-6-tert-butyl-1-methyl-1H-pyrazolo[3,4-b]pyridin-4-yl)-phenyl]-4-methoxy-benzamide | $^1$H-NMR: (DMSO, 300 MHz) 10.26 (1 H, s); 7.93-7.97 (4 H, m); 7.55 (2 H, d); 7.05 (2 H, d); 6.96 (1 H, s); 4.55-4.57 (2 H, m); 3.82 (3 H, s); 3.77 (3 H, s); 1.37 (9 H, s). |
| 10.3 | 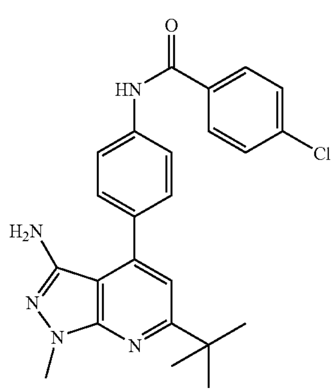 | N-[4-(3-Amino-6-tert-butyl-1-methyl-1H-pyrazolo[3,4-b]pyridin-4-yl)-phenyl]-4-chloro-benzamide | $^1$H-NMR: (DMSO, 300 MHz) 10.49 (1 H, s); 7.92-8.00 (4 H, m); 7.56-7.62 (4 H, m); 6.96 (1 H, s); 4.57 (2 H, br s); 3.77 (3 H, s); 1.37 (9 H, s). |

| Intermediate | Structure | Name | Analytical data |
|---|---|---|---|
| 10.4 | 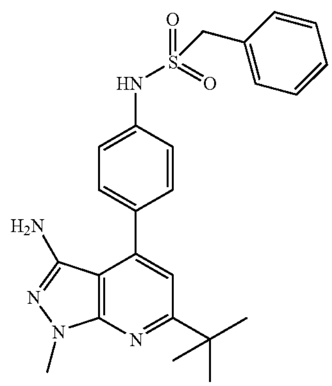 | N-[4-(3-Amino-6-tert-butyl-1-methyl-1H-pyrazolo[3,4-b]pyridin-4-yl)-phenyl]-C-phenyl-methanesulfonamide | ¹H-NMR: (DMSO, 400 MHz) 10.07 (1 H, s); 7.51 (2 H, s); 7.25-7.33 (7 H, s); 6.93 (1 H, s); 4.58-4.60 (2 H, m); 4.52 (2 H, s); 3.77 (3 H, s); 1.36 (9 H, s). |
| 10.5 | 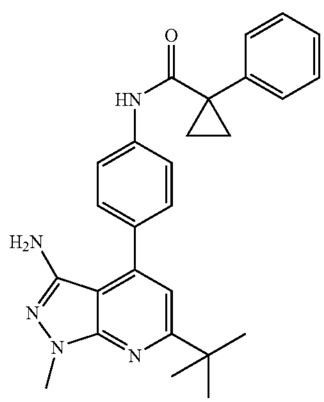 | 1-Phenyl-cyclopropanecarboxylic acid [4-(3-amino-6-tert-butyl-1-methyl-1H-pyrazolo[3,4-b]pyridin-4-yl)-phenyl]-amide | ¹H-NMR: (DMSO, 400 MHz) 9.31 (1 H, s); 7.72 (2 H, d); 7.47 (2 H, d); 7.24-7.39 (5 H, m); 6.90 (1 H, s); 4.53 (2 H, s); 3.76 (3 H, s); 1.42-1.45 (2 H, m); 1.35 (9 H, s); 1.10-1.13 (2 H, m). |
| 10.6 | 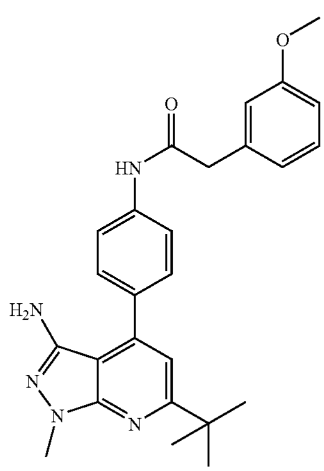 | N-[4-(3-Amino-6-tert-butyl-1-methyl-1H-pyrazolo[3,4-b]pyridin-4-yl)-phenyl]-2-(3-methoxy-phenyl)-acetamide | ¹H-NMR: (DMSO, 300 MHz) 10.33 (1 H, s); 7.74 (2 H, d); 7.51 (2 H, d); 7.19-7.24 (1 H, m); 6.88-6.92 (3 H, m); 6.78-6.81 (1 H, m); 4.55 (2 H, br s); 3.76 (3 H, s); 3.71 (3 H, s); 3.61 (2 H, s); 1.35 (9 H, s). |

-continued

| Intermediate | Structure | Name | Analytical data |
|---|---|---|---|
| 10.7 | 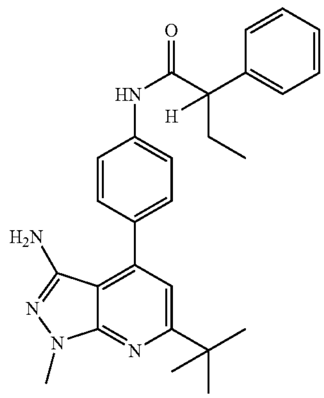 | N-[4-(3-Amino-6-tert-butyl-1-methyl-1H-pyrazolo[3,4-b]pyridin-4-yl)-phenyl]-2-phenyl-butyramide | $^1$H-NMR: (DMSO, 400 MHz) 10.27 (1 H, s); 7.75 (2 H, d); 7.49 (2 H, d); 7.37-7.39 (2 H, m); 7.28-7.32 (2 H, m); 7.19-7.23 (1 H, m); 6.90 (1 H, s); 4.54 (2 H, s); 3.75 (3 H, s); 3.56-3.60 (1 H, m); 1.99-2.10 (1 H, s); 1.63-1.74 (1 H, s); 1.34 (9 H, s); 0.85 (3 H, t). |
| 10.8 | 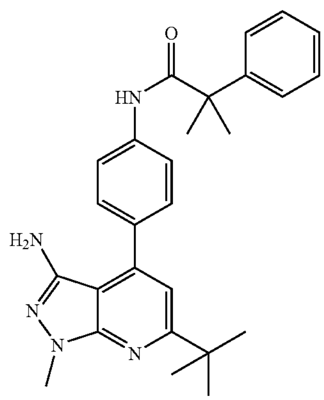 | N-[4-(3-Amino-6-tert-butyl-1-methyl-1H-pyrazolo[3,4-b]pyridin-4-yl)-phenyl]-2-phenyl-isobutyramide | $^1$H-NMR: (DMSO, 400 MHz) 9.28 (1 H, s); 7.78 (2 H, d); 7.48 (2 H, d); 7.31-7.36 (4 H, m); 7.20-7.24 (1 H, m); 6.90 (1 H, s); 4.54 (2 H, br s); 3.76 (3 H, s); 1.55 (6 H, s); 1.35 (9 H, s). |
| 10.9 | 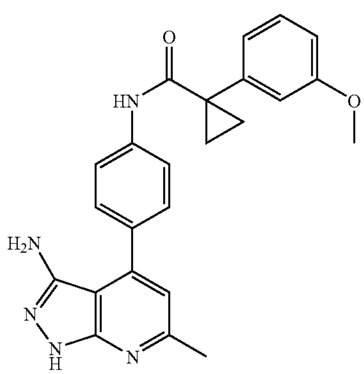 | 1-(3-Methoxy-phenyl)-cyclopropane-carboxylic acid [4-(3-amino-6-methyl-1H-pyrazolo[3,4-b]pyridin-4-yl)-phenyl]-amide | $^1$H-NMR: (DMSO, 400 MHz) 12.02 (s, 1 H); 9.21 (s, 1 H); 7.70 (d, 2 H); 7.45 (d, 2 H); 7.25 (t, 1 H); 6.97 (d, 1 H); 6.93 (t, 1 H); 6.84 (dd, 1 H); 6.73 (s, 1 H); 4.43 (s, 2 H); 3.73 (s, 3 H); 2.48 (s, 3 H); 1.40-1.43 (m, 2 H); 1.10-1.13 (m, 2 H).MS (ESI): [M + H]$^+$ = 414. |
| 10.10 | 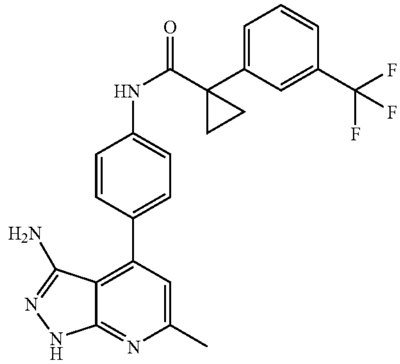 | 1-(3-Trifluoromethyl-phenyl)-cyclopropane-carboxylic acid [4-(3-amino-6-methyl-1H-pyrazolo[3,4-b]pyridin-4-yl)-phenyl]-amide | MS (ESI): [M + H]$^+$ = 452. |

| Intermediate | Structure | Name | Analytical data |
|---|---|---|---|
| 10.10 | 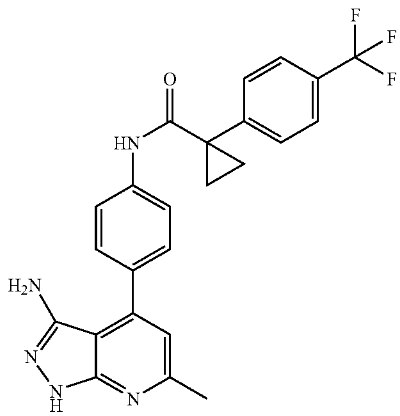 | 1-(4-Trifluoromethyl-phenyl)-cyclopropane-carboxylic acid [4-(3-amino-6-methyl-1H-pyrazolo[3,4-b]pyridin-4-yl)-phenyl]-amide | $^1$H-NMR: (DMSO, 400 MHz) 12.02 (s, 1 H); 9.52 (s, 1 H); 7.72 (d, 2 H); 7.69 (d, 2 H); 7.57 (d, 2 H); 7.46 (d, 2 H); 6.74 (s, 1 H); 4.44 (s, 2 H); 2.48 (s, 3 H); 1.50-1.53 (m, 2 H); 1.18-1.21 (m, 2 H). MS (ESI): [M + H]$^+$ = 452. |
| 10.11 | 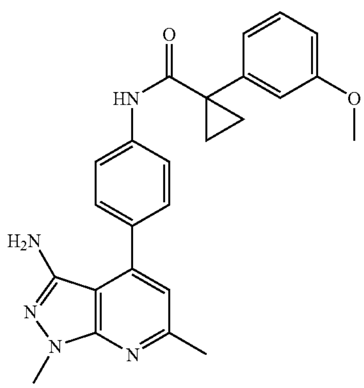 | 1-(3-Methoxy-phenyl)-cyclopropane-carboxylic acid [4-(3-amino-1,6-dimethyl-1H-pyrazolo[3,4-b]pyridin-4-yl)-phenyl]-amide | $^1$H-NMR: (CDCl$_3$, 400 MHz) 7.52 (d, 2 H); 7.46 (d, 2 H); 7.38 (t, 1 H); 7.27-7.31 (m, 1 H); 7.11 (d, 1 H); 7.04 (s, 1 H); 6.94 (dd, 1 H); 6.73 (S, 1 H); 4.00 (s, 3 H); 3.86 (s, 3 H); 2.71 (s, 3 H); 1.72-1.74 (m, 2 H); 1.19-1.22 (m, 2 H). MS (LC-MS): [M + H]$^+$ = 428. |
| 10.12 | 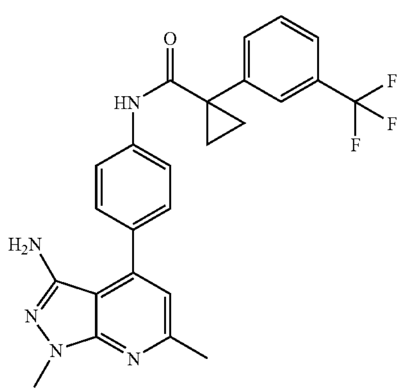 | 1-(3-Trifluoromethyl-phenyl)-cyclopropane-carboxylic acid [4-(3-amino-1,6-dimethyl-1H-pyrazolo[3,4-b]pyridin-4-yl)-phenyl]-amide | $^1$H-NMR: (DMSO, 300 MHz) 9.57 (s, 1 H); 7.72-7.78 (m, 4 H); 7.66 (t, 1 H); 7.60 (d, 1 H); 7.51 (d, 2 H); 6.80 (s, 1 H); 4.58 (br. 2 H); 3.78 (s, 3 H); 2.56 (s, 3 H); 1.53-1.57 (m, 2 H); 1.23-1.27 (m, 2 H). |

| Intermediate | Structure | Name | Analytical data |
|---|---|---|---|
| 10.13 | 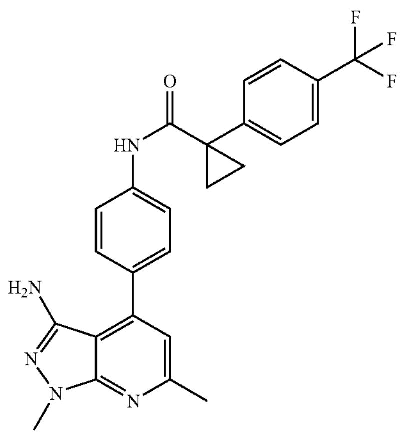 | 1-(4-Trifluoromethyl-phenyl)-cyclopropane-carboxylic acid [4-(3-amino-1,6-dimethyl-1H-pyrazolo[3,4-b]pyridin-4-yl)-phenyl]-amide | $^1$H-NMR: (DMSO, 300 MHz) 9.58 (s, 1 H); 7.77 (d, 2 H); 7.73 (d, 2 H); 7.61 (d, 2 H); 7.51 (d, 2 H); 6.80 (s, 1 H); 4.58 (br. s, 2 H); 3.78 (s, 3 H); 2.56 (s, 3 H); 1.54-1.58 (m, 2 H); 1.22-1.26 (m, 2 H). |
| 10.14 | 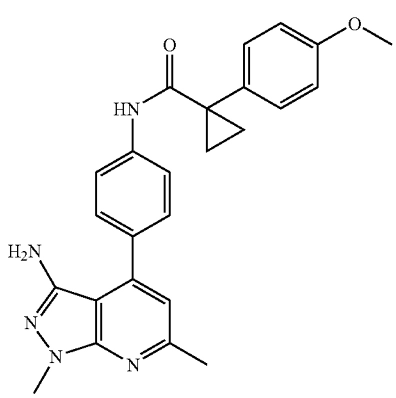 | 1-(4-Methoxy-phenyl)-cyclopropane-carboxylic acid [4-(3-amino-1,6-dimethyl-1H-pyrazolo[3,4-b]pyridin-4-yl)-phenyl]-amide | $^1$H-NMR: (CDCl$_3$, 400 MHz) 7.52 (d, 2 H); 7.46 (d, 2 H); 7.43 (d, 2 H); 6.98 (d, 2 H); 6.74 (s, 1 H); 4.01 (s, 3 H); 3.86 (s, 3 H); 2.71 (s, 3 H); 1.71-1.73 (m, 2 H); 1.16-1.18 (m, 2 H). |
| 10.15 | 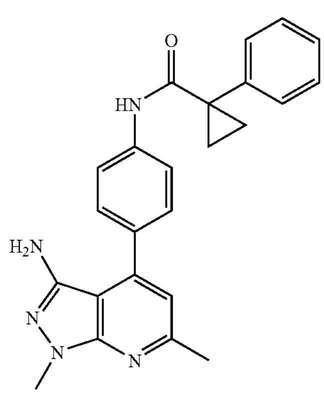 | 1-Phenyl-cyclopropanecarboxylic acid [4-(3-amino-1,6-dimethyl-1H-pyrazolo[3,4-b]pyridin-4-yl)-phenyl]-amide | $^1$H-NMR: (DMSO, 400 MHz) 9.28 (s, 1 H); 7.71 (d, 2 H); 7.45 (d, 2 H); 7.32-7.40 (m, 4 H); 7.24-7.28 (m, 1 H); 6.74 (s, 1 H); 4.53 (br. s, 2 H); 3.73 (s, 3 H); 2.51 (s, 3 H); 1.42-1.45 (m, 2 H); 1.10-1.13 (m, 2 H). |

Intermediate 11.1

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid

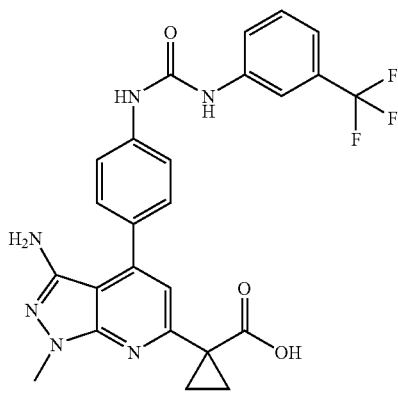

In analogy to GP 9, reaction of 0.96 g Intermediate 7.8 (1.78 mmol, 1 eq.) with 2.67 ml sodium hydroxide solution (2.67 mmol, 1.5 eq.) in 20 ml EtOH yielded 880 mg of the desired product (97% yield).

$^1$H-NMR (d$_6$-DMSO; 300 MHz): 12.61 (br. s, 1H); 9.15 (br. s, 1H); 9.07 (br. s, 1H); 8.04 (s, 1H); 7.68 (m, 2H); 7.60 (m, 1H); 7.55 (m, 3H); 7.33 (m, 1H); 7.05 (br. s, 1H); 4.65 (br. s, 2H); 3.79 (s, 3H); 1.53 (s, 2H); 1.50 (s, 2H).

Intermediate 11.2

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid methylamide

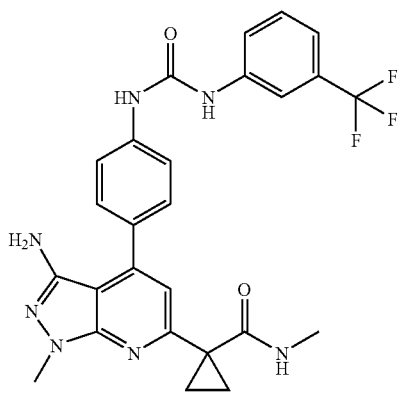

In analogy to GP 10, reaction of 234 mg Intermediate 11.1 (0.46 mmol, 1 eq.) with 0.23 ml methylamine (2M in THF; 0.46 mmol, 1 eq.), 0.25 ml 4-methylmorpholine (5 eq.) and 0.54 ml 2,4,6-tripropyl-[1,3,5,2,4,6]trioxatriphosphinane 2,4,6-trioxide (T3P; 2 eq.) in 10 ml DCM yielded after purification with flash column chromatography 40 mg of the desired product (17% yield).

$^1$H-NMR (d$_6$-DMSO; 400 MHz): 9.18 (br. s, 1H); 9.10 (br. s, 1H); 8.05 (s, 1H); 7.67 (m, 2H); 7.60 (m, 1H); 7.53 (m, 3H); 7.45 (m, 1H); 7.33 (m, 1H); 6.86 (s, 1H); 4.68 (br. s, 2H); 3.80 (s, 3H); 2.59 (d, 3H); 1.37 (m, 2H); 1.28 (m, 2H).

MS (ESI): [M+H]$^+$=524.

Intermediate 11.3

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethylamide

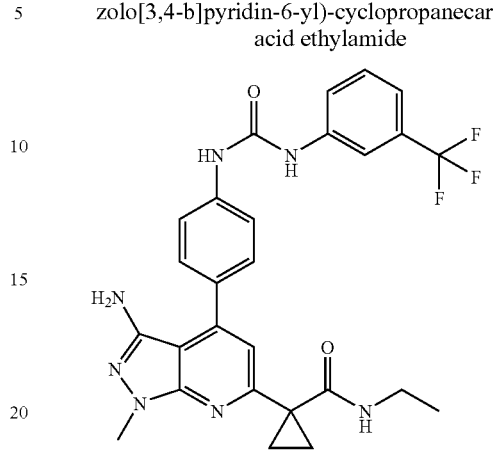

In analogy to GP 10, reaction of 430 mg Intermediate 11.1 (0.84 mmol, 1 eq.) with 0.7 ml ethylamine (2M in THF; 1.1 mmol, 1.3 eq.), 0.46 ml 4-methylmorpholine (5 eq.) and 1 ml 2,4,6-tripropyl-[1,3,5,2,4,6]trioxatriphosphinane 2,4,6-trioxide (T3P; 2 eq.) in 25 ml DCM yielded 440 mg of the desired product (97% yield).

$^1$H-NMR (d$_6$-DMSO; 400 MHz): 9.23 (br. s, 1H); 9.15 (br. s, 1H); 8.05 (s, 1H); 7.74 (m, 1H); 7.67 (m, 2H); 7.61 (m, 1H); 7.53 (m, 3H); 7.33 (m, 1H); 6.84 (s, 1H); 4.67 (br. s, 2H); 3.79 (s, 3H); 3.11 (q, 2H); 1.37 (m, 2H); 1.31 (m, 2H); 1.00 (t, 3H).

Intermediate 11.4

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid isopropyl-amide

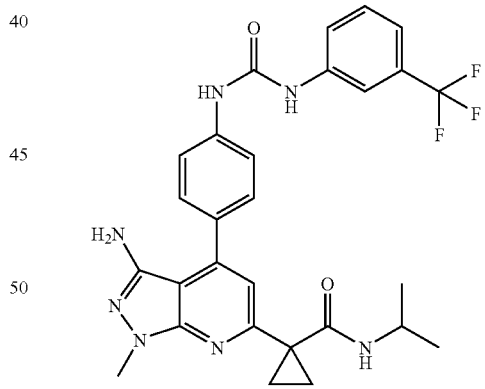

In analogy to GP 10, reaction of 205 mg Intermediate 11.1 (0.4 mmol, 1 eq.) with 0.07 ml isopropylamine (0.8 mmol, 2 eq.), 0.22 ml 4-methylmorpholine (5 eq.) and 0.47 ml 2,4,6-tripropyl-[1,3,5,2,4,6]trioxatriphosphinane 2,4,6-trioxide (T3P; 2 eq.) in 10 ml DCM yielded after purification with flash column chromatography 110 mg of the desired product (50% yield).

$^1$H-NMR (d$_6$-DMSO; 300 MHz): 9.16 (br. s, 1H); 9.07 (br. s, 1H); 8.04 (s, 1H); 7.89 (d, 1H); 7.66 (m, 2H); 7.60 (m, 1H); 7.53 (m, 3H); 7.32 (d, 1H); 6.80 (s, 1H); 4.67 (br. s, 2H); 3.96 (sept, 1H); 3.79 (s, 3H); 1.38 (m, 2H); 1.35 (m, 2H); 1.08 (d, 6H).

MS (ESI): [M+H]$^+$=552 (100%).

Intermediate 11.5

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid phenylamide

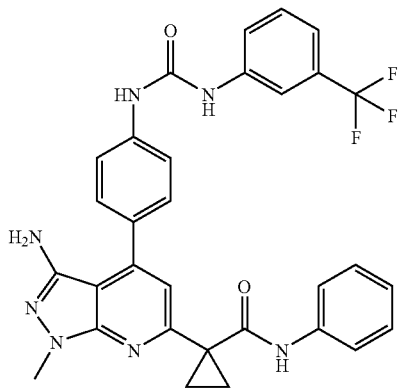

In analogy to GP 10, reaction of 202 mg Intermediate 11.1 (0.4 mmol, 1 eq.) with 36.85 mg aniline (0.4 mmol, 1 eq.), 0.22 ml 4-methylmorpholine (5 eq.) and 0.47 ml 2,4,6-tripropyl-[1,3,5,2,4,6]trioxatriphosphinane 2,4,6-trioxide (T3P; 2 eq.) in 9 ml DCM yielded after purification with flash column chromatography 123 mg of the desired product (53% yield).

$^1$H-NMR (d$_6$-DMSO; 300 MHz): 10.12 (s, 1H); 9.16 (br. s, 1H); 9.07 (br. s, 1H); 8.03 (s, 1H); 7.62 (m, 5H); 7.53 (m, 3H); 7.30 (m, 3H); 7.05 (m, 1H); 6.84 (s, 1H); 4.69 (br. s, 2H); 3.82 (s, 3H); 1.55 (m, 2H); 1.52 (m, 2H).

MS (ESI): [M+H]$^+$=586 (100%).

The following Intermediates 11.6 to 11.12 were prepared in analogy to GP10 and the before mentioned Intermediates 11.2 to 11.5 by reacting Intermediate 11.1 with the respective amines:

| Intermediate | Structure | Name | Analytical data |
|---|---|---|---|
| 11.6 | ![structure] | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-morpholin-4-yl-ethyl)-amide | $^1$H-NMR (d$_6$-DMSO; 400 MHz): 9.18 (br. s, 1 H); 9.11 (br. s, 1 H); 8.04 (br. s, 1 H); 7.67 (d, 2 H); 7.60 (d, 1 H); 7.54 (m, 4 H); 7.33 (d, 1 H); 6.89 (s, 1 H); 4.69 (br. s, 2 H); 3.81 (s, 3 H); 3.37 (m, 4 H); 3.19 (q, 2 H); 2.33 (t, 2 H); 2.27 (br. s, 4 H); 1.39 (m, 2 H); 1.32 (m, 2 H) MS (ESI): [M + H]$^+$ = 623 (100%) |

| Intermediate | Structure | Name | Analytical data |
|---|---|---|---|
| 11.7 | 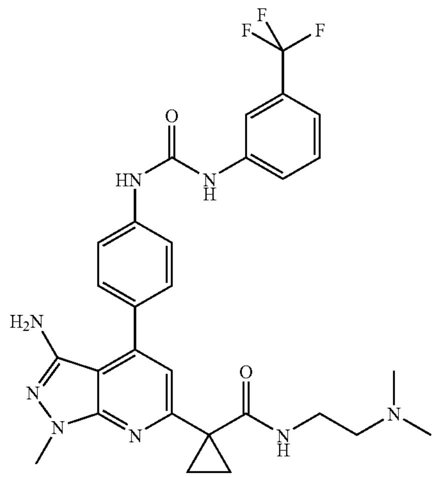 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-dimethylamino-ethyl)-amide | $^1$H-NMR ($d_6$-DMSO; 400 MHz): 9.16 (br. s, 1 H); 9.09 (br. s, 1 H); 8.04 (br. s, 1 H); 7.99 (m, 1 H); 7.67 (d, 2 H); 7.60 (d, 1 H); 7.54 (m, 3 H); 7.33 (d, 1 H); 6.86 (s, 1 H); 4.69 (br. s, 2 H); 3.82 (s, 3 H); 3.20 (m, 2 H); 2.29 (m, 2 H); 2.09 (s, 6 H); 1.41 (m, 2 H); 1.34 (m, 2 H) MS (ESI): $[M + H]^+ = 581$ (100%) |
| 11.8 | 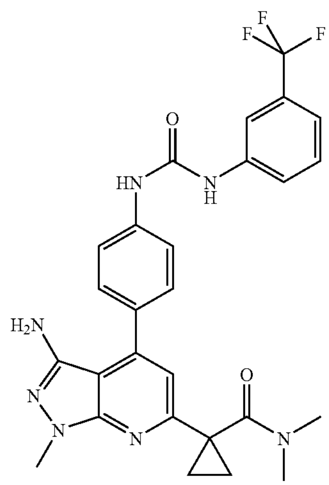 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid dimethylamide | $^1$H-NMR ($d_6$-DMSO; 400 MHz): 9.16 (br. s, 1 H); 9.09 (br. s, 1 H); 8.04 (s, 1 H); 7.66 (d, 2 H); 7.60 (d, 1 H); 7.53 (t, 1 H); 7.51 (d, 2 H); 7.33 (d, 1 H); 6.58 (s, 1 H); 4.67 (br. s, 2 H); 3.76 (s, 3 H); 2.91 (s, 3 H); 2.86 (s, 3 H); 1.54 (m, 2 H); 1.34 (m, 2 H) MS (ESI): $[M + H]^+ = 538$ (100%) |
| 11.9 | 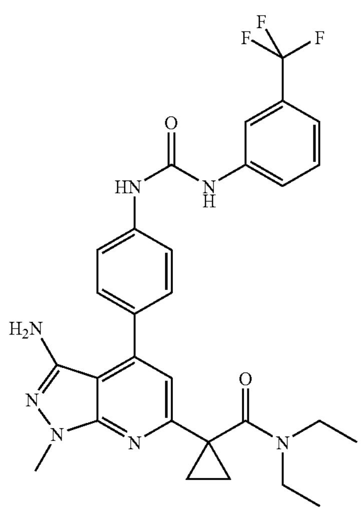 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid diethylamide | $^1$H-NMR ($d_6$-DMSO; 400 MHz): 9.15 (br. s, 1 H); 9.07 (br. s, 1 H); 8.04 (s, 1 H); 7.66 (d, 2 H); 7:60 (d, 1 H); 7:53 (t, 1 H); 7.49 (d, 2 H); 7.33 (d, 1 H); 6.62 (s, 1 H); 4.67 (br. s, 2 H); 3.76 (s, 3 H); 3.33 (q, 2 H); 3.30 (q, 2 H); 1.52 (m, 2 H); 1.33 (m, 2 H); 1.09 (t, 3 H); 0.86 (t, 3 H) MS (ESI): $[M + H]^+ = 566$ (100%) |

| Intermediate | Structure | Name | Analytical data |
|---|---|---|---|
| 11.10 | 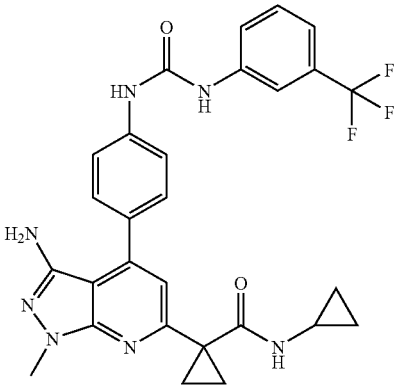 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid cyclopropylamide | ¹H-NMR (d₆-DMSO; 300 MHz): 9.15 (br. s, 1 H); 9.07 (br. s, 1 H); 8.04 (s, 1 H); 7.91 (d, 1 H); 7.67 (d, 2 H); 7.61 (d, 1 H); 7.53 (t, 1 H); 7.52 (d, 2 H); 7.33 (d, 1 H); 6.78 (s, 1 H); 4.66 (br. s, 2 H); 3.78 (s, 3 H); 2.69 (m, 1 H); 1.37 (m, 2 H); 1.34 (m, 2 H); 0.59 (m, 2 H); 0.43 (m, 2 H). MS (ESI): [M + H]⁺ = 550 (100%) |
| 11.11 | 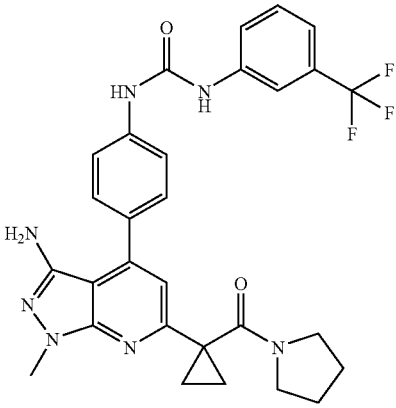 | 1-(4-{3-Amino-1-methyl-6-[1-(pyrrolidine-1-carbonyl)-cyclopropyl]-1H-pyrazolo[3,4-b]pyridin-4-yl}-phenyl)-3-(3-trifluoromethyl-phenyl)-urea | ¹H-NMR (d₆-DMSO; 300 MHz): 9.18 (br. s, 1 H); 9.10 (br. s, 1 H); 8.04 (s, 1 H); 7.67 (d, 2 H); 7.61 (d, 1 H); 7.53 (t, 1 H); 7.50 (d, 2 H); 7.33 (m, 1 H); 6.63 (s, 1 H); 4.66 (br. s, 2 H); 3.76 (s, 3 H); 3.40 (m, 2 H); 3.19 (m, 2 H); 1.74 (m, 4 H); 1.50 (m, 2 H); 1.35 (m, 2 H). MS (ESI): [M + H]⁺ = 564 (100%). |
| 11.12 | 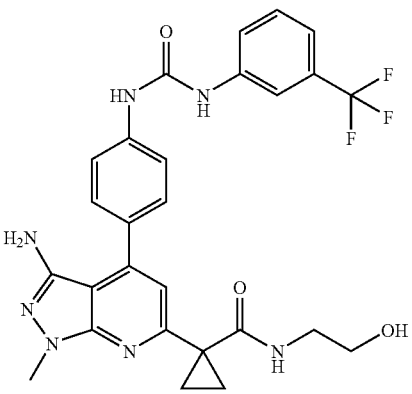 | 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid (2-hydroxy-ethyl)-amide | ¹H-NMR (d₆-DMSO; 400 MHz): 9.35 (br. s, 1 H); 9.27 (br. s, 1 H); 8.05 (br. s, 1 H); 7.97 (t, 1 H); 7.68 (d, 2 H); 7.63 (d, 1 H); 7.54 (d, 2 H); 7.52 (t, 1 H); 7.32 (d, 1 H); 6.84 (s, 1 H); 4.69 (br. s, 2 H); 3.81 (s, 3 H); 3.42 (t, 2 H); 3.19 (t, 1 H); 3.18 (t, 1 H); 1.42 (m, 2 H); 1.33 (m, 2 H). MS (ESI): [M + H]⁺ = 554 (100%). |

Intermediate 11.13

Preparation of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid amide

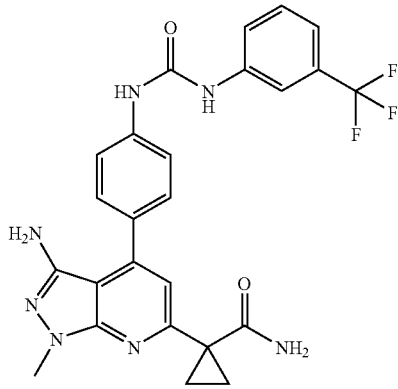

In analogy to *Synthetic Communications* 20(8), 1203-1208 (1990), reaction of 148 mg Intermediate 7.8 (0.27 mmol, 1.4 eq.) with 0.39 ml sodium methoxide solution (0.5 M in MeOH, 0.2 mmol, 1 eq.) and 42.44 mg formamide (0.94 mmol, 4.8 eq.) in 2 ml DMF yielded after purification with preparative HPLC 21 mg of the desired product (15% yield).

$^1$H-NMR (d$_6$-DMSO; 300 MHz): 9.16 (br. s, 1H); 9.08 (br. s, 1H); 8.04 (s, 1H); 7.67 (m, 2H); 7.60 (m, 1H); 7.54 (m, 3H); 7.33 (m, 1H); 7.11 (br. s, 2H); 6.89 (s, 1H); 4.66 (br. s, 2H); 3.79 (s, 3H); 1.39 (m, 2H); 1.31 (m, 2H).

Intermediate 11.14

Preparation of 1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid

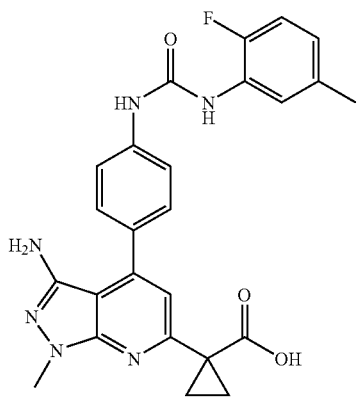

In analogy to GP 9, reaction of 0.7 g Intermediate 7.13 (1.39 mmol, 1 eq.) with 2.09 ml sodium hydroxide solution (2.09 mmol, 1.5 eq.) in 15 ml EtOH yielded 600 mg of the desired product (91% yield), which was used for the subsequent transformations without further purification.

Intermediate 11.15

Preparation of 1-(4-{3-Amino-1-methyl-6-[1-(pyrrolidine-1-carbonyl)-cyclopropyl]-1H-pyrazolo[3,4-b]pyridin-4-yl}-phenyl)-3-(2-fluoro-5-methyl-phenyl)-urea

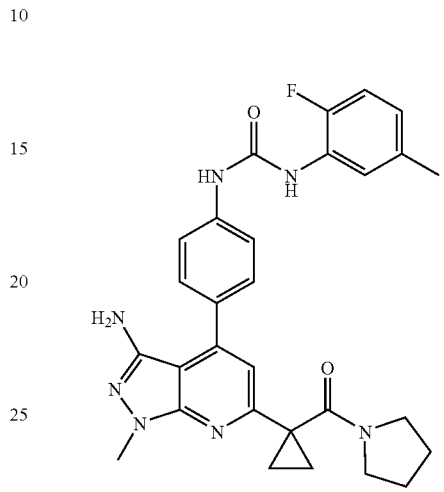

In analogy to GP 10, reaction of 200 mg Intermediate 11.14 (0.42 mmol, 1 eq.) with 0.052 ml pyrrolidine (0.63 mmol, 1.5 eq.), 0.23 ml 4-methylmorpholine (5 eq.) and 0.5 ml 2,4,6-tripropyl-[1,3,5,2,4,6]trioxatriphosphinane 2,4,6-trioxide (T3P; 2 eq.) in 15 ml DCM yielded 125 mg of the desired product (56% yield).

$^1$H-NMR (d$_6$-DMSO; 400 MHz): 9.31 (s, 1H); 8.57 (m, 1H); 8.00 (dd, 1H); 7.65 (d, 2H); 7.50 (d, 2H); 7.12 (dd, 1H); 6.82 (m, 1H); 6.62 (s, 1H); 4.66 (br. s, 2H); 3.76 (s, 3H); 3.39 (m, 2H); 3.18 (m, 2H); 2.28 (s, 3H); 1.74 (m, 4H); 1.49 (m, 2H); 1.35 (m, 2H).

Intermediate 11.16

Preparation of 1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid dimethylamide

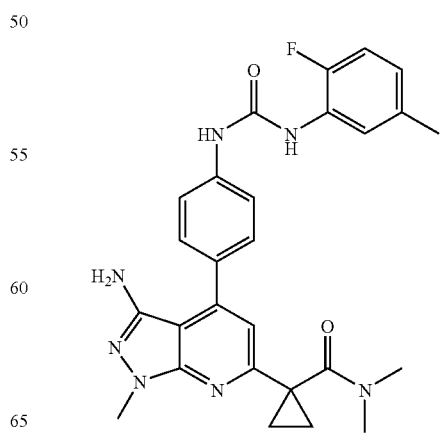

In analogy to GP 10, reaction of 200 mg Intermediate 11.14 (0.42 mmol, 1 eq.) with 0.32 ml dimethylamine (0.63 mmol, 1.5 eq.), 0.23 ml 4-methylmorpholine (5 eq.) and 0.5 ml 2,4,6-tripropyl-[1,3,5,2,4,6]trioxatriphosphinane 2,4,6-trioxide (T3P; 2 eq.) in 15 ml DCM yielded 136 mg of the desired product (64% yield).

¹H-NMR (d₆-DMSO; 300 MHz): 9.31 (s, 1H); 8.57 (m, 1H); 8.00 (dd, 1H); 7.65 (d, 2H); 7.51 (d, 2H); 7.12 (dd, 1H); 6.82 (m, 1H); 6.58 (s, 1H); 4.67 (br. s, 2H); 3.76 (s, 3H); 2.91 (s, 3H); 2.86 (s, 3H); 2.28 (s, 3H); 1.54 (m, 2H); 1.34 (m, 2H).

Intermediate 11.17

Preparation of 1-(3-Amino-4-{4-[3-(2-fluoro-5-methyl-phenyl)-ureido]-phenyl}-1-methyl-1H-pyrazolo[3,4-b]pyridin-6-yl)-cyclopropanecarboxylic acid cyclopropylamide

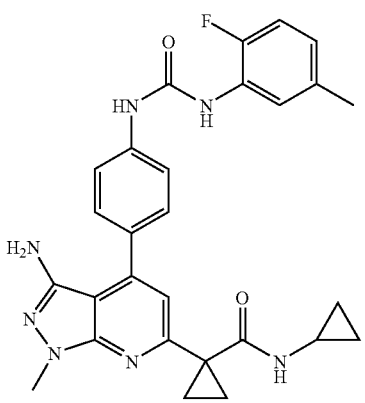

In analogy to GP 10, reaction of 200 mg Intermediate 11.14 (0.42 mmol, 1 eq.) with 36.1 mg cyclopropylamine (0.63 mmol, 1.5 eq.), 0.23 ml 4-methylmorpholine (5 eq.) and 0.5 ml 2,4,6-tripropyl-[1,3,5,2,4,6]trioxatriphosphinane 2,4,6-trioxide (T3P; 2 eq.) in 15 ml DCM yielded 178 mg of the desired product (82% yield).

¹H-NMR (d₆-DMSO; 300 MHz): 9.31 (s, 1H); 8.58 (m, 1H); 8.00 (dd, 1H); 7.91 (d, 1H); 7.65 (d, 2H); 7.51 (d, 2H); 7.12 (dd, 1H); 6.82 (m, 1H); 6.78 (s, 1H); 4.67 (br. s, 2H); 3.78 (s, 3H); 2.70 (m, 1H); 2.28 (s, 3H); 1.37 (m, 2H); 1.33 (m, 2H); 0.59 (m, 2H); 0.43 (m, 2H).

Intermediate 12.1

Preparation of 1,6-Dimethyl-4-(4-nitro-phenyl)-1H-pyrazolo[3,4-b]pyridin-3-ylamine

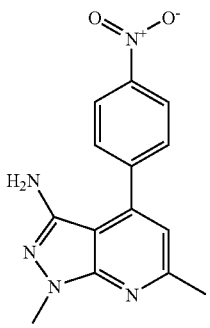

In an adoption of GP 4a (step 2), reaction of Intermediate 2.3 (2 g, 5.16 mmol, 1 eq.) with 270 μL methyl hydrazine (7.75 mmol, 1.5 eq.) in 90 mL 1-PrOH at 100° C. for 3 h followed by concentration of the reaction mixture and filtration yielded 745 mg of the target compound (51% yield). Extractive work-up of the filtrate and subsequent flash column chromatography provided a second batch of the target compound.

¹H-NMR (d₆-DMSO; 400 MHz): 8.33 (d, 2H); 7.81 (d, 2H); 6.88 (s, 1H); 4.67 (d, 2 H); 3.77 (s, 3H); 2.55 (s, 3H).

Intermediate 12.2

Preparation of 1,6-Dimethyl-4-(4-nitro-phenyl)-1H-pyrazolo[3,4-b]pyridine

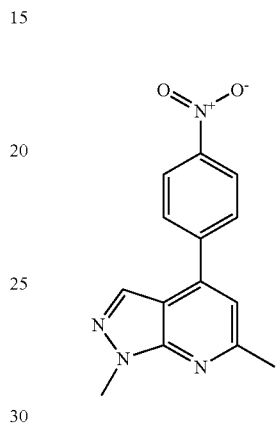

In an adoption of GP 6, reaction of Intermediate 12.1 (1010 mg, 3.57 mmol, 1 eq.) with 1.12 mL concentrated sulphuric acid and 1220 mg sodium nitrite (17.61 mmol, eq.) yielded the desired product in quantitative yield.

¹H-NMR (d₆-DMSO; 300 MHz): 8.36 (d, 2H); 8.24 (s, 1H); 8.11 (d, 2H); 7.39 (s, 1H); 4.04 (s, 3H); 2.66 (s, 3H).

Intermediate 12.3

Preparation of 4-(1,6-Dimethyl-1H-pyrazolo[3,4-b]pyridin-4-yl)-phenylamine

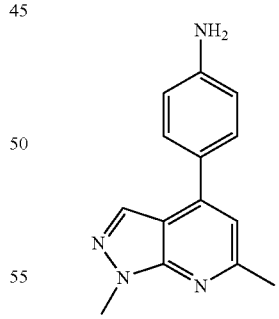

Hydrogenation of 958 mg of Intermediate 12.2 (3.57 mmol, 1 eq.) in 50 mL EtOH/THF (3:2) in the presence of 200 mg 10% Pd/C at room temperature for 4 h followed by filtration of the reaction slurry through Celite and concentration in vacuo provided 850 mg the target compound (quantitative yield) which was used without further purification steps.

¹H-NMR (d₆-DMSO; 300 MHz): 8.17 (s, 1H); 7.57 (d, 2H); 7.11 (s, 1H); 6.68 (d, 2H); 5.56 (s, 2H); 3.98 (s, 3H); 2.57 (s, 3H).

Intermediate 13.1 [For an Alternative Route, See Intermediates 17.1 to 17.7]

Preparation of 6-Bromomethyl-1-methyl-4-(4-nitrophenyl)-1H-pyrazolo[3,4-b]pyridine

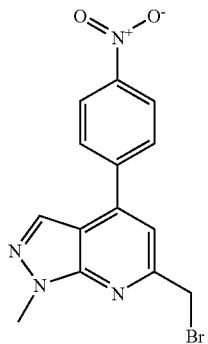

A mixture of Intermediate 12.2 (1690 mg, 6.3 mmol, 1 eq.), N-bromosuccinimide (NBS; 1680 mg, 9.5 mmol, 1.5 eq.) and azobisisobutyronitrile (AIBN; 50 mg, 5 mot %) in dry $CHCl_3$ (200 mL) was refluxed for 14 h under irradiation (300 W). Upon cooling to room temperature, the reaction mixture was quenched with sat. aq. $NaHCO_3$ solution and subsequently adjusted to pH ~8. The organic layer was separated, washed with brine, dried and concentrated in vacuo. Flash column chromatography provided 1070 mg (3.08 mmol, 49% yield) of the target compound.

$^1$H-NMR ($CDCl_3$; 300 MHz): 8.45 (d, 2H); 8.15 (s, 1H); 7.95 (d, 2H); 7.41 (s, 1H); 4.75 (s, 2H); 4.20 (s, 3H).

Intermediate 13.2

Preparation of 1-Methyl-6-morpholin-4-ylmethyl-4-(4-nitro-phenyl)-1H-pyrazolo[3,4-b]pyridine

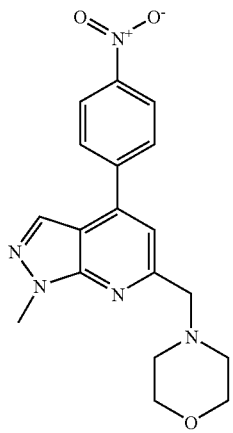

A mixture of Intermediate 13.1 (0.38 g, 1.1 mmol, 1 eq.) and morpholine (0.3 ml, 3.3 mmol, 3 eq.) in DMF (5 ml) was stirred at room temperature overnight. Upon addition of water to the reaction mixture, the precipitate was filtered, washed with water and dried to yield 0.23 g (0.65 mmol, 60%) of the target compound as a yellow solid.

$^1$H-NMR ($CDCl_3$; 300 MHz): 8.45 (d, 2H); 8.10 (s, 1H); 7.95 (d, 2H); 7.50 (s, 2H); 4.25 (s, 3H); 3.85 (s, 2H); 3.75-3.81 (m, 4H); 2.60-2.70 (m, 4H).

Intermediate 13.3

Preparation of 4-(1-Methyl-6-morpholin-4-ylmethyl-1H-pyrazolo[3,4-b]pyridin-4-yl)-phenylamine

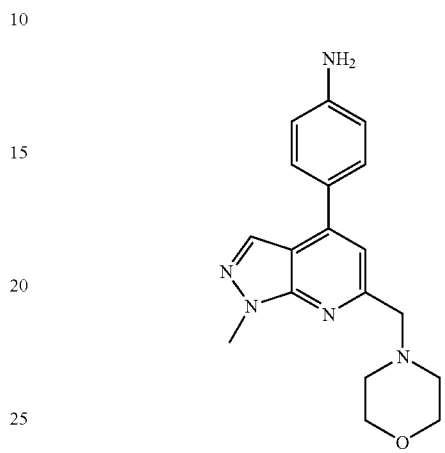

In an adoption of GP 3, reaction of Intermediate 13.2 (1000 mg, 2.83 mmol, 1 eq.) with 3.19 g tin(II)chloride dihydrate (14.15 mmol, 5 eq.) in 25 mL EtOH at reflux for 2 h followed by extractive workup as described in GP3 yielded after concentration in vacuo the desired product in quantitative yield which was used without further purification steps.

$^1$H-NMR ($d_6$-DMSO; 300 MHz): 8.23 (s, 1H); 7.57 (d, 2H); 7.33 (s, 1H); 6.70 (d, 2H); 5.61 (br. s, 2H); 4.00 (s, 3H); 3.66 (s, 2H); 3.54-3.60 (m, 4H); 2.41-2.45 (m, 4H).

Intermediate 14.1

Preparation of 1-[3-Amino-4-(4-nitro-phenyl)-1H-pyrazolo[3,4-b]pyridin-6-yl]-cyclopropanecarboxylic acid ethyl ester

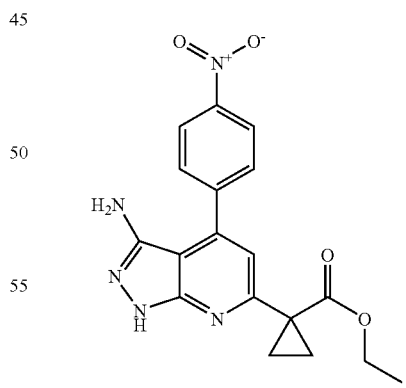

In an adoption of GP 4c (step 2), reaction of Intermediate 2.5 (1.1 g, 2.27 mmol, 1 eq.) with 330 μL 80% hydrazine hydrate (6.8 mmol, 3 eq.) in 55 mL 1-PrOH yielded 0.83 g of the 1H-pyrazolopyridine (2.26 mmol, 99% yield).

$^1$H-NMR ($d_6$-DMSO; 400 MHz): 12.37 (s, 1H); 8.38 (d, 2H); 7.87 (d, 2H); 7.16 (s, 1H); 4.67 (br. s, 2H); 4.09 (q, 2H); 1.54 (m, 2H); 1.52 (m, 2H); 1.13 (t, 3H).

MS (ESI): [M+H]$^+$=368 (100%).

Intermediate 14.2
Preparation of 1-[4-(4-Nitro-phenyl)-1H-pyrazolo[3,4-b]pyridin-6-yl]-cyclopropanecarboxylic acid ethyl ester

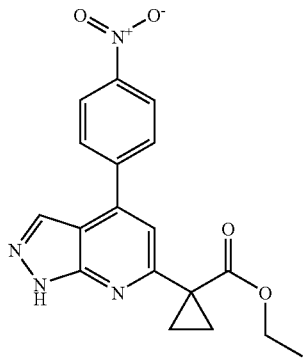

In an adoption of GP 6, reaction of Intermediate 14.1 (184 mg, 0.5 mmol, 1 eq.) in 2.5 ml EtOH with 40 μL concentrated sulphuric acid and 83 mg sodium nitrite (1.2 mmol, 2.4 eq.) yielded 70 mg of the desired product (40% yield).

$^1$H-NMR (d$_6$-DMSO; 400 MHz): 13.85 (s, 1H); 8.41 (d, 2H); 8.33 (s, 1H); 8.17 (d, 2H); 7.64 (s, 1H); 4.11 (q, 2H); 1.60 (m, 4H); 1.13 (t, 3H).
MS (ESI): [M+H]$^+$=353 (100%).

Intermediate 14.3
Preparation of 1-[4-(4-Amino-phenyl)-1H-pyrazolo[3,4-b]pyridin-6-yl]-cyclopropanecarboxylic acid ethyl ester

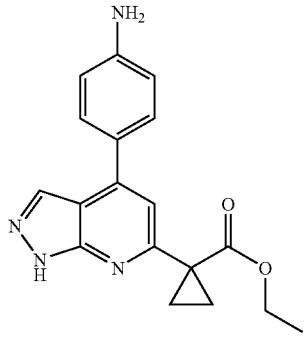

In analogy to GP 3, reaction of Intermediate 14.2 (70 mg, 0.2 mmol, 1 eq.) with 224.14 mg tin(II)chloride dihydrate (0.99 mmol, 5 eq.) in 5.2 mL EtOH yielded 40 mg of the amine (0.12 mmol, 62% yield).

$^1$H-NMR (d$_6$-DMSO; 400 MHz): 13.50 (br. s, 1H); 8.25 (s, 1H); 7.61 (d, 2H); 7.32 (s, 1H); 6.73 (d, 2H); 5.62 (br. s, 2H); 4.10 (q, 2H); 1.53 (m, 4H); 1.13 (t, 3H).
MS (ESI): [M+H]$^+$=323 (100%).

Intermediate 15.1

Preparation of 4-Iodo-1-methyl-1H-pyrazolo[3,4-b]pyridine

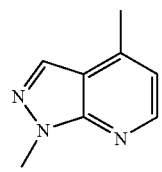

227 mg of 2-fluoro-4-iodo-pyridine-3-carbaldehyde (0.9 mmol, 1 eq.; prepared as described in *J. Org. Chem.* 1993, 58, 7832) were dissolved in 3.6 mL 1-PrOH, treated with 72 μL methyl hydrazine (1.36 mmol, 1.5 eq.) and heated to 100° C. for 30 min (Biotage Initiator 60®). The reaction mixture was concentrated in vacuo, the residue was partioned between water and ethyl acetate, the aq. layer was extracted with ethyl acetate, the combined organic layers were dried and concentrated in vacuo to provide the crude target compound.

$^1$H-NMR (d$_6$-DMSO; 400 MHz): 8.17 (d, 1H); 7.94 (s, 1H); 7.66 (d, 1H); 4.01 (s, 3 H).
MS (LC-MS): [M+H]$^+$=260.

The following synthetic intermediates 16.1 to 16.24 were synthesized in analogy to the before described reactions starting from Intermediate 3.4, commercially available 1-cyclopropyl-ethanone, 1-cyclobutyl-ethanone, 1-cyclohexyl-ethanone, 1-(2-phenyl-cyclopropyl)-ethanone, 1-thiazol-2-yl-ethanone, Intermediate 1.5, or (3-acetyl-2,2-dimethyl-cyclobutyl)-acetic acid methyl ester (accessible by standard esterification protocols, as known to the person skilled in the art, from commercially available cis-pinonic acid), respectively.

| Intermediate | Structure | Name | Analytical data |
|---|---|---|---|
| 16.1 | 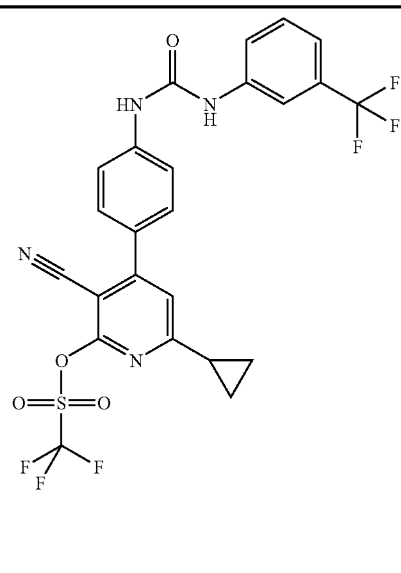 | Trifluoro-methanesulfonic acid 3-cyano-6-cyclopropyl-4-{4-[3-(3-trifluoromethyl-phenyl)-ureido]-phenyl}-pyridin-2-yl ester | $^1$H-NMR (d$_6$-DMSO; 300 MHz): 9.20 (s, 1 H); 9.19 (s, 1 H); 8.04 (s, 1 H); 7.88 (s, 1 H); 7.72 (m, 4 H); 7.60 (m, 1 H); 7.54 (t, 1 H); 7.34 (d, 1 H); 2.38 (m, 1 H); 1.23 (m, 2 H); 1.03 (m, 2 H). |

-continued

| Intermediate | Structure | Name | Analytical data |
|---|---|---|---|
| 16.2 | 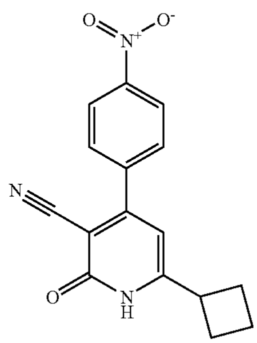 | 6-Cyclobutyl-4-(4-nitro-phenyl)-2-oxo-1,2-dihydro-pyridine-3-carbonitrile | $^1$H-NMR ($d_6$-DMSO; 300 MHz): 12.66 (br. s, 1 H); 8.39 (d, 2 H); 7.92 (d, 2 H); 6.42 (s, 1 H); 3.51 (m, 1 H); 2.26 (m, 4 H); 1.96 (m, 1 H); 1.80 (m, 1 H). |
| 16.3 | 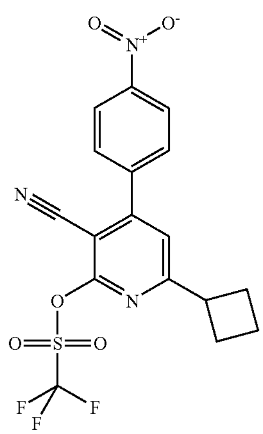 | Trifluoro-methanesulfonic acid 3-cyano-6-cyclobutyl-4-(4-nitro-phenyl)-pyridin-2-yl ester | $^1$H-NMR ($d_6$-DMSO; 400 MHz): 8.45 (d, 2 H); 8.03 (d, 2 H); 7.84 (s, 1 H); 3.86 (m, 1 H); 2.33 (m, 4 H); 2.04 (m, 1 H); 1.90 (m, 1 H). |
| 16.4 | 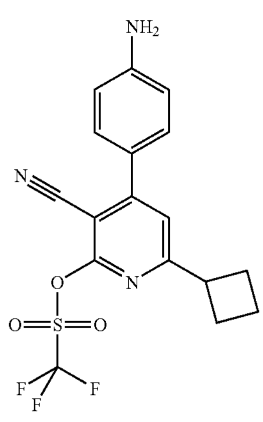 | Trifluoro-methanesulfonic acid 4-(4-amino-phenyl)-3-cyano-6-cyclobutyl-pyridin-2-yl ester | $^1$H-NMR ($d_6$-DMSO; 400 MHz): 7.59 (s, 1 H); 7.52 (d, 2 H); 6.70 (d, 2 H); 5.95 (br. s, 2 H); 2 H); 3.77 (m, 1 H); 2.29 (m, H); 2.02 (m, 1 H); 1.86 (m, 1 H). |

| Intermediate | Name | Analytical data |
|---|---|---|
| 16.5 | Trifluoromethanesulfonic acid 3-cyano-6-cyclobutyl-4-{4-[3-(3-trifluoromethyl-phenyl)-ureido]-phenyl}-pyridin-2-yl ester | $^1$H-NMR (d$_6$-DMSO; 400 MHz): 9.20 (s, 2 H); 8.03 (s, 1 H); 7.72 (m, 5 H); 7.60 (d, 1 H); 7.54 (t, 1 H); 7.34 (d, 1 H); 3.83 (qui, 1 H); 2.32 (m, 4 H); 2.04 (q, 1 H); 1.89 (m, 1 H). |
| 16.6 | 6-Cyclohexyl-4-(4-nitro-phenyl)-2-oxo-1,2-dihydro-pyridine-3-carbonitrile | $^1$H-NMR (d$_6$-DMSO; 300 MHz): 12.65 (br. s, 1 H); 8.38 (d, 2 H); 7.91 (d, 2 H); 6.36 (s, 1 H); 2.57 (m, 1 H); 1.81 (m, 4 H); 1.67 (m, 1 H); 1.50 (m, 2 H); 1.24 (m, 3 H). |
| 16.7 | Trifluoromethanesulfonic acid 3-cyano-6-cyclohexyl-4-(4-nitro-phenyl)-pyridin-2-yl ester | $^1$H-NMR (d$_6$-DMSO; 400 MHz): 8.45 (d, 2 H); 8.05 (d, 2 H); 7.89 (s, 1 H); 2.91 (m, 1 H); 1.92 (m, 2 H); 1.82 (m, 2 H); 1.71 (m, 1 H); 1.52 (m, 2 H); 1.38 (m, 2 H); 1.23 (m, 1 H). |

-continued

| Intermediate | Structure | Name | Analytical data |
|---|---|---|---|
| 16.8 | 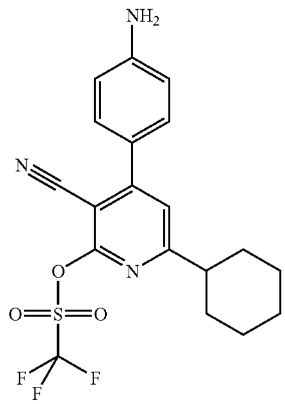 | Trifluoromethanesulfonic acid 4-(4-amino-phenyl)-3-cyano-6-cyclohexyl-pyridin-2-yl ester | $^1$H-NMR (d$_6$-DMSO; 300 MHz): 7.64 (s, 1 H); 7.54 (d, 2 H); 6.71 (d, 2 H); 5.95 (br. s, 2 H); 2.81 (m, 1 H); 1.93-1.64 (m, 5 H), 1.56-1.13 (m, 5 H). |
| 16.9 | 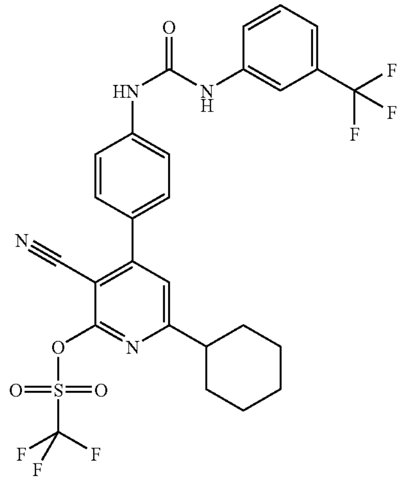 | Trifluoromethanesulfonic acid 3-cyano-6-cyclohexyl-4-{4-[3-(3-trifluoromethyl-phenyl)-ureido]-phenyl}-pyridin-2-yl ester | $^1$H-NMR (d$_6$-DMSO; 400 MHz): 9.20 (s, 1 H); 9.19 (s, 1 H); 8.03 (s, 1 H); 7.74 (m, 5 H); 7.60 (d, 1 H); 7.53 (m, 1 H); 7.34 (d, 1 H); 2.87 (t, 1 H); 1.90 (d, 2 H); 1.81 (d, 2 H); 1.71 (d, 1 H); 1.50 (q, 2 H); 1.37 (q, 2 H); 1.23 (t, 1 H). |
| 16.10 | 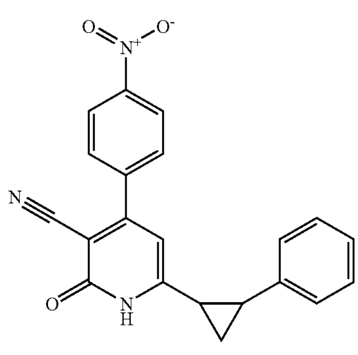 | 4-(4-Nitro-phenyl)-2-oxo-6-(2-phenyl-cyclopropyl)-1,2-dihydro-pyridine-3-carbonitrile | $^1$H-NMR (d$_6$-DMSO; 300 MHz): 12.84 (br. s, 1 H); 8.33 (d, 2 H); 7.51 (d, 2 H); 7.27 (m, 2 H); 7.22 (m, 3 H); 5.82 (s, 1 H); 2.82 (q, 1 H); 2.48 (q, 1 H); 2.00 (q, 1 H); 1.53 (q, 1 H). |

| Intermediate | Structure | Name | Analytical data |
|---|---|---|---|
| 16.11 | 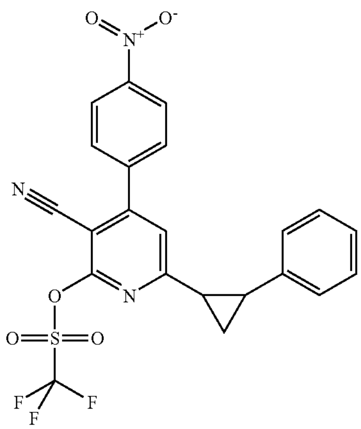 | Trifluoro-methanesulfonic acid 3-cyano-4-(4-nitro-phenyl)-6-(2-phenyl-cyclopropyl)-pyridin-2-yl ester | $^1$H-NMR ($d_6$-DMSO; 400 MHz): 8.41 (d, 2 H); 7.82 (d, 2 H); 7.68 (s, 1 H); 7.17 (m, 5 H); 2.98 (q, 1 H); 2.90 (q, 1 H); 2.03 (q, 1 H); 1.71 (q, 1 H). |
| 16.12 | 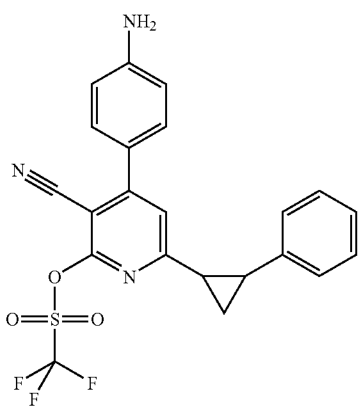 | Trifluoro-methanesulfonic acid 4-(4-amino-phenyl)-3-cyano-6-(2-phenyl-cyclopropyl)-pyridin-2-yl ester | $^1$H-NMR ($d_6$-DMSO; 300 MHz): 7.41 (s, 1 H); 7.31 (d, 2 H); 7.14 (m, 5 H); 6.66 (d, 2 H); 5.91 (br. s, 2 H); 2.88 (q, 1 H); 2.79 (q, 1 H); 1.96 (q, 1 H); 1.62 (q, 1 H). |
| 16.13 | 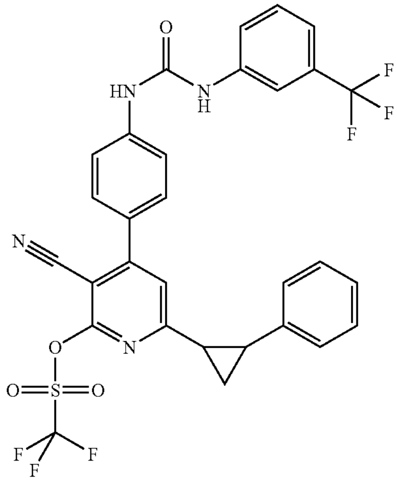 | Trifluoro-methanesulfonic acid 3-cyano-6-(2-phenyl-cyclopropyl)-4-{4-[3-(3-trifluoromethyl-phenyl)-ureido]-phenyl}-pyridin-2-yl ester | $^1$H-NMR ($d_6$-DMSO; 400 MHz): 9.20 (s, 1 H); 9.18 (s, 1 H); 8.03 (s, 1 H); 7.66 (d, 2 H); 7.60 (d, 1 H); 7.52 (m, 4 H); 7.34 (d, 1 H); 7.16 (m, 5 H); 2.94 (q, 1 H); 2.85 (q, 1 H); 2.01 (q, 1 H); 1.67 (q, 1 H). |

-continued

| Inter-mediate | Structure | Name | Analytical data |
|---|---|---|---|
| 16.14 | 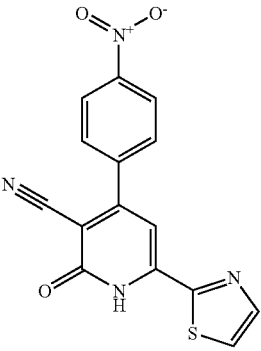 | 4-(4-Nitro-phenyl)-2-oxo-6-thiazol-2-yl-1,2-dihydro-pyridine-3-carbonitrile | $^1$H-NMR ($d_6$-DMSO; 300 MHz): 8.36 (d, 2 H); 7.95 (d, 1 H); 7.87 (d, 2 H); 7.84 (d, 1 H); 7.06 (br. s, 1 H). |
| 16.15 | 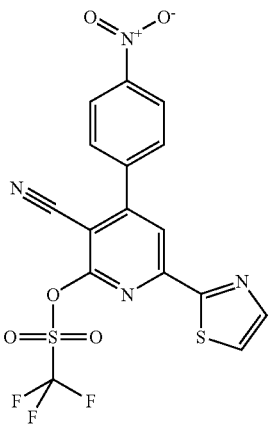 | Trifluoro-methanesulfonic acid 3-cyano-4-(4-nitro-phenyl)-6-thiazol-2-yl-pyridin-2-yl ester | $^1$H-NMR ($d_6$-DMSO; 300 MHz): 8.48 (d, 2 H); 8.45 (s, 1 H); 8.21 (d, 1 H); 8.20 (d, 1 H); 8.11 (d, 2 H). |
| 16.16 | 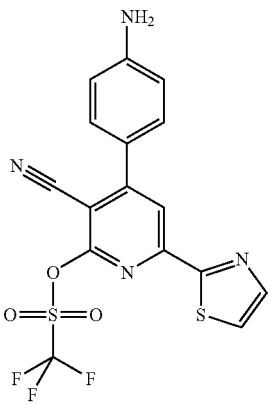 | Trifluoro-methanesulfonic acid 4-(4-amino-phenyl)-3-cyano-6-thiazol-2-yl-pyridin-2-yl ester | $^1$H-NMR ($d_6$-DMSO; 300 MHz): 8.27 (s, 1 H); 8.16 (d, 1 H); 8.12 (d, 1 H); 7.63 (d, 2 H); 6.74 (d, 2 H); 6.10 (br. s, 2 H). |

-continued

| Intermediate | Structure | Name | Analytical data |
|---|---|---|---|
| 16.17 | 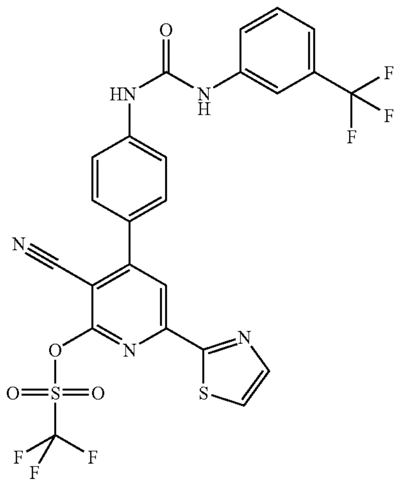 | Trifluoromethanesulfonic acid 3-cyano-6-thiazol-2-yl-4-{4-[3-(3-trifluoromethyl-phenyl)-ureido]-phenyl}-pyridin-2-yl ester | $^1$H-NMR (d$_6$-DMSO; 300 MHz): 9.25 (s, 1 H); 9.22 (s, 1 H); 8.36 (s, 1 H); 8.19 (d, 1 H); 8.16 (d, 1 H); 8.04 (s, 1 H); 7.83 (d, 2 H); 7.74 (d, 2 H); 7.62 (d, 1 H); 7.54 (t, 1 H); 7.34 (d, 1 H). |
| 16.18 | 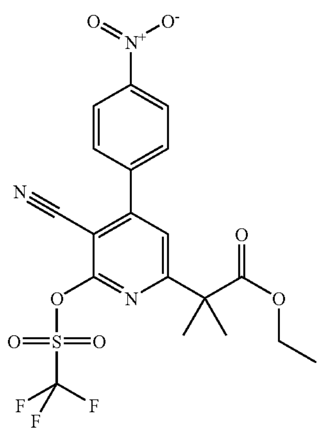 | 2-[5-Cyano-4-(4-nitro-phenyl)-6-trifluoromethanesulfonyloxy-pyridin-2-yl]-2-methyl-propionic acid ethyl ester | $^1$H-NMR (d$_6$-DMSO; 300 MHz): 8.46 (d, 2 H); 8.08 (d, 2 H); 7.99 (s, 1 H); 4.08 (q, 2 H); 1.59 (s, 6 H); 1.12 (t, 3 H). |
| 16.19 | 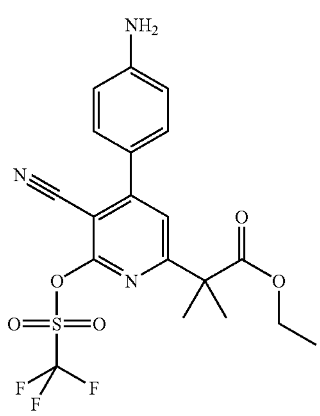 | 2-[4-(4-Amino-phenyl)-5-cyano-6-trifluoromethanesulfonyloxy-pyridin-2-yl]-2-methyl-propionic acid ethyl ester | $^1$H-NMR (d$_6$-DMSO; 400 MHz): 7.69 (s, 1 H); 7.58 (d, 2 H); 6.72 (d, 2 H); 6.00 (br. s, 2 H); 4.06 (q, 2 H); 1.55 (s, 6 H); 1.11 (t, 3 H). |

| Intermediate | Structure | Name | Analytical data |
|---|---|---|---|
| 16.20 | 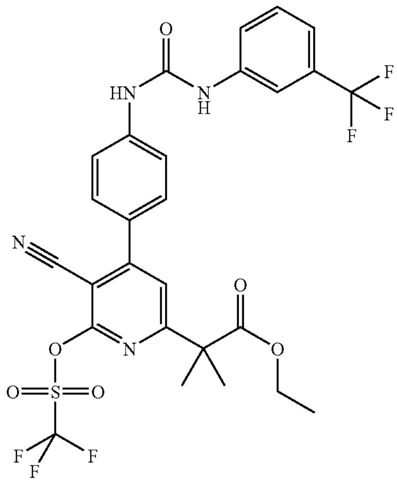 | 2-(5-Cyano-6-trifluoromethanesulfonyloxy-4-{4-[3-(3-trifluoromethyl-phenyl)-ureido]-phenyl}-pyridin-2-yl)-2-methyl-propionic acid ethyl ester | $^1$H-NMR (d$_6$-DMSO; 400 MHz): 9.22 (s, 1 H); 9.21 (s, 1 H); 8.03 (s, 1 H); 7.85 (s, 1 H); 7.80 (d, 2 H); 7.72 (d, 2 H); 7.62 (d, 1 H); 7.54 (t, 1 H); 7.35 (d, 1 H); 4.08 (q, 2 H); 1.59 (s, 6 H); 1.12 (t, 3 H). |
| 16.21 | 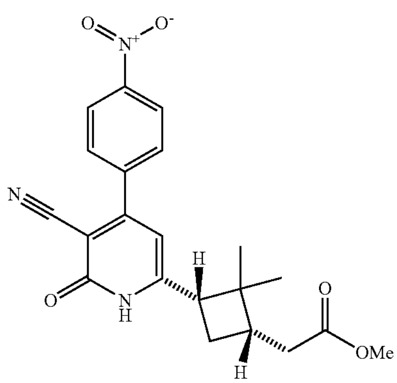 | {3-[5-Cyano-4-(4-nitro-phenyl)-6-oxo-1,6-dihydro-pyridin-2-yl]-2,2-dimethyl-cyclobutyl}-acetic acid methyl ester | $^1$H-NMR (d$_6$-DMSO; 300 MHz): 12.53 (br. s, 1 H); 8.39 (d, 2 H); 7.92 (d, 2 H); 6.42 (s, 1 H); 3.57 (s, 3 H); 3.14 (m, 1 H); 2.42 (m, 1 H); 2.35 (m, 2 H); 2.20 (m, 1 H); 2.08 (m, 1 H); 1.19 (s, 3 H); 0.76 (s, 3 H). |
| 16.22 | 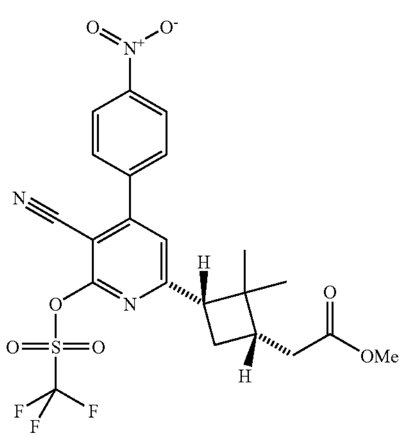 | 3-[5-Cyano-4-(4-nitro-phenyl)-6-trifluoromethane-sulfonyloxy-pyridin-2-yl]-2,2-dimethyl-cyclobutyl}-acetic acid methyl ester | $^1$H-NMR (d$_6$-DMSO; 300 MHz): 8.46 (d, 2 H); 8.06 (d, 2 H); 7.73 (s, 1 H); 3.59 (s, 3 H); 3.45 (m, 1 H); 2.55 (m, 1 H); 2.38 (m, 2 H); 2.24 (m, 2 H); 1.25 (s, 3 H); 0.64 (s, 3 H). |

-continued

| Intermediate | Structure | Name | Analytical data |
|---|---|---|---|
| 16.23 | 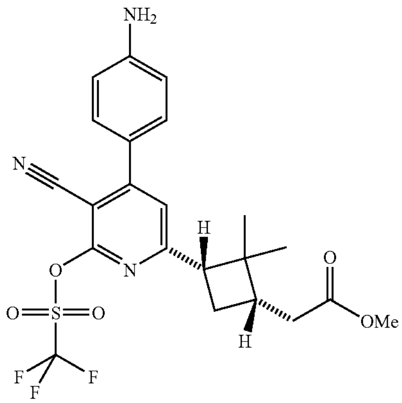 | {3-[4-(4-Amino-phenyl)-5-cyano-6-trifluoromethane-sulfonyloxy-pyridin-2-yl]-2,2-dimethyl-cyclobutyl}-acetic acid methyl ester | $^1$H-NMR (d$_6$-DMSO; 400 MHz): 7.55 (d, 2 H); 7.46 (s, 1 H); 6.71 (d, 2 H); 5.96 (br. s, 2 H); 3.58 (s, 3 H); 3.33 (m, 1 H); 2.54 (m, 1 H); 2.37 (m, 3 H); 2.19 (m, 1 H); 1.23 (s, 3 H); 0.62 (s, 3 H). |
| 16.24 | 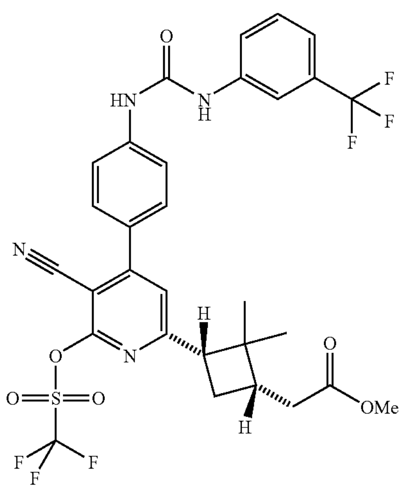 | [3-(5-Cyan-6-trifluoromethane-sulfonyloxy-4-{4-[3-(3-trifluoromethyl-phenyl)-ureido]-phenyl}-pyridin-2-yl)-2,2-dimethyl-cyclobutyl]-acetic acid methyl ester | $^1$H-NMR (d$_6$-DMSO; 400 MHz): 9.21 (s, 1 H); 9.20 (s, 1 H); 8.03 (s, 1 H); 7.76 (d, 2 H); 7.71 (d, 2 H); 7.61 (m, 2 H); 7.54 (m, 1 H); 7.34 (m, 1 H); 3.59 (s, 3 H); 3.41 (m, 1 H); 2.54 (m, 1 H); 2.38 (m, 3 H); 2.22 (m, 1 H); 1.25 (s, 3 H); 0.64 (s, 3 H). |

Intermediate 16.25

Preparation of 1-[4-(3-Amino-6-cyclopropyl-1-methyl-1H-pyrazolo[3,4-b]pyridin-4-yl)-phenyl]-3-(3-trifluoromethyl-phenyl)-urea

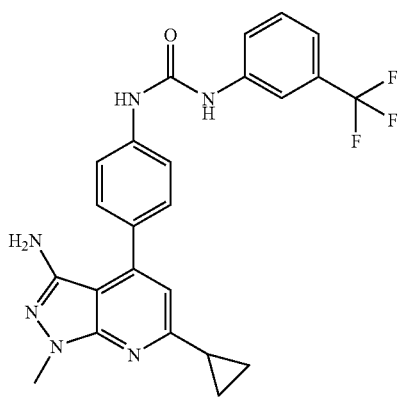

In analogy to GP 4a (step 2), reaction of 1.42 g Intermediate 16.1 (2.49 mmol) with 0.4 mL methyl hydrazine (7.47 mmol, 3 eq.) in 90 mL 1-PrOH yielded 1.1 g of the pyrazolopyridine (95 yield).

$^1$H-NMR (d$_6$-DMSO; 300 MHz): 9.15 (s, 1H); 9.05 (s, 1H); 8.04 (s, 1H); 7.66 (d, 2H); 7.61 (d, 1H); 7.54 (d, 2H); 7.53 (t, 1H); 7.33 (d, 1H); 6.83 (s, 1H); 4.58 (br. s, 2 H); 3.73 (s, 3H); 2.21 (m, 1H); 1.02 (m, 4H).

Intermediate 16.26

Preparation of 1-[4-(3-Amino-6-cyclobutyl-1-methyl-1H-pyrazolo[3,4-b]pyridin-4-yl)-phenyl]-3-(3-trifluoromethyl-phenyl)-urea

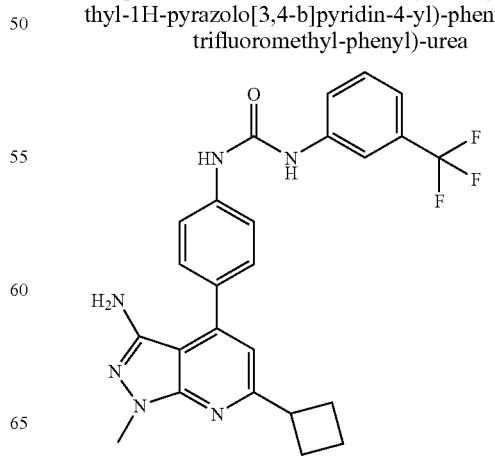

In analogy to GP 4a (step 2), reaction of 755 mg Intermediate 16.5 (1.29 mmol) with 0.21 mL methyl hydrazine (3.88 mmol, 3 eq.) in 41 mL 1-PrOH yielded 490 mg of the pyrazolopyridine (79% yield).

$^{1}$H-NMR (d$_6$-DMSO; 400 MHz): 9.14 (s, 1H); 9.05 (s, 1H); 8.04 (s, 1H); 7.66 (d, 2H); 7.60 (d, 1H); 7.53 (d, 2H); 7.53 (t, 1H); 7.33 (d, 1H); 6.78 (s, 1H); 4.62 (br. s, 2H); 3.81 (s, 3H); 3.74 (m, 1H); 2.38 (m, 2H); 2.31 (m, 2H); 2.02 (m, 1H); 1.87 (m, 1H).

Intermediate 16.27

Preparation of 1-[4-(3-Amino-6-cyclohexyl-1-methyl-1H-pyrazolo[3,4-b]pyridin-4-yl)-phenyl]-3-(3-trifluoromethyl-phenyl)-urea

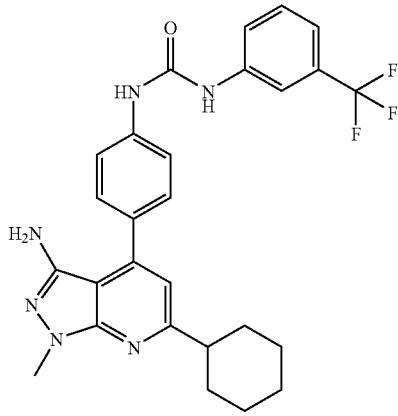

In analogy to GP 4a (step 2), reaction of 2.04 g Intermediate 16.9 (3.33 mmol) with 0.53 mL methyl hydrazine (9.99 mmol, 3 eq.) in 105 mL 1-PrOH yielded 1.38 g of the pyrazolopyridine (81% yield).

$^{1}$H-NMR (d$_6$-DMSO; 400 MHz): 9.13 (s, 1H); 9.05 (s, 1H); 8.04 (s, 1H); 7.66 (d, 2H); 7.60 (d, 1H); 7.54 (d, 2H); 7.53 (t, 1H); 7.33 (d, 1H); 6.80 (s, 1H); 4.61 (br. s, 2H); 3.79 (s, 3H); 2.77 (m, 1H); 1.91 (m, 2H); 1.82 (m, 2H); 1.72 (m, 1H); 1.61 (m, 2H); 1.39 (m, 2H); 1.27 (m, 1H).

Intermediate 16.28

Preparation of 1-{4-[3-Amino-1-methyl-6-(2-phenyl-cyclopropyl)-1H-pyrazolo[3,4-b]pyridin-4-yl]-phenyl}-3-(3-trifluoromethyl-phenyl)-urea

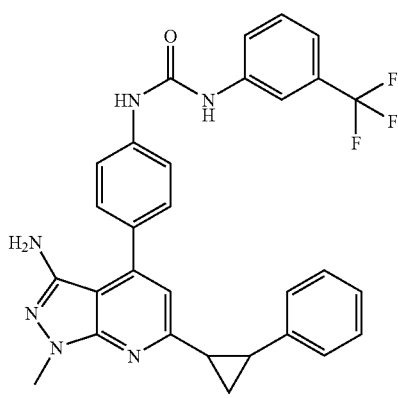

In analogy to GP 4a (step 2), reaction of 659 mg Intermediate 16.13 (1.02 mmol) with 0.16 mL methyl hydrazine (3.06 mmol, 3 eq.) in 32 mL 1-PrOH yielded 415 mg of the pyrazolopyridine (75% yield).

$^{1}$H-NMR (d$_6$-DMSO; 400 MHz): 9.13 (s, 1H); 9.02 (s, 1H); 8.04 (s, 1H); 7.60 (d, 3H); 7.53 (t, 1H); 7.33 (d, 3H); 7.22 (d, 2H); 7.13 (t, 2H); 7.05 (t, 1H); 6.59 (s, 1H); 4.52 (br. s, 2H); 3.66 (s, 3H); 2.73 (m, 2H); 2.01 (m, 1H); 1.51 (m, 1H).

Intermediate 16.29

Preparation of 1-[4-(3-Amino-1-methyl-6-thiazol-2-yl-1H-pyrazolo[3,4-b]pyridin-4-yl)-phenyl]-3-(3-trifluoromethyl-phenyl)-urea

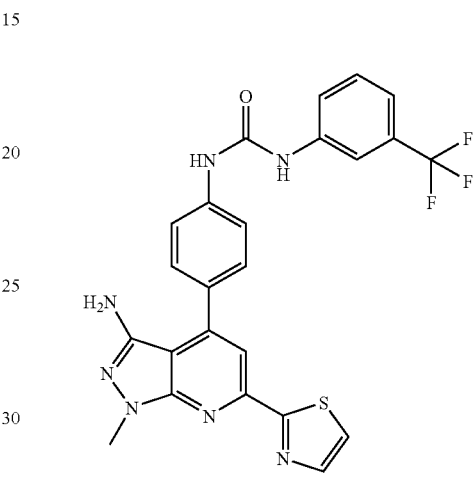

In analogy to GP 4a (step 2), reaction of 186 mg Intermediate 16.17 (0.3 mmol) with 0.048 mL methyl hydrazine (0.91 mmol, 3 eq.) in 11 mL 1-PrOH yielded 142 mg of the pyrazolopyridine (92% yield).

$^{1}$H-NMR (d$_6$-DMSO; 300 MHz): 9.16 (s, 1H); 9.10 (s, 1H); 8.05 (s, 1H); 8.02 (d, 1H); 7.93 (d, 1H); 7.71 (s, 1H); 7.70 (d, 2H); 7.63 (d, 2H); 7.61 (d, 1H); 7.54 (t, 1H); 7.33 (d, 1H); 4.82 (br. s, 2H); 3.88 (s, 3H).

Intermediate 16.30

Preparation of 2-(3-Amino-1-methyl-4-{4-[3-(3-trifluoromethyl-phenyl)-ureido]-phenyl}-1H-pyrazolo[3,4-b]pyridin-6-yl)-2-methyl-propionic acid ethyl ester

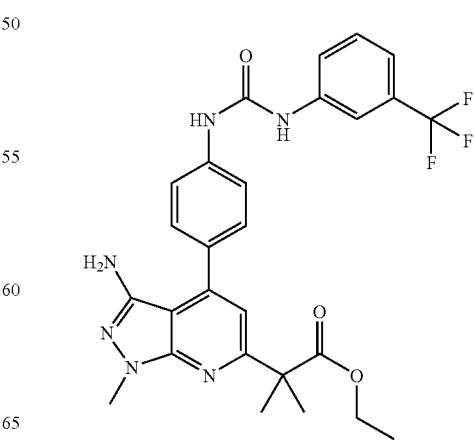

In analogy to GP 4a (step 2), reaction of 727 mg Intermediate 16.20 (1.13 mmol) with 0.18 ml methyl hydrazine (3.38 mmol, 3 eq.) in 35 mL 1-PrOH yielded 592 mg of the pyrazolopyridine (97% yield).

$^1$H-NMR (d$_6$-DMSO; 400 MHz): 9.14 (s, 1H); 9.07 (s, 1H); 8.04 (s, 1H); 7.67 (d, 2H); 7.61 (d, 1H); 7.54 (d, 2H); 7.53 (t, 1H); 7.33 (d, 1H); 6.86 (s, 1H); 4.68 (br. s, 2H); 4.12 (q, 2H); 3.78 (s, 3H); 1.59 (s, 6H); 1.14 (t, 3H).

Intermediate 16.31

Preparation of 2-(3-Amino-1-methyl-4-{4-[3-(3-trifluoromethyl-phenyl)-ureido]-phenyl}-1H-pyrazolo[3,4-b]pyridin-6-yl)-2-methyl-propionic acid

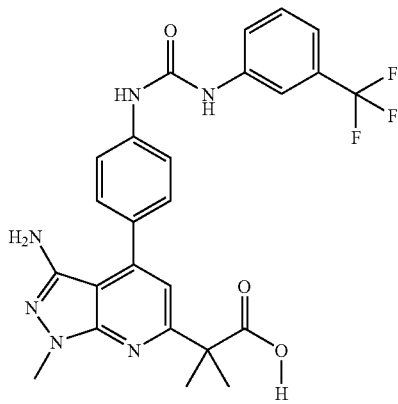

In analogy to GP 9, reaction of 592 mg Intermediate 16.30 (1.1 mmol, 1 eq.) with 1.8 ml sodium hydroxide solution (1.8 mmol, 1.64 eq.) in 15 ml EtOH yielded 477 mg of the desired product (85% yield).

$^1$H-NMR (d$_6$-DMSO; 400 MHz): 12.36 (br. s, 1H); 9.14 (s, 1H); 9.08 (s, 1H); 8.04 (s, 1H); 7.67 (d, 2H); 7.61 (d, 1H); 7.54 (d, 2H); 7.53 (t, 1H); 7.33 (d, 1H); 6.87 (s, 1H); 4.68 (br. s, 2H); 3.79 (s, 3H); 1.58 (s, 6H).

Intermediate 16.32

Preparation of 2-(3-Amino-1-methyl-4-{4-[3-(3-trifluoromethyl-phenyl)-ureido]-phenyl}-1H-pyrazolo[3,4-b]pyridin-6-yl)-N,N-dimethyl-isobutyramide

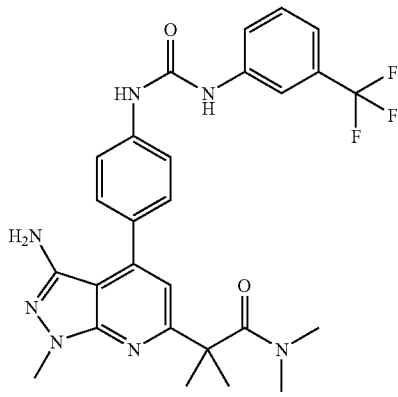

In analogy to GP 10, reaction of 442 mg Intermediate 16.31 (0.86 mmol, 1 eq.) with 0.65 ml dimethylamine (1.29 mmol, 1.5 eq.), 0.47 ml 4-methylmorpholine (5 eq.) and 1.02 ml 2,4,6-tripropyl-[1,3,5,2,4,6]trioxatriphosphinane 2,4,6-trioxide (T3P; 2 eq.) in 25.5 ml DCM yielded 137 mg of the desired product (29% yield).

$^1$H-NMR (d$_6$-DMSO; 300 MHz): 9.15 (s, 1H); 9.10 (s, 1H); 8.04 (s, 1H); 7.66 (d, 2H); 7.61 (d, 1H); 7.54 (d, 2H); 7.53 (t, 1H); 7.33 (d, 1H); 6.64 (s, 1H); 4.69 (br. s, 2H); 3.80 (s, 3H); 2.81 (br. s, 3H); 2.46 (br. s, 3H); 1.54 (s, 6H).

Intermediate 16.33

Preparation of 2-(3-Amino-1-methyl-4-{4-[3-(3-trifluoromethyl-phenyl)-ureido]-phenyl}-1H-pyrazolo[3,4-b]pyridin-6-yl)-N-cyclopropyl-isobutyramide

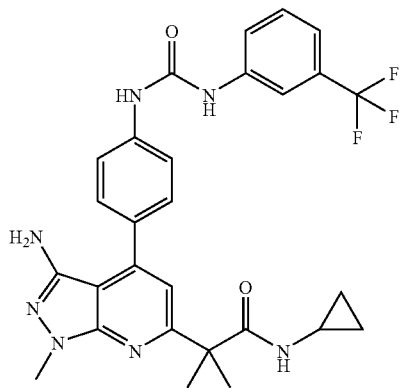

In analogy to GP 10, reaction of 228 mg Intermediate 16.31 (0.44 mmol, 1 eq.) with 0.36 ml cyclopropylamine (0.67 mmol, 1.5 eq.), 0.24 ml 4-methylmorpholine (5 eq.) and 0.52 ml 2,4,6-tripropyl-[1,3,5,2,4,6]trioxatriphosphinane 2,4,6-trioxide (T3P; 2 eq.) in 25 ml DCM yielded 210 mg of the desired product (86% yield).

$^1$H-NMR (d$_6$-DMSO; 400 MHz): 9.15 (s, 1H); 9.07 (s, 1H); 8.04 (s, 1H); 7.67 (d, 2H); 7.60 (d, 1H); 7.53 (t, 1H); 7.50 (d, 2H); 7.45 (m, 1H); 7.33 (d, 1H); 6.77 (s, 1H); 4.66 (br. s, 2H); 3.81 (s, 3H); 2.63 (m, 1H); 1.52 (s, 6H); 0.56 (m, 2H); 0.39 (m, 2H).

Intermediate 16.34

Preparation of [3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid methyl ester

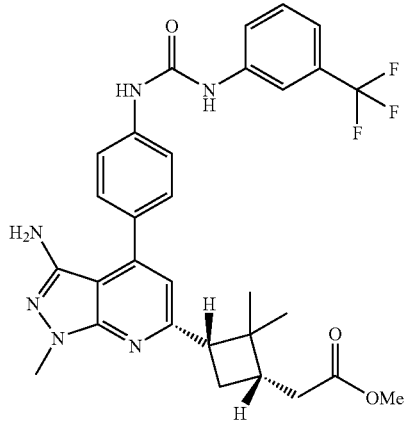

In analogy to GP 4a (step 2), reaction of 1.85 g Intermediate 16.24 (2.7 mmol) with 0.44 ml methyl hydrazine (8.28 mmol, 3.06 eq.) in 100 mL 1-PrOH yielded 1.13 g of the pyrazolopyridine (72% yield).

¹H-NMR (d₆-DMSO; 300 MHz): 9.13 (s, 1H); 9.05 (s, 1H); 8.04 (s, 1H); 7.66 (d, 2H); 7.61 (m, 1H); 7.54 (d, 2H); 7.53 (m, 1H); 7.33 (m, 1H); 6.64 (s, 1H); 4.62 (br. s, 2H); 3.81 (s, 3H); 3.59 (s, 3H); 3.44 (m, 1H); 2.54 (m, 1H); 2.38 (m, 3H); 2.19 (m, 1H); 1.27 (s, 3H); 0.62 (s, 3H).

Intermediate 16.35

Preparation of [3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-acetic acid

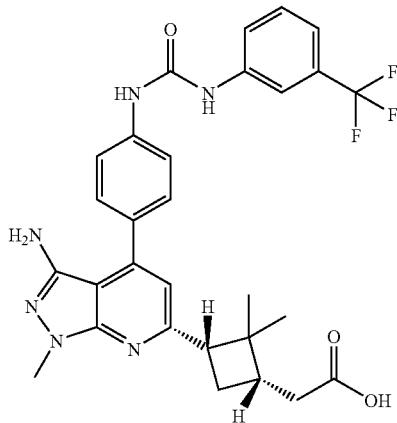

In analogy to GP 9, reaction of 407 mg Intermediate 16.34 (0.7 mmol, 1 eq.) with 1.05 ml sodium hydroxide solution (1.05 mmol, 1.5 eq.) in 17 ml EtOH yielded 384 mg of the desired product (97% yield).

¹H-NMR (d₆-DMSO; 300 MHz): 12.01 (br. s, 1H); 9.12 (s, 1H); 9.05 (s, 1H); 8.04 (s, 1H); 7.66 (d, 2H); 7.61 (m, 1H); 7.54 (d, 2H); 7.53 (m, 1H); 7.33 (m, 1H); 6.64 (s, 1H); 4.62 (br. s, 2H); 3.81 (s, 3H); 3.41 (m, 1H); 2.47-2.12 (m, 5H); 1.28 (s, 3H); 0.62 (s, 3H).

Intermediate 16.36

Preparation of 2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N,N-dimethylacetamide

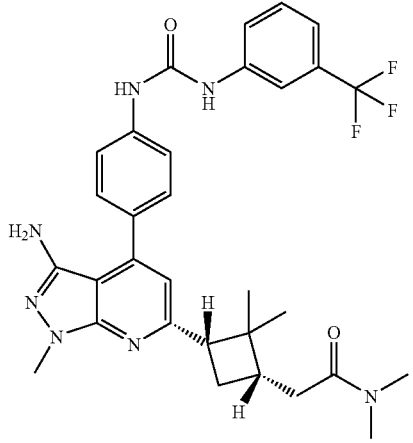

In analogy to GP 19, reaction of 369 mg Intermediate 16.35 (0.65 mmol, 1 eq.) with 0.49 ml dimethylamine (0.98 mmol, 1.5 eq.), 0.36 ml 4-methylmorpholine (5 eq.) and 0.77 ml 2,4,6-tripropyl-[1,3,5,2,4,6]trioxatriphosphinane 2,4,6-trioxide (T3P; 2 eq.) in 16.28 ml DCM yielded 181 mg of the desired product (31% yield).

¹H-NMR (d₆-DMSO; 300 MHz): 9.14 (s, 1H); 9.06 (s, 1H); 8.04 (s, 1H); 7.66 (d, 2H); 7.61 (m, 1H); 7.54 (d, 2H); 7.52 (m, 1H); 7.33 (m, 1H); 6.63 (s, 1H); 4.62 (br. s, 2H); 3.81 (s, 3H); 3.44 (m, 1H); 2.98 (s, 3H); 2.81 (s, 3H); 2.44 (m, 1H); 2.33 (m, 3H); 2.16 (m, 1H); 1.28 (s, 3H); 0.62 (s, 3H).

Intermediate 16.37

Preparation of 2-[3-(3-Amino-1-methyl-4-{4-[3-(3-trifluoromethyl-phenyl)-ureido]-phenyl}-1H-pyrazolo[3,4-b]pyridin-6-yl)-2,2-dimethyl-cyclobutyl]-N-cyclopropylacetamide

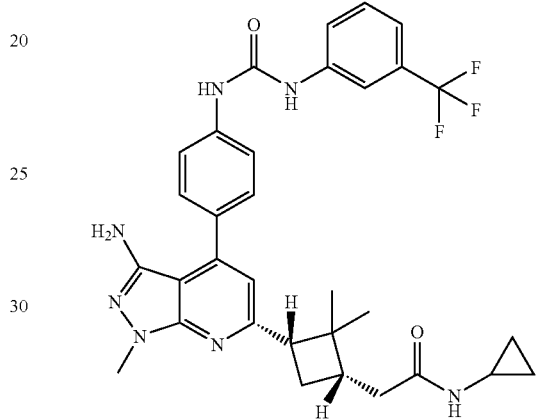

In analogy to GP 10, reaction of 691 mg Intermediate 16.35 (1.22 mmol, 1 eq.) with 0.17 ml cyclopropylamine (2.44 mmol, 2 eq.), 0.67 ml 4-methylmorpholine (5 eq.) and 1.44 ml 2,4,6-tripropyl-[1,3,5,2,4,6]trioxatriphosphinane 2,4,6-trioxide (T3P; 2 eq.) in 38.46 ml DCM yielded 354 mg of the desired product (48% yield).

¹H-NMR (d₆-DMSO; 300 MHz): 9.13 (s, 1H); 9.06 (s, 1H); 8.04 (s, 1H); 7.84 (d, 1H); 7.66 (d, 2H); 7.61 (m, 1H); 7.54 (d, 2H); 7.52 (m, 1H); 7.33 (m, 1H); 6.61 (s, 1H); 4.61 (br. s, 2H); 3.81 (s, 3H); 3.31 (m, 1H); 2.58 (m, 1H); 2.44-1.95 (m, 5H); 1.25 (s, 3H); 0.61 (s, 3H); 0.59 (m, 2H); 0.36 (m, 2H).

Intermediate 16.38

Preparation of 1-[4-(3-Amino-6-cyclopropyl-1H-pyrazolo[3,4-b]pyridin-4-yl)-phenyl]-3-(3-trifluoromethyl-phenyl)-urea

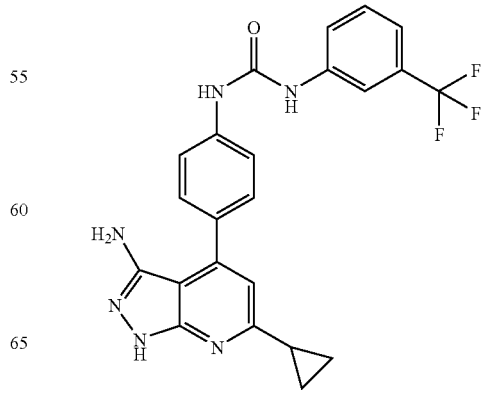

In analogy to GP 4c (step 2), reaction of 1.08 g Intermediate 16.1 (1.89 mmol) with 5.68 mL hydrazine hydrate (5.68 mmol, 3 eq.) in 60 mL 1-PrOH yielded 639 mg of the pyrazolopyridine (75% yield).

$^1$H-NMR (d$_6$-DMSO; 300 MHz): 9.13 (s, 1H); 9.04 (s, 1H); 8.04 (s, 1H); 7.66 (d, 2H); 7.58 (t, 1H); 7.54 (d, 2H); 7.51 (d, 1H); 7.32 (d, 1H); 6.87 (s, 1H); 2.21 (m, 1H); 1.01 (m, 4H).

Intermediate 17.1

Preparation of 2-Cyano-3-(4-nitro-phenyl)-acrylic acid ethyl ester

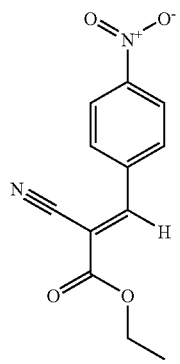

45.3 g (300 mmol, 1 eq.) 4-nitrobenzaldehyde and 32 mL cyano-acetic acid ethyl ester (300 mmol, 1 eq.) were dissolved in 90 mL 1,4-dioxane and treated at 0° C. with 1.2 mL (12 mmol, 4 mot %) piperidine. Upon precipitation additional 1,4-dioxane was added (350 mL) and stirring was continued at room temperature for 1 h. The solid was filtered off and washed with ice-cold ethanol. The filtrate was concentrated and the newly formed precipitate collected to give a combined yield of 66.5 g (270 mmol, 90% yield) of the acrylic ester.

$^1$H-NMR (d$_6$-DMSO; 400 MHz): 8.52 (s, 1H); 8.37 (d, 2H); 8.21 (d, 2H); 4.31 (q, 2H); 1.29 (t, 3H).

Intermediate 17.2

Preparation of 5-Cyano-4-(4-nitro-phenyl)-6-oxo-1,6-dihydro-pyridine-2-carboxylic acid ethyl ester

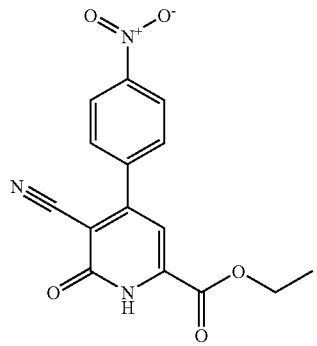

31.2 g 2-Cyano-3-(4-nitro-phenyl)-acrylic acid ethyl ester (Intermediate 17.1; 126.7 mmol, 1 eq.) were suspended in a solution of 12.67 g ammonium acetate (165 mmol, 1.3 eq.) in 1270 ml ethanol and treated at room temperature with 14.08 ml of 2-oxo-propionic acid ethyl ester (126.7 mmol. 1 eq.). The resulting mixture was refluxed for 2 h and stirred at rt overnight. The precipitate was filtered off, washed with ice-cold EtOH and dried to yield 11 g of the target pyridone (35 mmol, 28% yield).

$^1$H-NMR (d$_6$-DMSO; 300 MHz): 8.29 (d, 2H); 7.76 (d, 2H); 6.67 (s, 1H); 4.21 (q, 2H); 1.25 (t, 3H).

Intermediate 17.3

Preparation of 5-Cyano-4-(4-nitro-phenyl)-6-trifluoromethanesulfonyloxy-pyridine-2-carboxylic acid ethyl ester

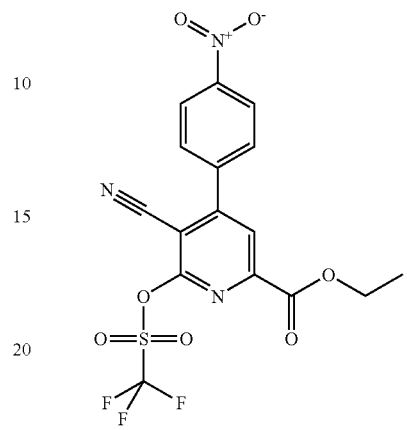

In analogy to GP2, 1 g of 5-cyano-4-(4-nitro-phenyl)-6-oxo-1,6-dihydro-pyridine-2-carboxylic acid ethyl ester (Intermediate 17.2; 3.19 mmol, 1 eq.) were dissolved in 150 mL CH$_2$Cl$_2$, cooled to 0° C. and treated sequentially with 0.39 mL pyridine (4.8 mmol, 1.5 eq.) and dropwise with 0.81 mL triflate anhydride (4.8 mmol, 1.5 eq.). The resulting brownish solution was stirred at rt for 2 h, quenched with saturated NaHCO$_3$ solution and extracted with CH$_2$Cl$_2$. The combined organic layers were dried and concentrated in vacuo. Flash column chromatography of the residue provided 1000 mg of the desired pyridyl triflate (2.24 mmol, 70% yield).

$^1$H-NMR (d$_6$-DMSO; 300 MHz): 8.45 (d, 2H); 8.39 (s, 1H); 8.04 (d, 2H); 4.39 (q, 2H); 1.31 (t, 3H).

Intermediate 17.4

Preparation of 3-Amino-1-methyl-4-(4-nitro-phenyl)-1H-pyrazolo[3,4-b]pyridine-6-carboxylic acid ethyl ester

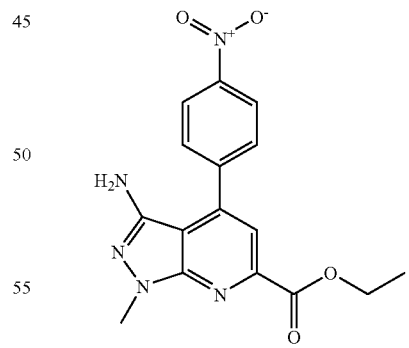

In analogy to GP4a (step 2), 15.4 g of 5-cyano-4-(4-nitro-phenyl)-6-trifluoromethanesulfonyloxy-pyridine-2-carboxylic acid ethyl ester (Intermediate 17.3; 34.6 mmol, 1 eq.) were dissolved in 820 mL 1-PrOH, treated with 3.22 mL methyl hydrazine (60.5 mmol, 1.75 eq.) and heated 110° C. for 2 h. The reaction mixture was cooled with ice and the precipitate filtered and washed with EtOH. The filtrate was concentrated, the newly formed solid was filtered and washed with ice-cold EtOH to provide a combined yield of 10.2 g of the 3-aminopyrazolopyridine (29.9 mmol, 86% yield).

¹H-NMR (d₆-DMSO; 300 MHz): 8.35 (d, 2H); 7.86 (d, 2H); 7.56 (s, 1H); 4.93 (br. s, 2H); 4.36 (q, 2H); 3.86 (s, 3H); 1.32 (t, 3H).

Intermediate 17.5

Preparation of 3-Amino-1-methyl-4-(4-nitro-phenyl)-1H-pyrazolo[3,4-b]pyridin-6-yl]-methanol

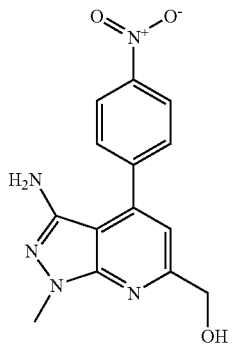

16.94 g of 3-amino-1-methyl-4-(4-nitro-phenyl)-1H-pyrazolo[3,4-b]pyridine-6-carboxylic acid ethyl ester (Intermediate 17.4; 49.6 mmol, 1 eq.) were dissolved in dry THF (1490 mL) and treated at 0° C. with 124 mL diisobutylaluminum hydride (DIBAH) solution (1.0 M in THF; 2.5 eq.; 20 min addition time) and subsequently stirred for 2 h at rt. Additional 74.4 mL DIBAH (74.4 mmol, 1.5 eq.) were added at 0° C. and stirring was continued at rt for 1.5 h. Aqueous work-up and extraction provided after concentration the crude benzylic alcohol (quantitative yield), which was used without further purification.

¹H-NMR (d₆-DMSO; 300 MHz): 8.35 (d, 2H); 7.82 (d, 2H); 7.09 (s, 1H); 5.54 (t, 1H); 4.71 (br. s, 2H); 4.63 (d, 2H); 3.78 (s, 3H).

Intermediate 17.6

Preparation of [1-Methyl-4-(4-nitro-phenyl)-1H-pyrazolo[3,4-b]pyridin-6-yl]-methanol

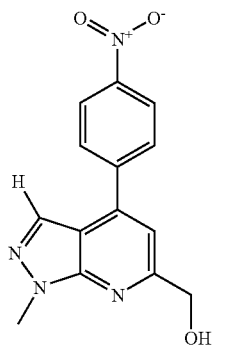

In analogy to GP 6, 14.8 g of 3-amino-1-methyl-4-(4-nitrophenyl)-1H-pyrazolo[3,4-b]pyridin-6-yl]-methanol (49.5 mmol, 1 eq.) were dissolved in 2200 mL EtOH, treated with 3.95 mL concentrated sulphuric acid (74.18 mmol, 1.5 eq.), heated to reflux and treated portionwise with 8.53 g NaNO₂ (123.6 mmol, 2.5 eq.). Stirring was continued after complete addition for 45 min upon which the reaction mixture was concentrated in vacuo. The residue was partitioned between CH₂Cl₂ and half-concentrated aq. NaHCO₃ solution, the organic layer was separated and the aqueous layer was re-extracted several times with CH₂Cl₂. The combined organic layers were dried, concentrated in vacuo and the residue (11.05 g, 38.8 mmol, 79% yield) was used without further purification in the subsequent transformations.

¹H-NMR (d₆-DMSO; 300 MHz): 8.38 (d, 2H); 8.29 (s, 1H); 8.11 (d, 2H); 7.57 (s, 1H); 5.64 (t, 1H); 4.73 (d, 2H); 4.05 (s, 3H).

Intermediate 17.7 [=Intermediate 13.1]

Preparation of 6-Bromomethyl-1-methyl-4-(4-nitrophenyl)-1H-pyrazolo[3,4-b]pyridine

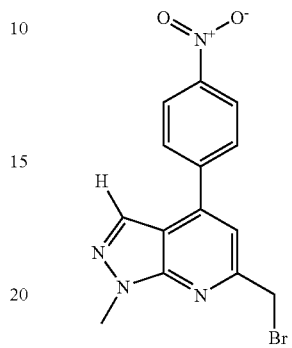

11 g of [1-Methyl-4-(4-nitro-phenyl)-1H-pyrazolo[3,4-b]pyridin-6-yl]-methanol (Intermediate 17.6; 38.7 mmol, 1 eq.) were dissolved in 68 mL HBr (32% in AcOH) and heated to reflux for 1 h. The reaction mixture was poured onto an ice/NaOH mixture and adjusted to neutral pH. The mixture was extracted with CH₂Cl₂ several times, the combined organic layers were dried and concentrated in vacuo. Recrystallization of the residue from hexane provided 8.18 g of the bromide (23.6 mmol, 61% yield).

¹H-NMR (d₆-DMSO; 300 MHz): 8.39 (d, 2H); 8.36 (s, 1H); 8.13 (d, 2H); 7.69 (s, 1H); 4.88 (s, 2H); 4.08 (s, 3H).

MS (LC-MS-ESI): [M+H]⁺=347, 349 (Br₁-isotope pattern).

Intermediate 17.8

Preparation of 1-Methyl-6-(4-methyl-piperazin-1-ylmethyl)-4-(4-nitro-phenyl)-1H-pyrazolo[3,4-b]pyridine

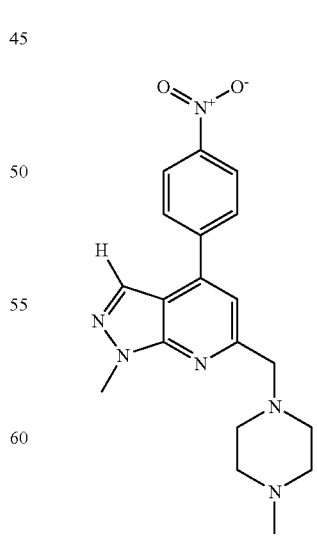

900 mg of 6-bromomethyl-1-methyl-4-(4-nitro-phenyl)-1H-pyrazolo[3,4-b]pyridine (Intermediate 17.7; 2.59 mmol, 1 eq.) were dissolved in 13.5 mL DMF and treated sequentially with 0.54 mL Et₃N (3.9 mmol, 1.5 eq.) and 0.35 mL methyl piperazine (3.11 mmol, 1.2 eq.). The reaction mixture was heated to 90° C. for 45 min, partitioned between $CH_2Cl_2$ and water, the aqueous layer was re-extracted and the combined organic layers were dried and concentrated in vacuo to yield the crude piperazine product, which was used without further purification.

¹H-NMR (d₆-DMSO; 300 MHz): 8.38 (d, 2H); 8.27 (s, 1H); 8.09 (d, 2H); 7.52 (s, 1H); 4.06 (s, 3H); 3.74 (s, 2H); 2.2-2.35 (m, 4H); 2.11 (s, 3H).

MS (ESI): $[M+H]^+$=367.

The following synthetic intermediates 17.9 to 17.10 were synthesized in analogy to the before described reaction by reacting Intermediate 17.7 with the corresponding amines.

| Intermediate | Structure | Name | Analytical data |
|---|---|---|---|
| 17.9 | 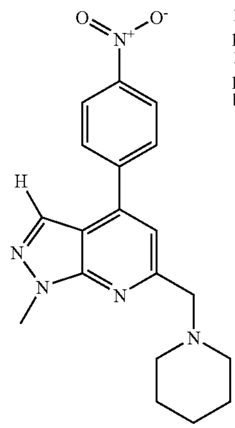 | 1-Methyl-4-(4-nitro-phenyl)-6-piperidin-1-ylmethyl-1H-pyrazolo[3,4-b]pyridine | ¹H-NMR (d₆-DMSO; 300 MHz): 8.37 (d, 2 H); 8.27 (s, 1 H); 8.09 (d, 2 H); 7.54 (s, 1 H); 4.05 (s, 3 H); 3.73 (s, 2 H); 2.38-2.45 (m, 4 H); 1.32-1.65 (m, 6 H). MS (ESI): $[M + H]^+ = 352$. |
| 17.10 | 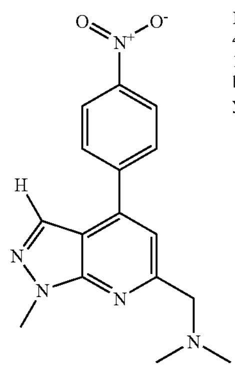 | Dimethyl-[1-methyl-4-(4-nitro-phenyl)-1H-pyrazolo[3,4-b]pyridin-6-ylmethyl]-amine | ¹H-NMR (d₆-DMSO; 300 MHz): 8.36 (d, 2 H); 8.28 (s, 1 H); 8.10 (d, 2 H); 7.53 (s, 1 H); 4.05 (s, 3 H); 3.68 (s, 2 H); 2.22 (s, 6 H). MS (ESI): $[M + H]^+ = 312$. |

Intermediate 17.11

Preparation of 4-[1-Methyl-6-(4-methyl-piperazin-1-ylmethyl)-1H-pyrazolo[3,4-b]pyridin-4-yl]-phenylamine

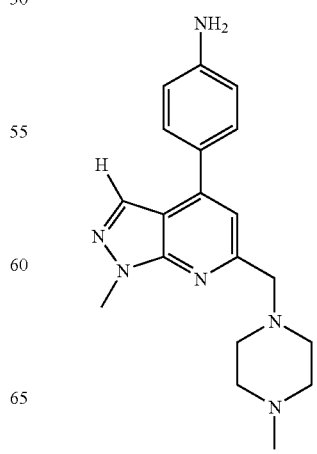

| Intermediate | Structure | Name | Analytical data |
|---|---|---|---|
| 17.12 | ![structure] | 4-(1-Methyl-6-piperidin-1-ylmethyl-1H-pyrazolo[3,4-b]pyridin-4-yl)-phenylamine | $^1$H-NMR (d$_6$-DMSO; 300 MHz): 8.20 (s, 1 H); 7.56 (d, 2 H); 7.30 (s, 1 H); 6.70 (d, 2 H); 5.59 (s, 2 H); 3.98 (s, 3 H); 3.61 (s, 2 H); 2.32-2.42 (m, 4 H); 1.43-1.52 (m, 4 H); 1.32-1.41 (m, 2 H). MS (ESI): [M + H]$^+$ = 322. |
| 17.13 | ![structure] | 4-(6-Dimethylaminomethyl-1-methyl-1H-pyrazolo[3,4-b]pyridin-4-yl)-phenylamine | $^1$H-NMR (d$_6$-DMSO; 300 MHz): 8.21 (s, 1 H); 7.57 (d, 2 H); 7.30 (s, 1 H); 6.69 (d, 2 H); 5.59 (s, 2 H); 3.99 (s, 3 H); 3.59 (s, 2 H); 2.20 (s, 6 H). MS (ESI): [M + H]$^+$ = 282. |

Intermediate 18.1

Preparation of 6-Methanesulfonylmethyl-1-methyl-4-(4-nitro-phenyl)-1H-pyrazolo[3,4-b]pyridine

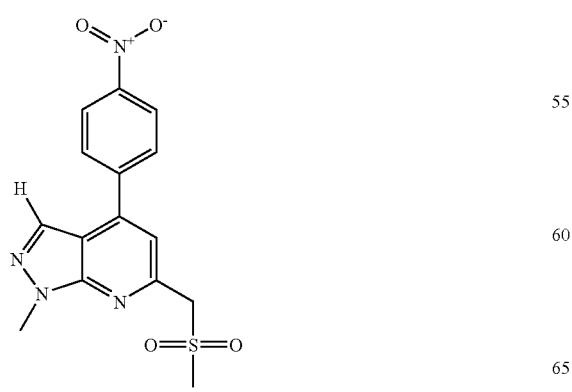

1.04 g 6-bromomethyl-1-methyl-4-(4-nitro-phenyl)-1H-pyrazolo[3,4-b]pyridine (Intermediate 13.1; 3 mmol, 1 eq.) were dissolved in 55 mL 10:1 EtOH/DMF, treated with 459 mg sodium methanesulfinate (4.5 mmol, 1.5 eq.) and refluxed for 150 min. The mixture was cooled to rt and concentrated in vacuo. Addition of water was followed by precipitation to yield 1040 mg of the crude product (quantitative yield).

$^1$H-NMR (d$_6$-DMSO; 300 MHz): 8.45 (d, 2H); 8.44 (s, 1H); 8.16 (d, 2H); 7.68 (s, 1H); 4.91 (s, 2H); 4.14 (s, 3H); 3.18 (s, 3H).

MS (ESI): [M+H]$^+$=347.

Intermediate 18.2

Preparation of 4-(6-Methanesulfonylmethyl-1-methyl-1H-pyrazolo[3,4-b]pyridin-4-yl)-phenylamine

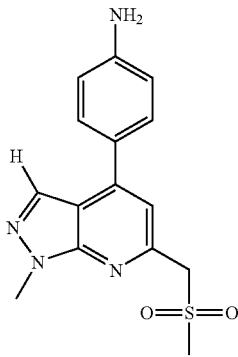

In analogy to GP3, reaction of 1000 mg 6-methanesulfonylmethyl-1-methyl-4-(4-nitro-phenyl)-1H-pyrazolo[3,4-b]pyridine (Intermediate 18.1; 2.89 mmol, 1 eq.) with 3.26 g SnCl$_2$.2H$_2$O (14.46 mmol, 5 eq.) in 56 mL 2.5:1 EtOH/THF at reflux for 3 h yielded after standard work-up the crude aniline which was used without further purification.

$^1$H-NMR (d$_6$-DMSO; 300 MHz): 8.36 (s, 1H); 7.64 (d, 2H); 7.42 (s, 1H); 6.76 (d, 2H); 5.73 (s, 2H); 4.79 (s, 2H); 4.07 (s, 3H); 3.15 (s, 3H).

MS (ESI): [M+H]$^+$=317.

PREPARATION OF EXAMPLE COMPOUNDS

Example Compound 1.1

Preparation of 1-[4-(6-tert-Butyl-1H-pyrazolo[3,4-b]pyridin-4-yl)-phenyl]-3-(3-ethylphenyl)-urea

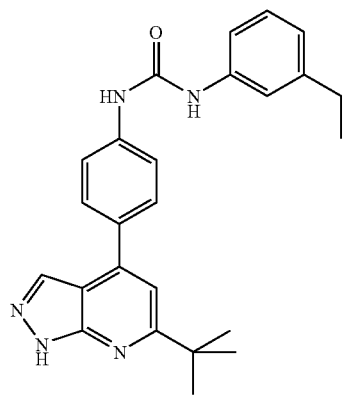

In analogy to GP 6, reaction of 95.6 mg of 1-[4-(3-amino-6-tert-butyl-1H-pyrazolo-[3,4-b]pyridin-4-yl)-phenyl]-3-(3-ethyl-phenyl)-urea (0.22 mmol, 1 eq.) with 35 μL concentrated sulphuric acid and 38 mg sodium nitrite (2.5 eq.) yielded 39 mg of the desired product (42% yield).

$^1$H-NMR (d$_6$-DMSO; 300 MHz): 8.91 (s, 1H); 8.64 (s, 1H); 8.24 (s, 1H); 7.81 (d, 2H); 7.64 (d, 2H); 7.36 (s, 1H); 7.31 (s, 1H); 7.25 (d, 1H); 7.16 (t, 1H); 6.81 (d, 1H); 2.55 (q, 2H); 1.40 (s, 9H); 1.15 (t, 3H) (salt form).

MS (ESI): [M+H]$^+$=414.

Example Compound 1.2

Preparation of 1-[4-(6-Isopropyl-1H-pyrazolo[3,4-b]pyridin-4-yl)-phenyl]-3-(3-trifluoromethyl-phenyl)-urea

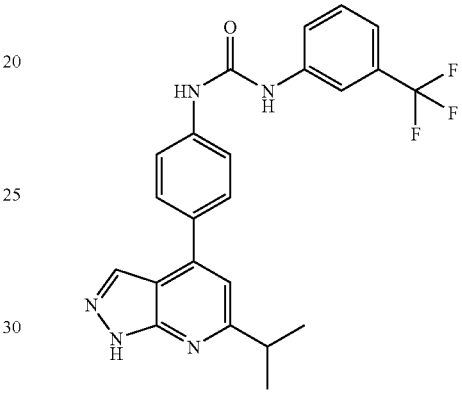

In analogy to GP 6, reaction of 100 mg of 1-[4-(3-Amino-6-isopropyl-1H-pyrazolo[3,4-b]pyridin-4-yl)-phenyl]-3-(3-trifluoromethyl-phenyl)-urea (0.22 mmol, 1 eq.) with 35 μL concentrated sulphuric acid and 37 mg sodium nitrite (2.5 eq.) yielded 72 mg of the desired product (74% yield).

$^1$H-NMR (d$_6$-DMSO; 400 MHz): 13.53 (br. s, 1H); 9.11 (s, 1H); 9.07 (s, 1H); 8.22 (s, 1H); 8.01 (s, 1H); 7.82 (d, 2H); 7.65 (d, 2H); 7.58 (d, 1H); 7.50 (t, 1H); 7.30 (d, 1H); 7.23 (s, 1H); 3.18 (sept., 1H); 1.30 (d, 6H). MS (ESI): [M+H]$^+$=440.

Example Compound 1.3

Preparation of 1-[4-(6-Isopropyl-1-methyl-1H-pyrazolo[3,4-b]pyridin-4-yl)-phenyl]-3-(3-trifluoromethyl-phenyl)-urea

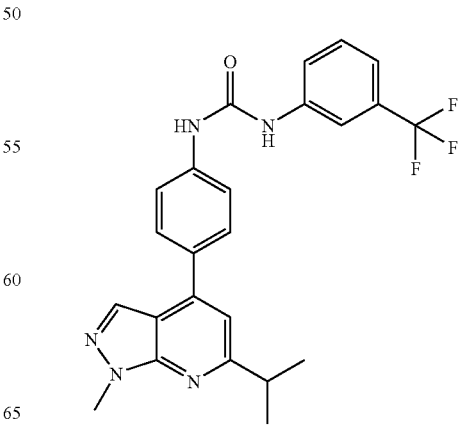

In analogy to GP 6, reaction of 200 mg of 1-[4-(3-Amino-6-isopropyl-1-methyl-1H-pyrazolo[3,4-b]pyridin-4-yl)-phenyl]-3-(3-trifluoromethyl-phenyl)-urea (0.43 mmol, 1 eq.) with 67 µL concentrated sulphuric acid and 146 mg sodium nitrite (5 eq.) yielded 23 mg of the desired product (12% yield).

$^1$H-NMR (d$_6$-DMSO; 300 MHz): 9.10 (s, 1H); 9.07 (s, 1H); 8.23 (s, 1H); 8.00 (s, 1H); 7.83 (d, 2H); 7.65 (d, 2H); 7.58 (d, 1H); 7.50 (t, 1H); 7.30 (d, 1H); 7.26 (s, 1H); 4.02 (s, 3H); 3.19 (sept., 1H); 1.32 (d, 6H).

MS (LC-MS): [M+H]$^+$=454.

Example Compound 1.4

Preparation of 1-[4-(1-Methyl-1H-pyrazolo[3,4-b]pyridin-4-yl)-phenyl]-3-(3-trifluoromethyl-phenyl)-urea

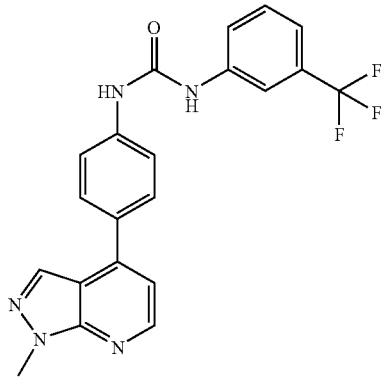

In analogy to GP 6, reaction of 171 mg of 1-[4-(3-Amino-1-methyl-1H-pyrazolo[3,4-b]pyridin-4-yl)-phenyl]-3-(3-trifluoromethyl-phenyl)-urea (0.4 mmol, 1 eq.) with 63 µL concentrated sulphuric acid and 68 mg sodium nitrite (2.5 eq.) in 3.75 mL EtOH yielded the desired product.

$^1$H-NMR (d$_6$-DMSO; 300 MHz): 9.11 (s, 1H); 9.09 (s, 1H); 8.55 (d, 1H); 8.34 (s, 1H); 8.00 (br. s, 1H); 7.84 (d, 2H); 7.67 (d, 2H); 7.58 (d, 1H); 7.50 (t, 1H); 7.36 (d, 1H); 7.30 (d, 1H); 4.06 (s, 3H).

Example Compound 1.5

Preparation of 1-(1-Methyl-4-{4-[3-(3-trifluoromethyl-phenyl)-ureido]-phenyl}-1H-pyrazolo[3,4-b]pyridin-6-yl)-cyclopropanecarboxylic acid ethyl ester

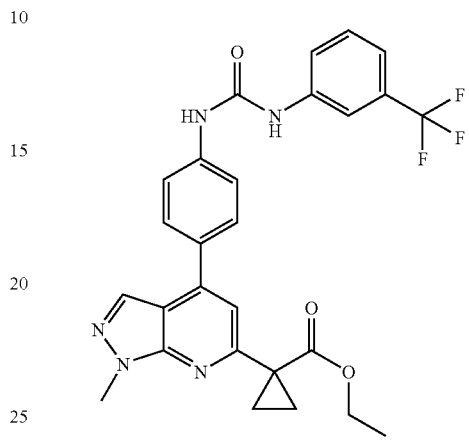

In analogy to GP 6, reaction of 210 mg of 1-(3-Amino-1-methyl-4-{4-[3-(3-trifluoromethyl-phenyl)-ureido]-phenyl}-1H-pyrazolo[3,4-b]pyridin-6-yl)-cyclopropanecarboxylic acid ethyl ester (0.39 mmol, 1 eq.) with 31 µL concentrated sulphuric acid and 64.6 mg sodium nitrite (0.94 mmol, 2.4 eq.) yielded 97 mg of the desired product (48% yield).

$^1$H-NMR (d$_6$-DMSO; 400 MHz): 9.14 (br. s, 1H); 9.12 (br. s, 1H); 8.31 (s, 1H); 8.03 (s, 1H); 7.87 (d, 2H); 7.70 (d, 2H); 7.62 (m, 1H); 7.54 (m, 1H); 7.51 (s, 1H); 7.34 (m, 1H); 4.13 (q, 2H); 4.05 (s, 3H); 1.60 (s, 4H); 1.15 (t, 3H).

MS (ESI): [M+H]$^+$=524.

The following example compounds 1.6 to 1.44 were prepared by applying GP 6 to the above described 3-aminopyrazolopyridine intermediates:

| Example | Structure | Name | Analytical data |
|---|---|---|---|
| 1.6 | 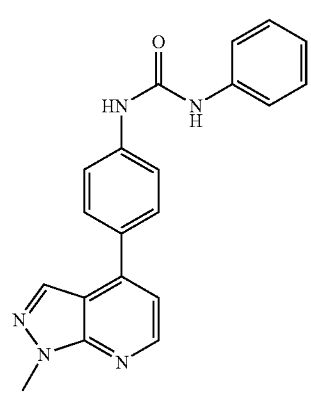 | 1-[4-(1-Methyl-1H-pyrazolo[3,4-b]-pyridin-4-yl)-phenyl]-3-phenyl-urea | $^1$H-NMR: (DMSO, 400 MHz) 8.95 (s, 1 H); 8.73 (s, 1 H); 8.54 (d, 1 H); 8.34 (s, 1 H); 7.83 (d, 2 H); 7.65 (d, 2 H); 7.45 (d, 2 H); 7.35 (d, 1 H); 7.26 (t, 2 H); 6.96 (t, 1 H); 4.06 (s, 3 H). MS (ESI): [M + H]$^+$ = 344. |

-continued

| Example | Structure | Name | Analytical data |
|---|---|---|---|
| 1.7 | 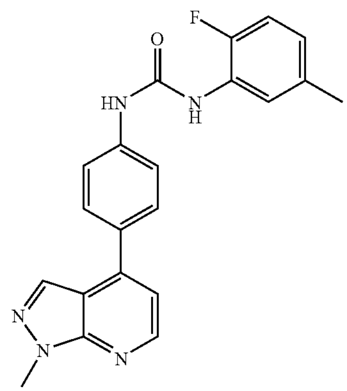 | 1-(2-Fluoro-5-methyl-phenyl)-3-[4-(1-methyl-1H-pyrazolo[3,4-b]pyridin-4-yl)-phenyl]-urea | $^1$H-NMR: (DMSO, 400 MHz) 9.36 (br. s, 1 H); 8.57 (br. s, 1 H); 8.54 (d, 1 H); 8.33 (s, 1 H); 7.96 (dd, 1 H); 7.84 (d, 2 H); 7.65 (d, 2 H); 7.35 (d, 1 H); 7.09 (dd, 1 H); 6.79 (m, 1 H); 4.06 (s, 3 H); 2.25 (s, 3 H). MS (ESI): [M + H]$^+$ = 376. |
| 1.8 | 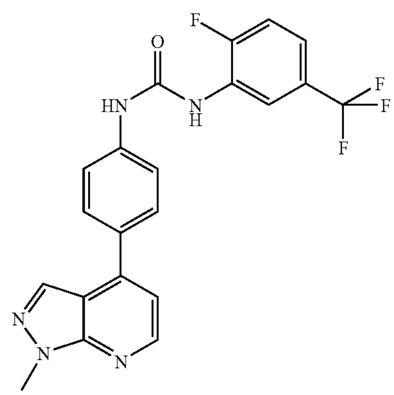 | 1-(2-Fluoro-5-trifluoromethyl-phenyl)-3-[4-(1-methyl-1H-pyrazolo[3,4-b]-pyridin-4-yl)-phenyl]-urea | $^1$H-NMR: (DMSO, 400MHz) 9.44 (s, 1 H); 8.95 (s, 1 H); 8.60 (dd, 1 H); 8.55 (d, 1 H); 8.33 (s, 1 H); 7.85 (d, 2 H); 7.66 (d, 2 H); 7.49 (t, 1 H); 7.37-7.41 (m, 1 H); 7.36 (d, 1 H); 4.06 (s, 3 H). |
| 1.9 | 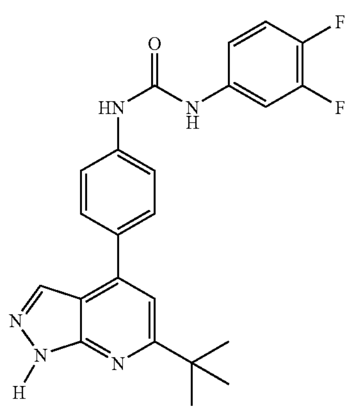 | 1-[4-(6-tert-Butyl-1H-pyrazolo[3,4-b]pyridin-4-yl)-phenyl]-3-(3,4-difluoro-phenyl)-urea | $^1$H-NMR: (DMSO, 400 MHz) 13.56 (s, 1 H); 9.06 (s, 1 H); 9.00 (s, 1 H); 8.21 (s, 1 H); 7.81 (d, 2 H); 7.65-7.70 (m, 1 H); 7.64 (d, 2 H); 7.36 (s, 1 H); 7.28-7.36 (m, 1 H); 7.10-7.16 (m, 1 H); 1.39 (s, 9 H). MS (ESI): [M + H]$^+$ = 422. |
| 1.10 | 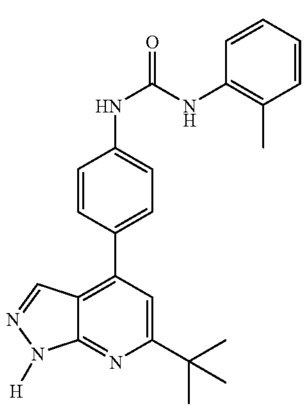 | 1-[4-(6-tert-Butyl-1H-pyrazolo[3,4-b]pyridin-4-yl)-phenyl]-3-o-tolyl-urea | $^1$H-NMR: (DMSO, 400 MHz) 13.55 (s, 1 H); 9.33 (s, 1 H); 8.22 (s, 1 H); 8.04 (s, 1 H); 7.80-7.83 (m, 3 H); 7.65 (d, 2 H); 7.36 (s, 1 H); 7.11-7.16 (m, 2 H); 6.93 (t, 1 H); 2.23 (s, 3 H); 1.40 (s, 9 H). MS (ESI): [M + H]$^+$ = 400. |

-continued

| Example | Structure | Name | Analytical data |
|---------|-----------|------|-----------------|
| 1.11 | 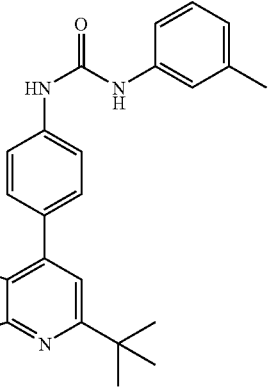 | 1-[4-(6-tert-Butyl-1H-pyrazolo[3,4-b]pyridin-4-yl)-phenyl]-3-m-tolyl-urea | $^1$H-NMR: (DMSO, 400 MHz) 13.56 (s, 1 H); 8.95 (s, 1 H); 8.67 (s, 1 H); 8.22 (s, 1 H); 7.80 (d, 2 H); 7.64 (d, 2 H); 7.35 (s, 1 H); 7.29 (s, 1 H); 7.23 (d, 1 H); 7.14 (t, 1 H); 6.77 (d, 1 H); 2.25 (s, 3 H); 1.40 (s, 9 H). MS (ESI): [M + H]$^+$ = 400. |
| 1.12 | 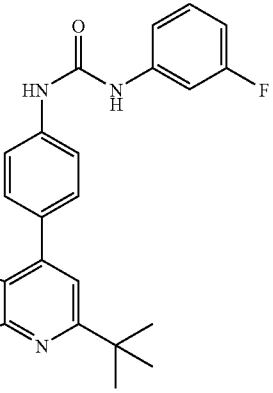 | 1-[4-(6-tert-Butyl-1H-pyrazolo[3,4-b]pyridin-4-yl)-phenyl]-3-(3-fluoro-phenyl)-urea | $^1$H-NMR: (DMSO, 300 MHz) 13.56 (s, 1 H); 9.04 (s, 1 H); 8.99 (s, 1 H); 8.21 (s, 1 H); 7.82 (d, 2 H); 7.64 (d, 2 H); 7.48 (dt, 1 H); 7.36 (s, 1 H); 7.29 (q, 1 H); 7.12 (dd, 1 H); 1.40 (s, 9 H). MS (ESI): [M + H]$^+$ = 404. |
| 1.13 | 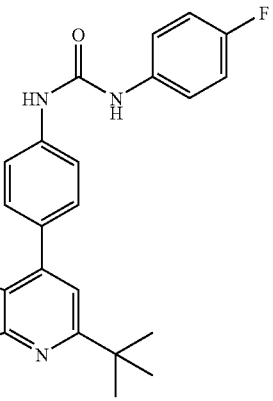 | 1-[4-(6-tert-Butyl-1H-pyrazolo[3,4-b]pyridin-4-yl)-phenyl]-3-(4-fluoro-phenyl)-urea | $^1$H-NMR: (DMSO, 400 MHz) 13.55 (s, 1 H); 9.10 (s, 1 H); 8.93 (s, 1 H); 8.21 (s, 1 H); 7.80 (d, 2 H); 7.65 (d, 2 H); 7.47 (dd, 2 H); 7.35 (s, 1 H); 7.10 (t, 2 H); 1.39 (s, 9 H). MS (ESI): [M + H]$^+$ = 404. |

-continued

| Example | Structure | Name | Analytical data |
|---|---|---|---|
| 1.14 | 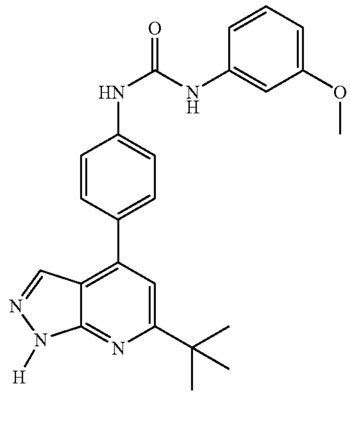 | 1-[4-(6-tert-Butyl-1H-pyrazolo[3,4-b]pyridin-4-yl)-phenyl]-3-(3-methoxy-phenyl)-urea | $^1$H-NMR: (DMSO, 400 MHz) 13.56 (s, 1 H); 8.93 (s, 1 H); 8.74 (s, 1 H); 8.21 (s, 1 H); 7.81 (d, 2 H); 7.63 (d, 2 H); 7.36 (s, 1 H); 7.18 (s, 1 H); 7.16 (t, 1 H); 6.93 (dd, 1 H); 6.54 (dd, 1 H); 3.71 (s, 3 H); 1.39 (s, 9 H). |
| 1.15 | 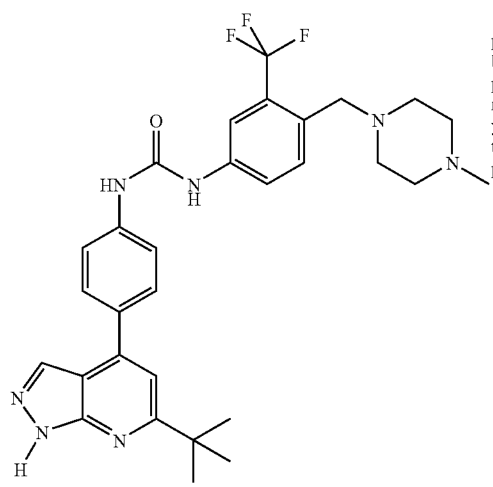 | 1-[4-(6-tert-Butyl-1H-pyrazolo[3,4-b]pyridin-4-yl)-phenyl]-3-[4-(4-methyl-piperazin-1-ylmethyl)-3-trifluoromethyl-phenyl]-urea | $^1$H-NMR: (DMSO, 300 MHz) 13.55 (s, 1 H); 9.10 (s, 1 H); 9.02 (s, 1 H); 8.21 (s, 1 H); 7.94 (d, 1 H); 7.81 (d, 2 H); 7.61 (d, 2 H); 7.55-7.70 (m, 2 H); 7.36 (s, 1 H); 3.49 (s, 2 H); 2.22-2.47 (m, 8 H); 2.12 (s, 3 H); 1.40 (s, 9 H). |
| 1.16 | 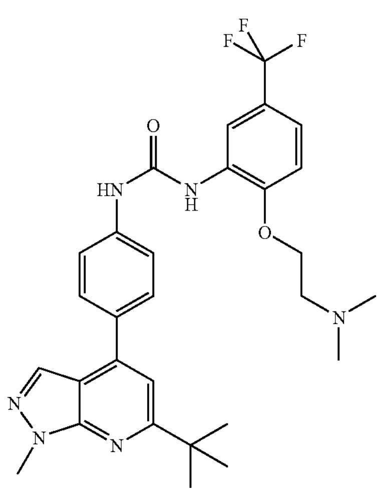 | 1-[4-(6-tert-Butyl-1-methyl-1H-pyrazolo[3,4-b]pyridin-4-yl)-phenyl]-3-[2-(2-dimethylamino-ethoxy)-5-trifluoromethyl-phenyl]-urea | $^1$H-NMR: (DMSO, 400 MHz) 9.79 (s, 1 H); 8.53 (d, 1 H); 8.38 (s, 1 H); 8.23 (s, 1 H); 7.84 (d, 2 H); 7.66 (d, 2 H); 7.40 (s, 1 H); 7.29 (d, 1 H); 7.23 (d, 1 H); 4.25 (t, 2 H); 4.03 (s, 3 H); 2.72 (t, 2 H); 2.22 (s, 6 H); 1.42 (s, 9 H). MS (ESI): [M + H]$^+$ = 555. |

-continued

| Example | Structure | Name | Analytical data |
|---|---|---|---|
| 1.17 | 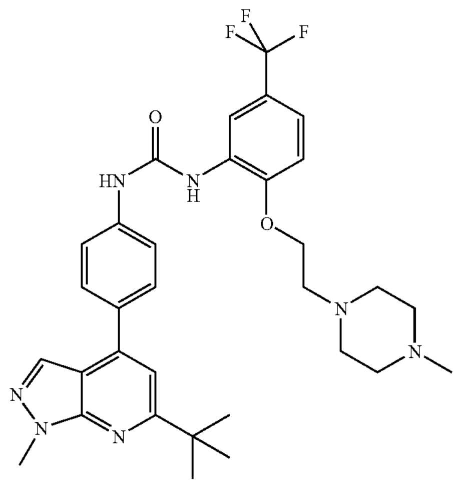 | 1-[4-(6-tert-Butyl-1-methyl-1H-pyrazolo[3,4-b]pyridin-4-yl)-phenyl]-3-{2-[2-(4-methyl-piperazin-1-yl)-ethoxy]-5-trifluoromethyl-phenyl}-urea | ¹H-NMR: (DMSO, 300 MHz) 9.84 (s, 1 H); 8.52 (d, 1 H); 8.41 (s, 1 H); 8.22 (s, 1 H); 7.84 (D, 2 H); 7.67 (d, 2 H); 7.39 (s, 1 H); 7.28 (dd, 1 H); 7.23 (d, 1 H); 4.27 (t, 2 H); 4.03 (s, 3 H); 2.77 (t, 2 H); 2.17-2.43 (m, 8 H); 2.08 (s, 3 H); 1.42 (s, 9 H). MS (ESI): [M + H]⁺ = 610. |
| 1.18 | 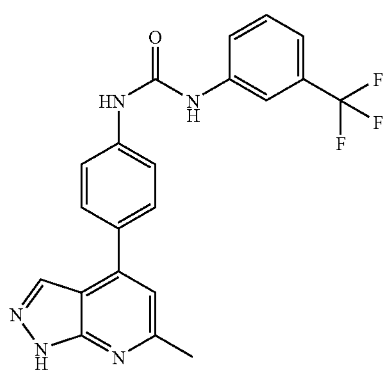 | 1-[4-(6-Methyl-1H-pyrazolo[3,4-b]pyridin-4-yl)-phenyl]-3-(3-trifluoromethyl-phenyl)-urea | ¹H-NMR: (DMSO, 400 MHz) 13.48 (s, 1 H); 9.15 (s, 1 H); 9.10 (s, 1 H); 8.22 (s, 1 H); 8.01 (s, 1 H); 7.80 (d, 2 H); 7.65 (d, 2 H); 7.58 (d, 1 H); 7.50 (t, 1 H); 7.30 (d, 1 H); 7.21 (s, 1 H); 2.59 (s, 3 H). MS (ESI): [M + H]⁺ = 412. |
| 1.19 | 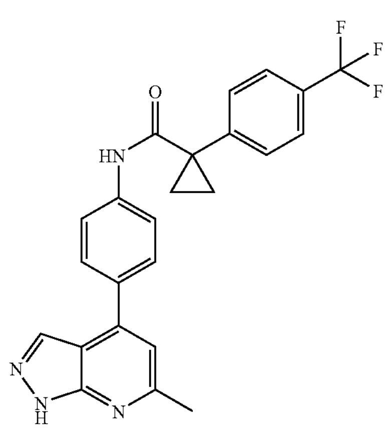 | 1-(4-Trifluoromethyl-phenyl)-cyclopropanecarboxylic acid [4-(6-methyl-1H-pyrazolo[3,4-b]pyridin-4-yl)-phenyl]-amide | ¹H-NMR: (DMSO, 300 MHz) 13.47 (s, 1 H); 9.56 (s, 1 H); 8.19 (s, 1 H); 7.73-7.80 (m, 4 H); 7.69 (d, 2 H); 7.57 (d, 2 H); 7.20 (s, 1 H); 2.58 (s, 3 H); 1.51-1.54 (m, 2 H); 1.18-1.22 (m, 2 H). MS (ESI): [M + H]⁺ = 437. |

| Example | Structure | Name | Analytical data |
|---------|-----------|------|-----------------|
| 1.20 | 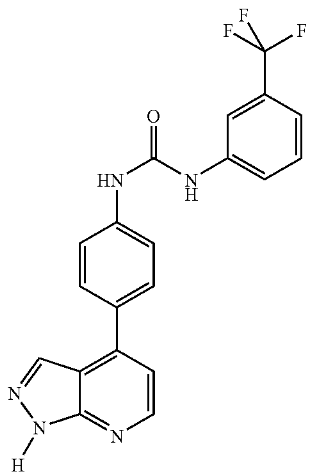 | 1-[4-(1H-Pyrazolo[3,4-b]pyridin-4-yl)-phenyl]-3-(3-trifluoromethyl-phenyl)-urea | ¹H-NMR: (DMSO, 300 MHz) 13.70 (s, 1 H); 9.12 (s, 1 H); 9.08 (s, 1 H); 8.50 (d, 1 H); 8.32 (s, 1 H); 8.00 (s, 1 H); 7.83 (d, 2 H); 7.66 (d, 2 H); 7.58 (d, 1 H); 7.50 (t, 1 H); 7.31 (d, 1 H); 7.30 (d, 1 H). |
| 1.21 | 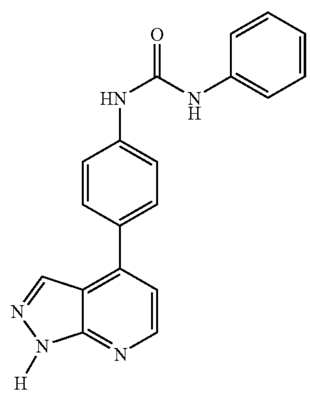 | 1-Phenyl-3-[4-(1H-pyrazolo[3,4-b]-pyridin-4-yl)-phenyl]-urea | ¹H-NMR: (DMSO, 400 MHz) 13.70 (s, 1 H); 8.94 (s, 1 H); 8.73 (s, 1 H); 8.50 (d, 1 H); 8.33 (s, 1 H); 7.82 (d, 2 H); 7.65 (d, 2 H); 7.45 (d, 2 H); 7.31 (d, 1 H); 7.27 (t, 2 H); 6.96 (t, 1 H). |
| 1.22 | 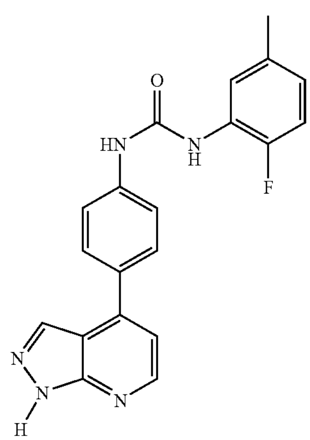 | 1-(2-Fluoro-5-methyl-phenyl)-3-[4-(1H-pyrazolo[3,4-b]pyridin-4-yl)-phenyl]-urea | ¹H-NMR: (DMSO, 400 MHz) 13.70 (s, 1 H); 9.31 (s, 1 H); 8.54 (s, 1 H); 8.50 (d, 1 H); 8.33 (s, 1 H); 7.97 (dd, 1 H); 7.83 (d, 2 H); 7.65 (d, 2 H); 7.31 (d, 1 H); 7.09 (dd, 1 H); 6.77-6.81 (m, 1 H), 2.25 (s, 3 H). |

| Example | Name | Analytical data |
|---|---|---|
| 1.23 | 1-[4-(1-Methyl-piperidin-4-yloxy)-3-trifluoromethyl-phenyl]-3-[4-(1-methyl-1H-pyrazolo[3,4-b]pyridin-4-yl)-phenyl]-urea | $^1$H-NMR: (DMSO, 400 MHz) 9.03 (s, 1 H); 8.88 (s, 1 H); 8.59 (d, 1 H); 8.38 (s, 1 H); 7.86-7.89 (m, 3 H); 7.70 (d, 2 H); 7.57 (dd, 1 H); 7.40 (d, 1 H); 7.32 (d, 1 H); 4.42-4.52 (m, 1 H); 4.11 (s, 3 H); 2.87-2.94 (m, 1 H); 2.56-2.63 (m, 1 H); 1.91-2.03 (m, 3 H); 1.67-1.77 (m, 1 H); 1.47-1.63 (m, 1 H); 1.23-1.36 (m, 1 H). MS (ESI): [M + H]$^+$ = 525. |
| 1.24 | 1-[4-(4-Methyl-piperazin-1-ylmethyl)-3-trifluoromethyl-phenyl]-3-[4-(1-methyl-1H-pyrazolo[3,4-b]pyridin-4-yl)-phenyl]-urea | $^1$H-NMR: (DMSO, 300 MHz) 9.07 (s, 1 H); 9.06 (s, 1 H); 8.54 (d, 1 H); 8.33 (s, 1 H); 7.95 (d, 1 H); 7.83 (d, 2 H); 7.66 (d, 2 H); 7.54-7.62 (m, 2 H); 7.35 (d, 1 H); 4.06 (s, 3 H); 3.50 (s, 2 H); 2.23-2.41 (m, 8 H); 2.13 (s, 3 H). |
| 1.25 | 1-{4-[6-Isopropyl-1-(3-morpholin-4-yl-propyl)-1H-pyrazolo[3,4-b]pyridin-4-yl]-phenyl}-3-(3-trifluoromethyl-phenyl)-urea | $^1$H-NMR: (DMSO, 400 MHz) 9.15 (s, 1 H); 9.12 (s, 1 H); 8.22 (s, 1 H); 8.00 (s, 1 H); 7.81 (d, 2 H); 7.65 (d, 2 H); 7.58 (d, 1 H); 7.49 (t, 1 H); 7.29 (d, 1 H); 7.25 (s, 1 H); 4.48 (t, 2 H); 3.43-3.51 (m, 4 H); 3.17 (sept., 1 H); 2.15-2.30 (m, 6 H); 1.99 (quint., 2 H); 1.30 (d, 6 H). MS (ESI): [M + H]$^+$ = 567. |

-continued

| Example | Structure | Name | Analytical data |
|---|---|---|---|
| 1.26 | 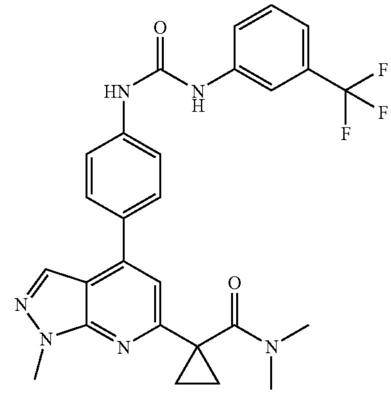 | 1-(1-Methyl-4-{4-[3-(3-trifluoromethyl-phenyl)-ureido]-phenyl}-1H-pyrazolo[3,4-b]pyridin-6-yl)-cyclopropane-carboxylic acid dimethylamide | $^1$H-NMR: (DMSO, 400 MHz) 9.11 (s, 1 H); 9.10 (s, 1 H); 8.24 (s, 1 H); 8.00 (s, 1 H); 7.76 (d, 2 H); 7.66 (d, 2 H); 7.58 (d, 1 H); 7.50 (t, 1 H); 7.30 (d, 1 H); 6.97 (s, 1 H); 3.99 (s, 3 H); 2.91 (s, 3 H); 2.82 (s, 3 H); 1.55-1.58 (m, 2 H); 1.35-1.38 (m, 2 H). MS (ESI): [M + H]$^+$ = 523. |
| 1.27 | 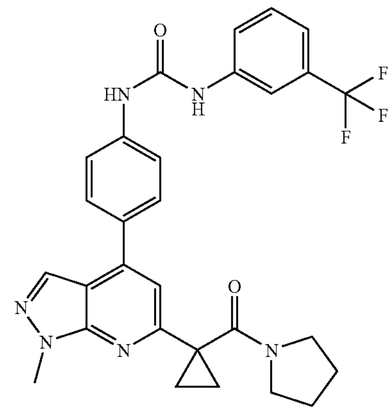 | 1-(4-{1-Methyl-6-[1-(pyrrolidine-1-carbonyl)-cyclopropyl]-1H-pyrazolo[3,4-b]pyridin-4-yl}-phenyl)-3-(3-trifluoromethyl-phenyl)-urea | $^1$H-NMR: (DMSO, 400 MHz) 9.12 (s, 1 H); 9.11 (s, 1 H); 8.24 (s, 1 H); 8.00 (s, 1 H); 7.76 (d, 2 H); 7.66 (d, 2 H); 7.58 (d, 1 H); 7.50 (t, 1 H); 7.30 (d, 1 H); 7.02 (s, 1 H); 3.99 (s, 3 H); 3.40 (t, 2 H); 3.13 (t, 2 H); 1.64-1.77 (m, 4 H); 1.49-1.55 (m, 2 H); 1.35-1.39 (m, 2 H). MS (ESI): [M + H]$^+$ = 549. |
| 1.28 | 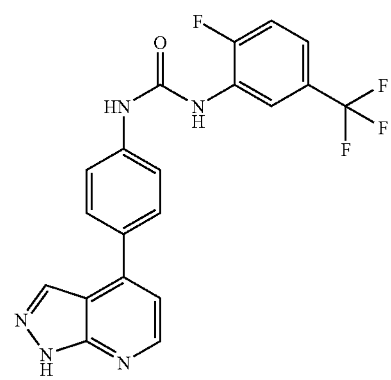 | 1-(2-Fluoro-5-trifluoromethyl-phenyl)-3-[4-(1H-pyrazolo[3,4-b]pyridin-4-yl)-phenyl]-urea | $^1$H-NMR: (DMSO, 400MHz) 8.59 (dd, 1 H); 8.50 (d, 1 H); 8.32 (s, 1 H); 7.84 (d, 2 H); 7.67 (d, 2 H); 7.47 (dd, 1 H); 7.35-7.40 (m, 1 H); 7.31 (d, 1 H). (TFA salt) |
| 1.29 | 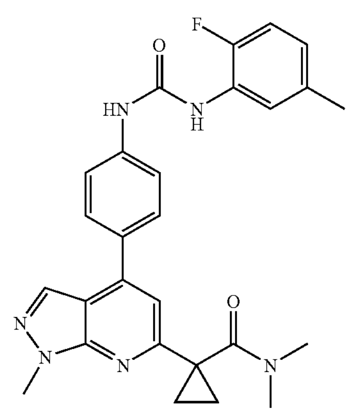 | 1-(4-{4-[3-(2-Fluoro-5-methyl-phenyl)-ureido]-phenyl}-1-methyl-1H-pyrazolo[3,4-b]pyridin-6-yl)-cyclopropane-carboxylic acid dimethylamide | $^1$H-NMR: (DMSO, 300 MHz) 9.36 (s, 1 H); 8.56 (s, 1 H); 8.28 (s, 1 H); 8.00 (dd, 1 H); 7.80 (d, 2 H); 7.68 (d, 2 H); 7.12 (dd, 1 H); 7.01 (s, 1 H); 6.83 (m, 1 H); 5.76 (s, 1 H); 4.03 (s, 3 H); 2.94 (br. s, 3 H); 2.86 (br. s, 3 H); 2.29 (s, 3 H); 1.60 (m, 2 H); 1.40 (m, 2 H). |

-continued

| Example | Structure | Name | Analytical data |
|---|---|---|---|
| 1.30 | 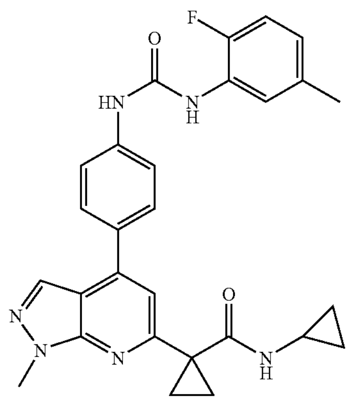 | 1-(4-{4-[3-(2-Fluoro-5-methyl-phenyl)-ureido]-phenyl}-1-methyl-1H-pyrazolo[3,4-b]pyridin-6-yl)-cyclopropane-carboxylic acid cyclopropylamide | $^1$H-NMR: (DMSO, 300 MHz) 9.35 (s, 1 H); 8.57 (s, 1 H); 8.30 (s, 1 H); 8.01 (dd, 1 H); 7.83 (d, 2 H); 7.68 (d, 2 H); 7.24 (s, 1 H); 7.12 (dd, 1 H); 6.82 (m, 1 H); 4.05 (s, 3 H); 2.71 (m, 1 H); 2.29 (s, 3 H); 1.42 (m, 2 H); 1.39 (m, 2 H); 0.59 (m, 2 H); 0.44 (m, 2 H). |
| 1.31 | 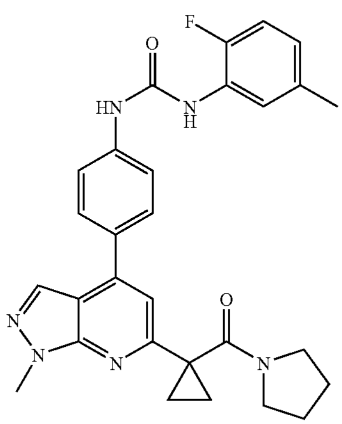 | 1-(2-Fluoro-5-methyl-phenyl)-3-(4-{1-methyl-6-[1-(pyrrolidine-1-carbonyl)-cyclopropyl]-1H-pyrazolo[3,4-b]-pyridin-4-yl}-phenyl)-urea | $^1$H-NMR: (DMSO, 300 MHz) 9.36 (s, 1 H); 8.57 (s, 1 H); 8.28 (s, 1 H); 8.00 (dd, 1 H); 7.80 (d, 2 H); 7.68 (d, 2 H); 7.12 (dd, 1 H); 7.06 (s, 1 H); 6.82 (m, 1 H); 4.02 (s, 3 H); 3.43 (m, 2 H); 3.16 (m, 2 H); 2.28 (s, 3 H); 1.74 (m, 4 H); 1.56 (m, 2 H); 1.41 (m, 2 H). |
| 1.32 | 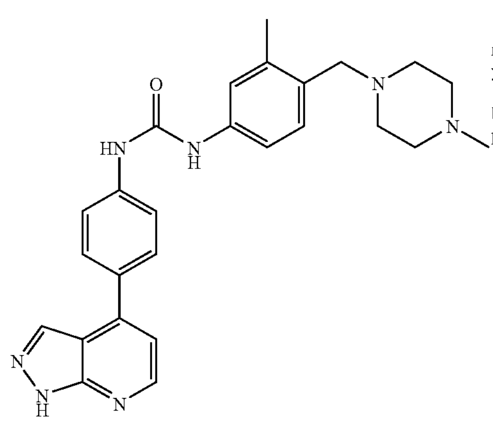 | 1-[3-Methyl-4-(4-methyl-piperazin-1-yl-methyl)-phenyl]-3-[4-(1H-pyrazolo-[3,4-b]pyridin-4-yl)-phenyl]-urea | $^1$H-NMR: (DMSO, 300 MHz) 13.69 (s, 1 H); 8.91 (s, 1 H); 8.62 (s, 1 H); 8.49 (d, 1 H); 8.32 (s, 1 H); 7.81 (d, 2 H); 7.64 (d, 2 H); 7.30 (d, 1 H); 7.18-7.23 (m, 2 H); 7.06 (d, 1 H); 2.21-2.37 (m, 8 H); 2.26 (s, 3 H); 2.11 (s, 3 H). |

-continued

| Example | Structure | Name | Analytical data |
|---|---|---|---|
| 1.33 | 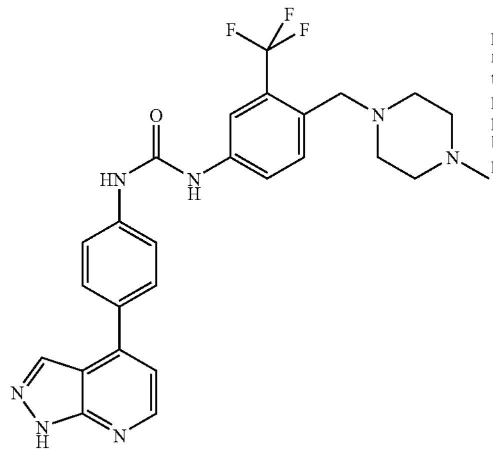 | 1-[4-(4-Methyl-piperazin-1-yl-methyl)-3-trifluoromethyl-phenyl]-3-[4-(1H-pyrazolo[3,4-b]pyridin-4-yl)-phenyl]-urea | $^1$H-NMR: (DMSO, 400 MHz) 13.71 (s, 1 H); 9.16 (s, 1 H); 9.19 (s, 1 H); 8.50 (d, 1 H); 8.32 (s, 1 H); 7.96 (s, 1 H); 7.82 (d, 2 H); 7.66 (d, 2 H); 7.55-7.61 (m, 2 H); 7.30 (d, 1 H); 3.49 (s, 2 H); 2.20-2.41 (m, 8 H); 2.12 (s, 3 H). MS (ESI): [M + H]$^+$ = 510. |
| 1.34 | 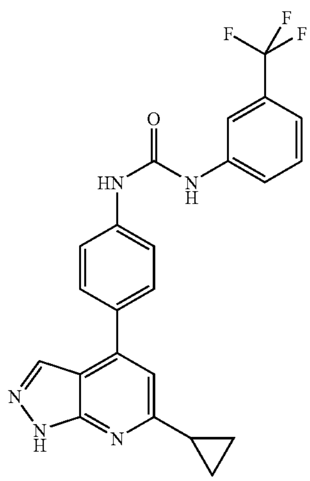 | 1-[4-(6-Cyclopropyl-1H-pyrazolo[3,4-b]pyridin-4-yl)-phenyl]-3-(3-trifluoromethyl-phenyl)-urea | $^1$H-NMR: (DMSO, 300 MHz) 13.45 (s, 1 H); 9.13 (s, 1 H); 9.08 (s, 1 H); 8.21 (s, 1 H); 8.04 (s, 1 H); 7.86 (d, 2 H); 7.69 (d, 2 H); 7.62 (d, 1 H); 7.53 (t, 1 H); 7.33 (d, 1 H); 7.31 (s, 1 H); 2.30 (m, 1 H); 1.05 (m, 4 H). |
| 1.35 | 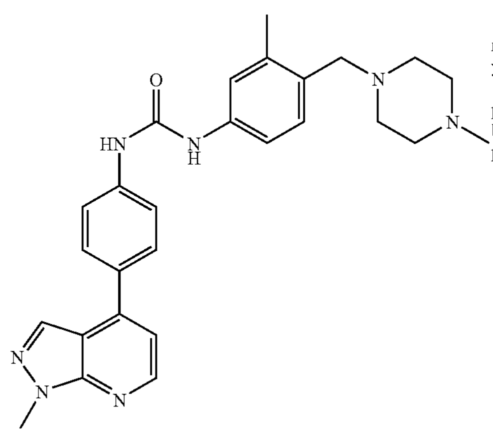 | 1-[3-Methyl-4-(4-methyl-piperazin-1-ylmethyl)-phenyl]-3-[4-(1-methyl-1H-pyrazolo[3,4-b]pyridin-4-yl)-phenyl]-urea | $^1$H-NMR: (DMSO, 300 MHz) 8.93 (s, 1 H); 8.63 (s, 1 H); 8.54 (d, 1 H); 8.33 (s, 1 H); 7.82 (d, 2 H); 7.64 (d, 2 H); 7.34 (d, 1 H); 7.18-7.23 (m, 2 H); 7.06 (d, 1 H); 4.06 (s, 3 H); 2.20-2.36 (m, 8 H); 2.26 (s, 3 H); 2.10 (s, 3 H). |

| Example | Structure | Name | Analytical data |
| --- | --- | --- | --- |
| 1.36 | 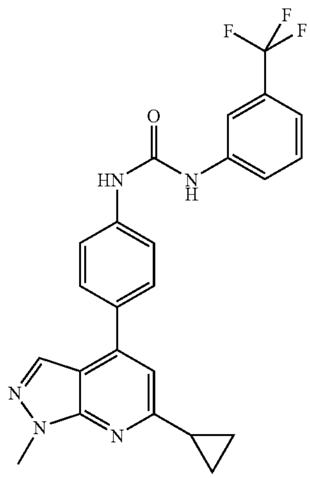 | 1-[4-(6-Cyclopropyl-1-methyl-1H-pyrazolo[3,4-b]pyridin-4-yl)-phenyl]-3-(3-trifluoromethyl-phenyl)-urea | $^1$H-NMR: (DMSO, 400 MHz) 9.14 (s, 1 H); 9.10 (s, 1 H); 8.22 (s, 1 H); 8.04 (s, 1 H); 7.86 (d, 2 H); 7.69 (d, 2 H); 7.61 (d, 1 H); 7.53 (t, 1 H); 7.33 (d, 1 H); 7.30 (s, 1 H); 4.00 (s, 3 H); 2.32 (m, 1 H); 1.11 (m, 2 H); 1.06 (m, 2 H). |
| 1.37 | 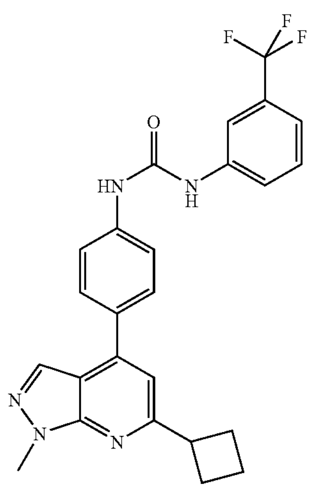 | 1-[4-(6-Cyclobutyl-1-methyl-1H-pyrazolo[3,4-b]pyridin-4-yl)-phenyl]-3-(3-trifluoromethyl-phenyl)-urea | $^1$H-NMR: (DMSO, 400 MHz) 9.13 (s, 1 H); 9.11 (s, 1 H); 8.26 (s, 1 H); 8.03 (s, 1 H); 7.85 (d, 2 H); 7.68 (d, 2 H); 7.61 (d, 1 H); 7.53 (t, 1 H); 7.33 (d, 1 H); 7.25 (s, 1 H); 4.07 (s, 3 H); 3.85 (m, 1 H); 2.43 (m, 2 H); 2.34 (m, 2 H); 2.05 (m, 1 H); 1.90 (m, 1 H). |
| 1.38 | 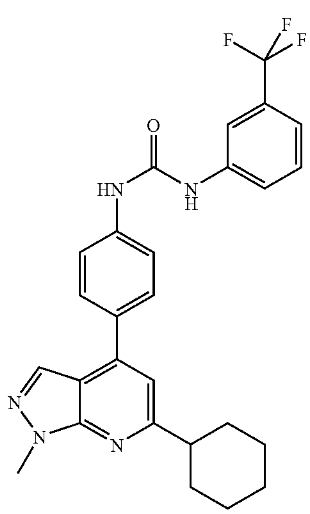 | 1-[4-(6-Cyclohexyl-1-methyl-1H-pyrazolo[3,4-b]pyridin-4-yl)-phenyl]-3-(3-trifluoromethyl-phenyl)-urea | $^1$H-NMR: (DMSO, 400 MHz) 9.15 (s, 1 H); 9.12 (s, 1 H); 8.26 (s, 1 H); 8.04 (s, 1 H); 7.86 (d, 2 H); 7.69 (d, 2 H); 7.61 (d, 1 H); 7.53 (t, 1 H); 7.33 (d, 1 H); 7.28 (s, 1 H); 4.05 (s, 3 H); 2.88 (m, 1 H); 1.95 (m, 2 H); 1.85 (m, 2 H); 1.68 (m, 2 H); 1.43 (m, 2 H); 1.30 (m, 2 H). |

| Example | Structure | Name | Analytical data |
|---|---|---|---|
| 1.39 | 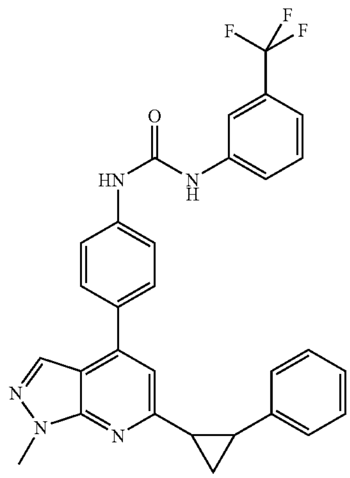 | 1-{4-[1-Methyl-6-(2-phenyl-cyclopropyl)-1H-pyrazolo[3,4-b]pyridin-4-yl]-phenyl}-3-(3-trifluoromethyl-phenyl)-urea | ¹H-NMR: (DMSO, 400 MHz) 9.14 (s, 1 H); 9.09 (s, 1 H); 8.12 (s, 1 H); 8.04 (s, 1 H); 7.66 (d, 2 H); 7.63 (d, 2 H); 7.60 (d, 1 H); 7.53 (t, 1 H); 7.33 (d, 1 H); 7.24 (d, 2 H); 7.12 (t, 2 H); 7.07 (s, 1 H); 7.02 (t, 1 H); 3.92 (s, 3 H); 2.86 (m, 1 H); 2.76 (m, 1 H); 2.10 (m, 1 H); 1.57 (m, 1 H). |
| 1.40 | 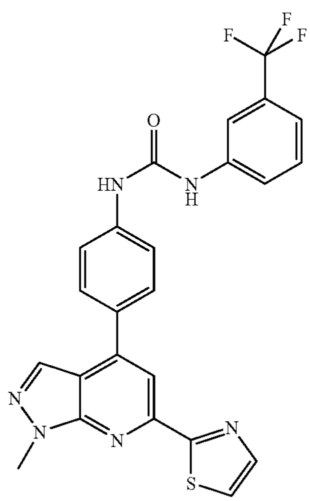 | 1-[4-(1-Methyl-6-thiazol-2-yl-1H-pyrazolo[3,4-b]pyridin-4-yl)-phenyl]-3-(3-trifluoromethyl-phenyl)-urea | ¹H-NMR: (DMSO, 300 MHz) 9.18 (s, 1 H); 9.16 (s, 1 H); 8.43 (s, 1 H); 8.16 (s, 1 H); 8.07 (d, 1 H); 8.05 (s, 1 H); 7.97 (d, 1 H); 7.93 (d, 2 H); 7.74 (d, 2 H); 7.63 (d, 1 H); 7.54 (t, 1 H); 7.34 (d, 1 H); 4.15 (s, 3 H). |
| 1.41 | 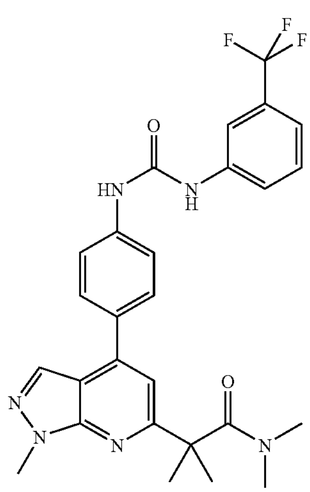 | N,N-Dimethyl-2-(1-methyl-4-{4-[3-(3-trifluoromethyl-phenyl)-ureido]-phenyl}-1H-pyrazolo[3,4-b]pyridin-6-yl)-isobutyramide | ¹H-NMR: (DMSO, 300 MHz) 9.17 (s, 2 H); 8.31 (s, 1 H); 8.03 (s, 1 H); 7.84 (d, 2 H); 7.70 (d, 2 H); 7.62 (d, 1 H); 7.53 (t, 1 H); 7.33 (d, 1 H); 7.09 (s, 1 H); 4.07 (s, 3 H); 2.84 (br. s, 3 H); 2.42 (br. s, 3 H); 1.59 (s, 6 H). |

-continued

| Example | Structure | Name | Analytical data |
|---|---|---|---|
| 1.42 | 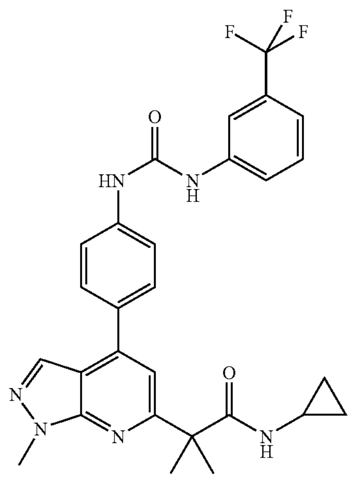 | N-Cyclopropyl-2-(1-methyl-4-{4-[3-(3-trifluoromethyl-phenyl)-ureido]-phenyl}-1H-pyrazolo[3,4-b]pyridin-6-yl)-isobutyramide | $^1$H-NMR: (DMSO, 400 MHz) 9.14 (s, 1 H); 9.13 (s, 1 H); 8.29 (s, 1 H); 8.04 (d, 1 H); 7.81 (d, 2 H); 7.70 (d, 2 H); 7.61 (d, 1 H); 7.53 (t, 1 H); 7.47 (m, 1 H); 7.34 (d, 1 H); 7.21 (s, 1 H); 4.07 (s, 3 H); 2.65 (m, 1 H); 1.58 (s, 6 H); 0.57 (m, 2 H); 0.40 (m, 2 H). |
| 1.43 | 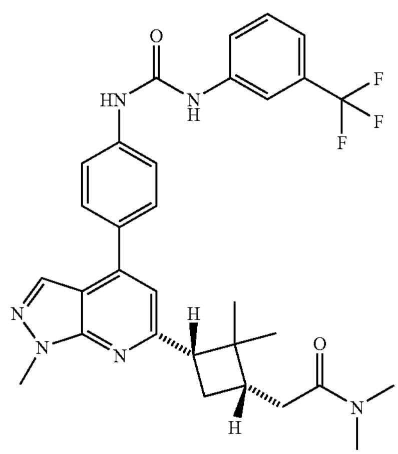 | 2-[2,2-Dimethyl-3-(1-methyl-4-{4-[3-(3-trifluoromethyl-phenyl)-ureido]-phenyl}-1H-pyrazolo[3,4-b]pyridin-6-yl)-cyclobutyl]-N,N-dimethyl-acetamide | $^1$H-NMR: (DMSO, 300 MHz) 9.16 (s, 1 H); 9.14 (s, 1 H); 8.26 (s, 1 H); 8.03 (s, 1 H); 7.85 (d, 2 H); 7.69 (d, 2 H); 7.62 (d, 1 H); 7.53 (t, 1 H); 7.33 (d, 1 H); 7.09 (s, 1 H); 4.07 (s, 3 H); 3.43 (m, 1 H); 2.99 (s, 3 H); 2.81 (s, 3 H); 2.42 (m, 4 H); 2.25 (m, 1 H); 1.32 (s, 3 H); 0.61 (s, 3 H). |
| 1.44 | 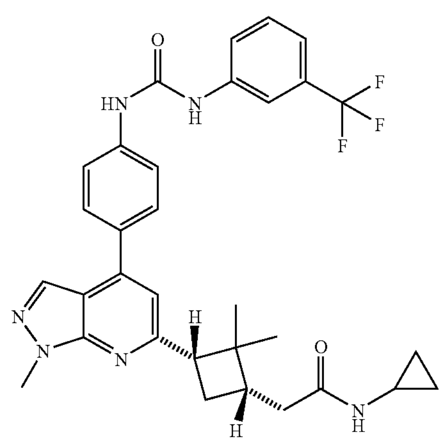 | N-Cyclopropyl-2-[2,2-dimethyl-3-(1-methyl-4-{4-[3-(3-trifluoromethyl-phenyl)-ureido]-phenyl}1H-pyrazolo[3,4-b]pyridin-6-yl)-cyclobutyl]-acetamide | $^1$H-NMR: (DMSO, 300 MHz) 9.14 (s, 1 H); 9.12 (s, 1 H); 8.26 (s, 1 H); 8.03 (s, 1 H); 7.88 (m, 1 H); 7.85 (d, 2 H); 7.69 (d, 2 H); 7.62 (d, 1 H); 7.53 (t, 1 H); 7.33 (d, 1 H); 7.07 (s, 1 H); 4.07 (s, 3 H); 3.44 (m, 1 H); 2.60 (m, 1 H); 2.40 (m, 2 H); 2.27 (m, 1 H); 2.10 (m, 2 H); 1.29 (s, 3 H); 0.60 (s, 3 H); 0.57 (m, 2 H); 0.37 (m, 2 H). |

Example Compound 2.1

Preparation of 1-[4-(1,6-Dimethyl-1H-pyrazolo[3,4-b]pyridin-4-yl)-phenyl]-3-phenyl-urea

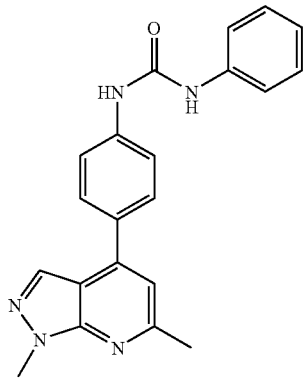

In an adoption of GP 4a (step 1), reaction of 83.4 mg of Intermediate 12.3 (0.35 mmol, 1 eq.) with 42 µL phenylisocyanate (0.38 mmol, 1.1 eq.) in 3.5 mL DCM yielded after extractive work-up and flash column chromatography 70 mg of Example Compound 2.1 as a beige solid (0.2 mmol, 56% yield).

$^1$H-NMR (d$_6$-DMSO; 400 MHz): 8.94 (s, 1H); 8.73 (s, 1H); 8.23 (s, 1H); 7.80 (d, 2H); 7.63 (d, 2H); 7.45 (d, 2H); 7.26 (t, 2H); 7.25 (s, 1H); 6.96 (t, 1H); 4.01 (s, 3H); 2.62 (s, 2H).

MS (ESI): [M+H]$^+$=358.

Example Compound 2.2

Preparation of 1-[4-(1,6-Dimethyl-1H-pyrazolo[3,4-b]pyridin-4-yl)-phenyl]-3-(3-trifluoromethyl-phenyl)-urea

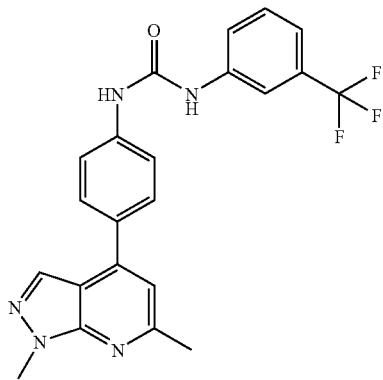

In an adoption of GP 4a (step 1), reaction of 83.4 mg of Intermediate 12.3 (0.35 mmol, 1 eq.) with 49 µL 1-isocyanato-3-trifluoromethyl-benzene (0.38 mmol, 1.1 eq.) in 3.5 mL DCM yielded after extractive work-up and flash column chromatography 85 mg of Example Compound 2.2 as a beige solid (0.2 mmol, 58% yield; mp 226° C.).

$^1$H-NMR (d$_6$-DMSO; 400 MHz): 9.11 (s, 1H); 9.08 (s, 1H); 8.23 (s, 1H); 8.01 (s, 1H); 7.81 (d, 2H); 7.65 (d, 2H); 7.58 (d, 1H); 7.50 (t, 1H); 7.30 (d, 1H); 7.25 (s, 1H); 4.01 (s, 3H); 2.62 (s, 2H).

MS (ESI): [M+H]$^+$=426.

Example Compound 2.3

Preparation of 1-[4-(1,6-Dimethyl-1H-pyrazolo[3,4-b]pyridin-4-yl)-phenyl]-3-(2-fluoro-5-trifluoromethyl-phenyl)-urea

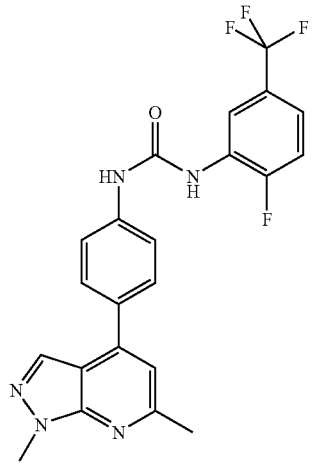

In an adoption of GP 4a (step 1), reaction of 83.4 mg of Intermediate 12.3 (0.35 mmol, 1 eq.) with 56 µL 1-fluoro-2-isocyanato-4-trifluoromethyl-benzene (0.38 mmol, 1.1 eq.) in 3.5 mL DCM yielded after extractive work-up and flash column chromatography 64 mg of Example Compound 2.3 as a beige solid (0.144 mmol, 41% yield; mp 225° C.).

$^1$H-NMR (d$_6$-DMSO; 400 MHz): 9.42 (br. s, 1H); 8.95 (br. s, 1H); 8.60 (dd, 1H); 8.22 (s, 1H); 7.83 (d, 2H); 7.65 (d, 2H); 7.48 (dd, 1H); 7.36-7.40 (m, 1H); 7.26 (s, 1H); 4.01 (s, 3H); 2.62 (s, 2H).

MS (ESI): [M+H]$^+$=444.

Example Compound 2.4

Preparation of 1-[4-(1,6-Dimethyl-1H-pyrazolo[3,4-b]pyridin-4-yl)-phenyl]-3-(3-fluoro-5-trifluoromethyl-phenyl)-urea

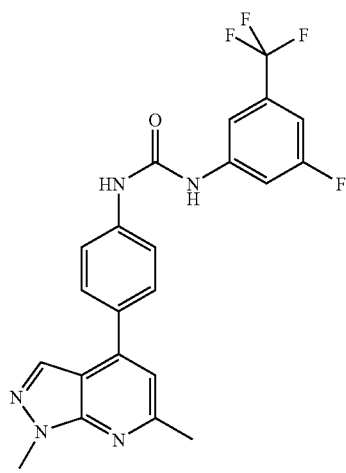

In an adoption of GP 4a (step 1), reaction of 83.4 mg of Intermediate 12.3 (0.35 mmol, 1 eq.) with 79 mg 1-fluoro-3-isocyanato-5-trifluoromethyl-benzene (0.38 mmol, 1.1 eq.) in 3.5 mL DCM yielded after extractive work-up and flash column chromatography 84 mg of Example Compound 2.4 as a beige solid (0.190 mmol, 54% yield; mp 213° C.).

¹H-NMR (d₆-DMSO; 400 MHz): 9.31 (br. s, 1H); 9.19 (br. s, 1H); 8.23 (s, 1H); 7.82 (d, 2H); 7.70 (s, 1H); 7.66 (d, 2H); 7.61 (br. d, 1H); 7.25 (s, 1H); 7.22 (br. d, 1H); 4.01 (s, 3H); 2.62 (s, 2H).

MS (ESI): [M+H]⁺=444.

Example Compound 2.5

Preparation of 1-[4-(1,6-Dimethyl-1H-pyrazolo[3,4-b]pyridin-4-yl)-phenyl]-3-(4-fluoro-3-trifluoromethyl-phenyl)-urea

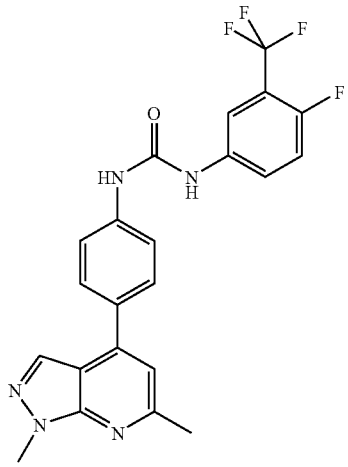

In an adoption of GP 4a (step 1), reaction of 83.4 mg of Intermediate 12.3 (0.35 mmol, 1 eq.) with 79 mg 1-fluoro-4-isocyanato-2-trifluoromethyl-benzene (0.38 mmol, 1.1 eq.) in 3.5 mL DCM yielded after extractive work-up and flash column chromatography 93 mg of Example Compound 2.5 as a beige solid (0.21 mmol, 60% yield; mp 232° C.).

¹H-NMR (d₆-DMSO; 400 MHz): 9.11 (s, 1H); 9.10 (s, 1H); 8.22 (s, 1H); 7.99 (dd, 1H); 7.81 (d, 2H); 7.62-7.66 (m, 3H); 7.42 (t, 1H); 7.25 (s, 1H); 4.01 (s, 3H); 2.62 (s, 2H).

MS (ESI): [M+H]⁺=444.

Example Compound 2.6

Preparation of 1-[4-(1,6-Dimethyl-1H-pyrazolo[3,4-b]pyridin-4-yl)-phenyl]-3-(2-fluoro-3-trifluoromethyl-phenyl)-urea

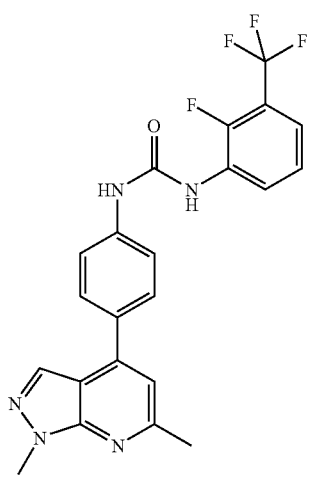

In an adoption of GP 4a (step 1), reaction of 83.4 mg of Intermediate 12.3 (0.35 mmol, 1 eq.) with 79 mg 2-fluoro-1-isocyanato-3-trifluoromethyl-benzene (0.38 mmol, 1.1 eq.) in 3.5 mL DCM yielded after extractive work-up and flash column chromatography 69 mg of Example Compound 2.6 as a white solid (0.156 mmol, 45% yield; mp 234° C.).

¹H-NMR (d₆-DMSO; 400 MHz): 9.40 (br. s, 1H); 8.89 (br. s, 1H); 8.41-8.46 (m, 1H); 8.23 (s, 1H); 7.83 (d, 2H); 7.65 (d, 2H); 7.32-7.37 (m, 2H); 7.26 (s, 1H); 4.01 (s, 3H); 2.62 (s, 2H).

MS (ESI): [M+H]⁺=444.

Example Compound 2.7

Preparation of 1-[4-(1,6-Dimethyl-1H-pyrazolo[3,4-b]pyridin-4-yl)-phenyl]-3-(2-methoxy-5-trifluoromethyl-phenyl)-urea

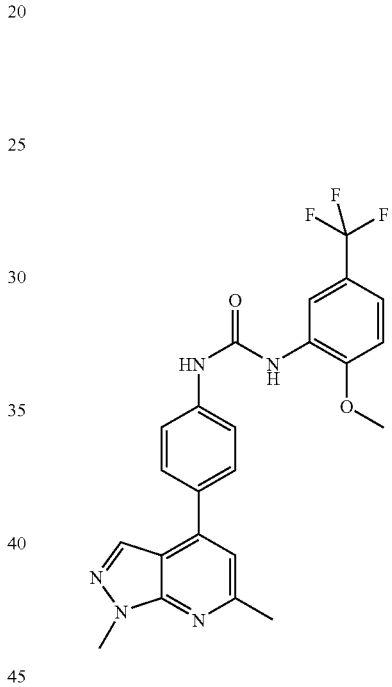

In an adoption of GP 4b (step 1), 80.3 mg 2-methoxy-5-trifluoromethyl-phenylamine (0.42 mmol, 1.2 eq.) was reacted at rt with 41.5 mg triphosgene (0.14 mmol, 0.4 eq.) in 7 mL acetonitrile and stirred for 1 h before addition of 83.4 mg of Intermediate 12.3 (0.35 mmol, 1 eq.). Stirring at rt was continued for 48 h. The mixture was quenched with water, extracted with ethyl acetate, the combined organic layers were dried and concentrated in vacuo. Flash column chromatography of the residue followed by preparative HPLC purification provided 29.4 mg of Example Compound 2.7 as a white solid (0.065 mmol, 13% yield).

¹H-NMR (d₆-DMSO; 400 MHz): 9.68 (s, 1H); 8.56 (s, 1H); 8.54 (d, 1H); 8.22 (s, 1H); 7.82 (d, 2H); 7.64 (d, 2H); 7.31 (dd, 1H); 7.25 (s, 1H); 7.19 (d, 1H); 4.01 (s, 3H); 3.95 (s, 3H); 2.62 (s, 3H).

MS (LC-MS): [M+H]⁺=456 (99.1%).

Example Compound 2.8

Preparation of 1-[4-(1,6-Dimethyl-1H-pyrazolo[3,4-b]pyridin-4-yl)-phenyl]-3-(2-pyrrolidin-1-yl-5-trifluoromethyl-phenyl)-urea

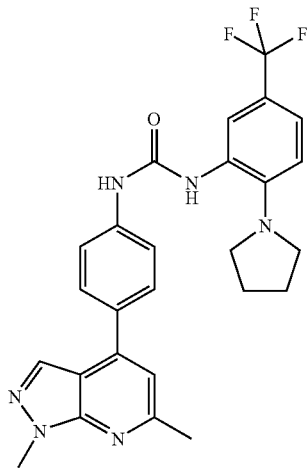

In an adoption of GP 4b (step 1), 97 mg 2-pyrrolidin-1-yl-5-trifluoromethyl-phenylamine (0.42 mmol, 1.2 eq.) was reacted at rt with 41.5 mg triphosgene (0.14 mmol, 0.4 eq.) in 7 mL acetonitrile and stirred for 1 h before addition of 83.4 mg of Intermediate 12.3 (0.35 mmol, 1 eq.). Stirring at rt was continued for 48 h. The mixture was quenched with water, extracted with ethyl acetate, the combined organic layers were dried and concentrated in vacuo. Flash column chromatography of the residue provided 43 mg of Example Compound 2.8 as a white solid (0.087 mmol, 29% yield, mp 236° C.).

$^1$H-NMR (d$_6$-DMSO; 400 MHz): 9.41 (s, 1H); 8.23 (s, 1H); 8.06 (s, 1H); 7.92 (d, 1H); 7.80 (d, 2H); 7.65 (d, 2H); 7.28 (dd, 1H); 7.25 (s, 1H); 7.04 (d, 1H); 4.01 (s, 3H); 3.19-3.23 (m, 4H); 2.62 (s, 3H); 1.88-1.91 (m, 4H).

MS (ESI): [M+H]$^+$=495.

Example Compound 3.1

Preparation of 1-[4-(1-Methyl-6-morpholin-4-ylmethyl-1H-pyrazolo[3,4-b]pyridin-4-yl)-phenyl]-3-phenyl-urea

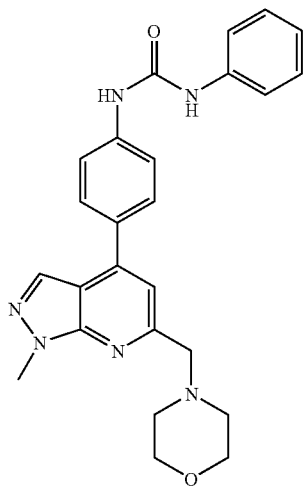

In an adoption of GP 4a (step 1), reaction of 97 mg of Intermediate 13.3 (0.3 mmol, 1 eq.) with 36 μL phenylisocyanate (0.33 mmol, 1.1 eq.) in 3 mL DCM yielded after extractive work-up, flash column chromatography and trituration with diisopropylether 59 mg of Example Compound 3.1 as a beige solid (0.133 mmol, 44% yield; mp 232° C.).

$^1$H-NMR (d$_6$-DMSO; 400 MHz): 8.96 (s, 1H); 8.73 (s, 1H); 8.27 (s, 1H); 7.80 (d, 2H); 7.65 (d, 2H); 7.45 (d, 2H); 7.42 (s, 1H); 7.26 (t, 2H); 6.95 (t, 1H); 4.03 (s, 3H); 3.72 (s, 2H); 3.56-3.59 (m, 4H); 2.43-2.50 (obscured by d$_6$-DMSO, 4H).

MS (ESI): [M+H]$^+$=443.

Example Compound 3.2

Preparation of 1-[4-(1-Methyl-6-morpholin-4-ylmethyl-1H-pyrazolo[3,4-b]pyridin-4-yl)-phenyl]-3-(3-trifluoromethyl-phenyl)-urea

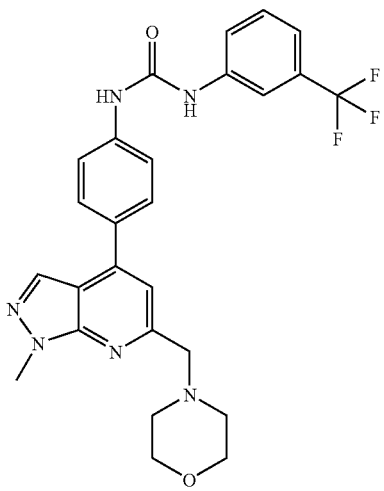

In an adoption of GP 4a (step 1), reaction of 162 mg of Intermediate 13.3 (0.5 mmol, 1 eq.) with 77 μL 1-isocyanato-3-trifluoromethyl-benzene (0.55 mmol, 1.1 eq.) in 5 mL DCM yielded after extractive work-up and flash column chromatography 75 mg of Example Compound 3.2 (0.147 mmol, 30% yield).

$^1$H-NMR (d$_6$-DMSO; 400 MHz): 9.11 (s, 1H); 9.10 (s, 1H); 8.27 (s, 1H); 8.01 (s, 1H); 7.81 (d, 2H); 7.67 (d, 2H); 7.58 (d, 1H); 7.50 (t, 1H); 7.43 (s, 1H); 7.30 (d, 1H); 4.03 (s, 3H); 3.72 (s, 2H); 3.56-3.59 (m, 4H); 2.43-2.50 (obscured by d$_6$-DMSO, 4H).

MS (ESI): [M+H]$^+$=511.

Example Compound 3.3

Preparation of 1-[4-(1-Methyl-6-morpholin-4-ylmethyl-1H-pyrazolo[3,4-b]pyridin-4-yl)-phenyl]-3-m-tolyl-urea

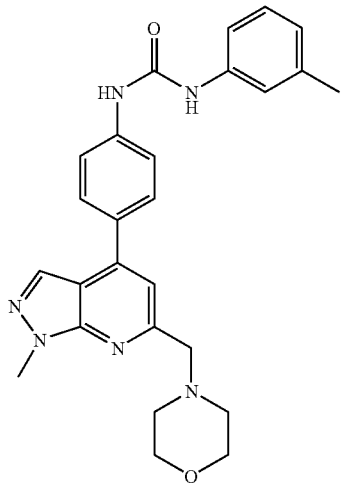

In an adoption of GP 4a (step 1), reaction of 162 mg of Intermediate 13.3 (0.5 mmol, 1 eq.) with 71 μL 1-isocyanato-3-methyl-benzene (0.55 mmol, 1.1 eq.) in 5 mL DCM yielded after extractive work-up and flash column chromatography 54 mg of Example Compound 3.3 as a yellowish resin (0.118 mmol, 24% yield).

$^1$H-NMR (d$_6$-DMSO; 400 MHz): 8.94 (s, 1H); 8.65 (s, 1H); 8.27 (s, 1H); 7.79 (d, 2H); 7.67 (d, 2H); 7.43 (s, 1H); 7.29 (s, 1H); 7.22 (d, 1H); 7.14 (t, 1H); 6.77 (d, 1H); 4.03 (s, 3H); 3.72 (s, 2H); 3.55-3.59 (m, 4H); 2.43-2.50 (obscured by d$_6$-DMSO, 4H); 2.25 (s, 3H).

MS (ESI): [M+H]$^+$=457.

Example Compound 3.4

Preparation of 1-(3-Ethyl-phenyl)-3-[4-(1-methyl-6-morpholin-4-ylmethyl-1H-pyrazolo[3,4-b]pyridin-4-yl)-phenyl]-urea

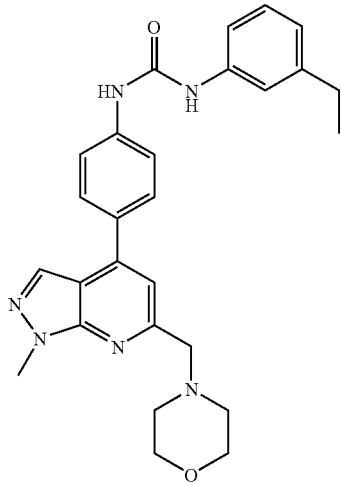

In an adoption of GP 4a (step 1), reaction of 162 mg of Intermediate 13.3 (0.5 mmol, 1 eq.) with 78 μL 1-ethyl-3-isocyanato-benzene (0.55 mmol, 1.1 eq.) in 5 mL DCM yielded after extractive work-up and flash column chromatography 116 mg of Example Compound 3.4 (0.25 mmol, 50% yield).

$^1$H-NMR (d$_6$-DMSO; 400 MHz): 8.95 (s, 1H); 8.68 (s, 1H); 8.27 (s, 1H); 7.80 (d, 2H); 7.65 (d, 2H); 7.43 (s, 1H); 7.31 (s, 1H); 7.25 (d, 1H); 7.16 (t, 1H); 6.81 (d, 1H); 4.03 (s, 3H); 3.71 (s, 2H); 3.56-3.59 (m, 4H); 2.55 (q, 2H); 2.43-2.50 (obscured by d$_6$-DMSO, 4H); 1.15 (t, 3H).

MS (ESI): [M+H]$^+$=471.

Example Compound 3.5

Preparation of 1-(2-Fluoro-5-methyl-phenyl)-3-[4-(1-methyl-6-morpholin-4-ylmethyl-1H-pyrazolo[3,4-b]pyridin-4-yl)-phenyl]-urea

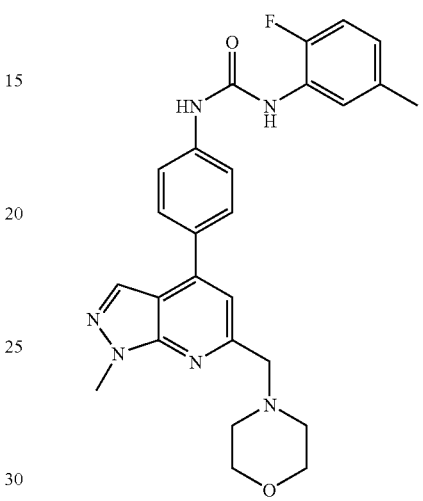

In an adoption of GP 4a (step 1), reaction of 87 mg of Intermediate 13.3 (0.27 mmol, 1 eq.) with 39 μL 1-fluoro-2-isocyanato-4-methyl-benzene (0.3 mmol, 1.1 eq.) in 2.7 mL DCM yielded after concentration in vacuo and flash column chromatography of the residue 68 mg of Example Compound 3.5 (0.143 mmol, 53% yield, mp 238° C.).

$^1$H-NMR (d$_6$-DMSO; 300 MHz): 9.31 (s, 1H); 8.52 (d, 1H); 8.27 (s, 1H); 7.97 (dd, 1H); 7.81 (d, 2H); 7.65 (d, 2H); 7.43 (s, 1H); 7.09 (dd, 1H); 6.76-6.81 (m, 1H); 4.03 (s, 3H); 3.72 (s, 2H); 3.55-3.60 (m, 4H); 2.42-2.50 (obscured by d$_6$-DMSO, 4H); 2.25 (s, 3H).

MS (ESI): [M+H]$^+$=475.

Example Compound 3.6

Preparation of 1-(2-Fluoro-5-trifluoromethyl-phenyl)-3-[4-(1-methyl-6-morpholin-4-ylmethyl-1H-pyrazolo[3,4-b]pyridin-4-yl)-phenyl]-urea

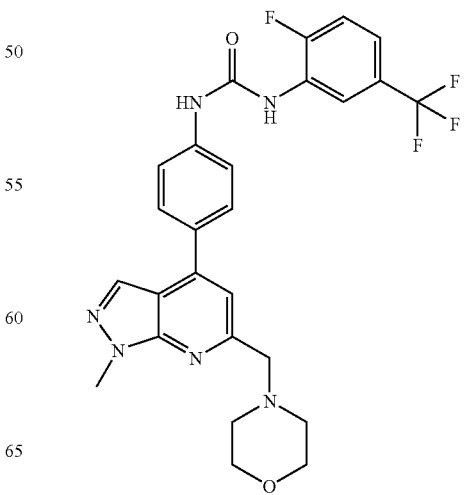

In an adoption of GP 4a (step 1), reaction of 162 mg of Intermediate 13.3 (0.5 mmol, 1 eq.) with 80 µL 1-Fluoro-2-isocyanato-4-trifluoromethyl-benzene (0.55 mmol, 1.1 eq.) in 5 mL DCM yielded after extractive work-up and flash column chromatography 113 mg of Example Compound 3.6 (0.214 mmol, 43% yield).

$^1$H-NMR (d$_6$-DMSO; 400 MHz): 9.44 (s, 1H); 8.95 (s, 1H); 8.60 (dd, 1H); 8.26 (s, 1H); 7.82 (d, 2H); 7.66 (d, 2H); 7.49 (t, 1H); 7.43 (s, 1H); 7.36-7.40 (m, 1H); 4.03 (s, 3H); 3.72 (s, 2H); 3.56-3.60 (m, 4H); 2.42-2.50 (obscured by d$_6$-DMSO, 4H).

MS (ESI): [M+H]$^+$=529.

The following example compounds 3.7 to 3.14 were prepared in analogy to the example compounds 3.1 to 3.6 by reacting the respective aniline intermediates with the respective commercially available isocyanates:

| Example | Structure | Name | Analytical data |
|---|---|---|---|
| 3.7 | 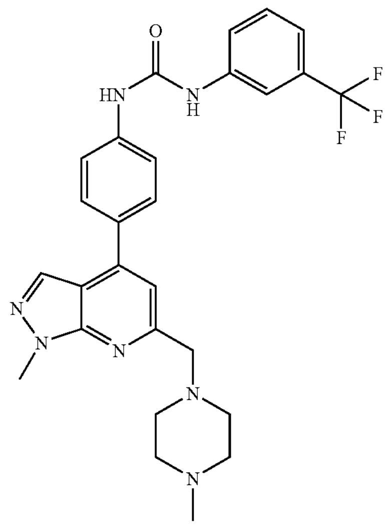 | 1-{4-[1-Methyl-6-(4-methyl-piperazin-1-ylmethyl)-1H-pyrazolo[3,4-b]pyridin-4-yl]-phenyl}-(3-trifluoromethyl-phenyl)-urea | $^1$H-NMR: (DMSO, 300 MHz) 9.12 (s, 1 H); 9.10 (s, 1 H); 8.26 (s, 1 H); 8.01 (br. s, 1 H); 7.80 (d, 2 H); 7.67 (d, 2 H); 7.58 (d, 1 H); 7.50 (t, 1 H); 7.40 (s, 1 H); 7.30 (d, 1 H); 4.03 (s, 3 H); 3.70 (s, 2 H); 2.26-2.37 (m, 4 H); 2.12 (s, 3 H). MS (LC-MS-ESI): [M + H]$^+$ = 524. |
| 3.8 | 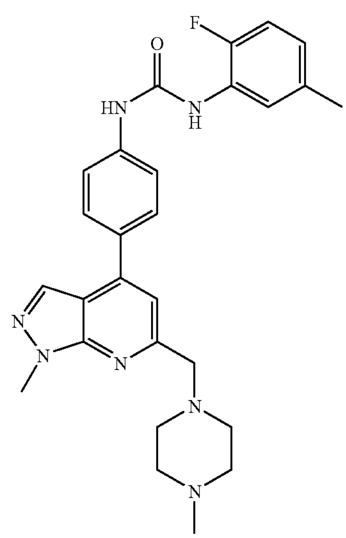 | 1-(2-Fluoro-5-methyl-phenyl)-3-{4-[1-methyl-6-(4-methyl-piperazin-1-ylmethyl)-1H-pyrazolo[3,4-b]pyridin-4-yl]-phenyl}-urea | $^1$H-NMR: (DMSO, 300 MHz) 9.34 (s, 1 H); 8.54 (d, 1 H); 8.26 (s, 1 H); 7.96 (dd, 1 H); 7.79 (d, 2 H); 7.65 (d, 2 H); 7.41 (s, 1 H); 7.08 (dd, 1 H); 6.76-6.82 (m, 1 H); 4.03 (s, 3 H); 3.70 (s, 2 H); 2.27-2.37 (m, 4 H); 2.25 (s, 3 H); 2.11 (s, 3 H). MS (ESI): [M + H]$^+$ = 488. |

-continued

| Example | Structure | Name | Analytical data |
|---------|-----------|------|-----------------|
| 3.9 | 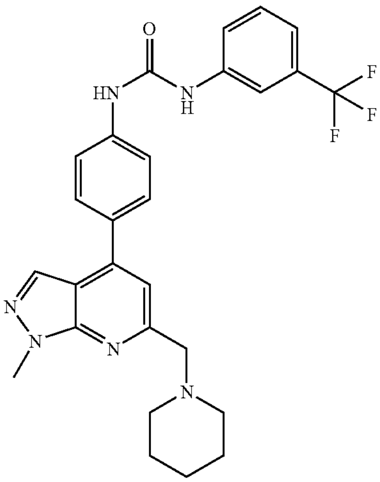 | 1-[4-(1-Methyl-6-piperidin-1-ylmethyl-1H-pyrazolo[3,4-b]pyridin-4-yl)-phenyl]-3-(3-trifluoromethyl-phenyl)-urea | $^1$H-NMR: (DMSO, 300 MHz) 9.12 (s, 1 H); 9.10 (s, 1 H); 8.26 (s, 1 H); 8.00 (s, 1 H); 7.80 (d, 2 H); 7.66 (d, 2 H); 7.58 (d, 1 H); 7.50 (t, 1 H); 7.42 (s, 1 H); 7.30 (d, 1 H); 4.03 (s, 1 H); 3.67 (s, 2 H); 2.24-2.40 (m, 4 H); 1.45-1.55 (m, 4 H); 1.33-1.42 (m, 2 H). MS (ESI): [M + H]$^+$ = 509. |
| 3.10 | 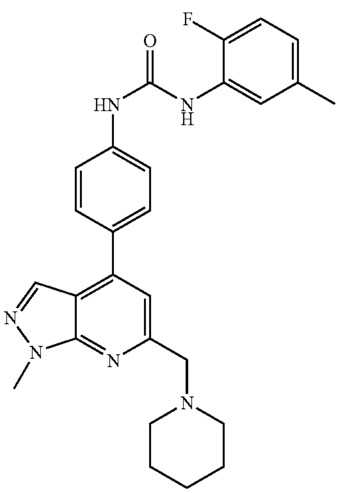 | 1-(2-Fluoro-5-methyl-phenyl)-3-[4-(1-methyl-6-piperidin-1-ylmethyl-1H-pyrazolo[3,4-b]pyridin-4-yl)-phenyl]-urea | $^1$H-NMR: (DMSO, 300 MHz) 9.34 (s, 1 H); 8.54 (d, 1 H); 8.25 (s, 1 H); 7.97 (dd, 1 H); 7.80 (d, 2 H); 7.65 (d, 2 H); 7.42 (s, 1 H); 7.08 (dd, 1 H); 6.76-6.81 (m, 1 H); 4.02 (s, 3 H); 3.67 (s, 2 H); 2.36-2.43 (m, 4 H); 2.25 (s, 3 H); 1.45-1.54 (m, 4 H); 1.33-1.42 (m, 2 H). MS (ESI): [M + H]$^+$ = 473. |
| 3.11 | 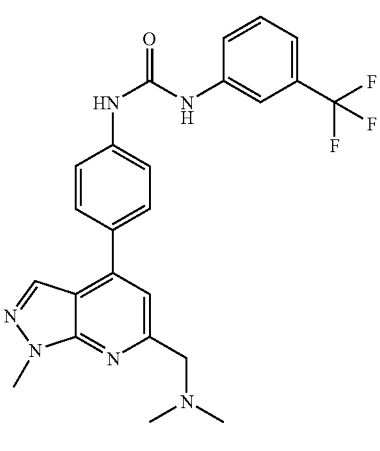 | 1-[4-(6-Dimethylaminomethyl-1-methyl-1H-pyrazolo[3,4-b]pyridin-4-yl)-phenyl]-3-(3-trifluoromethyl-phenyl)-urea | $^1$H-NMR: (DMSO, 300 MHz) 9.13 (s, 1 H); 9.12 (s, 1 H); 8.26 (s, 1 H); 8.01 (s, 1 H); 7.81 (d, 2 H); 7.66 (d, 2 H); 7.58 (d, 1 H); 7.49 (t, 1 H); 7.41 (s, 1 H); 7.30 (d, 1 H); 4.03 (s, 3 H); 3.65 (s, 2 H); 2.22 (s, 6 H). MS (ESI): [M + H]$^+$ = 469. |

| Example | Structure | Name | Analytical data |
|---|---|---|---|
| 3.12 | 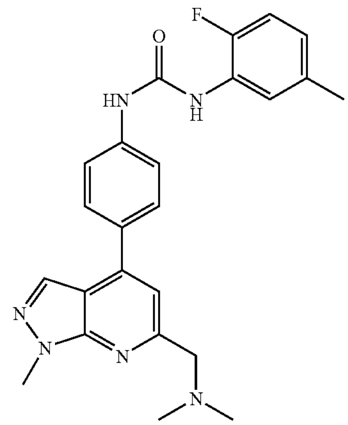 | 1-[4-(6-Dimethylaminomethyl-1-methyl-1H-pyrazolo[3,4-b]pyridin-4-yl)-phenyl]-3-(2-fluoro-5-methyl-phenyl)-urea | $^1$H-NMR: (DMSO, 300 MHz) 9.35 (s, 1 H); 8.54 (d, 1 H); 8.27 (s, 1 H); 7.97 (dd, 1 H); 7.81 (d, 2 H); 7.64 (d, 2 H); 7.42 (s, 1 H); 7.08 (dd, 1 H); 6.76-6.81 (m, 1 H); 4.03 (s, 3 H); 3.65 (s, 2 H); 2.25 (s, 3 H), 2.23 (s, 6 H). MS (ESI): [M + H]$^+$ = 433. |
| 3.13 | 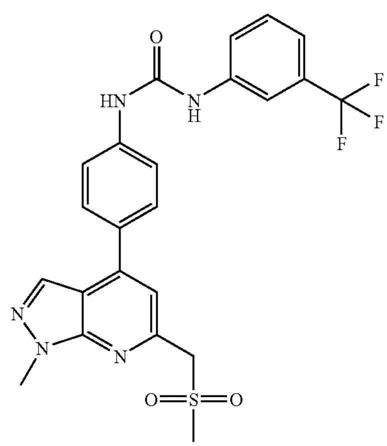 | 1-[4-(6-Methanesulfonylmethyl-1-methyl-1H-pyrazolo[3,4-b]pyridin-4-yl)-phenyl]-3-(3-trifluoromethyl-phenyl)-urea | $^1$H-NMR: (DMSO, 300 MHz) 9.19 (s, 2 H); 8.42 (s, 1 H); 8.05 (s, 1 H); 7.88 (d, 2 H); 7.74 (d, 2 H); 7.63 (d, 1 H); 7.55 (s, 1 H); 7.54 (t, 1 H); 7.35 (d, 1 H); 4.85 (s, 2 H); 4.11 (s, 3 H); 3.17 (s, 3 H). MS (ESI): [M + H]$^+$ = 504. |
| 3.14 | 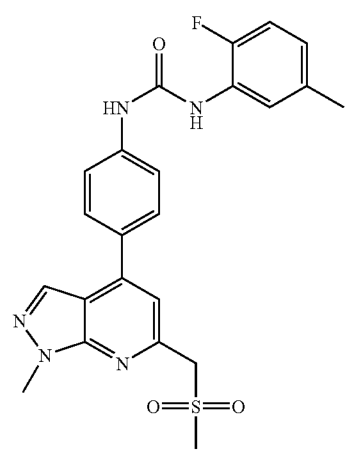 | 1-(2-Fluoro-5-methyl-phenyl)-3-[4-(6-methanesulfonylmethyl-1-methyl-1H-pyrazolo[3,4-b]pyridin-4-yl)-phenyl]-urea | $^1$H-NMR: (DMSO, 400 MHz) 9.45 (s, 1 H); 8.61 (d, 1 H); 8.42 (s, 1 H); 8.02 (dd, 1 H); 7.88 (d, 2 H); 7.72 (d, 2 H); 7.55 (s, 1 H); 7.13 (dd, 1 H); 6.80-6.87 (m, 1 H); 4.85 (s, 2 H); 4.11 (s, 3 H); 3.17 (s, 3 H); 2.29 (s, 3 H). MS (ESI): [M + H]$^+$ = 468. |

Example Compound 3.15

Preparation of 1-[4-(6-Methanesulfonylmethyl-1-methyl-1H-pyrazolo[3,4-b]pyridin-4-yl)-phenyl]-3-(4-trifluoromethyl-pyridin-2-yl)-urea

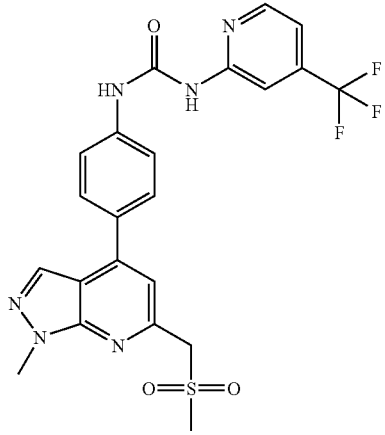

In analogy to *J. Org. Chem.* 2005, 70, 6960, 200 mg of Intermediate 18.2 (0.63 mmol, 1 eq.) were treated with 311 mg of (4-trifluoromethyl-pyridin-2-yl)-carbamic acid isopropenyl ester (1.26 mmol, 2 eq.) in 10 mL THF in the presence of 13 µL N-methylpyrrolidine (0.13 mmol, 0.2 eq.) and stirred at 55° C. for 16 h. The reaction mixture was concentrated in vacuo, the residue was partitioned between ethyl acetate and water, the organic phase was dried and concentrated. HPLC purification of the residue provided the analytically pure target compound.

$^1$H-NMR (d$_6$-DMSO; 300 MHz): 10.03 (s, 1H); 9.82 (s, 1H); 8.58 (d, 1H); 8.42 (s, 1H); 8.11 (s, 1H); 7.90 (d, 2H); 7.77 (d, 2H); 7.56 (s, 1H); 7.40 (d, 1H); 4.86 (s, 2H); 4.12 (s, 3H); 3.17 (s, 3H).

MS (LC-MS-ESI): [M+H]$^+$=505.

The following example compounds 3.16 to 3.18 were prepared in analogy to the example compounds 3.15 by reacting the respective aniline intermediates with (4-trifluoromethyl-pyridin-2-yl)-carbamic acid isopropenyl ester.

| Example | Structure | Name | Analytical data |
|---|---|---|---|
| 3.16 | 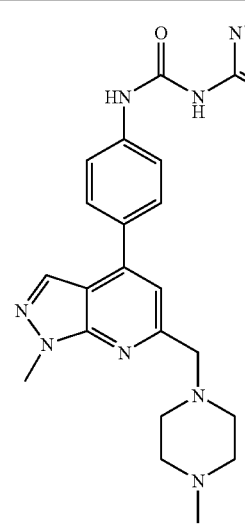 | 1-{4-[1-Methyl-6-(4-methyl piperazin-1-ylmethyl)-1H-pyrazolo[3,4-b]pyridin-4-yl]-phenyl}-3-(4-trifluoromethyl-pyridin-2-yl)-urea | MS (LC-MS-ESI): [M + H]$^+$ = 525. |
| 3.17 | 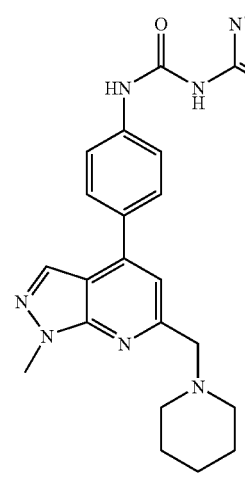 | 1-[4-(1-Methyl-6-piperidin-1-ylmethyl-1H-pyrazolo[3,4-b]pyridin-4-yl)-phenyl]-3-(4-trifluoromethyl-pyridin-2-yl)-urea | MS (LC-MS-ESI): [M + H]$^+$ = 510. |

| Example | Structure | Name | Analytical data |
|---|---|---|---|
| 3.18 | 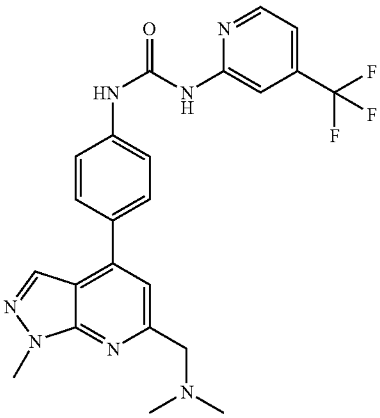 | 1-[4-(6-Dimethylaminomethyl-1-methyl-1H-pyrazolo[3,4-b]pyridin-4-yl)-phenyl]-3-(4-trifluoromethyl-pyridin-2-yl)-urea | MS (LC-MS-ESI): [M + H]⁺ = 470. |

The following example compounds 3.19 to 3.29 were prepared either from Intermediate 17.7 by amination with the respective commercially available amines and subsequent nitro reduction and urea formation in analogy to the afore described procedures or from Intermediate 17.8 by methylation employing standard conditions as known to the person skilled in the art and subsequent nitro reduction and urea formation in analogy to the aforementioned procedures.

| Example | Structure | Name | Analytical data |
|---|---|---|---|
| 3.19 | 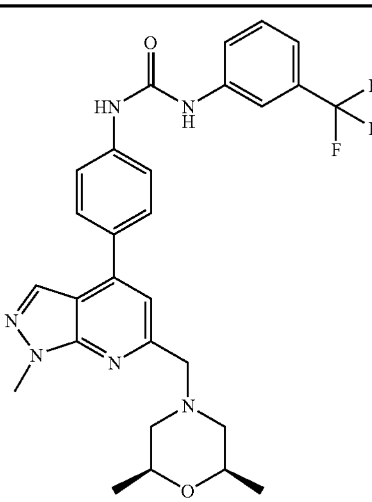 | 1-{4-[1-Methyl-6-(2,6-dimethyl-morpholin-4-ylmethyl)-1H-pyrazolo[3,4-b]pyridin-4-yl]-phenyl}-3-(3-trifluoromethyl-phenyl)-urea; | ¹H-NMR: (DMSO, 300 MHz) 9.16 (s, 1 H); 9.15 (s, 1 H); 8.31 (s, 1 H); 8.05 (s, 1 H); 7.85 (d, 2 H); 7.71 (d, 2 H); 7.63 (d, 1 H); 7.54 (t, 1 H); 7.47 (s, 1 H); 7.35 (d, 1 H); 4.08 (s, 3 H); 3.74 (s, 2 H); 3.63 (mc, 2 H); 2.77 (d, 2 H); 1.81 (t, 2 H); 1.04 (d, 6 H). MS (ESI): [M + H]⁺ = 539. |

| Example | Structure | Name | Analytical data |
|---|---|---|---|
| 3.20 | 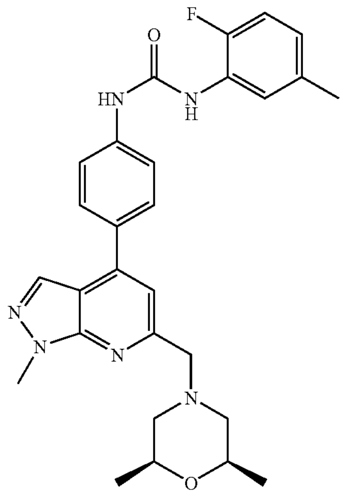 | 1-(2-Fluoro-5-methyl-phenyl)-3-{4-[1-methyl-6-(2,6-di-methyl-morpholin-4-ylmethyl)-1H-pyrazolo[3,4-b]pyridin-4-yl]-phenyl}-urea; | $^1$H-NMR: (DMSO, 300 MHz) 9.37 (s, 1 H); 8.58 (d, 1 H); 8.31 (s, 1 H); 8.01 (dd, 1 H); 7.85 (d, 2 H); 7.69 (d, 2 H); 7.46 (s, 1 H); 7.13 (dd, 2 H); 6.81-6.85 (m, 1 H); 4.08 (s, 3 H); 3.73 (s, 2 H); 3.62 (mc, 2 H); 2.77 (d, 2 H); 2.30 (s, 3 H); 1.80 (t, 2 H); 1.04 (d, 6 H). MS (ESI): [M + H]$^+$ = 503. |
| 3.21 | 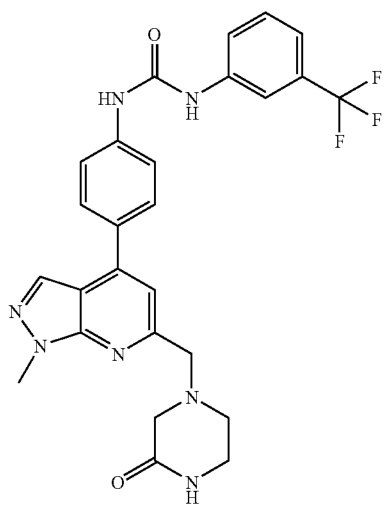 | 1-{4-[1-Methyl-6-(3-oxo-piperazin-1-ylmethyl)-1H-pyrazolo[3,4-b]pyridin-4-yl]-phenyl}-3-(3-trifluoromethyl-phenyl)-urea | $^1$H-NMR: (DMSO, 300 MHz) 9.15 (br. s, 2 H); 8.33 (s, 1 H); 8.05 (s, 1 H); 7.87 (d, 2 H); 7.79 (br. s, 1 H); 7.71 (d, 2 H); 7.63 (d, 1 H); 7.54 (t, 1 H); 7.48 (s, 1 H); 7.34 (d, 1 H); 4.08 (s, 3 H); 3.85 (s, 2 H); 3.17-3.22 (m, 2 H); 3.09 (br. s, 2 H); 2.69 (t, 2 H). MS (ESI): [M + H]$^+$ = 524. |
| 3.22 | 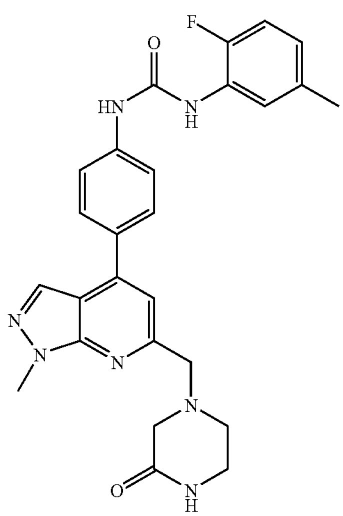 | 1-(2-Fluoro-5-methyl-phenyl)-3-{4-[1-methyl-6-(3-oxo-piperazin-1-ylmethyl)-1H-pyrazolo[3,4-b]pyridin-4-yl]-phenyl}-urea | $^1$H-NMR: (DMSO, 300 MHz) 9.37 (s, 1 H); 8.58 (d, 1 H); 8.33 (s, 1 H); 8.01 (dd, 1 H); 7.87 (d, 2 H); 7.79 (br. s, 1 H); 7.69 (d, 2 H); 7.48 (s, 1 H); 7.13 (dd, 1 H); 6.80-6.86 (m, 1 H); 4.08 (s, 3 H); 3.85 (s, 2 H); 3.17-3.22 (m, 2 H); 3.09 (br. s, 2 H); 2.69 (t, 2 H); 2.29 (s, 3 H). MS (ESI): [M + H]$^+$ = 488. |

| Example | Structure | Name | Analytical data |
|---|---|---|---|
| 3.23 | 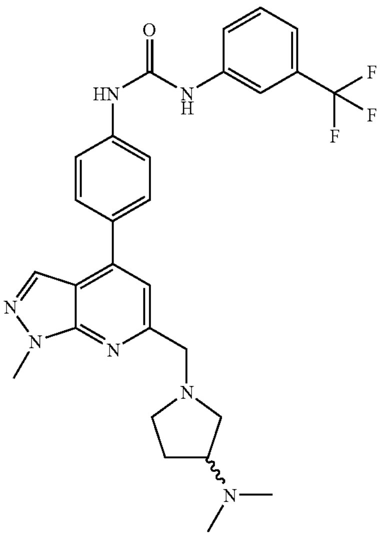 | 1-{4-[6-(3-Dimethylamino-pyrrolidin-1-ylmethyl)-1-methyl-1H-pyrazolo[3,4-b]pyridin-4-yl]-phenyl}-3-(3-trifluoromethyl-phenyl)-urea | $^1$H-NMR: (DMSO, 300 MHz) 9.22 (br. s, 2 H); 8.30 (s, 1 H); 8.05 (s, 1 H); 7.85 (d, 2 H); 7.71 (d, 2 H); 7.63 (d, 1 H); 7.54 (t, 1 H); 7.44 (s, 1 H); 7.34 (d, 1 H); 4.07 (s, 3 H); 3.85 (mc, 2 H); 2.66-2.81 (m, 3 H); 2.55-2.62 (m, 1 H); 2.37-2.46 (m, 1 H); 2.10 (s, 6 H); 1.83-1.95 (m, 1 H); 1.60-1.71 (m, 1 H). MS (ESI): [M + H]$^+$ = 538. |
| 3.24 | 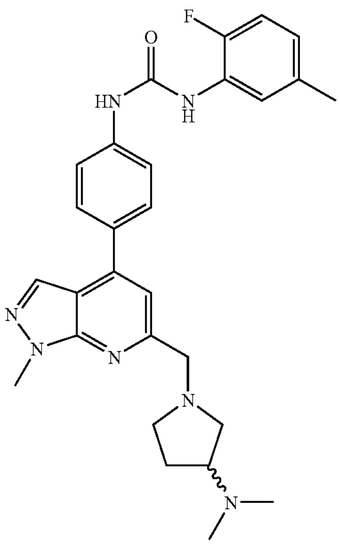 | 1-{4-[6-(3-Dimethylamino-pyrrolidin-1-ylmethyl)-1-methyl-1H-pyrazolo[3,4-b]pyridin-4-yl]-phenyl}-3-(2-fluoro-5-methyl-phenyl)-urea | $^1$H-NMR: (DMSO, 300 MHz) 9.39 (s, 1 H); 8.58 (br. s, 1 H); 8.31 (s, 1 H); 8.01 (dd, 1 H); 7.84 (d, 2 H); 7.69 (d, 2 H); 7.43 (s, 1 H); 7.13 (dd, 1 H); 6.80-6.86 (m, 1 H); 4.07 (s, 3 H); 3.85 (mc, 2 H); 2.66-2.81 (m, 3 H); 2.53-2.61 (m, 1 H); 2.37-2.46 (m, 1 H); 2.29 (s, 3 H); 2.09 (s, 6 H); 1.83-1.94 (m, 1 H); 1.59-1.73 (m, 1 H). MS (ESI): [M + H]$^+$ = 502. |
| 3.25 | 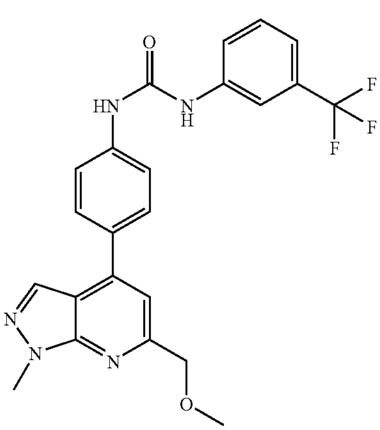 | 1-[4-(6-Methoxymethyl-1-methyl-1H-pyrazolo[3,4-b]pyridin-4-yl)-phenyl]-3-(3-trifluoromethyl-phenyl)-urea | MS (LC-MS-ESI): [M + H]$^+$ = 455. |

| Example | Structure | Name | Analytical data |
|---------|-----------|------|-----------------|
| 3.26 | 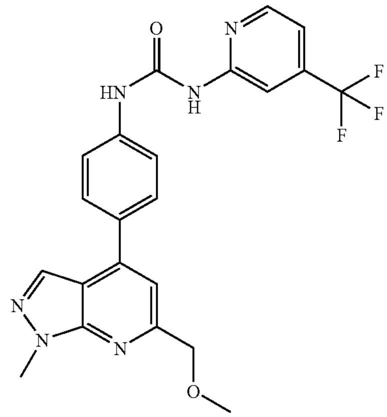 | 1-[4-(6-Methoxymethyl-1-methyl-1H-pyrazolo[3,4-b]pyridin-4-yl)-phenyl]-3-(4-trifluoromethyl-pyridin-2-yl)-urea | MS (LC-MS-ESI): [M + H]$^+$ = 456. |
| 3.27 | 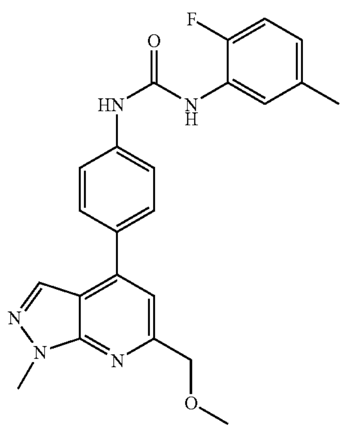 | 1-(2-Fluoro-5-methyl-phenyl)-3-[4-(6-methoxymethyl-1-methyl-1H-pyrazolo[3,4-b]pyridin-4-yl)-phenyl]-urea | MS (LC-MS-ESI): [M + H]$^+$ = 419. |
| 3.28 | 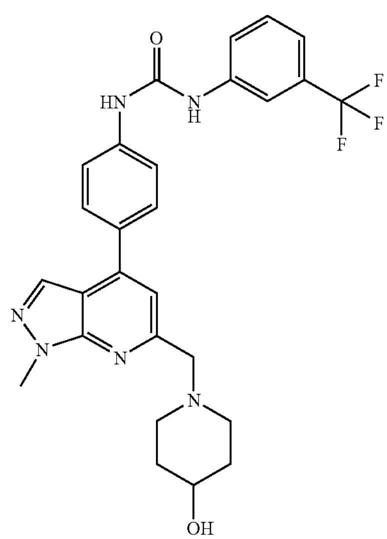 | 1-{4-[6-(4-Hydroxy-piperidin-1-ylmethyl)-1-methyl-1H-pyrazolo[3,4-b]pyridin-4-yl]-phenyl}-3-(3-trifluoromethyl-phenyl)-urea | $^1$H-NMR: (DMSO, 300 MHz) 9.16 (s, 1 H); 9.16 (s, 1 H); 8.30 (s, 1 H); 8.05 (s, 1 H); 7.85 (d, 2 H); 7.71 (d, 2 H); 7.63 (d, 1 H); 7.54 (t, 1 H); 7.46 (s, 1 H); 7.35 (d, 1 H); 4.56 (d, 1 H); 4.07 (s, 3 H); 3.73 (s, 2 H); 3.48 (mc, 1 H); 2.72-2.81 (m, 2 H); 2.18 (t, 2 H); 1.70-1.78 (m, 2 H); 1.38-1.50 (m, 2 H). MS (ESI): [M + H]$^+$ = 525. |

| Example | Structure | Name | Analytical data |
|---|---|---|---|
| 3.29 | 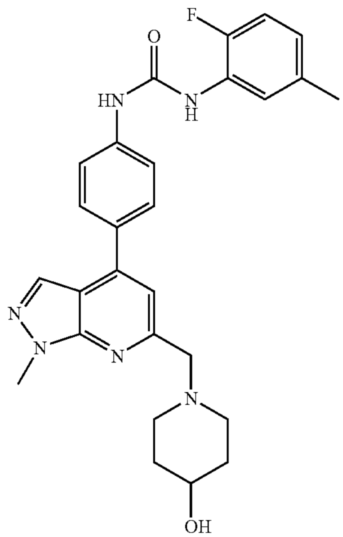 | 1-(2-Fluoro-5-methyl-phenyl)-3-{4-[6-(4-hydroxy-piperidin-1-ylmethyl)-1-methyl-1H-pyrazolo[3,4-b]pyridin-4-yl]-phenyl}-urea | $^1$H-NMR: (DMSO, 300 MHz) 9.37 (s, 1 H); 8.58 (d, 1 H); 8.31 (s, 1 H); 8.02 (dd, 1 H); 7.85 (d, 2 H); 7.68 (d, 2 H); 7.46 (s, 1 H); 7.13 (dd, 1 H); 6.80- 6.86 (m, 1 H); 4.57 (d, 1 H); 4.07 (s, 3 H); 3.73 (s, 2 H); 3.48 (mc, 1 H); 2.73-2.81 (m, 2 H); 2.30 (s, 3 H); 2.18 (t, 2 H); 1.70-1.78 (m, 2 H); 1.38-1.50 (m, 2 H). MS (ESI): $[M + H]^+ = 489$. |

Example Compound 4.1

Preparation of 1-{4-[4-(3-Phenyl-ureido)-phenyl]-1H-pyrazolo[3,4-b]pyridin-6-yl}-cyclopropanecarboxylic acid ethyl ester

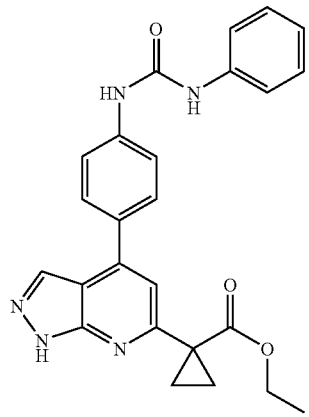

In analogy to GP 4c (step 1), reaction of Intermediate 14.3 (40 mg, 0.12 mmol, 1 eq.) with 16 μL phenylisocyanate (0.15 mmol, 1.2 eq.) in 2 mL DCM yielded 19 mg of the phenylurea (0.043 mmol, 35% yield).

$^1$H-NMR (d$_6$-DMSO; 300 MHz): 13.65 (br. s, 1H); 8.98 (br. s, 1H); 8.77 (br. s, 1H); 8.31 (br. s, 1H); 7.85 (m, 2H); 7.69 (m, 2H); 7.47 (m, 3H); 7.30 (m, 2H); 6.99 (m, 1H); 4.11 (q, 2H); 1.56 (m, 4H); 1.14 (t, 3H).

The following example compounds 5.1 to 5.63 are accessible from the above described intermediates by applying GP 6 or by alternative processes described above:

Example 5.1

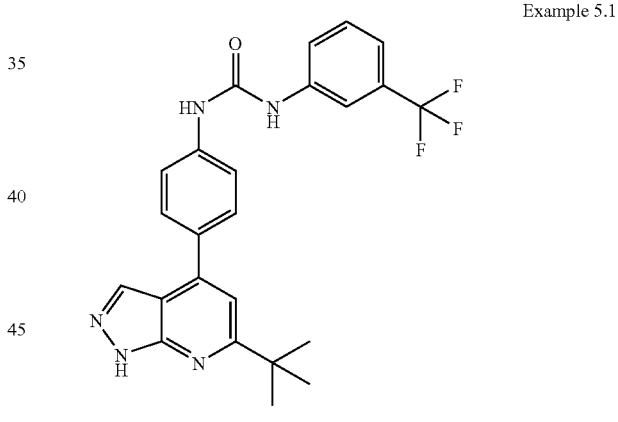

Example 5.2

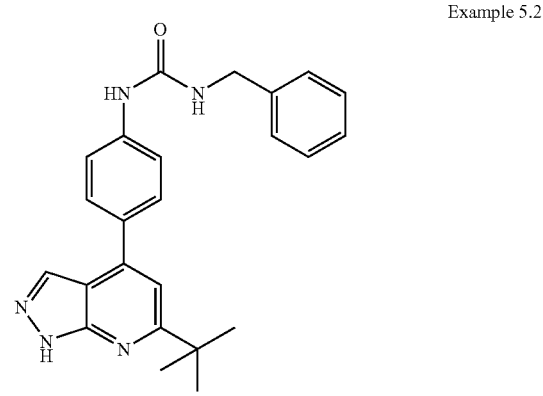

-continued
Example 5.3
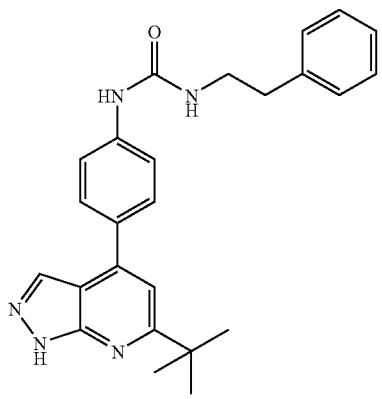
Example 5.4
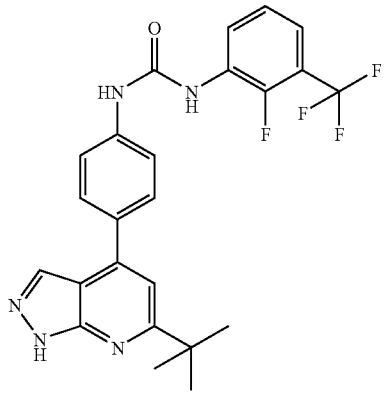
Example 5.5
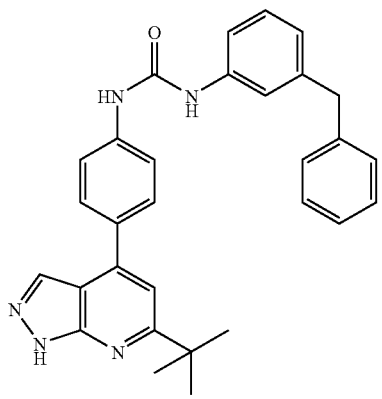
Example 5.6
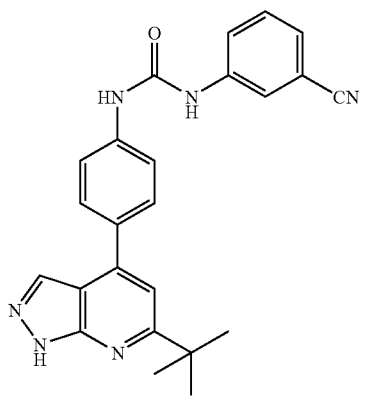
-continued
Example 5.7
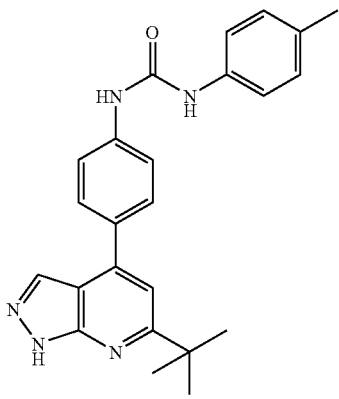
Example 5.8
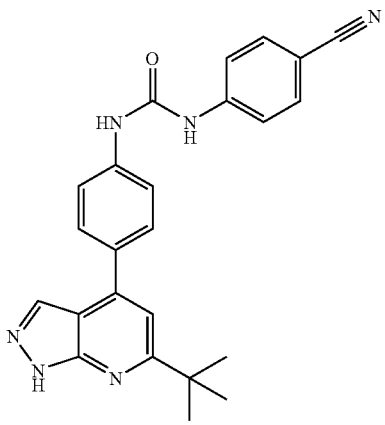
Example 5.9
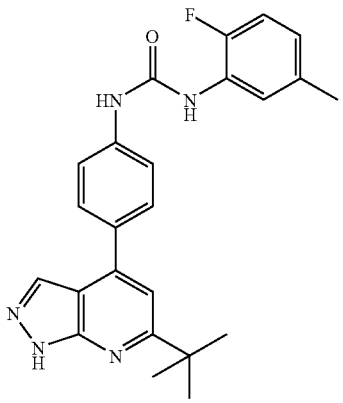
Example 5.10
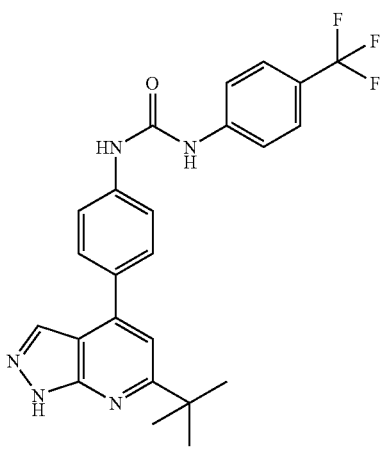

-continued
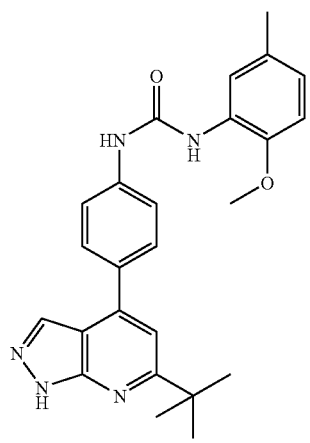
Example 5.11
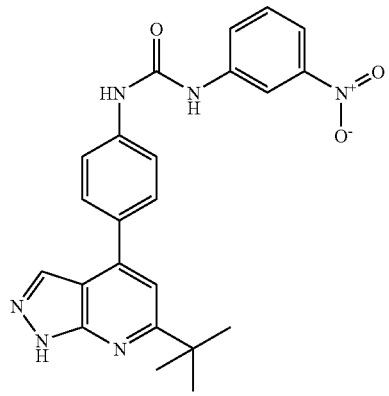
Example 5.12
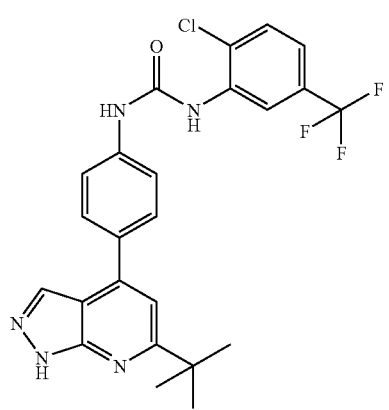
Example 5.13
-continued
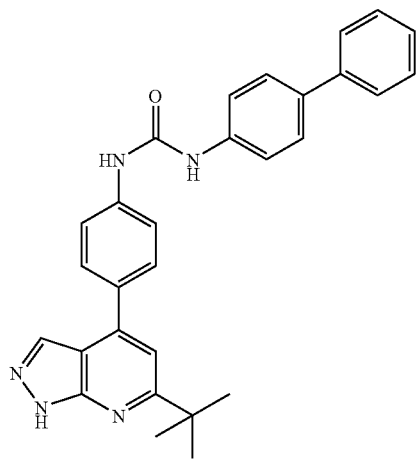
Example 5.14
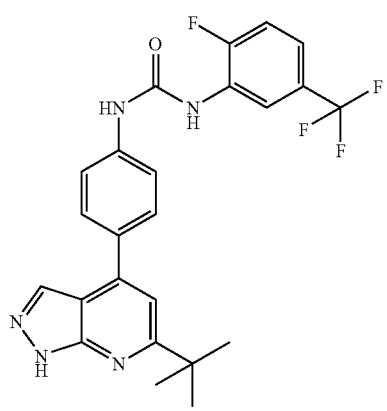
Example 5.15
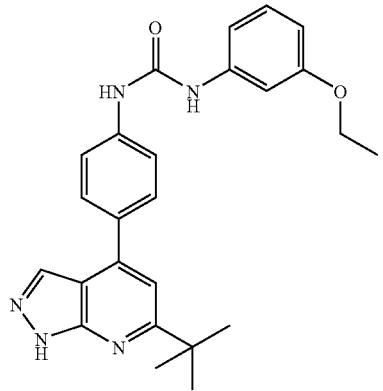
Example 5.16

-continued
Example 5.17
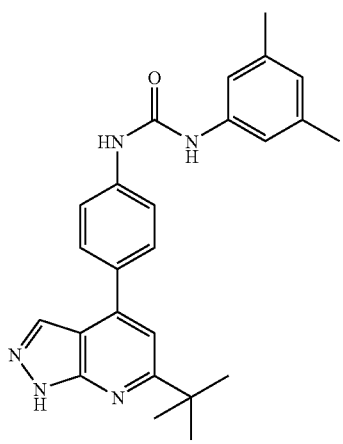
Example 5.18
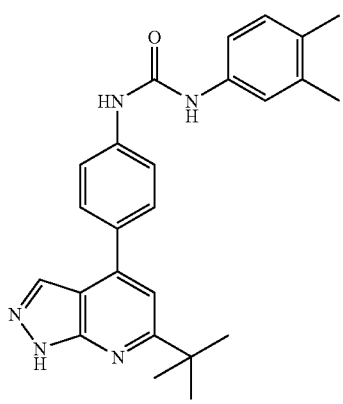
Example 5.19
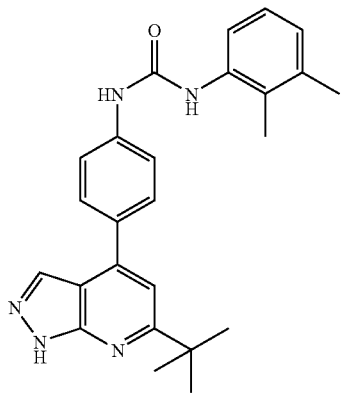
Example 5.20
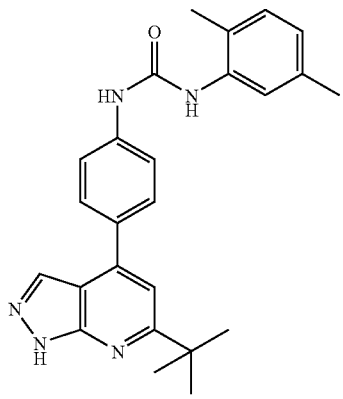
-continued
Example 5.21
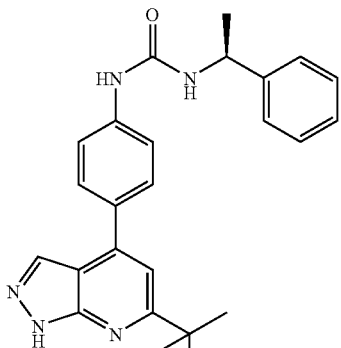
Example 5.22
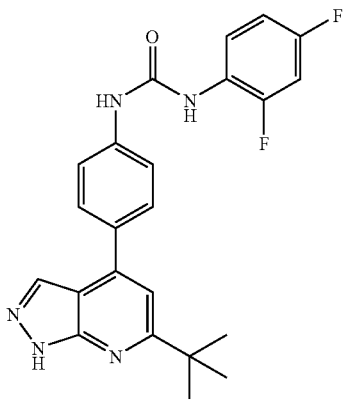
Example 5.23
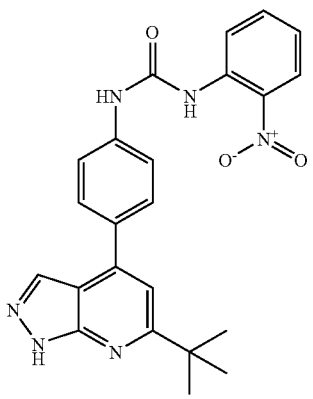
Example 5.24
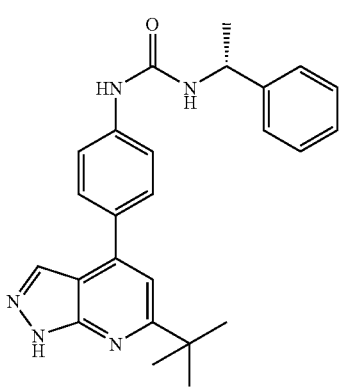

-continued
Example 5.25
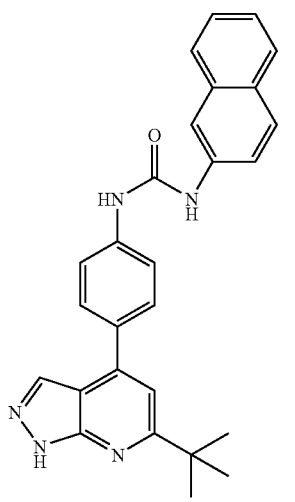
Example 5.26
Example 5.27
-continued
Example 5.28
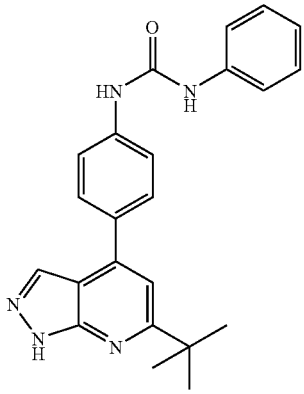
Example 5.29
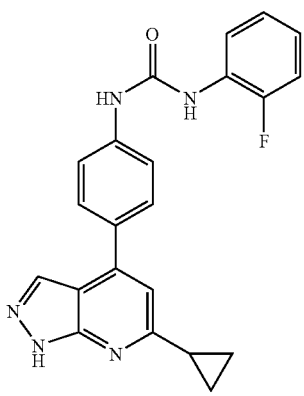
Example 5.30
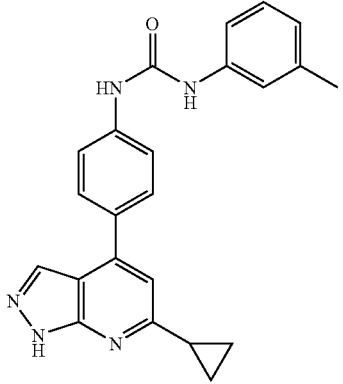
Example 5.31

-continued
Example 5.32
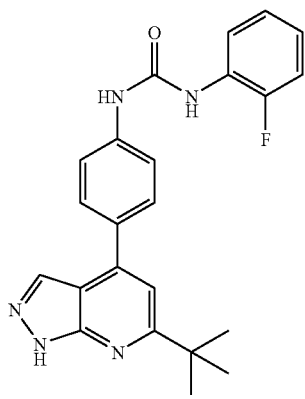
Example 5.33
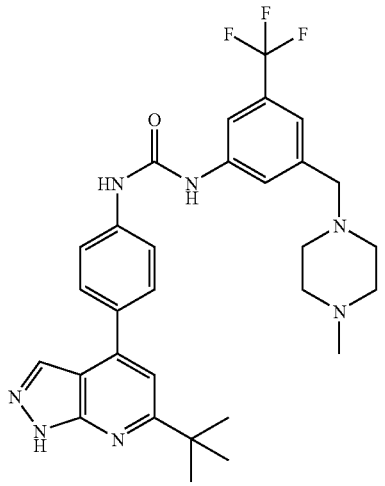
Example 5.34
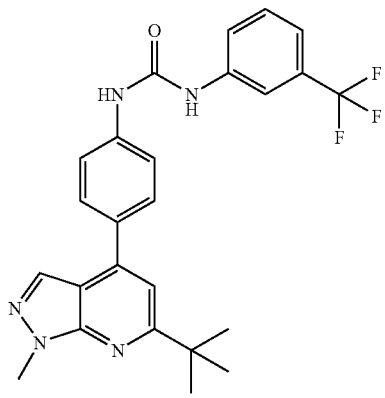
-continued
Example 5.35
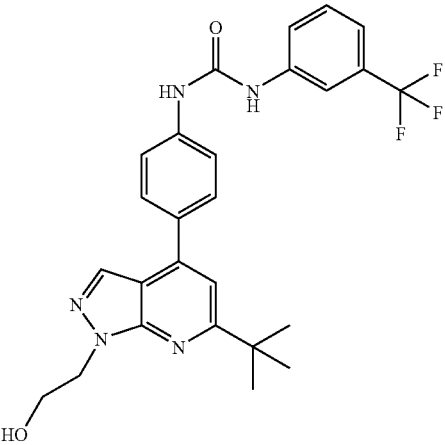
Example 5.36
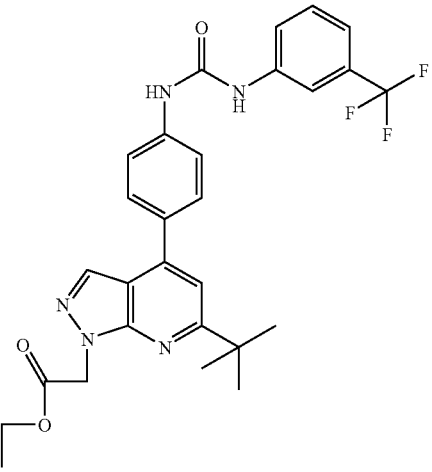
Example 5.37
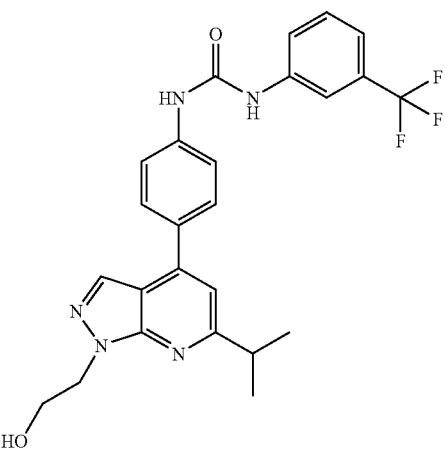

-continued
Example 5.38
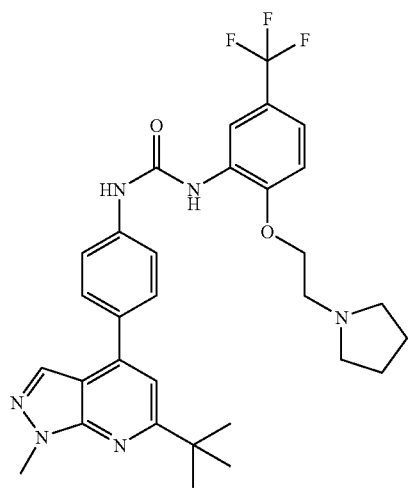
Example 5.39
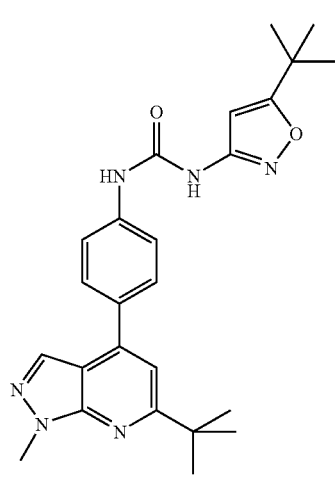
Example 5.40
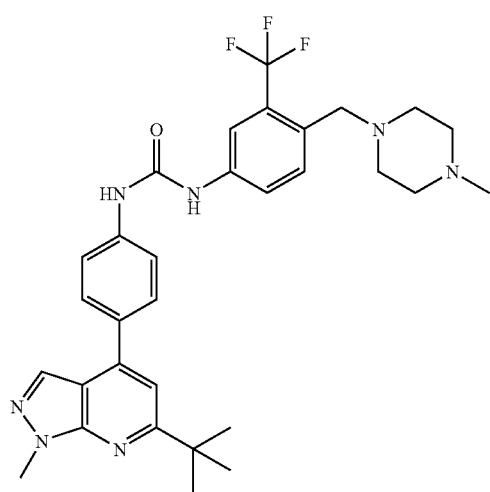
-continued
Example 5.41
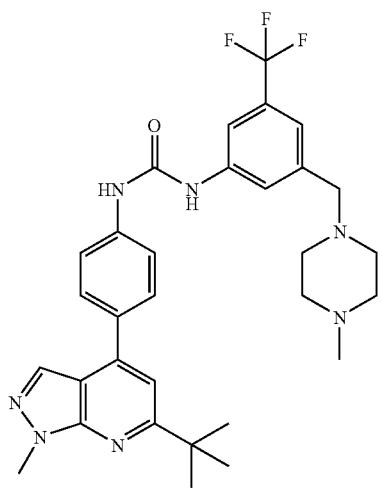
Example 5.42
Example 5.43
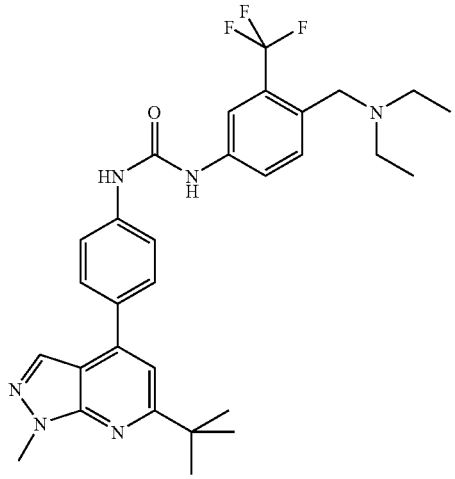

-continued
Example 5.44
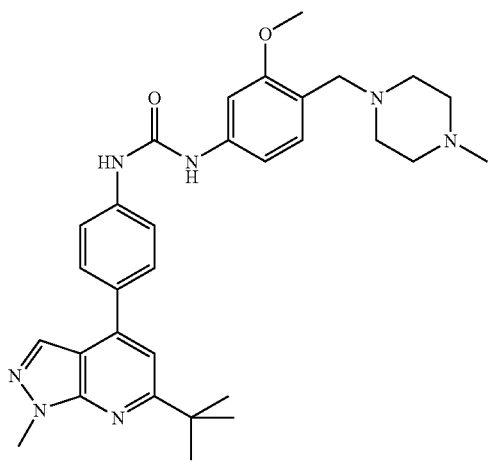
Example 5.45
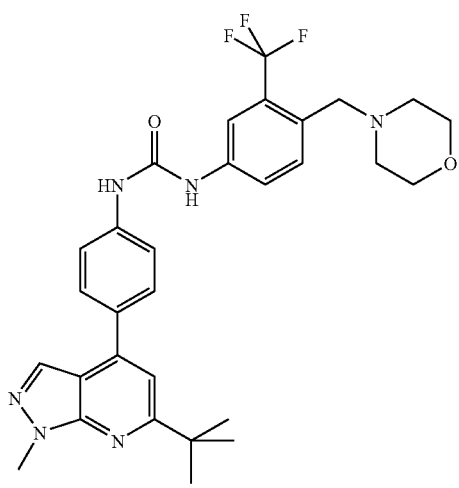
Example 5.46
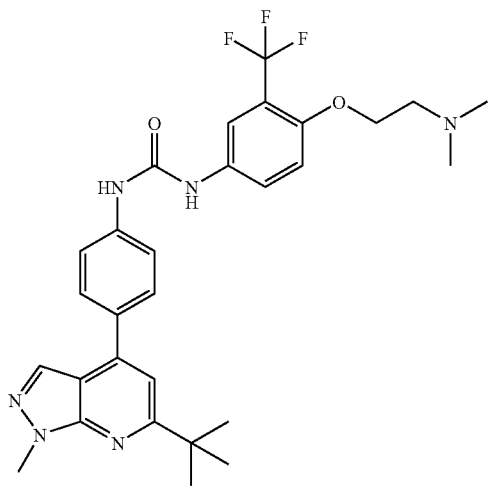
-continued
Example 5.47
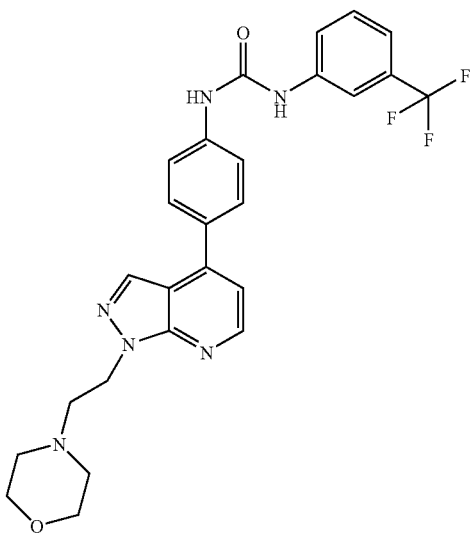
Example 5.48
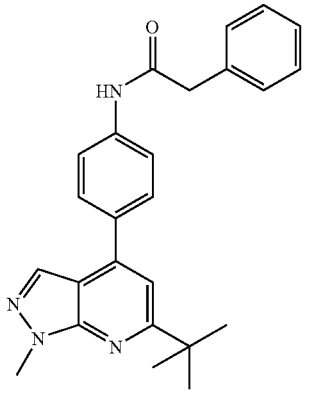
Example 5.49
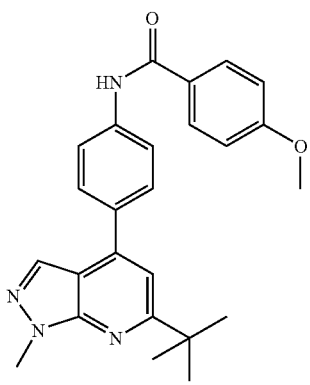

-continued
Example 5.50
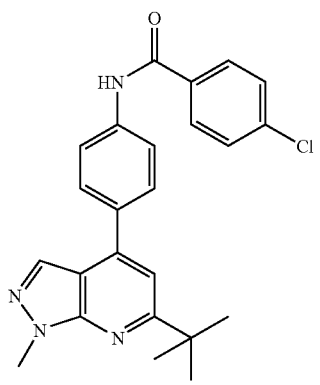
Example 5.51
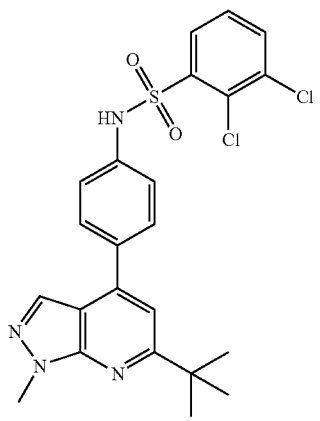
Example 5.52
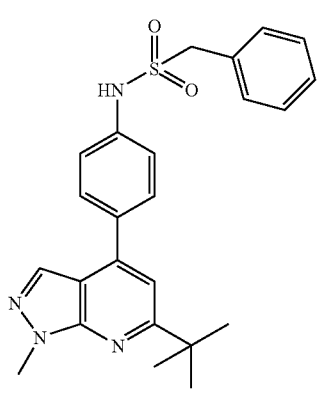
Example 5.53
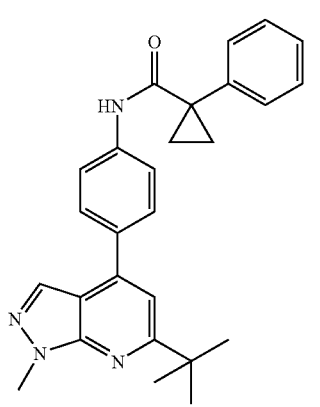
-continued
Example 5.54
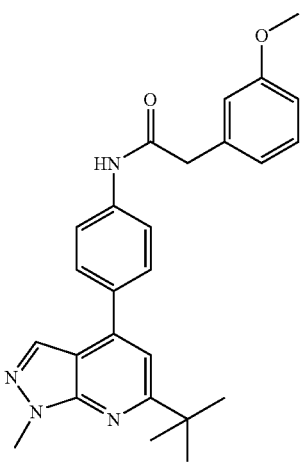
Example 5.55
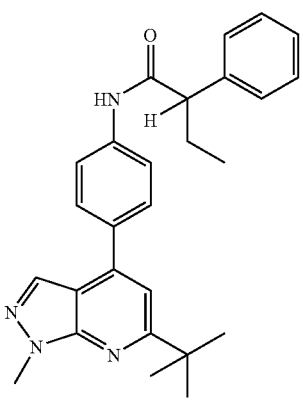
Example 5.56
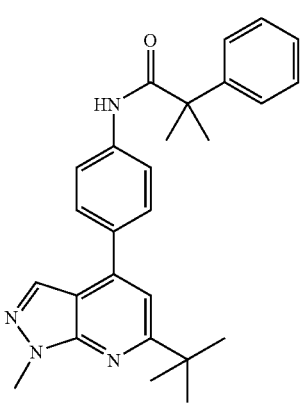
Example 5.57
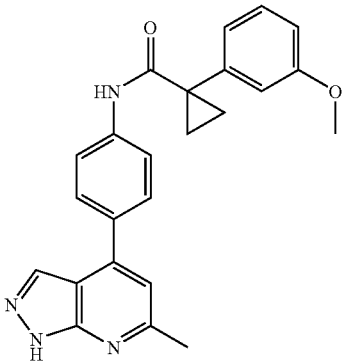

-continued
Example 5.58
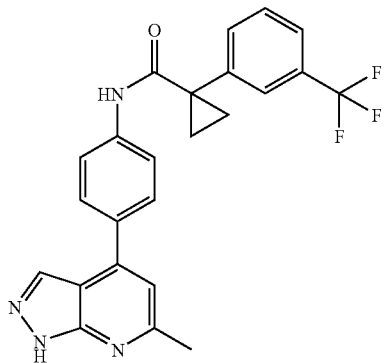
Example 5.59
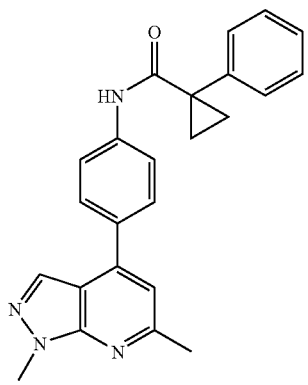
Example 5.60
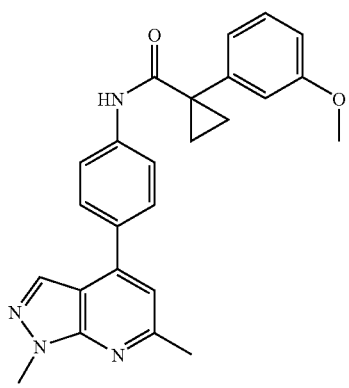
Example 5.61
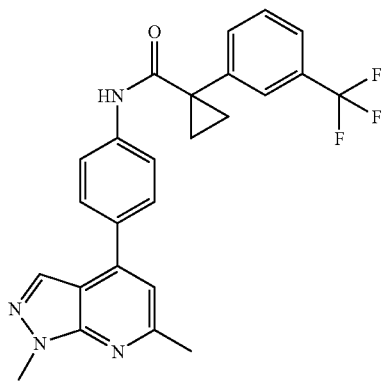
-continued
Example 5.62
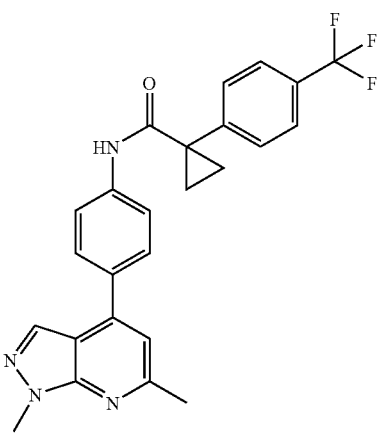
Example 5.63
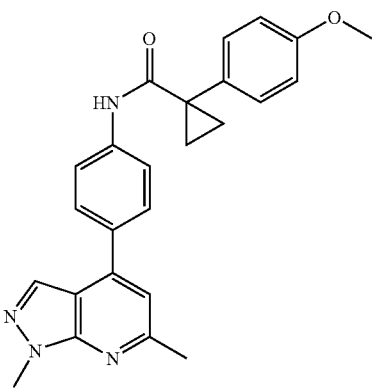
Example 5.64
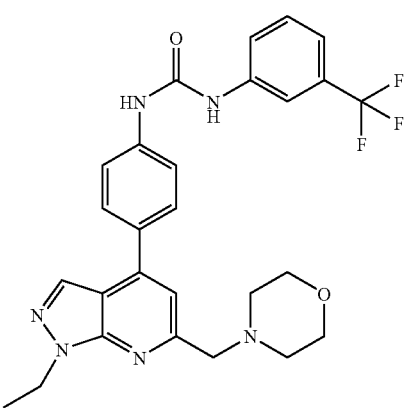

-continued
Example 5.65
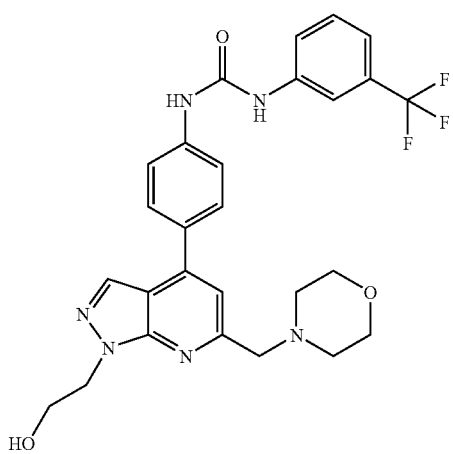
Example 5.66
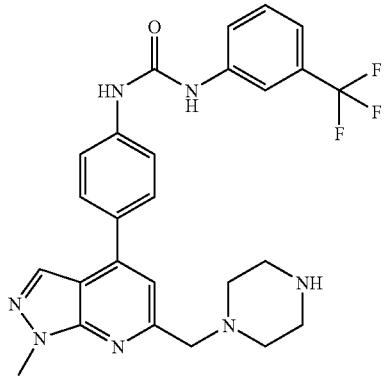
Example 5.67
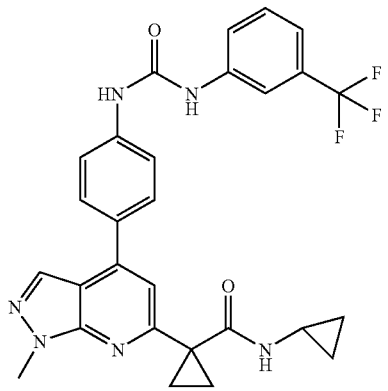
Example 5.68
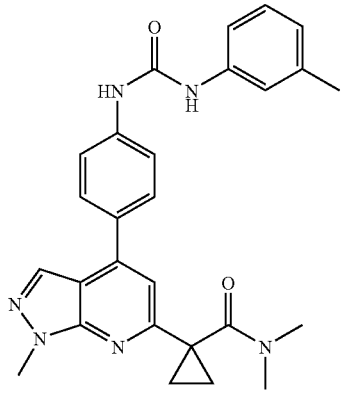
-continued
Example 5.69
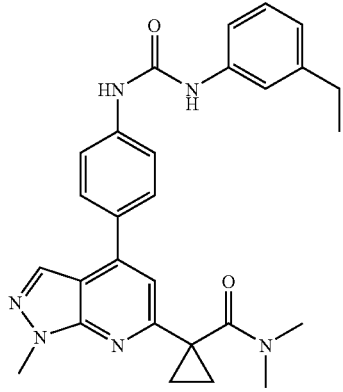
Example 5.70
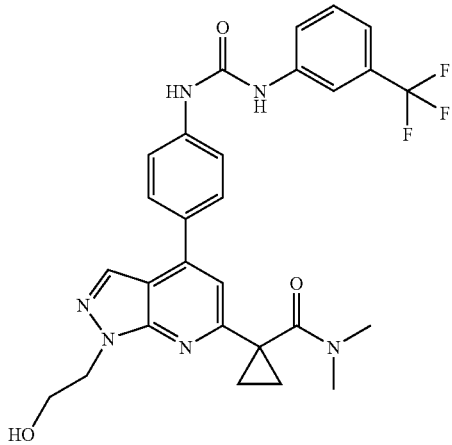
Example 5.71
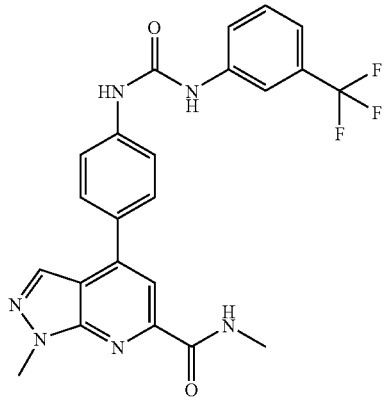

Example 5.72
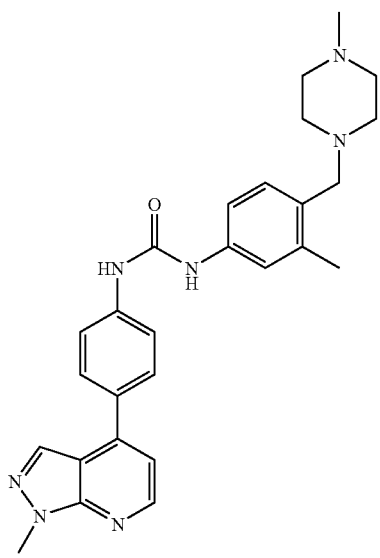
Example 5.75
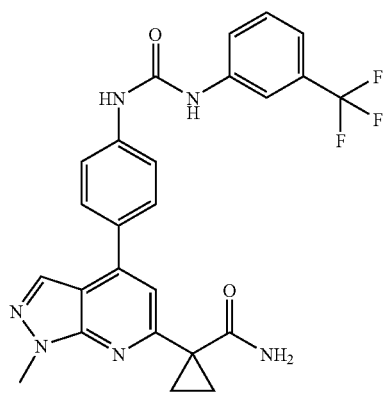
Example 5.73
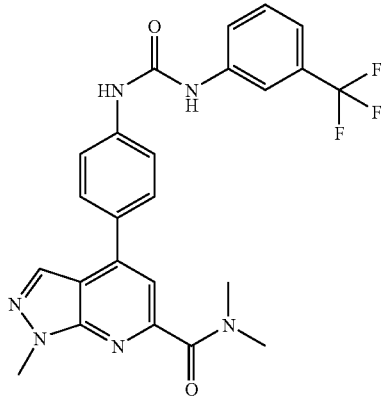
Example 5.76
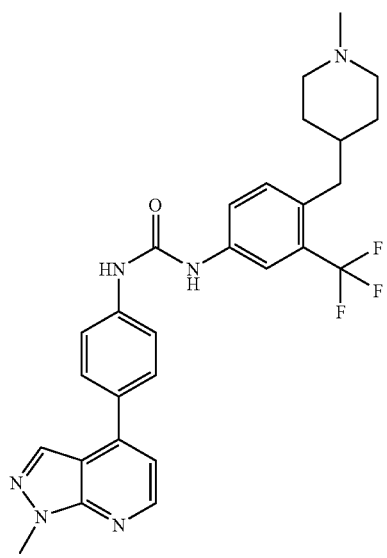
Example 5.74
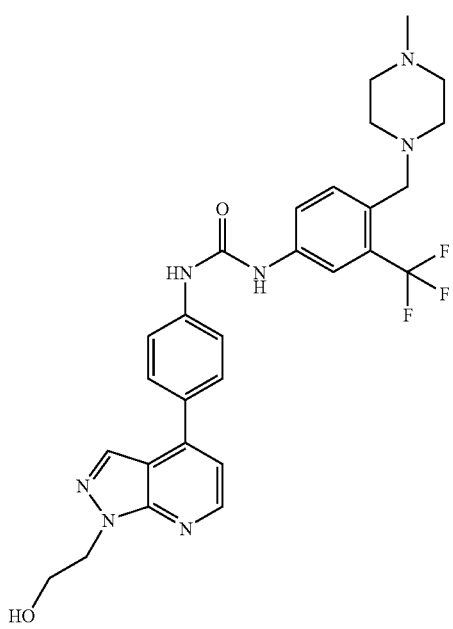
Example 5.77
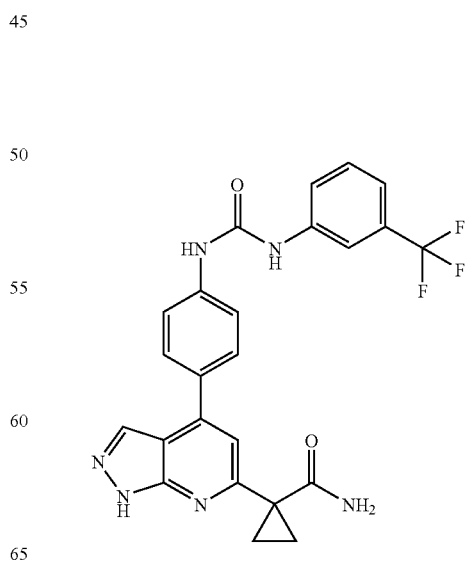

Example 5.78

Example 5.79

Example 5.80

Example 5.81

Example 5.82

Biological Data

Assay 1: Tie2 ELISA Assay

Cellular activity of compounds of the present invention as inhibitors of Tie2 kinase activity was measured employing a Tie2 ELISA assay as described in the following paragraphs. Herein CHO cell-cultures, which are stably transfected by known techniques with Tie2 using DHFR deficiency as selection marker, are stimulated by angiopoietin-2. The specific autophosphorylation of Tie2 receptors is quantified with a sandwich-ELISA using anti-Tie2 antibodies for catch and anti-phosphotyrosine antibodies coupled to HRP for detection.

Materials:
96 well tissue culture plate, sterile, Greiner
96 well FluoroNunc plate MaxiSorp Surface C, Nunc
96 well plate polypropylene for compound dilution in DMSO
CHO Tie2/DHFR (transfected cells)
PBS−; PBS++, DMSO
MEM alpha Medium with Glutamax-I without Ribonucleosides and
  Deoxyribonucleosides (Gibco #32561-029)
  with 10% FCS after dialysis! and 1% PenStrep Lysis buffer: 1 Tablet "Complete" protease inhibitor
1 cap Vanadate (1 mL>40 mg/mL; working solution 2 mM)
ad 50 mL with Duschl-Puffer
pH 7.6
Anti-Tie2-antibody 1:425 in Coating Buffer pH 9.6
Stock solution: 1.275 mg/mL>working: 3 µg/mL
PBST: 2 bottles PBS(10×)+10 ml Tween, fill up with VE-water
RotiBlock 1:10 in VE-water
Anti-Phosphotyrosine HRP-Conjugated 1:10000 in 3% TopBlock
3% TopBlock in PBST
BM Chemiluminescence ELISA Substrate (POD) solution B1:100 solution A
SF9 cell culture medium
Ang2-Fc in SF9 cell culture medium Cell Experiment:
Dispense $5 \times 10^4$ cells/well/98 µL in 96 well tissue culture plate
Incubate at 37° C./5% $CO_2$
After 24 h add compounds according to desired concentrations
Add also to control and stimulated values without compounds 2 µL DMSO
And mix for a few min at room temperature
Add 100 µL Ang2-Fc to all wells except control, which receives insect medium
Incubate 20 min at 37° C.
Wash 3× with PBS++
Add 100 µl Lysis buffer/well and shake a couple of min at room temperature
Store lysates at 20° C. before utilizing for the ELISA Performance of Sandwich-ELISA
Coat 96 well FluoroNunc Plate MaxiSorp Surface C with anti-Tie2 mAb
1:425 in Coating buffer pH 9.6; 100 µL/well overnight at 4° C.
Wash 2× with PBST
Block plates with 250 µL/well RotiBlock 1:10 in VE-water
Incubate for 2 h at room temperature or overnight at 4° C. shaking
Wash 2× in PBST
Add thawed lysates to wells and incubate overnight shaking at 4° C.
Wash 2× with PBST
Add 100 µL/well anti-Phosphotyrosine HRP-Conjugated 1:10000 in 3%
TopBlock (3% TopBlock in PBST) and incubate overnight under shaking
Wash 6× with PBST
Add 100 µL/well BM Chemiluminescence ELISA Substrate (POD)
solutions 1 und 2 (1:100)
Determine luminescence with the LumiCount.

Assay 2: Tie-2-Kinase HTRF-Assay without Kinase Preactivation

Tie2-inhibitory activity of compounds of the present invention was quantified employing two Tie2 HTRF assay as described in the following paragraphs.

A recombinant fusion protein of GST and the intracellular domains of Tie-2, expressed in insect cells (Hi-5) and purified by Glutathion-Sepharose affinity chromatography was used as kinase. Alternatively, commercially available GST-Tie2-fusion protein (Upstate Biotechnology, Dundee, Scotland) can be used As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany). Detection of phosphorylated product is achieved specifically by a trimeric detection complex consisting of the phosphorylated substrate, streptavidin-XLent (SA-XLent) which binds to biotin, and Europium Cryptate-labeled anti-phosphotyrosine antibody PT66 which binds to phosphorylated tyrosine.

Tie-2 (3.5 ng/measurement point) was incubated for 60 min at 22° C. in the presence of 10 µM adenosine-tri-phosphate (ATP) and 1 µM substrate peptide (biotin-Ahx-EPKDDAYPLYSDFG-$NH_2$) with different concentrations of test compounds (0 µM and concentrations in the range 0.001-20 µM) in 5 µl assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointernational, Marcoule, France) and PT66-Eu-Chelate (0.3 ng/µl; a europium-chelate labelled anti-phospho-tyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Assay 3: Tie-2-Kinase HTRF-Assay with Kinase Preactivation

A recombinant fusion protein of GST and the intracellular domains of Tie-2, expressed in insect cells (Hi-5) and purified by Glutathion-Sepharose affinity chromatography was used as kinase. As substrate for the kinase reaction the biotinylated peptide biotin-Ahx-EPKDDAYPLYSDFG (C-terminus in amid form) was used which can be purchased e.g. from the company Biosynthan GmbH (Berlin-Buch, Germany).

For activation, Tie-2 was incubated at a conc. 12.5 ng/µl of for 20 min at 22° C. in the presence of 250 µM adenosine-tri-phosphate (ATP) in assay buffer [50 mM Hepes/NaOH pH 7, 10 mM $MgCl_2$, 0.5 mM $MnCl_2$, 1.0 mM dithiothreitol, 0.01% NP40, protease inhibitor mixture ("Complete w/o EDTA" from Roche, 1 tablet per 2.5 ml)].

For the subsequent kinase reaction, the preactivated Tie-2 (0.5 ng/measurement point) was incubated for 20 min at 22° C. in the presence of 10 µM adenosine-tri-phosphate (ATP) and 1 µM substrate peptide (biotin-Ahx-EPKDDAYPLYS-DFG-$NH_2$) with different concentrations of test compounds (0 µM and concentrations in the range 0.001-20 µM) in 5 µl assay buffer [50 mM Hepes/NaOH pH 7, 10 mM $MgCl_2$, 0.5 mM $MnCl_2$, 0.1 mM sodium ortho-vanadate, 1.0 mM dithiothreitol, 0.01% NP40, protease inhibitor mixture ("Complete w/o EDTA" from Roche, 1 tablet per 2.5 ml), 1% (v/v) dimethylsulfoxide]. The reaction was stopped by the addition of 5 µl of an aqueous buffer (25 mM Hepes/NaOH pH 7.5, 0.28% (w/v) bovine serum albumin) containing EDTA (90 mM) and the HTRF (Homogeneous Time Resolved Fluorescence) detection reagents streptavidine-XLent (0.2 µM, from Cis Biointernational, Marcoule, France) and PT66-Eu-Chelate (0.3 ng/µl; a europium-chelate labelled anti-phosphotyrosine antibody from Perkin Elmer).

The resulting mixture was incubated 1 h at 22° C. to allow the binding of the biotinylated phosphorylated peptide to the streptavidine-XLent and the PT66-Eu-Chelate. Subsequently the amount of phosphorylated substrate peptide was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate peptide. The data were normalised (enzyme reaction without inhibitor=0% inhibition, all other assay components but no enzyme=100% inhibition) and $IC_{50}$ values were calculated by a 4 parameter fit using an inhouse software.

Assay 4: InsR HTRF Assay

Inhibitory activity of compounds against the kinase activity of the insulin receptor was quantified employing the Ins-R HTRF assay as described in the following paragraphs.

GST-tagged recombinant kinase domain of the human insuline receptor (Ins-R, purchase from ProQinase, Freiburg, Germany) expressed in SF-9 cells was used as kinase. As substrate for the kinase reaction biotinylated poly-(Glu,Tyr) (Cis biointernational, France) was used.

Ins-R was incubated for 20 min at 22° C. in the presence of different concentrations of test compounds in 5 µl assay buffer [50 mM Hepes/NaOH pH 7, 15 mM $MnCl_2$, 1 mM dithiothreitol, 0.1 µM sodium ortho-vanadate, 0.015% (v/v) PEG20000, 10 µM adenosine-tri-phosphate (ATP), 0.3 µg/ml substrate, 1% (v/v) dimethylsulfoxide]. The concentration of Ins-R was adjusted depending of the activity of the enzyme lot and was chosen appropriate to have the assay in the linear range, typical concentrations were in the range of 10 pg/µl. The reaction was stopped by the addition of 5 µl of a solution of HTRF detection reagents (0.1 µM streptavidine-XLent and 1 nM PT66-Eu-Chelate, an europium-chelate labelled anti-phosphotyrosine antibody from Perkin Elmer) in an aqueous EDTA-solution (80 mM EDTA, 0.2% (w/v) bovine serum albumin in 50 mM HEPES/NaOH pH 7.0).

The resulting mixture was incubated 1 h at 22° C. to allow the binding of the biotinylated phosphorylated peptide to the streptavidine-XLent and the PT66-Eu-Chelate. Subsequently the amount of phosphorylated substrate was evaluated by measurement of the resonance energy transfer from the PT66-Eu-Chelate to the streptavidine-XLent. Therefore, the fluorescence emissions at 620 nm and 665 nm after excitation at 350 nm was measured in a HTRF reader, e.g. a Rubystar (BMG Labtechnologies, Offenburg, Germany) or a Viewlux (Perkin-Elmer). The ratio of the emissions at 665 nm and at 622 nm was taken as the measure for the amount of phosphorylated substrate. The data were normalised (enzyme reaction without inhibitor=0% inhibition, all other assay components but no enzyme=100% inhibition) and IC50 values were calculated by a 4 parameter fit using an inhouse software.

Compounds of the present invention were found to possess enzymatic and cellular activity as inhibitors of Tie2 kinase. Compounds of the present invention inhibit Tie2 kinase activity and cellular Tie2 autophosphorylation with $IC_{50}$ values below 1 µM, more preferred compounds inhibit Tie2 autophosphorylation with $IC_{50}$ values below 0.5 µM. Compounds of the present invention possess inhibitory selectivity for Tie2 kinase vs. insulin receptor (as defined below).

Selected data are given in the following table. The $IC_{50}$ values were converted to $pIC_{50}$ values, i.e. $-\log IC_{50}$ in molar concentration.

TABLE

| Example No. | Tie 2 activity (assay 1) | Tie 2 activity (assay 2) | Selectivity vs. InsR |
|---|---|---|---|
| 1.1 | +++ | +++ | >20 fold |
| 1.2 | +++ | +++ | >20 fold |
| 1.3 | +++ | +++ | >20 fold |
| 1.4 | +++ | +++ | >20 fold |
| 1.7 | +++ | +++ | >20 fold |
| 1.8 | +++ | +++ | >20 fold |
| 1.11 | ++ | ++ | >20 fold |
| 1.15 | +++ | +++ | >20 fold |
| 1.18 | +++ | +++ | >20 fold |
| 1.20 | +++ | +++ | >20 fold |
| 1.22 | +++ | ++ | >20 fold |
| 1.23 | +++ | +++ | >20 fold |
| 1.24 | +++ | +++ | >20 fold |
| 1.25 | +++ | + | |
| 1.26 | +++ | +++ | >20 fold |
| 1.27 | +++ | +++ | |
| 1.29 | +++ | +++ | >20 fold |
| 1.33 | +++ | +++ | >20 fold |
| 1.37 | +++ | +++ | >20 fold |
| 1.38 | +++ | +++ | >20 fold |
| 2.4 | +++ | +++ | >20 fold |
| 2.5 | ++ | ++ | >20 fold |
| 2.7 | +++ | +++ | >20 fold |
| 3.2 | +++ | +++ | >20 fold |
| 3.4 | +++ | +++ | >20 fold |
| 3.5 | +++ | +++ | >20 fold |

+ stands for $pIC_{50}$ 5.0-6.0
++ stands for $pIC_{50}$ 6.0-6.3
+++ stands for $pIC_{50}$ >6.3
Selectivity vs. InsR: $IC_{50}$ assay 4/$IC_{50}$ assay 2

GENERAL REMARKS

It is believed that one skilled in the art, using the preceding information and information available in the art, can utilize the present invention to its fullest extent. It should be apparent to one of ordinary skill in the art that changes and modifications can be made to this invention without departing from the spirit or scope of the invention as it is set forth herein. All publications, applications and patents cited above are incorporated herein by reference.

The topic headings set forth above and below are meant as guidance where certain information can be found in the application, but are not intended to be the only source in the application where information on such topic can be found.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 06090109.7, filed Jun. 13, 2006 and European application No. 07090020.4 filed Feb. 15, 2007, and U.S. Provisional Application Ser. No. 60/816,626 filed Jun. 27, 2006 and U.S. Provisional Application Ser. No. 60/890,937 filed Feb. 21, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A compound of formula (I):

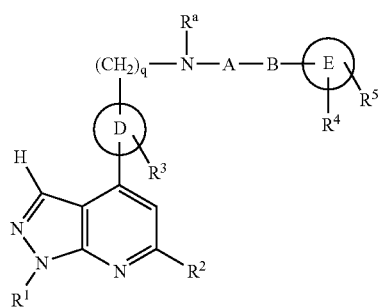

(I)

wherein:
- $R^1$ is H or —C(O)$R^b$, or is a group which is $C_1$-$C_6$-alkyl, $C_2$-$C_6$-alkenyl, $C_2$-$C_6$-alkynyl, $C_3$-$C_{10}$-cycloalkyl, or $C_3$-$C_{10}$-heterocycloalkyl, wherein said groups are optionally substituted one or more times, independently from each other, with $R^6$;
- $R^2$ is hydrogen, —NR$^{d1}$R$^{d2}$, —C(O)$R^b$, or is a group which is $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, or heteroaryl, wherein said groups are unsubstituted or singly or multiply substituted independently from each other with $R^7$;
- $R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, halogen, or cyano;
- $R^4$, $R^5$, $R^6$, $R^7$, and $R^8$ are each, independently from each other, hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, aryl, heteroaryl, hydroxy, amino, halogen, cyano, nitro, —C(O)$R^b$, —S(O)$_2$R$^b$, —OR$^c$, —NR$^{d1}$R$^{d2}$, or —OP(O)(OR$^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;
- $R^a$ is hydrogen or $C_1$-$C_6$-alkyl;
- $R^b$ is hydroxyl, —OR$^c$, —SR$^c$, —NR$^{d1}$R$^{d2}$, or $C_1$-$C_6$-alkyl;
- $R^c$ is hydrogen, —C(O)$R^b$, $C_1$-$C_6$-alkyl, $C_1$-$C_6$-haloalkyl $C_3$-$C_{10}$-cycloalkyl, or $C_3$-$C_{10}$-heterocycloalkyl, wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted one or more times, independently of one another, with hydroxyl, halogen, aryl, or —NR$^{d1}$R$^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —OR$^c$, or —OP(O)(OR$^c$)$_2$;
- $R^{d1}$, and $R^{d2}$ are, independently from each other, hydrogen, $C_1$-$C_6$-alkyl, $C_3$-$C_{10}$-cycloalkyl, $C_3$-$C_{10}$-heterocycloalkyl, aryl, heteroaryl, or a group —C(O)$R^c$, —S(O)$_2$R$^b$, or —C(O)NR$^{d1}$R$^{d2}$, wherein $C_1$-$C_6$-alkyl, $C_3$-$C_{10}$-cycloalkyl, $C_3$-$C_{10}$-heterocycloalkyl are optionally substituted one or more times, independently of one another, with halogen, hydroxy or an —OR$^c$, —C(O)$R^b$, —S(O)$_2$R$^b$, or —OP(O)(OR$^c$)$_2$ group, and wherein $C_1$-$C_6$-alkyl, $C_3$-$C_{10}$-cycloalkyl, $C_3$-$C_{10}$-heterocycloalkyl are optionally substituted once with an —NR$^{d1}$R$^{d2}$ group; or
- $R^{d1}$ and $R^{d2}$ together with the nitrogen atom to which they are attached, form a 3 to 10 membered heterocycloalkyl ring, wherein the carbon backbone of the heterocycloalkyl ring is optionally interrupted one or more times, independently, with NH, NR$^{d1}$, oxygen or sulphur, and is optionally interrupted one or more times, independently, with a —C(O)—, —S(O)—, or —S(O)$_2$— group, and wherein said heterocycloalkyl ring optionally comprises one or more double bonds;
- A is —C(O)—, —C(S)—, —C(=NR$^a$)—, —C(O)NR$^a$—, —C(=NR$^a$)NR$^a$—, —S(O)$_2$—, —S(O)(=NR$^a$)—, —S(=NR$^a$)$_2$—, —C(S)NR$^a$—, —C(O)C(O)—, —C(O)C(O)NR$^a$—, —C(O)NR$^a$C(O)—, —C(S)NR$^a$C(O)—, or —C(O)NR$^a$C(S)—;
- B is a bond or a group which is $C_1$-$C_6$-alkylene, $C_3$-$C_{10}$-cycloalkylene, or $C_3$-$C_{10}$-heterocycloalkylene;
- D, E are, independently from each other, arylene or heteroarylene;

and q is an integer of 0, 1, or 2;

or a salt or an N-oxide thereof, wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

2. The compound according to claim 1, wherein:
- $R^1$ is H or —C(O)$R^b$, or is a group which is $C_1$-$C_6$-alkyl, $C_2$-$C_6$-alkenyl, $C_2$-$C_6$-alkynyl, $C_3$-$C_{10}$-cycloalkyl, $C_3$-$C_{10}$- or heterocycloalkyl, wherein said groups are optionally substituted one or more times, independently from each other, with $R^6$;
- $R^2$ is hydrogen, —NR$^{d1}$R$^{d2}$, —C(O)$R^b$, or is a group which is $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, or heteroaryl, wherein said groups are unsubstituted or singly or multiply substituted independently from each other with $R^7$;
- $R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, or halogen;
- $R^4$, $R^5$, $R^6$, $R^7$, and $R^8$ independently from each other, are hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, hydroxy, amino, halogen, —C(O)R S(O)$_2$R$^b$, OR$^c$, NR$^{d1}$R$^{d2}$, or OP(O)(OR$^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is hydrogen or $C_1$-$C_6$-alkyl;

$R^b$ is hydroxyl, $OR^c$, $SR^c$, or $NR^{d1}R^{d2}$;

$R^c$ is hydrogen, —C(O)$R^b$, $C_1$-$C_6$-alkyl, $C_1$-$C_6$-haloalkyl $C_3$-$C_{10}$-cycloalkyl, or $C_3$-$C_{10}$-heterocycloalkyl, wherein $C_1$-$C_6$ alkyl, $C_1$-$C_6$-haloalkyl, $C_3$-$C_{10}$-cycloalkyl, $C_3$-$C_{10}$-heterocycloalkyl are optionally substituted one or more times, in the same way or differently, with hydroxyl, halogen, aryl, or —$NR^{d1}R^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —$OR^c$, or —OP(O)($OR^c$)$_2$;

$R^{d1}$, and $R^{d2}$ independently from each other are hydrogen, $C_1$-$C_6$-alkyl, $C_3$-$C_{10}$-cycloalkyl, $C_3$-$C_{10}$-heterocycloalkyl, $C_6$-$C_{11}$-aryl, $C_5$-$C_{10}$-heteroaryl, or a group —C(O)$R^c$, —S(O)$_2R^b$, or C(O)$NR^{d1}R^{d2}$, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —$OR^c$, —C(O)$R^b$, —S(O)$_2R^b$, or —OP(O)($OR^c$)$_2$ group, and wherein $C_1$-$C_6$-alkyl, $C_3$-$C_{10}$-cycloalkyl, $C_3$-$C_{10}$-heterocycloalkyl are optionally substituted once with an —$NR^{d1}R^{d2}$ group; or $R^{d1}$ and $R^{d2}$ together with the nitrogen atom to which they are attached, form a 3 to 10 membered heterocycloalkyl ring, whereby the carbon backbone of the this heterocycloalkyl ring is optionally interrupted one or more times, the same way or differently, by NH, $NR^{d1}$, oxygen or sulphur, and is optionally interrupted one or more times, the same way or differently, with a —C(O)—, —S(O)—, or —S(O)$_2$— group, and wherein said heterocycloalkyl ring optionally comprises one or more double bonds;

A is —C(O)—, —C(O)$NR^a$—, —S(O)$_2$—, —S(O)(=$NR^a$)—, —C(S)$NR^a$—, —C(O)C(O)—, —C(O)C(O)$NR^a$—, —C(O)$NR^aC$(O)—, —C(S)$NR^aC$(O)—, or —C(O)$NR^aC$(S)—;

B is a bond or a group which $C_1$-$C_6$-alkylene, $C_3$-$C_{10}$-cycloalkylene, or $C_3$-$C_{10}$-heterocycloalkylene;

D is phenylene;

E is phenylene or 5- or 6-membered heteroarylene; and q is an integer of 0 or 1;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

3. The compound according to claim 1, wherein:

$R^1$ is H or —C(O)$R^b$, or is a group which is $C_1$-$C_6$-alkyl, $C_2$-$C_6$-alkenyl, $C_2$-$C_6$-alkynyl, $C_3$-$C_{10}$-cycloalkyl, or $C_3$-$C_{10}$-heterocycloalkyl, wherein said groups are unsubstituted or substituted one or more times, independently from each other, with $R^6$;

$R^2$ is hydrogen, $NR^{d1}R^{d2}$, —C(O)$R^b$, or is a group which is $C_1$-$C_6$-alkyl, $C_2$-$C_6$-alkenyl, $C_2$-$C_6$-alkynyl, $C_3$-$C_{10}$-cycloalkyl, $C_3$-$C_{10}$-heterocycloalkyl, aryl, heteroaryl, wherein said groups are unsubstituted or singly or multiply substituted independently from each other with $R^7$;

$R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, or halogen;

$R^4$, $R^5$, $R^6$, $R^7$, and $R^8$ independently from each other, are hydrogen, $C_1$-$C_6$-alkyl, $C_3$-$C_{10}$-cycloalkyl, $C_3$-$C_{10}$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, $NR^{d1}R^{d2}$, or OP(O)($OR^c$)$_2$, wherein $C_1$-$C_6$-alkyl, $C_3$-$C_{10}$-heterocycloalkyl and $C_3$-$C_{10}$-cycloalkyl of $R^4$, $R^5$, $R^6$, and $R^7$, are optionally substituted one or more times with $R^8$, and wherein $C_1$-$C_6$-alkyl, $C_3$-$C_{10}$-heterocycloalkyl and $C_3$-$C_{10}$-cycloalkyl of $R^8$, are optionally substituted once with $R^8$;

$R^a$ is hydrogen or $C_1$-$C_6$-alkyl;

$R^b$ is hydroxyl, $OR^c$, $SR^c$, or $NR^{d1}R^{d2}$;

$R^c$ is hydrogen, —C(O)$R^b$, $C_1$-$C_6$ alkyl, $C_1$-$C_6$-haloalkyl $C_3$-$C_{10}$-cycloalkyl, or $C_3$-$C_{10}$-heterocycloalkyl, wherein $C_1$-$C_6$ alkyl, $C_1$-$C_6$-haloalkyl, $C_3$-$C_{10}$-cycloalkyl, $C_3$-$C_{10}$-heterocycloalkyl are optionally substituted one or more times, in the same way or differently, with hydroxyl, halogen, aryl, or —$NR^{d1}R^{d2}$, and wherein $C_1$-$C_6$-alkyl, $C_1$-$C_6$-haloalkyl, $C_3$-$C_{10}$-cycloalkyl, $C_3$-$C_{10}$-heterocycloalkyl are optionally substituted once with —$OR^c$, or —OP(O)($OR^c$)$_2$;

$R^{d1}$, and $R^{d2}$ independently from each other are hydrogen, $C_1$-$C_6$-alkyl, $C_3$-$C_{10}$-cycloalkyl, $C_3$-$C_{10}$-heterocycloalkyl, $C_6$-$C_{11}$-aryl, $C_5$-$C_{10}$-heteroaryl, or a group —C(O)$R^c$, —S(O)$_2R^b$, or C(O)$NR^{d1}R^{d2}$, wherein $C_1$-$C_6$-alkyl, $C_3$-$C_{10}$-cycloalkyl, $C_3$-$C_{10}$-heterocycloalkyl are optionally substituted one or more times, in the same way or differently, with halogen, hydroxy or an —$OR^c$, —C(O)$R^b$, —S(O)$_2R^b$, or —OP(O)($OR^c$)$_2$ group, and wherein $C_1$-$C_6$-alkyl, $C_3$-$C_{10}$-cycloalkyl, $C_3$-$C_{10}$-heterocycloalkyl are optionally substituted once with an —$NR^{d1}R^{d2}$ group; or $R^{d1}$ and $R^{d2}$ together with the nitrogen atom to which they are attached, form a 3 to 10 membered heterocycloalkyl ring, whereby the carbon backbone of the heterocycloalkyl ring is optionally interrupted one or more times, the same way or differently, by NH, $NR^{d1}$, oxygen or sulphur, and is optionally interrupted one or more times, the same way or differently, with a —C(O)—, —S(O)—, or —S(O)$_2$— group, and wherein said heterocycloalkyl ring optionally comprises one or more double bonds;

A is —C(O)—, —C(O)$NR^a$—, or —S(O)$_2$—;

B is a bond or a group which is $C_1$-$C_6$-alkylene, or $C_3$-$C_{10}$-cycloalkylene;

D is phenylene;

E is phenylene or 5- or 6-membered heteroarylene; and q is an integer of 0 or 1;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

4. The compound according to claim 1, wherein:

$R^1$ is H or —C(O)$R^b$, or is a group which is $C_1$-$C_6$-alkyl, $C_3$-$C_6$-cycloalkyl, or $C_3$-$C_6$-heterocycloalkyl, wherein said groups are unsubstituted or substituted one or more times, independently from each other, with $R^6$;

$R^2$ is hydrogen or is a group which $C_1$-$C_6$-alkyl, $C_3$-$C_6$-cycloalkyl, $C_3$-$C_6$-heterocycloalkyl, aryl, or heteroaryl, wherein said groups are unsubstituted or singly or multiply substituted independently from each other with $R^7$;

$R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, or halogen;

$R^4$ is hydrogen, $C_1$-$C_6$-alkyl, $C_1$-$C_6$-haloalkyl, $C_1$-$C_6$-haloalkoxy, hydroxy, amino, halogen, or $OR^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^6$ is hydrogen, $C_3$-$C_6$-heterocycloalkyl, $C_1$-$C_6$-haloalkoxy, hydroxy, amino, —C(O)$R^b$, —S(O)$_2R^b$, $OR^c$, or $NR^{d1}R^{d2}$, wherein $C_3$-$C_6$-heterocycloalkyl is optionally substituted one or more times with $R^8$;

$R^7$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^8$ is $C_1$-$C_6$-haloalkoxy, hydroxy, amino, halogen, —C(O)$R^b$, —S(O)$_2R^b$, $OR^c$, or $NR^{d1}R^{d2}$;

$R^a$ is hydrogen;

$R^b$ is, $OR^c$, or $NR^{d1}R^{d2}$;

$R^c$ is hydrogen, $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times, in the same way or differently, with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, and $R^{d2}$ independently from each other are, hydrogen, $C_1$-$C_6$-alkyl, $C_3$-$C_6$-cycloalkyl, or a —C(O)$R^c$ or C(O)$NR^{d1}R^{d2}$ group, wherein $C_1$-$C_6$-alkyl and $C_3$-$C_6$-cycloalkyl are optionally substituted one or more times, in the same way or differently, with an —$OR^c$, or —C(O)$R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of the heterocycloalkyl ring is optionally interrupted one or more times, the same way or differently, by NH, $NR^{d1}$, or oxygen;

A is —C(O)—, —C(O)$NR^a$—, or —S(O)$_2$—;

B is a bond or a group which is $C_1$-$C_3$-alkylene, or $C_3$-cycloalkylene;

D and E are phenylene;

and q is an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

5. The compound according to claim 1, wherein:

$R^1$ is H or —C(O)$R^b$, or is a group which is $C_1$-$C_6$-alkyl, $C_3$-$C_6$-cycloalkyl, or $C_3$-$C_6$-heterocycloalkyl, wherein said groups are unsubstituted or substituted one or more times, independently from each other, with $R^6$;

$R^2$ is hydrogen or is $C_3$-$C_6$-cycloalkyl, $C_3$-$C_6$-heterocycloalkyl, aryl, or heteroaryl, wherein said groups are unsubstituted or singly or multiply substituted independently from each other with $R^7$;

$R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, or halogen;

$R^4$ is hydrogen, $C_1$-$C_6$-alkyl, $C_1$-$C_6$-haloalkyl, $C_1$-$C_6$-haloalkoxy, hydroxy, amino, halogen, or $OR^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^6$ is hydrogen, $C_3$-$C_6$-heterocycloalkyl, $C_1$-$C_6$-haloalkoxy, hydroxy, amino, —C(O)$R^b$, —S(O)$_2R^b$, $OR^c$, or $NR^{d1}R^{d2}$, wherein $C_3$-$C_6$-heterocycloalkyl is optionally substituted one or more times with $R^8$;

$R^7$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^8$ is $C_1$-$C_6$-haloalkoxy, hydroxy, amino, halogen, —C(O)$R^b$, —S(O)$_2R^b$, $OR^c$, or $NR^{d1}R^{d2}$;

$R^a$ is hydrogen;

$R^b$ is, $OR^c$, or $NR^{d1}R^{d2}$;

$R^c$ is hydrogen, $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, and $R^{d2}$ independently from each other are hydrogen, $C_1$-$C_6$-alkyl, $C_3$-$C_6$-cycloalkyl, or a —C(O)$R^c$ or C(O)$NR^{d1}R^{d2}$ group, wherein $C_1$-$C_6$-alkyl and $C_3$-$C_6$-cycloalkyl are optionally substituted one or more times, in the same way or differently, with an —$OR^c$ or —C(O)$R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of the this heterocycloalkyl ring is optionally interrupted one or more times, the same way or differently, by NH, $N^{d1}$, or oxygen;

A is —C(O)$NR^a$—;

B is a bond or a group which is $C_1$-$C_3$-alkylene, or $C_3$-cycloalkylene;

D and E are phenylene;

and q is an integer of 0;

wherein, when one or more of $R^a$, $R^b$, $R^c$, $R^{d1}R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

6. The compound according to claim 1, wherein:

$R^1$ is H or —C(O)$R^b$, or is a group which is $C_1$-$C_6$-alkyl, $C_3$-$C_6$-cycloalkyl, $C_3$-$C_6$-heterocycloalkyl, wherein said groups are unsubstituted or substituted one or more times, independently from each other, with $R^6$;

$R^2$ is hydrogen or is $C_1$-$C_6$-alkyl, or $C_3$-cycloalkyl;

$R^3$ is hydrogen, methyl, fluoro, or chloro;

$R^4$ is hydrogen, $C_1$-$C_6$-alkyl, $C_1$-$C_6$-haloalkyl, $C_1$-$C_6$-haloalkoxy, hydroxy, amino, halogen, or $OR^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^6$ is hydrogen, $C_3$-$C_6$-heterocycloalkyl, $C_1$-$C_6$-haloalkoxy, hydroxy, amino, —C(O)$R^b$, —S(O)$_2R^b$, $OR^c$, or $NR^{d1}R^{d2}$, wherein $C_3$-$C_6$-heterocycloalkyl is optionally substituted one or more times with $R^8$;

$R^8$ is $C_1$-$C_6$-haloalkoxy, hydroxy, amino, halogen, —C(O)$R^b$, —S(O)$_2R^b$, $OR^c$, or $NR^{d1}R^{d2}$;

$R^a$ is hydrogen;

$R^b$ is $OR^c$, or $NR^{d1}R^{d2}$;

$R^c$ is hydrogen, $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, and $R^{d2}$ independently from each other are hydrogen, $C_1$-$C_6$-alkyl, $C_3$-$C_6$-cycloalkyl, or a —C(O)$R^c$ or C(O)$NR^{d1}R^{d2}$ group, wherein $C_1$-$C_6$-alkyl and $C_3$-$C_6$-cycloalkyl are optionally substituted one or more times, in the same way or differently, with an —$OR^c$ or —C(O)$R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of the heterocycloalkyl ring is optionally interrupted one or more times, the same way or differently, by NH, $NR^{d1}$, or oxygen;

A is —C(O)$NR^a$—;

B is a bond or a group which is $C_1$-$C_3$-alkylene, or $C_3$-cycloalkylene;

D and E are phenylene;

and q is an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

7. The compound according to claim 1, wherein:

$R^1$ is H or $C_1$-$C_6$-alkyl;

$R^2$ is hydrogen or is a group which is $C_1$-$C_6$-alkyl, $C_3$-$C_6$-cycloalkyl, $C_3$-$C_6$-heterocycloalkyl, aryl, heteroaryl, wherein said groups are unsubstituted or singly or multiply substituted independently from each other with $R^7$;

$R^3$ is hydrogen, methyl, fluor, or chloro;

$R^4$ is hydrogen, $C_1$-$C_6$-alkyl, $C_1$-$C_6$-haloalkyl, $C_1$-$C_6$-haloalkoxy, hydroxy, amino, halogen, or $OR^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^7$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^8$ is $C_1$-$C_6$-haloalkoxy, hydroxy, amino, halogen, —C(O)$R^b$, —S(O)$_2R^b$, $OR^c$, or $NR^{d1}R^{d2}$;

$R^a$ is hydrogen;

$R^b$ is $OR^c$, or $NR^{d1}R^{d2}$;

$R^c$ is hydrogen, $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, and $R^{d2}$ independently from each other are hydrogen, $C_1$-$C_6$-alkyl, $C_3$-$C_6$-cycloalkyl, or a —C(O)$R^c$ or C(O)$NR^{d1}R^{d2}$ group, wherein $C_1$-$C_6$-alkyl and $C_3$-$C_6$-cycloalkyl are optionally substituted one or more times, in the same way or differently, with an —$OR^c$ or —C(O)$R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of the heterocycloalkyl ring is optionally interrupted one or more times, the same way or differently, by NH, $NR^{d1}$, or oxygen;

A is —C(O)$NR^a$—;

B is a bond or a group which is $C_1$-$C_3$-alkylene, or $C_3$-cycloalkylene;

D and E are phenylene;

and q is an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

8. The compound according to claim 1, wherein:

$R^1$ is H or $C_1$-$C_6$-alkyl;

$R^2$ is hydrogen or is a group which is $C_1$-$C_6$-alkyl, $C_3$-$C_6$-heterocycloalkyl, aryl, or heteroaryl, wherein said groups are unsubstituted or singly or multiply substituted independently from each other with $R^7$;

$R^3$ is hydrogen, methyl, fluor, or chloro;

$R^4$ is hydrogen, $C_1$-$C_6$-alkyl, $C_1$-$C_6$-haloalkyl, $C_1$-$C_6$-haloalkoxy, hydroxy, amino, halogen, or $OR^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^7$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^8$ is $C_1$-$C_6$-haloalkoxy, hydroxy, amino, halogen, —C(O)$R^b$, —S(O)$_2R^b$, $OR^c$, or $NR^{d1}R^{d2}$;

$R^a$ is hydrogen;

$R^b$ is $OR^c$, or $NR^{d1}R^{d2}$;

$R^c$ is hydrogen, $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, and $R^{d2}$ independently from each other are hydrogen, $C_1$-$C_6$-alkyl, $C_3$-$C_6$-cycloalkyl, or a —$C(O)R^c$ or $C(O)NR^{d1}R^{d2}$ group, wherein $C_1$-$C_6$-alkyl and $C_3$-$C_6$-cycloalkyl are optionally substituted one or more times, in the same way or differently, with an —$OR^c$ or —$C(O)R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of the heterocycloalkyl ring is optionally interrupted one or more times, the same way or differently, by NH, $NR^{d1}$, or oxygen;

A is —$C(O)NR^a$—;

B is a bond or a group which is $C_1$-$C_3$-alkylene, or $C_3$-cycloalkylene;

D and E are phenylene;

and q is an integer of 0;

wherein, when one or more of $R^a$, $R^b$, $R^c$, $R^{d1}$, $R^{d2}$ or $R^8$ is (are) present in one position in the, molecule as well as in one or more further positions in the molecule, said $R^a$, $R^b$, $R^c$, $R^{d1}$ $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

9. The compound according to claim 1, wherein:

$R^1$ is H or $C_1$-$C_3$-alkyl;

$R^2$ is hydrogen or is $C_1$-$C_6$-alkyl, or $C_3$-cycloalkyl;

$R^3$ is hydrogen, methyl, or fluoro;

$R^4$ is hydrogen, halogen, $C_1$-$C_3$-alkyl, or $C_1$-$C_3$-haloalkyl;

$R^5$ is hydrogen, $C_1$-$C_3$-alkyl, $C_1$-$C_3$-haloalkyl, $C_1$-$C_3$-haloalkoxy, halogen, —$OR^c$, or —$NR^{d1}R^{d2}$, wherein $C_1$-$C_3$-alkyl is optionally substituted by $R^8$;

$R^8$ is —$OR^c$, or —$NR^{d1}R^{d2}$;

$R^a$ is hydrogen;

$R^c$ is hydrogen, or $C_1$-$C_3$-alkyl, wherein $C_1$-$C_3$-alkyl is optionally substituted one or more times with —$NR^{d1}R^{d2}$, and wherein $C_1$-$C_3$-alkyl is optionally substituted once with —$OR^c$;

$R^{d1}$, and $R^{d2}$ independently from each other are hydrogen, or $C_1$-$C_3$-alkyl, wherein $C_1$-$C_3$-alkyl is optionally substituted one or more times with an —$OR^c$ group, and wherein $C_1$-$C_3$-alkyl is optionally substituted once with an —$NR^{d1}R^{d2}$ group; or, $R^{d1}$ and $R^{d2}$ together with the nitrogen atom to which they are attached, form a 6 membered heterocycloalkyl ring, whereby the carbon backbone of the this heterocycloalkyl ring is optionally interrupted one time, by NH, $NR^{d1}$, or oxygen;

A is —$C(O)NR^a$—;

B is a bond;

D is para-phenylene;

E is phenylene;

q is an integer of 0;

wherein, when one or more of $R^a$, $R^b$, $R^c$, $R^{d1}$ or $R^{d2}$ is (are) present in one position in the molecule as well as in one or more further positions in the molecule, said $R^a$, $R^b$, $R^c$, $R^{d1}$ or $R^{d2}$ has (have), independently from each other, the same meanings as defined above in said first position in the molecule and in said second or further positions in the molecule, it being possible for the two or more occurrences of $R^a$, $R^b$, $R^c$, $R^{d1}$ or $R^{d2}$ within a single molecule to be identical or different.

10. The compound according to claim 1, wherein:

$R^1$ represents is H or —$C(O)R^b$, or is a group which is $C_1$-$C_6$-alkyl, $C_3$-$C_6$-cycloalkyl, or $C_3$-$C_6$-heterocycloalkyl, wherein said groups are unsubstituted or substituted one or more times, independently from each other, with $R^6$;

$R^2$ is hydrogen or is a group which is $C_1$-$C_6$-alkyl, $C_3$-$C_6$-cycloalkyl, $C_3$-$C_6$-heterocycloalkyl, aryl, or heteroaryl, wherein said groups are unsubstituted or singly or multiply substituted independently from each other with $R^7$;

$R^3$ is hydrogen, $C_1$-$C_6$-alkyl, $C_1$-$C_6$-alkoxy, $C_1$-$C_6$-haloalkyl, $C_1$-$C_6$-haloalkoxy, hydroxy, amino, or halogen;

$R^4$ is hydrogen, $C_1$-$C_6$-alkyl, $C_1$-$C_6$-haloalkyl, $C_1$-$C_6$-haloalkoxy, hydroxy, amino, halogen, or $OR^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —$C(O)R^b$, —$S(O)_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^6$ is hydrogen, $C_3$-$C_6$-heterocycloalkyl, $C_1$-$C_6$-haloalkoxy, hydroxy, amino, —$C(O)R^b$, —$S(O)_2R^b$, $OR^c$, or $NR^{d1}R^{d2}$, wherein $C_3$-$C_6$-heterocycloalkyl is optionally substituted one or more times with $R^8$;

$R^7$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —$C(O)R^b$, —$S(O)_2R^b$, $OR^c$, or $NR^{d1}R^{d2}$, wherein $C_1$-$C_6$-alkyl and $C_3$-$C_6$-heterocycloalkyl are optionally substituted one or more times with $R^8$;

$R^8$ is $C_1$-$C_6$-haloalkoxy, hydroxy, amino, halogen, —$C(O)R^b$, —$S(O)_2R^b$, $OR^c$, or $NR^{d1}R^{d2}$;

$R^a$ is hydrogen;

$R^b$ is, $OR^c$, or $NR^{d1}R^{d2}$;

$R^c$ is hydrogen, $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —$NR^{d1}R^{d2}$, and wherein $C_1$-$C_6$-alkyl, $C_3$-$C_6$-cycloalkyl, $C_3$-$C_6$-heterocycloalkyl are optionally substituted once with —$OR^c$;

$R^{d1}$, and $R^{d2}$ independently from each other are, hydrogen, $C_1$-$C_6$-alkyl, $C_3$-$C_6$-cycloalkyl, or a —$C(O)R^c$ or $C(O)NR^{d1}R^{d2}$ group, wherein $C_1$-$C_6$-alkyl and $C_3$-$C_6$-cycloalkyl are optionally substituted one or more times, in the same way or differently, with an —$OR^c$ or —$C(O)R^b$ group, and wherein $C_1$-$C_6$-alkyl and $C_3$-$C_6$-cycloalkyl are optionally substituted once with an —$NR^{d1}R^{d2}$ group; or, $R^{d1}$ and $R^{d2}$ together with the nitrogen atom to which they are attached, form a 3 to 6 membered heterocycloalkyl ring, whereby the carbon backbone of the heterocycloalkyl ring is optionally interrupted one or more times, the same way or differently, by NH, $NR^{d1}$, or oxygen;

A is —$C(O)$— or —$S(O)_2$—;

B is a bond or a group which is $C_1$-$C_3$-alkylene, or $C_3$-cycloalkylene;

D and E are phenylene;

and q is an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

11. The compound according to claim 1, wherein:

$R^1$ is H or —C(O)$R^b$, or is a group which is $C_1$-$C_6$-alkyl, $C_3$-$C_6$-cycloalkyl, or $C_3$-$C_6$-heterocycloalkyl, wherein said groups are unsubstituted or substituted one or more times, independently from each other, with $R^6$;

$R^2$ is hydrogen or is $C_1$-$C_6$-alkyl, or $C_3$-cycloalkyl;

$R^3$ is hydrogen, methyl, fluoro, or chloro;

$R^4$ is hydrogen, $C_1$-$C_6$-alkyl, $C_1$-$C_6$-haloalkyl, $C_1$-$C_6$-haloalkoxy, hydroxy, amino, halogen, or O$R^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2$$R^b$, O$R^c$, or N$R^{d1}$$R^{d2}$, wherein $C_1$-$C_6$-alkyl and $C_3$-$C_6$-heterocycloalkyl are optionally substituted one or more times with $R^8$;

$R^6$ is hydrogen, $C_3$-$C_6$-heterocycloalkyl, $C_1$-$C_6$-haloalkoxy, hydroxy, amino, —C(O)$R^b$, —S(O)$_2$$R^b$, O$R^c$, or N$R^{d1}$$R^{d2}$, wherein $C_3$-$C_6$-heterocycloalkyl is optionally substituted one or more times with $R^8$;

$R^8$ is $C_1$-$C_6$-haloalkoxy, hydroxy, amino, halogen, —C(O)$R^b$, —S(O)$_2$$R^b$, O$R^c$, or N$R^{d1}$$R^{d2}$;

$R^a$ is hydrogen;

$R^b$ is O$R^c$, N$R^{d1}$$R^{d2}$;

$R^c$ is hydrogen, $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —N$R^{d1}$$R^{d2}$, and wherein $C_1$-$C_6$-alkyl, $C_3$-$C_6$-cycloalkyl, $C_3$-$C_6$-heterocycloalkyl are optionally substituted once with —O$R^c$;

$R^{d1}$, and $R^{d2}$ independently from each other are hydrogen, $C_1$-$C_6$-alkyl, $C_3$-$C_6$-cycloalkyl, or a —C(O)$R^c$ or C(O)N$R^{d1}$$R^{d2}$ group, wherein $C_1$-$C_6$-alkyl and $C_3$-$C_6$-cycloalkyl are optionally substituted one or more times, in the same way or differently, with an —O$R^c$ or —C(O)$R^b$ group, and wherein $C_1$-$C_6$-alkyl and $C_3$-$C_6$-cycloalkyl are optionally substituted once with an —N$R^{d1}$$R^{d2}$ group; or, $R^{d1}$ and $R^{d2}$ together with the nitrogen atom to which they are attached, form a 3 to 6 membered heterocycloalkyl ring, whereby the carbon backbone of the heterocycloalkyl ring is optionally interrupted one or more times, the same way or differently, by NH, N$R^{d1}$, or oxygen;

A is —C(O)— or —S(O)$_2$—;

B is a bond or a group which is $C_1$-$C_3$-alkylene, or $C_3$-cycloalkylene;

D and E are phenylene;

and q is an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

12. The compound according to claim 1, wherein:

$R^1$ is H or $C_1$-$C_6$-alkyl;

$R^2$ is hydrogen or is a group which is $C_1$-$C_6$-alkyl, $C_3$-$C_6$-cycloalkyl, $C_3$-$C_6$-heterocycloalkyl, aryl, or heteroaryl, wherein said groups are unsubstituted or singly or multiply substituted independently from each other with $R^7$;

$R^3$ is hydrogen, methyl, fluor, or chloro;

$R^4$ is hydrogen, $C_1$-$C_6$-alkyl, $C_1$-$C_6$-haloalkyl, $C_1$-$C_6$-haloalkoxy, hydroxy, amino, halogen, or O$R^c$, wherein $C_1$-$C_6$-alkyl is optionally substituted one or more times with $R^8$;

$R^5$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, halogen, —C(O)$R^b$, —S(O)$_2$$R^b$, O$R^c$, or N$R^{d1}$$R^{d2}$, wherein $C_1$-$C_6$-alkyl and $C_3$-$C_6$-heterocycloalkyl are optionally substituted one or more times with $R^8$;

$R^7$ is hydrogen, $C_1$-$C_6$-alkyl, $C_3$-$C_6$-heterocycloalkyl, $C_1$-$C_6$-haloalkyl, $C_1$-$C_6$-haloalkoxy, hydroxy, amino, —C(O)$R^b$, —S(O)$_2$$R^b$, O$R^c$, or N$R^{d1}$$R^{d2}$, wherein $C_1$-$C_6$-alkyl and $C_3$-$C_6$-heterocycloalkyl are optionally substituted one or more times with $R^8$;

$R^8$ is $C_1$-$C_6$-haloalkoxy, hydroxy, amino, halogen, —C(O)$R^b$, —S(O)$_2$$R^b$, O$R^c$, or N$R^{d1}$$R^{d2}$;

$R^a$ is hydrogen;

$R^b$ is O$R^c$, N$R^{d1}$, $R^{d2}$;

$R^c$ is $C_1$-$C_6$-alkyl, $C_3$-$C_6$-cycloalkyl, or $C_3$-$C_6$-heterocycloalkyl, wherein $C_1$-$C_6$-alkyl, $C_3$-$C_6$-cycloalkyl, $C_3$-$C_6$-heterocycloalkyl are optionally substituted one or more times with —N$R^{d1}$$R^{d2}$, and wherein $C_1$-$C_6$-alkyl, $C_3$-$C_6$-cycloalkyl, $C_3$-$C_6$-heterocycloalkyl are optionally substituted once with —O$R^c$;

$R^{d1}$, and $R^{d2}$ are independently from each other hydrogen, $C_1$-$C_6$-alkyl, $C_3$-$C_6$-cycloalkyl, or a —C(O)$R^c$ or C(O)N$R^{d1}$$R^{d2}$ group, wherein $C_1$-$C_6$-alkyl and $C_3$-$C_6$-cycloalkyl are optionally substituted one or more times, in the same way or differently, with an —O$R^c$ or —C(O)$R^b$ group, and wherein $C_1$-$C_6$-alkyl and $C_3$-$C_6$-cycloalkyl are optionally substituted once with an —N$R^{d1}$$R^{d2}$ group; or, $R^{d1}$ and $R^{d2}$ together with the nitrogen atom to which they are attached, form a 3 to 6 membered heterocycloalkyl ring, wherein the carbon backbone of the heterocycloalkyl ring is optionally interrupted one or more times, the same way or differently, by NH, N$R^{d1}$, or oxygen;

A is —C(O)— or —S(O)$_2$—;

B is a bond or a group which is $C_1$-$C_3$-alkylene, or $C_3$-cycloalkylene;

D and E are each, independently, phenylene;

and q is an integer of 0;

wherein, when one or more of $R^a$, $R^b$, $R^c$, $R^{d1}$, $R^{d2}$ or $R^8$ is (are) present in one position in the molecule as well as in one or more further positions in the molecule, said $R^a$, $R^b$, $R^c$, $R^{d1}$, $R^{d2}$ or $R^8$ has (have), independently from each other, the same meanings as defined above in said first position in the molecule and in said second or further positions in the molecule, it being possible for the two or more occurrences of $R^a$, $R^b$, $R^c$, $R^{d1}$, $R^{d2}$ or $R^8$ within a single molecule to be identical or different.

13. The compound according to claim 1, wherein:

$R^1$ is H or $C_1$-$C_3$-alkyl;

$R^2$ is hydrogen $C_1$-$C_6$-alkyl, or $C_3$-cycloalkyl;

$R^3$ is hydrogen, methyl, or fluoro;

$R^4$ is hydrogen, halogen, $C_1$-$C_3$-alkyl, or $C_1$-$C_3$-haloalkyl;

$R^5$ is hydrogen, $C_1$-$C_3$-alkyl, $C_1$-$C_3$-haloalkyl, $C_1$-$C_3$-haloalkoxy, halogen, —O$R^c$, or —N$R^{d1}$$R^{d2}$, wherein $C_1$-$C_3$-alkyl is optionally substituted by $R^8$;

$R^8$ is —$OR^c$, and or —$NR^{d1}R^{d2}$;

$R^a$ is hydrogen;

$R^c$ is hydrogen, or $C_1$-$C_3$-alkyl, wherein $C_1$-$C_3$-alkyl is optionally substituted one or more times with —$NR^{d1}R^{d2}$, and wherein $C_1$-$C_3$-alkyl is optionally substituted once with —$OR^c$;

$R^{d1}$, and $R^{d2}$ are each, independently from each other, hydrogen, or $C_1$-$C_3$-alkyl, wherein $C_1$-$C_3$-alkyl is optionally substituted one or more times with an —$OR^c$ group, and wherein $C_1$-$C_3$-alkyl is optionally substituted once with an —$NR^{d1}R^{d2}$ group; or, $R^{d1}$ and $R^{d2}$ together with the nitrogen atom to which they are attached, form a 6 membered heterocycloalkyl ring, wherein the carbon backbone of the heterocycloalkyl ring is optionally interrupted one time, by NH, $NR^{d1}$, or oxygen;

A is —C(O)—;

B is $C_1$-alkylene or $C_3$-cycloalkylene;

D is para-phenylene;

E is phenylene;

q is an integer of 0;

wherein, when one or more of $R^a$, $R^b$, $R^c$, $R^{d1}$ or $R^{d2}$ is (are) present in one position in the molecule as well as in one or more further positions in the molecule, said $R^a$, $R^b$, $R^c$, $R^{d1}$ or $R^{d2}$ has (have), independently from each other, the same meanings as defined above in said first position in the molecule and in said second or further positions in the molecule, it being possible for the two or more occurrences of $R^a$, $R^b$, $R^c$, $R^{d1}$ or $R^{d2}$ within a single molecule to be identical or different.

14. The compound according to claim 1 which is

1-[4-(6-tert-Butyl-1H-pyrazolo[3,4-b]pyridin-4-yl)-phenyl]-3-(3-ethyl-phenyl)-urea;

1-[4-(6-Isopropyl-1H-pyrazolo[3,4-b]pyridin-4-yl)-phenyl]-3-(3-trifluoromethyl-phenyl)-urea;

1-[4-(6-Isopropyl-1-methyl-1H-pyrazolo[3,4-b]pyridin-4-yl)-phenyl]-3-(3-trifluoromethyl-phenyl)-urea;

1-[4-(1-Methyl-1H-pyrazolo[3,4-b]pyridin-4-yl)-phenyl]-3-(3-trifluoromethyl-phenyl)-urea;

1-(1-Methyl-4-{4-[3-(3-trifluoromethyl-phenyl)-ureido]-phenyl}-1H-pyrazolo[3,4-b]pyridin-6-yl)-cyclopropanecarboxylic acid ethyl ester;

1-[4-(1-Methyl-1H-pyrazolo[3,4-b]-pyridin-4-yl)-phenyl]-3-phenyl-urea;

1-(2-Fluoro-5-methyl-phenyl)-3-[4-(1-methyl-1H-pyrazolo[3,4-b]pyridin-4-yl)-phenyl]-urea;

1-(2-Fluoro-5-trifluoromethyl-phenyl)-3-[4-(1-methyl-1H-pyrazolo[3,4-b]pyridin-4-yl)-phenyl]-urea;

1-[4-(6-tert-Butyl-1H-pyrazolo[3,4-b]pyridin-4-yl)-phenyl]-3-(3,4-difluoro-phenyl)-urea;

1-[4-(6-tert-Butyl-1H-pyrazolo[3,4-b]pyridin-4-yl)-phenyl]-3-o-tolyl-urea;

1-[4-(6-tert-Butyl-1H-pyrazolo[3,4-b]pyridin-4-yl)-phenyl]-3-m-tolyl-urea; 1-[4-(6-tert-Butyl-1H-pyrazolo[3,4-b]pyridin-4-yl)-phenyl]-3-(3-fluoro-phenyl)-urea;

1-[4-(6-tert-Butyl-1H-pyrazolo[3,4-b]pyridin-4-yl)-phenyl]-3-(4-fluoro-phenyl)-urea;

1-[4-(6-tert-Butyl-1H-pyrazolo[3,4-b]pyridin-4-yl)-phenyl]-3-(3-methoxy-phenyl)-urea;

1-[4-(6-tert-Butyl-1H-pyrazolo[3,4-b]pyridin-4-yl)-phenyl]-3-[4-(4-methyl-piperazin-1-ylmethyl)-3-trifluoromethyl-phenyl]-urea;

1-[4-(6-tert-Butyl-1-methyl-1H-pyrazolo[3,4-b]pyridin-4-yl)-phenyl]-3-[2-(2-dimethylamino-ethoxy)-5-trifluoromethyl-phenyl]-urea;

1-[4-(6-tert-Butyl-1-methyl-1H-pyrazolo[3,4-b]pyridin-4-yl)-phenyl]-3-[2-[2-(4-methyl-piperazin-1-yl)-ethoxy]-5-trifluoromethyl-phenyl]-urea;

1-[4-(6-Methyl-1H-pyrazolo[3,4-b]pyridin-4-yl)-phenyl]-3-(3-trifluoromethyl-phenyl)-urea;

1-(4-Trifluoromethyl-phenyl)-cyclopropanecarboxylic acid [4-(6-methyl-1H-pyrazolo[3,4-b]pyridin-4-yl)-phenyl]-amide;

1-[4-(1H-pyrazolo[3,4-b]pyridin-4-yl)-phenyl]-3-(3-trifluoromethyl-phenyl)-urea;

1-Phenyl-3-[4-(1H-pyrazolo[3,4-b]-pyridin-4-yl)-phenyl]-urea;

1-(2-Fluoro-5-methyl-phenyl)-3-[4-(1H-pyrazolo[3,4-b]pyridin-4-yl)-phenyl]-urea;

1-[4-(1-Methyl-piperidin-4-yloxy)-3-trifluoromethyl-phenyl]-3-[4-(1-methyl-1H-pyrazolo[3,4-b]pyridin-4-yl)-phenyl]-urea;

1-[4-(4-Methyl-piperazin-1-ylmethyl)-3-trifluoromethyl-phenyl]-3-[4-(1-methyl-1H-pyrazolo[3,4-b]pyridin-4-yl)-phenyl]-urea;

1-{4-[6-Isopropyl-1-(3-morpholin-4-yl-propyl)-1H-pyrazolo[3,4-b]pyridin-4-yl]-phenyl}-3-(3-trifluoromethyl-phenyl)-urea;

1-(1-Methyl-4-{4-[3-(3-trifluoromethyl-phenyl)-ureido]-phenyl}-1H-pyrazolo[3,4-b]pyridin-6-yl)-cyclopropane-carboxylic acid dimethylamide;

1-(4-{1-Methyl-6-[1-(pyrrolidine-1-carbonyl)-cyclopropyl]-1H-pyrazolo[3,4-b]pyridin-4-yl}-phenyl)-3-(3-trifluoromethyl-phenyl)-urea;

1-(2-Fluoro-5-trifluoromethyl-phenyl)-3-[4-(1H-pyrazolo[3,4-b]pyridin-4-yl)-phenyl]-urea;

1-[4-(1,6-Dimethyl-1H-pyrazolo[3,4-b]pyridin-4-yl)-phenyl]-3-phenyl-urea;

1-[4-(1,6-Dimethyl-1H-pyrazolo[3,4-b]pyridin-4-yl)-phenyl]-3-(3-trifluoromethyl-phenyl)-urea;

1-[4-(1,6-Dimethyl-1H-pyrazolo[3,4-b]pyridin-4-yl)-phenyl]-3-(2-fluoro-5-trifluoromethyl-phenyl)-urea;

1-[4-(1,6-Dimethyl-1H-pyrazolo[3,4-b]pyridin-4-yl)-phenyl]-3-(3-fluoro-5-trifluoromethyl-phenyl)-urea;

1-[4-(1,6-Dimethyl-1H-pyrazolo[3,4-b]pyridin-4-yl)-phenyl]-3-(4-fluoro-3-trifluoromethyl-phenyl)-urea;

1-[4-(1,6-Dimethyl-1H-pyrazolo[3,4-b]pyridin-4-yl)-phenyl]-3-(2-fluoro-3-trifluoromethyl-phenyl)-urea;

1-[4-(1,6-Dimethyl-1H-pyrazolo[3,4-b]pyridin-4-yl)-phenyl]-3-(2-methoxy-5-trifluoromethyl-phenyl)-urea;

1-[4-(1,6-Dimethyl-1H-pyrazolo[3,4-b]pyridin-4-yl)-phenyl]-3-(2-pyrrolidin-1-yl-5-trifluoromethyl-phenyl)-urea;

1-[4-(1-Methyl-6-morpholin-4-ylmethyl-1H-pyrazolo[3,4-b]pyridin-4-yl)-phenyl]-3-phenyl-urea;

1-[4-(1-Methyl-6-morpholin-4-ylmethyl-1H-pyrazolo[3,4-b]pyridin-4-yl)-phenyl]-3-(3-trifluoromethyl-phenyl)-urea;

1-[4-(1-Methyl-6-morpholin-4-ylmethyl-1H-pyrazolo[3,4-b]pyridin-4-yl)-phenyl]-3-m-tolyl-urea;

1-(3-Ethyl-phenyl)-3-[4-(1-methyl-6-morpholin-4-ylmethyl-1H-pyrazolo[3,4-b]pyridin-4-yl)-phenyl]-urea;

1-(2-Fluoro-5-methyl-phenyl)-3-[4-(1-methyl-6-morpholin-4-ylmethyl-1H-pyrazolo[3,4-b]pyridin-4-yl)-phenyl]-urea;

1-(2-Fluoro-5-trifluoromethyl-phenyl)-3-[4-(1-methyl-6-morpholin-4-ylmethyl-1H-pyrazolo[3,4-b]pyridin-4-yl)-phenyl]-urea;

1-{4-[6-(4-Hydroxy-piperidin-1-ylmethyl)-1-methyl-1H-pyrazolo[3,4-b]pyridin-4-yl]-phenyl}-3-(3-trifluoromethyl-phenyl)-urea;

1-(2-Fluoro-5-methyl-phenyl)-3-{4-[6-(4-hydroxy-piperidin-1-ylmethyl)-1-methyl-1H-pyrazolo[3,4-b]pyridin-4-yl]-phenyl}-urea;
1-{4-[4-(3-Phenyl-ureido)-phenyl]-1H-pyrazolo[3,4-b]pyridin-6-yl}-cyclopropanecarboxylic acid ethyl ester;
1-(4-{4-[3-(2-Fluoro-5-methyl-phenyl)-ureido]-phenyl}-1-methyl-1H-pyrazolo[3,4-b]pyridin-6-yl)-cyclopropane-carboxylic acid dimethylamide;
1-(4-{4-[3-(2-Fluoro-5-methyl-phenyl)-ureido]-phenyl}-1-methyl-1H-pyrazolo[3,4-b]pyridin-6-yl)-cyclopropane-carboxylic acid cyclopropylamide;
1-(2-Fluoro-5-methyl-phenyl)-3-(4-{1-methyl-6-[1-(pyrrolidine-1-carbonyl)-cyclopropyl]-1H-pyrazolo[3,4-b]-pyridin-4-yl}-phenyl)-urea;
1-[3-Methyl-4-(4-methyl-piperazin-1-yl-methyl)-phenyl]-3-[4-(1H-pyrazolo-[3,4-b]pyridin-4-yl)-phenyl]-urea;
1-[4-(4-Methyl-piperazin-1-yl-methyl)-3-trifluoromethyl-phenyl]-3-[4-(1H-pyrazolo[3,4-b]pyridin-4-yl)-phenyl]-urea;
1-[4-(6-Cyclopropyl-1H-pyrazolo[3,4-b]pyridin-4-yl)-phenyl]-3-(3-trifluoromethyl-phenyl)-urea;
1-[3-Methyl-4-(4-methyl-piperazin-1-ylmethyl)-phenyl]-3-[4-(1-methyl-1H-pyrazolo[3,4-b]pyridin-4-yl)-phenyl]-urea;
1-[4-(6-Cyclopropyl-1-methyl-1H-pyrazolo[3,4-b]pyridin-4-yl)-phenyl]-3-(3-trifluoromethyl-phenyl)-urea;
1-[4-(6-Cyclobutyl-1-methyl-1H-pyrazolo[3,4-b]pyridin-4-yl)-phenyl]-3-(3-trifluoromethyl-phenyl)-urea;
1-[4-(6-Cyclohexyl-1-methyl-1H-pyrazolo[3,4-b]pyridin-4-yl)-phenyl]-3-(3-trifluoromethyl-phenyl)-urea;
1-{4-[1-Methyl-6-(2-phenyl-cyclopropyl)-1H-pyrazolo[3,4-b]pyridin-4-yl]-phenyl}-3-(3-trifluoromethyl-phenyl)-urea;
1-[4-(1-Methyl-6-thiazol-2-yl-1H-pyrazolo[3,4-b]pyridin-4-yl)-phenyl]-3-(3-trifluoromethyl-phenyl)-urea;
N,N-Dimethyl-2-(1-methyl-4-{4-[3-(3-trifluoromethyl-phenyl)-ureido]-phenyl}-1H-pyrazolo[3,4-b]pyridin-6-yl)-isobutyramide;
N-Cyclopropyl-2-(1-methyl-4-{4-[3-(3-trifluoromethyl-phenyl)-ureido]-phenyl}-1H-pyrazolo[3,4-b]pyridin-6-yl)-isobutyramide;
2-[2,2-Dimethyl-3-(1-methyl-4-{4-[3-(3-trifluoromethyl-phenyl)-ureido]-phenyl}-1H-pyrazolo[3,4-b]pyridin-6-yl)-cyclobutyl]-N,N-dimethyl-acetamide;
N-Cyclopropyl-2-[2,2-dimethyl-3-(1-methyl-4-{4-[3-(3-trifluoromethyl-phenyl)-ureido]-phenyl}-1H-pyrazolo[3,4-b]pyridin-6-yl)-cyclobutyl]-acetamide;
1-{4-[1-Methyl-6-(4-methyl-piperazin-1-ylmethyl)-1H-pyrazolo[3,4-b]pyridin-4-yl]-phenyl}-(3-trifluoromethyl-phenyl)-urea;
1-(2-Fluoro-5-methyl-phenyl)-3-{4-[1-methyl-6-(4-methyl-piperazin-1-ylmethyl)-1H-pyrazolo[3,4-b]pyridin-4-yl]-phenyl}-urea;
1-[4-(1-Methyl-6-piperidin-1-ylmethyl-1H-pyrazolo[3,4-b]pyridin-4-yl)-phenyl]-3-(3-trifluoromethyl-phenyl)-urea;
1-(2-Fluoro-5-methyl-phenyl)-3-[4-(1-methyl-6-piperidin-1-ylmethyl-1H-pyrazolo[3,4-b]pyridin-4-yl)-phenyl]-urea;
1-[4-(6-Dimethylaminomethyl-1-methyl-1H-pyrazolo[3,4-b]pyridin-4-yl)-phenyl]-3-(3-trifluoromethyl-phenyl)-urea;
1-[4-(6-Dimethylaminomethyl-1-methyl-1H-pyrazolo[3,4-b]pyridin-4-yl)-phenyl]-3-(2-fluoro-5-methyl-phenyl)-urea;
1-[4-(6-Methanesulfonylmethyl-1-methyl-1H-pyrazolo[3,4-b]pyridin-4-yl)-phenyl]-3-(3-trifluoromethyl-phenyl)-urea;
1-(2-Fluoro-5-methyl-phenyl)-3-[4-(6-methanesulfonylmethyl-1-methyl-1H-pyrazolo[3,4-b]pyridin-4-yl)-phenyl]-urea;
1-[4-(6-Methanesulfonylmethyl-1-methyl-1H-pyrazolo[3,4-b]pyridin-4-yl)-phenyl]-3-(4-trifluoromethyl-pyridin-2-yl)-urea;
1-{4-[1-Methyl-6-(4-methyl-piperazin-1-ylmethyl)-1H-pyrazolo[3,4-b]pyridin-4-yl]-phenyl}-3-(4-trifluoromethyl-pyridin-2-yl)-urea;
1-[4-(1-Methyl-6-piperidin-1-ylmethyl-1H-pyrazolo[3,4-b]pyridin-4-yl)-phenyl]-3-(4-trifluoromethyl-pyridin-2-yl)-urea;
1-[4-(6-Dimethylaminomethyl-1-methyl-1H-pyrazolo[3,4-b]pyridin-4-yl)-phenyl]-3-(4-trifluoromethyl-pyridin-2-yl)-urea;
1-{4-[1-Methyl-6-(2,6-dimethyl-morpholin-4-ylmethyl)-1H-pyrazolo[3,4-b]pyridin-4-yl]-phenyl}-3-(3-trifluoromethyl-phenyl)-urea;
1-(2-Fluoro-5-methyl-phenyl)-3-{4-[1-methyl-6-(2,6-dimethyl-morpholin-4-ylmethyl)-1H-pyrazolo[3,4-b]pyridin-4-yl]-phenyl}-urea;
1-{4-[1-Methyl-6-(3-oxo-piperazin-1-ylmethyl)-1H-pyrazolo[3,4-b]pyridin-4-yl]-phenyl}-3-(3-trifluoromethyl-phenyl)-urea;
1-(2-Fluoro-5-methyl-phenyl)-3-{4-[1-methyl-6-(3-oxo-piperazin-1-ylmethyl)-1H-pyrazolo[3,4-b]pyridin-4-yl]-phenyl}-urea;
1-{4-[6-(3-Dimethylamino-pyrrolidin-1-ylmethyl)-1-methyl-1H-pyrazolo[3,4-b]pyridin-4-yl]-phenyl}-3-(3-trifluoromethyl-phenyl)-urea;
1-{4-[6-(3-Dimethylamino-pyrrolidin-1-ylmethyl)-1-methyl-1H-pyrazolo[3,4-b]pyridin-4-yl]-phenyl}-3-(2-fluoro-5-methyl-phenyl)-urea;
1-[4-(6-Methoxymethyl-1-methyl-1H-pyrazolo[3,4-b]pyridin-4-yl)-phenyl]-3-(3-trifluoromethyl-phenyl)-urea;
1-[4-(6-Methoxymethyl-1-methyl-1H-pyrazolo[3,4-b]pyridin-4-yl)-phenyl]-3-(4-trifluoromethyl-pyridin-2-yl)-urea; or
1-(2-Fluoro-5-methyl-phenyl)-3-[4-(6-methoxymethyl-1-methyl-1H-pyrazolo[3,4-b]pyridin-4-yl)-phenyl]-urea;

or a salt or an N-oxide thereof.

15. A method of preparing a compound of formula (I) according to claim 1, comprising deaminating via diazotization and de-diazotization an intermediate compound of formula 1:

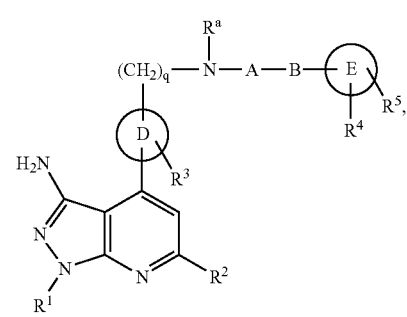

wherein A, B, D, E, $R^a$, $R^1$, $R^2$, $R^3$, $R^4$, $R^5$ and q are each, independently, as defined in claim 1, to form a compound of formula (I):

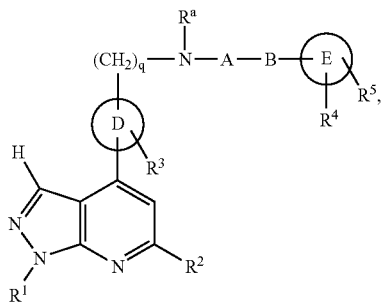

(I)

wherein A, B, D, E, $R^a$, $R^1$, $R^2$, $R^3$, $R^4$, $R^5$ and q are each, independently, as defined in claim 1.

16. A method of preparing a compound of formula (I) according to claim 1, comprising reacting an intermediate compound of formula 8″:

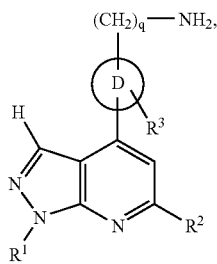

8″ wherein D, $R^1$, $R^2$, $R^3$ and q are each, independently, as defined in claim 1, with an isocyanate of formula (Ia′):

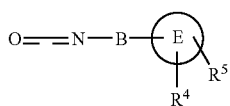

Ia′ wherein B, E, $R^4$, and $R^5$ are each, independently, as defined in claim 1, to form a compound of formula (Ia):

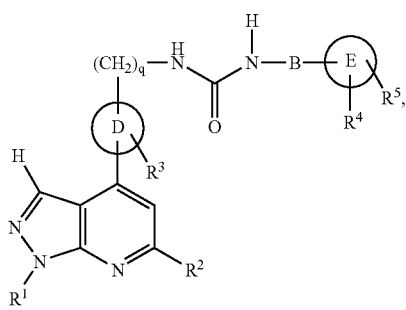

Ia wherein B, D, E, $R^1$, $R^2$, $R^3$, $R^4$, $R^5$ and q are each, independently, as defined in claim 1.

17. A method of preparing a compound of formula (I) according to claim 1, comprising reacting an intermediate compound of formula 8″:

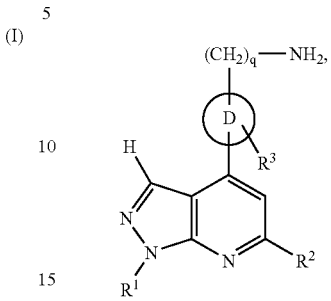

8″ wherein D, $R^1$, $R^2$, $R^3$, and q are each, independently, as defined in claim 1, with a compound of formula Ia″:

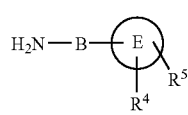

Ia″ wherein B, E, $R^4$, and $R^5$ are each, independently, defined as in claim 1;
in the presence of a phosgene equivalent, to form a compound of formula (Ia):

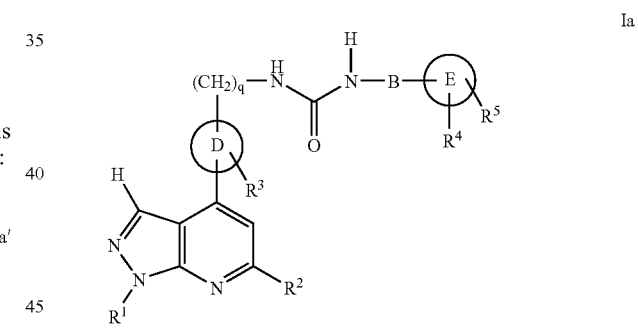

Ia wherein B, D, E, $R^1$, $R^2$, $R^3$, $R^4$, $R^5$ and q are each, independently, as defined in claim 1.

18. A method of preparing a compound of formula (I) according to claim 1, comprising reacting an intermediate compound of formula 7:

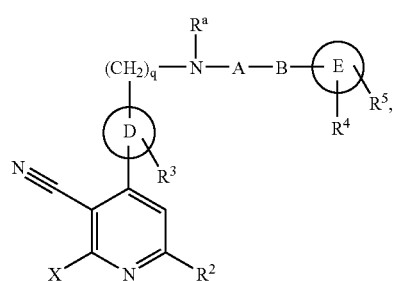

7 wherein, X is OTf, Cl, F, OAc, OMe, and A, B, D, E, $R^a$, $R^2$, $R^3$, $R^4$, $R^5$ and q are each, independently, as defined in claim 1, with a substituted hydrazine of formula 6':

  6' wherein $R^1$ is as defined in claim 1, to form a compound of formula 1:

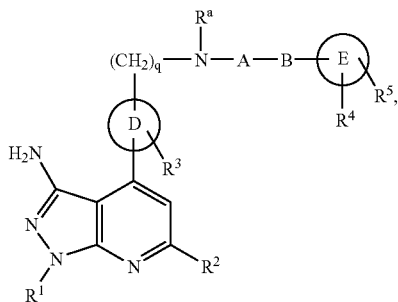

wherein A, B, D, E, $R^a$, $R_1$, $R_2$, $R_3$, $R_4$, $R_5$ and q are each, independently, as defined claim 1.

19. A method of preparing a compound of formula (I) according to claim 1, comprising deprotecting an intermediate compound of formula 11:

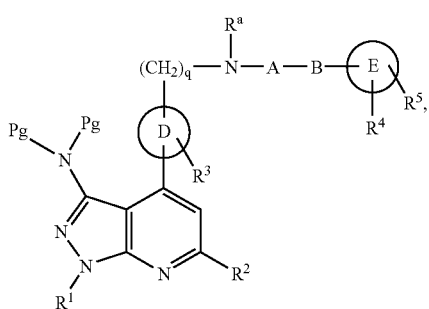

wherein, formula 10' Pg is a protecting group

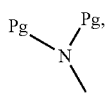  10' and wherein, A, B, D, E, $R^a$, $R^1$, $R^2$, $R^3$, $R^4$, $R^5$ and q are each, independently, as defined in claim 1, to form a compound of formula 1:

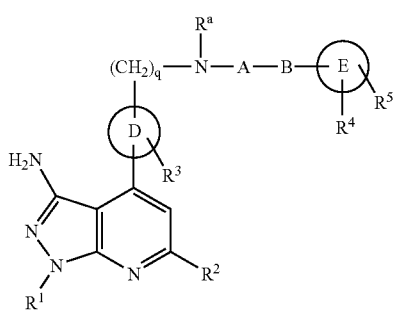

wherein, A, B, D, E, $R^a$, $R^1$, $R^2$, $R^3$, $R^4$, $R^5$ and q are each, independently, as defined in claim 1.

20. A method of preparing a compound of formula (I) according to claim 1, comprising reacting an intermediate compound of formula 12:

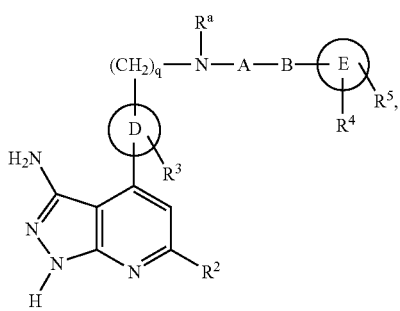

wherein, A, B, D, E, $R^a$, $R^2$, $R^3$, $R^4$, $R^5$ and q are each, independently, as defined in claim 1, with a compound of formula 12':

  12', wherein, R1 is defined as in claim 1, and X' OTf, Cl, F, OAc, or OMe, to form a compound of formula 1:

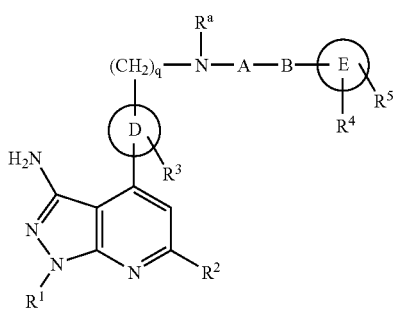

wherein, A, B, D, E, $R^a$, $R^1$, $R^2$, $R^3$, $R^4$, $R^5$ and q are each, independently, as defined in claim 1.

21. A method of preparing a compound of formula (I) according to claim 1, comprising reacting, in a coupling reaction, an intermediate compound of formula 15:

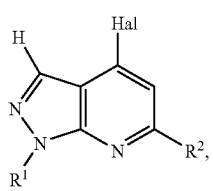

wherein, $R^1$ and $R^2$ are each, independently, as defined in claim 1, and Hal is Cl, Br, or I, with a compound of formula 16:

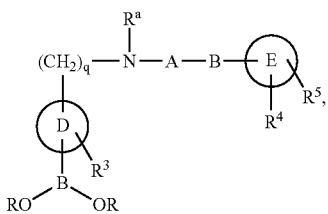

wherein, A, B, D, E, $R^a$, $R^3$, $R^4$, $R^5$ and q are each, independently, as defined in claim 1, and R is H, alkyl;
to form a compound of formula (I):

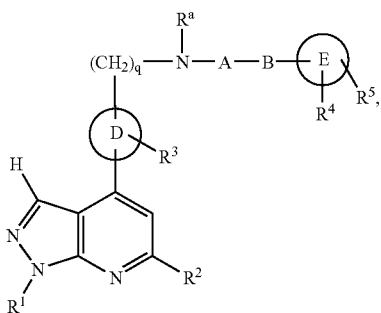

wherein, A, B, D, E, $R^a$, $R^1$, $R^2$, $R^3$, $R^4$, $R^5$ and q are each, independently, as defined in claim 1.

22. A pharmaceutical composition which comprises a compound of formula (I) according to claim 1, or a pharmaceutically acceptable salt or an N-oxide thereof, and a pharmaceutically-acceptable diluent or carrier.

23. The method according to claim 15, wherein the deamination comprises diazotization with $NaNO_2$ and further de-diazotization with an acid which is hydrochloric acid or sulphuric acid.

24. The method according to claim 17, wherein the phosgene equivalent is triphosgene.

25. The method according to claim 19, wherein formula 10'-Pg is a phthalimide-protected amine of formula 10"

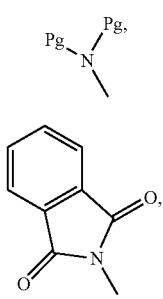

and the deprotecting step is carried out by reacting said compound of formula 11 with hydrazine.

26. A salt or an N-oxide of the compound according to claim 2.

27. A salt or an N-oxide of the compound according to claim 3.

28. A salt or an N-oxide of the compound according to claim 4.

29. A salt or an N-oxide of the compound according to claim 5.

30. A salt or an N-oxide of the compound according to claim 6.

31. A salt or an N-oxide of the compound according to claim 7.

32. A salt or an N-oxide of the compound according to claim 8.

33. A salt or an N-oxide of the compound according to claim 9.

34. A salt or an N-oxide of the compound according to claim 10.

35. A salt or an N-oxide of the compound according to claim 11.

36. A salt or an N-oxide of the compound according to claim 12.

37. A salt or an N-oxide of the compound according to claim 13.

38. A salt or an N-oxide of the compound according to claim 14.

39. A pharmaceutical composition which comprises at least one compound which is

1-[4-(6-tert-Butyl-1H-pyrazolo[3,4-b]pyridin-4-yl)-phenyl]-3-(3-ethyl-phenyl)-urea;

1-[4-(6-Isopropyl-1H-pyrazolo[3,4-b]pyridin-4-yl)-phenyl]-3-(3-trifluoromethyl-phenyl)-urea;

1-[4-(6-Isopropyl-1-methyl-1H-pyrazolo[3,4-b]pyridin-4-yl)-phenyl]-3-(3-trifluoromethyl-phenyl)-urea;

1-[4-(1-Methyl-1H-pyrazolo[3,4-b]pyridin-4-yl)-phenyl]-3-(3-trifluoromethyl-phenyl)-urea;

1-(1-Methyl-4-{4-[3-(3-trifluoromethyl-phenyl)-ureido]-phenyl}-1H-pyrazolo[3,4-b]pyridin-6-yl)-cyclopropanecarboxylic acid ethyl ester;

1-[4-(1-Methyl-1H-pyrazolo[3,4-b]-pyridin-4-yl)-phenyl]-3-phenyl-urea;

1-(2-Fluoro-5-methyl-phenyl)-3-[4-(1-methyl-1H-pyrazolo[3,4-b]pyridin-4-yl)-phenyl]-urea;

1-(2-Fluoro-5-trifluoromethyl-phenyl)-3-[4-(1-methyl-1H-pyrazolo[3,4-b]-pyridin-4-yl)-phenyl]-urea;

1-[4-(6-tert-Butyl-1H-pyrazolo[3,4-b]pyridin-4-yl)-phenyl]-3-(3,4-difluoro-phenyl)-urea;

1-[4-(6-tert-Butyl-1H-pyrazolo[3,4-b]pyridin-4-yl)-phenyl]-3-o-tolyl-urea;

1-[4-(6-tert-Butyl-1H-pyrazolo[3,4-b]pyridin-4-yl)-phenyl]-3-m-tolyl-urea; 1-[4-(6-tert-Butyl-1H-pyrazolo[3,4-b]pyridin-4-yl)-phenyl]-3-(3-fluoro-phenyl)-urea;

1-[4-(6-tert-Butyl-1H-pyrazolo[3,4-b]pyridin-4-yl)-phenyl]-3-(4-fluoro-phenyl)-urea;

1-[4-(6-tert-Butyl-1H-pyrazolo[3,4-b]pyridin-4-yl)-phenyl]-3-(3-methoxy-phenyl)-urea;

1-[4-(6-tert-Butyl-1H-pyrazolo[3,4-b]pyridin-4-yl)-phenyl]-3-[4-(4-methyl-piperazin-1-ylmethyl)-3-trifluoromethyl-phenyl]-urea;

1-[4-(6-tert-Butyl-1-methyl-1H-pyrazolo[3,4-b]pyridin-4-yl)-phenyl]-3-[2-(2-dimethylamino-ethoxy)-5-trifluoromethyl-phenyl-urea;

1-[4-(6-tert-Butyl-1-methyl-1H-pyrazolo[3,4-b]pyridin-4-yl)-phenyl]-3-[2-[2-(4-methyl-piperazin-1-yl)-ethoxy]-5-trifluoromethyl-phenyl]-urea;

1-[4-(6-Methyl-1H-pyrazolo[3,4-b]pyridin-4-yl)-phenyl]-3-(3-trifluoromethyl-phenyl)-urea;

1-(4-Trifluoromethyl-phenyl)-cyclopropanecarboxylic acid [4-(6-methyl-1H-pyrazolo[3,4-b]pyridin-4-yl)-phenyl]-amide;

1-[4-(1H-Pyrazolo[3,4-b]pyridin-4-yl)-phenyl]-3-(3-trifluoromethyl-phenyl)-urea;
1-Phenyl-3-[4-(1H-pyrazolo[3,4-b]-pyridin-4-yl)-phenyl]-urea;
1-(2-Fluoro-5-methyl-phenyl)-3-[4-(1H-pyrazolo[3,4-b]pyridin-4-yl)-phenyl]-urea;
1-[4-(1-Methyl-piperidin-4-yloxy)-3-trifluoromethyl-phenyl]-3-[4-(1-methyl-1H-pyrazolo[3,4-b]pyridin-4-yl)-phenyl]-urea;
1-[4-(4-Methyl-piperazin-1-ylmethyl)-3-trifluoromethyl-phenyl]-3-[4-(1-methyl-1H-pyrazolo[3,4-b]pyridin-4-yl)-phenyl]-urea;
1-{4-[6-Isopropyl-1-(3-morpholin-4-yl-propyl)-1H-pyrazolo[3,4-b]pyridin-4-yl]-phenyl}-3-(3-trifluoromethyl-phenyl)-urea;
1-(1-Methyl-4-{4-[3-(3-trifluoromethyl-phenyl)-ureido]-phenyl}-1H-pyrazolo[3,4-b]pyridin-6-yl)-cyclopropane-carboxylic acid dimethylamide;
1-(4-{1-Methyl-6-[1-(pyrrolidine-1-carbonyl)-cyclopropyl]-1H-pyrazolo[3,4-b]pyridin-4-yl}phenyl)-3-(3-trifluoromethyl-phenyl)-urea;
1-(2-Fluoro-5-trifluoromethyl-phenyl)-3-[4-(1H-pyrazolo[3,4-b]pyridin-4-yl)-phenyl]-urea;
1-[4-(1,6-Dimethyl-1H-pyrazolo[3,4-b]pyridin-4-yl)-phenyl]-3-phenyl-urea;
1-[4-(1,6-Dimethyl-1H-pyrazolo[3,4-b]pyridin-4-yl)-phenyl]-3-(3-trifluoromethyl-phenyl)-urea;
1-[4-(1,6-Dimethyl-1H-pyrazolo[3,4-b]pyridin-4-yl)-phenyl]-3-(2-fluoro-5-trifluoromethyl-phenyl)-urea;
1-[4-(1,6-Dimethyl-1H-pyrazolo[3,4-b]pyridin-4-yl)-phenyl]-3-(3-fluoro-5-trifluoromethyl-phenyl)-urea;
1-[4-(1,6-Dimethyl-1H-pyrazolo[3,4-b]pyridin-4-yl)-phenyl]-3-(4-fluoro-3-trifluoromethyl-phenyl)-urea;
1-[4-(1,6-Dimethyl-1H-pyrazolo[3,4-b]pyridin-4-yl)-phenyl]-3-(2-fluoro-3-trifluoromethyl-phenyl)-urea;
1-[4-(1,6-Dimethyl-1H-pyrazolo[3,4-b]pyridin-4-yl)-phenyl]-3-(2-methoxy-5-trifluoromethyl-phenyl)-urea;
1-[4-(1,6-Dimethyl-1H-pyrazolo[3,4-b]pyridin-4-yl)-phenyl]-3-(2-pyrrolidin-1-yl-5-trifluoromethyl-phenyl)-urea;
1-[4-(1-Methyl-6-morpholin-4-ylmethyl-1H-pyrazolo[3,4-b]pyridin-4-yl)-phenyl]-3-phenyl-urea;
1-[4-(1-Methyl-6-morpholin-4-ylmethyl-1H-pyrazolo[3,4-b]pyridin-4-yl)-phenyl]-3-(3-trifluoromethyl-phenyl)-urea;
1-[4-(1-Methyl-6-morpholin-4-ylmethyl-1H-pyrazolo[3,4-b]pyridin-4-yl)-phenyl]-3-m-tolyl-urea;
1-(3-Ethyl-phenyl)-3-[4-(1-methyl-6-morpholin-4-ylmethyl-1H-pyrazolo[3,4-b]pyridin-4-yl)-phenyl]-urea;
1-(2-Fluoro-5-methyl-phenyl)-3-[4-(1-methyl-6-morpholin-4-ylmethyl-1H-pyrazolo[3,4-b]pyridin-4-yl)-phenyl]-urea;
1-(2-Fluoro-5-trifluoromethyl-phenyl)-3-[4-(1-methyl-6-morpholin-4-ylmethyl-1H-pyrazolo[3,4-b]pyridin-4-yl)-phenyl]-urea;
1-{4-[6-(4-Hydroxy-piperidin-1-ylmethyl)-1-methyl-1H-pyrazolo[3,4-b]pyridin-4-yl]-phenyl}-3-(3-trifluoromethyl-phenyl)-urea;
1-(2-Fluoro-5-methyl-phenyl)-3-{4-[6-(4-hydroxy-piperidin-1-ylmethyl)-1-methyl-1H-pyrazolo[3,4-b]pyridin-4-yl]-phenyl}-urea;
1-{4-[4-(3-Phenyl-ureido)-phenyl]-1H-pyrazolo[3,4-b]pyridin-6-yl}-cyclopropanecarboxylic acid ethyl ester;
1-(4-{4-[3-(2-Fluoro-5-methyl-phenyl)-ureido]-phenyl}-1-methyl-1H-pyrazolo[3,4-b]pyridin-6-yl)-cyclopropane-carboxylic acid dimethylamide;
1-(4-{4-[3-(2-Fluoro-5-methyl-phenyl)-ureido]-phenyl}-1-methyl-1H-pyrazolo[3,4-b]pyridin-6-yl)-cyclopropane-carboxylic acid cyclopropylamide;
1-(2-Fluoro-5-methyl-phenyl)-3-(4-{1-methyl-6-[1-(pyrrolidine-1-carbonyl)-cyclopropyl]-1H-pyrazolo[3,4-b]-pyridin-4-yl}-phenyl)-urea;
1-[3-Methyl-4-(4-methyl-piperazin-1-yl-methyl)-phenyl]-3-[4-(1H-pyrazolo-[3,4-b]pyridin-4-yl)-phenyl]-urea;
1-[4-(4-Methyl-piperazin-1-yl-methyl)-3-trifluoromethyl-phenyl]-3-[4-(1H-pyrazolo[3,4-b]pyridin-4-yl)-phenyl]-urea;
1-[4-(6-Cyclopropyl-1H-pyrazolo[3,4-b]pyridin-4-yl)-phenyl]-3-(3-trifluoromethyl-phenyl)-urea;
1-[3-Methyl-4-(4-methyl-piperazin-1-ylmethyl)-phenyl]-3-[4-(1-methyl-1H-pyrazolo[3,4-b]pyridin-4-yl)-phenyl]-urea;
1-[4-(6-Cyclopropyl-1-methyl-1H-pyrazolo[3,4-b]pyridin-4-yl)-phenyl]-3-(3-trifluoromethyl-phenyl)-urea;
1-[4-(6-Cyclobutyl-1-methyl-1H-pyrazolo[3,4-b]pyridin-4-yl)-phenyl]-3-(3-trifluoromethyl-phenyl)-urea;
1-[4-(6-Cyclohexyl-1-methyl-1H-pyrazolo[3,4-b]pyridin-4-yl)-phenyl]-3-(3-trifluoromethyl-phenyl)-urea;
1-{4-[1-Methyl-6-(2-phenyl-cyclopropyl)-1H-pyrazolo[3,4-b]pyridin-4-yl]-phenyl}-3-(3-trifluoromethyl-phenyl)-urea;
1-[4-(1-Methyl-6-thiazol-2-yl-1H-pyrazolo[3,4-b]pyridin-4-yl)-phenyl]-3-(3-trifluoromethyl-phenyl)-urea;
N,N-Dimethyl-2-(1-methyl-4-{4-[3-(3-trifluoromethyl-phenyl)-ureido]-phenyl}-1H-pyrazolo[3,4-b]pyridin-6-yl)-isobutyramide;
N-Cyclopropyl-2-(1-methyl-4-{4-[3-(3-trifluoromethyl-phenyl)-ureido]-phenyl}-1H-pyrazolo[3,4-b]pyridin-6-yl)-isobutyramide;
2-[2,2-Dimethyl-3-(1-methyl-4-{4-[3-(3-trifluoromethyl-phenyl)-ureido]-phenyl}-1H-pyrazolo[3,4-b]pyridin-6-yl)-cyclobutyl]-N,N-dimethyl-acetamide;
N-Cyclopropyl-2-[2,2-dimethyl-3-(1-methyl-4-{4-[3-(3-trifluoromethyl-phenyl)-ureido]-phenyl}-1H-pyrazolo[3,4-b]pyridin-6-yl)-cyclobutyl]-acetamide;
1-{4-[1-Methyl-6-(4-methyl-piperazin-1-ylmethyl)-1H-pyrazolo[3,4-b]pyridin-4-yl]-phenyl}-(3-trifluoromethyl-phenyl)-urea;
1-(2-Fluoro-5-methyl-phenyl)-3-{4-[1-methyl-6-(4-methyl-piperazin-1-ylmethyl)-1H-pyrazolo[3,4-b]pyridin-4-yl]-phenyl}-urea;
1-[4-(1-Methyl-6-piperidin-1-ylmethyl-1H-pyrazolo[3,4-b]pyridin-4-yl)-phenyl]-3-(3-trifluoromethyl-phenyl)-urea;
1-(2-Fluoro-5-methyl-phenyl)-3-[4-(1-methyl-6-piperidin-1-ylmethyl-1H-pyrazolo[3,4-b]pyridin-4-yl)-phenyl]-urea;
1-[4-(6-Dimethylaminomethyl-1-methyl-1H-pyrazolo[3,4-b]pyridin-4-yl)-phenyl]-3-(3-trifluoromethyl-phenyl)-urea;
1-[4-(6-Dimethylaminomethyl-1-methyl-1H-pyrazolo[3,4-b]pyridin-4-yl)-phenyl]-3-(2-fluoro-5-methyl-phenyl)-urea;
1-[4-(6-Methanesulfonylmethyl-1-methyl-1H-pyrazolo[3,4-b]pyridin-4-yl)-phenyl]-3-(3-trifluoromethyl-phenyl)-urea;
1-(2-Fluoro-5-methyl-phenyl)-3-[4-(6-methanesulfonylmethyl-1-methyl-1H-pyrazolo[3,4-b]pyridin-4-yl)-phenyl]-urea;
1-[4-(6-Methanesulfonylmethyl-1-methyl-1H-pyrazolo[3,4-b]pyridin-4-yl)-phenyl]-3-(4-trifluoromethyl-pyridin-2-yl)-urea;

1-{4-[1-Methyl-6-(4-methyl-piperazin-1-ylmethyl)-1H-pyrazolo[3,4-b]pyridin-4-yl]-phenyl}-3-(4-trifluoromethyl-pyridin-2-yl)-urea;

1-[4-(1-Methyl-6-piperidin-1-ylmethyl-1H-pyrazolo[3,4-b]pyridin-4-yl)-phenyl]-3-(4-trifluoromethyl-pyridin-2-yl)-urea;

1-[4-(6-Dimethylaminomethyl-1-methyl-1H-pyrazolo[3,4-b]pyridin-4-yl)-phenyl]-3-(4-trifluoromethyl-pyridin-2-yl)-urea;

1-{4-[1-Methyl-6-(2,6-dimethyl-morpholin-4-ylmethyl)-1H-pyrazolo[3,4-b]pyridin-4-yl]-phenyl}-3-(3-trifluoromethyl-phenyl)-urea;

1-(2-Fluoro-5-methyl-phenyl)-3-{4-[1-methyl-6-(2,6-dimethyl-morpholin-4-ylmethyl)-1H-pyrazolo[3,4-b]pyridin-4-yl]-phenyl}-urea;

1-{4-[1-Methyl-6-(3-oxo-piperazin-1-ylmethyl)-1H-pyrazolo[3,4-b]pyridin-4-yl]-phenyl}-3-(3-trifluoromethyl-phenyl)-urea;

1-(2-Fluoro-5-methyl-phenyl)-3-{4-[1-methyl-6-(3-oxo-piperazin-1-ylmethyl)-1H-pyrazolo[3,4-b]pyridin-4-yl]-phenyl}-urea;

1-{4-[6-(3-Dimethylamino-pyrrolidin-1-ylmethyl)-1-methyl-1H-pyrazolo[3,4-b]pyridin-4-yl]-phenyl}-3-(3-trifluoromethyl-phenyl)-urea;

1-{4-[6-(3-Dimethylamino-pyrrolidin-1-ylmethyl)-1-methyl-1H-pyrazolo[3,4-b]pyridin-4-yl]-phenyl}-3-(2-fluoro-5-methyl-phenyl)-urea;

1-[4-(6-Methoxymethyl-1-methyl-1H-pyrazolo[3,4-b]pyridin-4-yl)-phenyl]-3-(3-trifluoromethyl-phenyl)-urea;

1-[4-(6-Methoxymethyl-1-methyl-1H-pyrazolo[3,4-b]pyridin-4-yl)-phenyl]-3-(4-trifluoromethyl-pyridin-2-yl)-urea; or 1-(2-Fluoro-5-methyl-phenyl)-3-[4-(6-methoxymethyl-1-methyl-1H-pyrazolo[3,4-b]pyridin-4-yl)-phenyl]-urea;

and a pharmaceutically-acceptable diluent or carrier.

* * * * *